US012503497B2

(12) United States Patent
Lu et al.

(10) Patent No.: US 12,503,497 B2
(45) Date of Patent: Dec. 23, 2025

(54) MINIMAL ARRESTIN DOMAIN CONTAINING PROTEIN 1(ARRDC1) CONSTRUCTS

(71) Applicant: President and Fellows of Harvard College, Cambridge, MA (US)

(72) Inventors: Quan Lu, Cambridge, MA (US); Qiyu Wang, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 840 days.

(21) Appl. No.: 17/764,013

(22) PCT Filed: Sep. 25, 2020

(86) PCT No.: PCT/US2020/052784

§ 371 (c)(1),
(2) Date: Mar. 25, 2022

(87) PCT Pub. No.: WO2021/062196

PCT Pub. Date: Apr. 1, 2021

(65) Prior Publication Data

US 2022/0403003 A1 Dec. 22, 2022

Related U.S. Application Data

(60) Provisional application No. 62/906,685, filed on Sep. 26, 2019.

(51) Int. Cl.

| | |
|---|---|
| ***C07K 14/74*** | (2006.01) |
| ***A61K 9/127*** | (2025.01) |
| ***A61K 31/7088*** | (2006.01) |
| ***A61K 38/46*** | (2006.01) |
| ***A61K 47/55*** | (2017.01) |
| ***A61K 47/64*** | (2017.01) |
| ***A61K 47/69*** | (2017.01) |
| ***C07K 14/47*** | (2006.01) |
| ***C12N 5/00*** | (2006.01) |
| ***C12N 9/22*** | (2006.01) |
| ***C12N 15/62*** | (2006.01) |

(52) U.S. Cl.

CPC ........ *C07K 14/70539* (2013.01); *A61K 9/127* (2013.01); *A61K 31/7088* (2013.01); *A61K 38/465* (2013.01); *A61K 47/552* (2017.08); *A61K 47/64* (2017.08); *A61K 47/6911* (2017.08); *C07K 14/47* (2013.01); *C12N 5/00* (2013.01); *C12N 9/22* (2013.01); *C12N 15/62* (2013.01)

(58) Field of Classification Search

CPC ...................................................... C07K 14/47

See application file for complete search history.

(56) References Cited

U.S. PATENT DOCUMENTS

| | | | |
|---|---|---|---|
| 4,182,449 | A | 1/1980 | Kozlow |
| 4,880,635 | A | 11/1989 | Janoff et al. |
| 4,906,477 | A | 3/1990 | Kurono et al. |
| 4,911,928 | A | 3/1990 | Wallach |
| 4,917,951 | A | 4/1990 | Wallach |
| 4,920,016 | A | 4/1990 | Allen et al. |
| 4,921,757 | A | 5/1990 | Wheatley et al. |
| 5,270,163 | A | 12/1993 | Gold et al. |
| 5,449,639 | A | 9/1995 | Wei et al. |
| 5,475,096 | A | 12/1995 | Gold et al. |
| 5,496,938 | A | 3/1996 | Gold et al. |
| 5,595,887 | A | 1/1997 | Coolidge et al. |
| 5,767,099 | A | 6/1998 | Harris et al. |
| 5,780,053 | A | 7/1998 | Ashley et al. |
| 5,817,785 | A | 10/1998 | Gold et al. |
| 5,830,430 | A | 11/1998 | Unger et al. |
| 5,851,548 | A | 12/1998 | Dattagupta et al. |
| 5,855,910 | A | 1/1999 | Ashley et al. |
| 5,861,254 | A | 1/1999 | Schneider et al. |
| 5,958,691 | A | 9/1999 | Pieken et al. |
| 5,962,219 | A | 10/1999 | Gold et al. |
| 6,013,443 | A | 1/2000 | Heilig et al. |
| 6,030,776 | A | 2/2000 | Eaton et al. |
| 6,083,696 | A | 7/2000 | Biesecker et al. |
| 6,110,900 | A | 8/2000 | Gold et al. |
| 6,127,119 | A | 10/2000 | Stephens et al. |
| 6,147,204 | A | 11/2000 | Gold et al. |
| 6,376,019 | B1 | 4/2002 | Leung |
| 7,314,923 | B2 | 1/2008 | Kaneko et al. |
| 7,335,765 | B2 | 2/2008 | Kaneko et al. |
| 7,399,845 | B2 | 7/2008 | Seth et al. |

(Continued)

FOREIGN PATENT DOCUMENTS

| | | |
|---|---|---|
| CN | 111088283 A | 5/2020 |
| EP | 2 604 255 A1 | 6/2013 |

(Continued)

OTHER PUBLICATIONS

Extended European Search Report for EP 20869845.6, mailed Sep. 12, 2023.

Wang et al., Engineering of ARMMs for efficient delivery of Cas9 genome editors. International Society for Extracellular Vesicles (Isev) Annual Meeting 2019. Kyoto, Japan. Apr. 28, 2019; 8: 381. DOI: https://doi.org/ 10.1080/20013078.2019.

Extended European Search Report for Application No. 21821526.7, mailed Dec. 13, 2024.

(Continued)

*Primary Examiner* — Robert J Yamasaki

(74) *Attorney, Agent, or Firm* — Wolf, Greenfield & Sacks, P.C.

(57) ABSTRACT

Disclosed herein are minimal arrestin domain containing protein 1 (ARRDC1) constructs, which drive the formation of ARRDC1-mediated microvesicles (ARMMs). These vesicles can be harnessed to package and deliver a variety of molecular cargos such as small molecules, nucleic acids, and proteins. An example of such cargo is the genome editor Cas9.

33 Claims, 7 Drawing Sheets

Specification includes a Sequence Listing.

(56) References Cited

U.S. PATENT DOCUMENTS 7,479,573 B2 1/2009 Chu et al.
7,569,686 B1 8/2009 Bhat et al.
7,741,457 B2 6/2010 Seth et al.
7,816,333 B2 10/2010 Seth et al.
8,022,193 B2 9/2011 Seth et al.
8,569,065 B2 10/2013 Polach et al.
8,680,069 B2 3/2014 de Fougerolles et al.
8,795,965 B2 8/2014 Zhang et al.
9,061,043 B2 6/2015 Sullenger et al.
9,737,480 B2 8/2017 Lu et al.
9,816,080 B2 11/2017 Lu et al.
10,260,055 B2 4/2019 Lu et al.
10,945,954 B2 3/2021 Lu et al.
11,001,817 B2 5/2021 Lu et al.
11,730,823 B2 8/2023 Lu et al.
11,827,910 B2 11/2023 Lu et al.
2003/0083294 A1 5/2003 Sullenger et al.
2003/0175703 A1 9/2003 Sullenger et al.
2006/0024780 A1 2/2006 Aldaz et al.
2006/0188560 A1 8/2006 Cheresh et al.
2008/0318882 A1 12/2008 Wang et al.
2011/0009471 A1 1/2011 Kaneko et al.
2011/0046208 A1 2/2011 Rossi et al.
2011/0053157 A1 3/2011 Skog et al.
2011/0151460 A1 6/2011 Klass et al.
2011/0223188 A1 9/2011 Langermann
2012/0129759 A1 5/2012 Liu et al.
2013/0202559 A1 8/2013 Skog et al.
2014/0005126 A1 1/2014 Ullman et al.
2014/0273226 A1 9/2014 Wu
2014/0364588 A1 12/2014 Haugwitz et al.
2015/0037421 A1 2/2015 Lu et al.
2015/0050699 A1 2/2015 Siksnys et al.
2015/0071903 A1 3/2015 Liu et al.
2015/0071906 A1 3/2015 Liu et al.
2015/0093433 A1 4/2015 Leonard et al.
2015/0118216 A1 4/2015 Liu et al.
2015/0315252 A1 11/2015 Haugwitz et al.
2016/0200779 A1 7/2016 Liu et al.
2016/0201089 A1 7/2016 Gersbach et al.
2016/0206566 A1 7/2016 Lu et al.
2017/0073382 A1 3/2017 Wong et al.
2017/0130197 A1 5/2017 Haugwitz et al.
2018/0055768 A1 3/2018 Lu et al.
2018/0119118 A1 5/2018 Lu et al.
2018/0362603 A1 12/2018 Gilbert et al.
2019/0144885 A1 5/2019 Fejoz et al.
2019/0241876 A1 8/2019 Lu et al.
2020/0060980 A1 2/2020 Von Maltzahn et al.
2020/0138938 A1 5/2020 Wegmann et al.
2021/0213139 A1 7/2021 Lu
2021/0261930 A1 8/2021 Lu et al.
2021/0315814 A1 10/2021 Lu et al.
2023/0227852 A1 7/2023 Lu et al.
2023/0390382 A1 12/2023 Lu et al.
2023/0391834 A1 12/2023 Lu et al.
2023/0398202 A1 12/2023 Lu et al.
2024/0082420 A1 3/2024 Lu
2024/0327478 A1 10/2024 Lu et al.

FOREIGN PATENT DOCUMENTS

JP 2008-528485 A 7/2008
WO WO 2001/038547 A2 5/2001
WO WO 2006/078221 A1 7/2006
WO WO 2011/127219 A1 10/2011
WO WO 2013/013105 A2 1/2013
WO WO 2013/119602 A1 8/2013
WO WO 2014/093655 A2 6/2014
WO WO 2014/165825 A2 10/2014
WO WO 2015/002956 A1 1/2015
WO WO 2015/042308 A2 3/2015
WO WO 2018/067546 A1 4/2018
WO WO 2018/208728 A1 11/2018
WO WO 2019/155060 A1 8/2019
WO WO 2020/102485 A1 5/2020
WO WO 2020/191361 A2 9/2020
WO WO 2021/062196 A1 4/2021
WO WO 2021/252924 A1 12/2021
WO WO 2022/136503 A1 6/2022

OTHER PUBLICATIONS

International Preliminary Report on Patentability for Application No. PCT/US2021/037053, mailed Dec. 22, 2022.
Extended European Search Report for Application No. 21881181.8, mailed Jan. 9, 2025.
International Preliminary Report on Patentability for Application No. PCT/US2021/055203, mailed Apr. 27, 2023.
Extended European Search Report for Application No. 21881163.6, mailed Dec. 11, 2024.
International Preliminary Report on Patentability for Application No. PCT/US2021/055158, mailed Apr. 27, 2023.
Extended European Search Report for Application No. 21881160.2, mailed Dec. 10, 2024.
International Preliminary Report on Patentability for Application No. PCT/US2021/055154, mailed Apr. 27, 2023.
Invitation to Pay Additional Fees for Application No. PCT/US2023/064262, mailed May 30, 2023.
International Search Report and Written Opinion for PCT/US2023/064262, mailed Aug. 21, 2023.
International Preliminary Report on Patentability for Application No. PCT/US2023/064262, mailed Sep. 26, 2024.
International Search Report and Written Opinion for Application No. PCT/US2024/061424, mailed Mar. 5, 2025.
Bender et al., Receptor-Targeted Nipah Virus Glycoproteins Improve Cell-Type Selective Gene Delivery and Reveal a Preference for Membrane-Proximal Cell Attachment. PLoS Pathog. Jun. 9, 2016;12(6):e1005641. doi: 10.1371/journal.ppat.1005641. eCollection Jun. 2016.
Chesarino et al., E3 Ubiquitin Ligase NEDD4 Promotes Influenza Virus Infection by Decreasing Levels of the Antiviral Protein IFITM3. Plos Pathog. Aug. 11, 2015;11(8):e1005095. doi: 10.1371/journal.ppat.1005095. eCollection Aug. 2015.
Chin et al., RNA localization: Making its way to the center stage. Biochim Biophys Acta Gen Subj. Nov. 2017;1861(11 Pt B):2956-2970. doi: 10.1016/j.bbagen.2017.06.011. Epub Jun. 16, 2017.
Choi et al., Displaying and delivering viral membrane antigens via WW domain-activated extracellular vesicles. Sci Adv. Jan. 27, 2023;9(4):eade2708. doi: 10.1126/sciadv.ade2708. Epub Jan. 27, 2023.
Fleming et al., Respiratory syncytial virus F envelope protein associates with lipid rafts without a requirement for other virus proteins. J Virol. Dec. 2006;80(24):12160-70. doi: 10.1128/JVI.00643-06. Epub Sep. 27, 2006.
Frank et al., Surface-Engineered Lentiviral Vectors for Selective Gene Transfer into Subtypes of Lymphocytes. Mol Ther Methods Clin Dev. Oct. 17, 2018;12:19-31. doi: 10.1016/j.omtm.2018.10.006. eCollection Mar. 15, 2019.
Gao, Progress and perspectives on targeting nanoparticles for brain drug delivery. Acta Pharm Sin B. Jul. 2016;6(4):268-86. doi: 10.1016/j.apsb.2016.05.013. Epub Jun. 14, 2016.
GENBANK Submission, NIH/NCBI, Accession No. AJ318514.1. Cloning vector pHCMV-VSV-G, complete sequence, No Author Listed, Jan. 23, 2002. 3 pages.
GENBANK Submission, NIH/NCBI, Accession No. M38452.1. Rabies virus glycoprotein mRNA, complete cds, No Author Listed, Aug. 3, 1993, 2 pages.
GENBANK Submission, NIH/NCBI, Accession No. NP_006283.1. tumor susceptibility gene 101 protein [*Homo sapiens*], No Author Listed, May 17, 2020. 3 pages.
GENBANK Submission, NIH/NCBI, Accession No. NP_068684.1. tumor susceptibility gene 101 protein isoform 1 [Mus musculus], No Author Listed, May 6, 2020. 3 pages.
GENBANK Submission, NIH/NCBI, Accession No. NP_853659.2. tumor susceptibility gene 101 protein [Rattus norvegicus], No Author Listed, Apr. 30, 2020. 3 pages.

(56) References Cited

OTHER PUBLICATIONS

GENBANK Submission, NIH/NCBI, Accession No. QHD43416.1. surface glycoprotein [Severe acute respiratory syndrome coronavirus 2], No Author Listed, Mar. 18, 2020, 3 pages.
GENBANK Submission, NIH/NCBI, Accession No. QHD43418.1. envelope protein [Severe acute respiratory syndrome coronavirus 2], No Author Listed, Mar. 18, 2020, 1 page.
GENBANK Submission, NIH/NCBI, Accession No. QHD43419.1. membrane glycoprotein [Severe acute respiratory syndrome coronavirus 2], No Author Listed, Mar. 18, 2020, 2 pages.
Gjoneska et al., Conserved epigenomic signals in mice and humans reveal immune basis of Alzheimer's disease. Nature. Feb. 19, 2015;518(7539):365-9. doi: 10.1038/nature14252.
Hayashita-Kinoh et al., Down-regulation of α-synuclein expression can rescue dopaminergic cells from cell death in the substantia nigra of Parkinson's disease rat model. Biochem Biophys Res Commun. Mar. 24, 2006;341(4):1088-95. doi: 10.1016/j.bbrc.2006.01.057. Epub Jan. 25, 2006.
Huang et al., Construction of a high sensitive *Escherichia coli* alkaline phosphatase reporter system for screening affinity peptides. J Biochem Biophys Methods. Apr. 10, 2007;70(3):435-9. doi: 10.1016/j.jbbm.2006.10.006. Epub Oct. 21, 2006.
Kasuya et al., In vivo protein delivery to human liver-derived cells using hepatitis B virus envelope pre-S region. J Biosci Bioeng. Jul. 2008;106(1):99-102. doi: 10.1263/jbb.106.99.
Keren-Shaul et al., A Unique Microglia Type Associated with Restricting Development of Alzheimer's Disease. Cell. Jun. 15, 2017;169(7):1276-1290.e17. doi: 10.1016/j.cell.2017.05.018. Epub Jun. 8, 2017.
Langlois et al., Hammerhead ribozyme-mediated destruction of nuclear foci in myotonic dystrophy myoblasts. Mol Ther. May 2003;7(5 Pt 1):670-80. doi: 10.1016/s1525-0016(03)00068-6.
Lueck et al., Engineered transfer RNAs for suppression of premature termination codons. Nat Commun. Feb. 18, 2019;10(1):822. doi: 10.1038/s41467-019-08329-4.
Mastroyiannopoulos et al., The application of ribozymes and DNAzymes in muscle and brain. Molecules. Aug. 9, 2010;15(8):5460-72. doi: 10.3390/molecules15085460.
Mathys et al., Temporal Tracking of Microglia Activation in Neurodegeneration at Single-Cell Resolution. Cell Rep. Oct. 10, 2017;21(2):366-380. doi: 10.1016/j.celrep.2017.09.039.
McCully et al., Peptide Mediated Brain Delivery of Nano-and Submicroparticles: A Synergistic Approach. Curr Pharm Des. 2018;24(13):1366-1376. doi: 10.2174/1381612824666171201115126.
Mellios et al., MeCP2-regulated miRNAs control early human neurogenesis through differential effects on ERK and AKT signaling. Mol Psychiatry. Apr. 2018;23(4):1051-1065. doi: 10.1038/mp.2017.86. Epub Apr. 25, 2017.
Naskalska et al., Influenza recombinant vaccine: matrix protein M1 on the platform of the adenovirus dodecahedron. Vaccine. Dec. 9, 2009;27(52):7385-93. doi: 10.1016/j.vaccine.2009.09.021. Epub Sep. 18, 2009.
No Author Listed, GENBANK Submission; NIH/NCBI, Accession No. NP_056287.1. Oct. 22, 2020.
No Author Listed, Two-Hybrid screening. Wikipedia. Published Jan. 31, 2012. Accessed from https://en.wikipedia.org/w/index.php?title=Two-hybrid_screening&oldid=474234791. Last accessed: Mar. 14, 2024. 10 pages.
Pasca et al., Functional cortical neurons and astrocytes from human pluripotent stem cells in 3D culture. Nat Methods. Jul. 2015;12(7):671-8. doi: 10.1038/nmeth.3415. Epub May 25, 2015.
Phylactou et al., Ribozyme-mediated trans-splicing of a trinucleotide repeat. Nat Genet. Apr. 1998;18(4):378-81. doi: 10.1038/ng0498-378.
Schulze et al., Fine Mapping of Pre-S Sequence Requirements for Hepatitis B Virus Large Envelope Protein-Mediated Receptor Interaction. J Virol. Feb. 2010;84(4):1989-2000. doi: 10.1128/JVI.01902-09. Epub Dec. 9, 2009.
Sheridan et al., Epigenetic characterization of the FMR1 gene and aberrant neurodevelopment in human induced pluripotent stem cell models of fragile X syndrome. PLoS One. 2011;6(10):e26203. doi: 10.1371/journal.pone.0026203. Epub Oct. 12, 2011.
Shi et al., Reprogramming Extracellular Vesicles with Engineered Proteins. Methods. May 1, 2020:177:95-102. doi: 10.1016/j.ymeth.2019.09.017. Epub Sep. 27, 2019.
Stagljar et al., A genetic system based on split-ubiquitin for the analysis of interactions between membrane proteins in vivo. Proc Natl Acad Sci U S A. Apr. 28, 1998;95(9):5187-92. doi: 10.1073/pnas.95.9.5187.
Sterzenbach et al., Engineered Exosomes as Vehicles for Biologically Active Proteins. Mol Ther. Jun. 7, 2017;25(6):1269-1278. doi: 10.1016/j.ymthe.2017.03.030. Epub Apr. 13, 2017.
UniProt Submission; UniProt, Accession No. Q9IH62. Last modified May 3, 2023, version 124. https://www.uniprot.org/uniprotkb/Q9IH62/entry.
UniProt Submission; UniProt, Accession No. Q9IH63. Last modified May 3, 2023, version 111. https://www.uniprot.org/uniprotkb/Q9IH63/entry.
Van Der Zee et al., Dementia in 2013: frontotemporal lobar degeneration-building on breakthroughs. Nat Rev Neurol. Feb. 2014;10(2):70-2. doi: 10.1038/nrneurol.2013.270. Epub Jan. 7, 2014.
Walls et al., Tagging recombinant proteins to enhance solubility and aid purification. Methods Mol Biol. 2011;681:151-75. doi: 10.1007/978-1-60761-913-0_9.
Wang et al., Plasma membrane-derived extracellular microvesicles mediate non-canonical intercellular NOTCH signaling. Nature Commun. Sep. 27, 2017;8(1):709. doi: 10.1038/s41467-017-00767-2.
Wu et al., Crossing the blood-brain-barrier with nanoligand drug carriers self-assembled from a phage display peptide. Nat Commun. Oct. 11, 2019;10(1):4635. doi: 10.1038/s41467-019-12554-2.
Yang et al., Investigating protein-ligand interactions with a mutant FKBP possessing a designed specificity pocket. J Med Chem. Mar. 23, 2000;43(6):1135-42. doi: 10.1021/jm9904396.
International Search Report and Written Opinion for PCT/US2013/024839, mailed May 28, 2013.
International Preliminary Report on Patentability for PCT/US2013/024839, mailed Aug. 21, 2014.
Extended European Search Report for EP 17859007.1, mailed May 12, 2020.
Invitation to Pay Additional Fees for PCT/US/2017/54912, mailed Dec. 12, 2017.
International Search Report and Written Opinion for PCT/US/2017/54912, mailed Feb. 13, 2018.
International Preliminary Report on Patentability for PCT/US/2017/54912, mailed Apr. 18, 2019.
International Search Report and Written Opinion for PCT/US2020/052784, mailed Jan. 27, 2021.
International Preliminary Report on Patentability for PCT/US2020/052784, mailed Apr. 7, 2022.
International Search Report and Written Opinion for PCT/US2021/037053, mailed Oct. 6, 2021.
International Search Report and Written Opinion for PCT/US2021/055203, mailed Mar. 17, 2022.
Invitation to Pay Additional Fees for PCT/US2021/055203, mailed Dec. 29, 2021.
International Search Report and Written Opinion for PCT/US2021/055158, mailed Feb. 23, 2022.
Invitation to Pay Additional Fees for PCT/US2021/055158, mailed Dec. 8, 2021.
Invitation to Pay Additional Fees for PCT/US2021/055154, mailed Dec. 23, 2021.
International Search Report and Written Opinion for PCT/US2021/055154, mailed Mar. 10, 2022.
[No Author Listed], A minimal ARRDC1 for ARMM budding and Cargo Packaging powerpoint and written description. Feb. 21, 2019. 7 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.

(56) References Cited

OTHER PUBLICATIONS

[No Author Listed], Thermo Fisher Scientific—How Cationic Lipid Mediated Transfection Works, retrieved from the internet Aug. 27, 2015. 2 pages.
Abbas et al., Plasma membrane signaling in HIV-1 infection. Biochim Biophys Acta. Apr. 2014;1838(4):1132-42. doi: 10.1016/j.bbamem.2013.06.020. Epub Jun. 24, 2013.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/6904878b. Epub May 11, 2009.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Altschul et al., Basic local alignment search tool. J Mol Biol. Oct. 5, 1990;215(3):403-10.
Alvarez, On the origins of arrestin and rhodopsin. BMC Evol Biol. Jul. 29, 2008;8:222. doi: 10.1186/1471-2148-8-222.
Andriole et al., Mortality results from a randomized prostate-cancer screening trial. N Engl J Med. Mar. 26, 2009;360(13):1310-9. doi: 10.1056/NEJMoa0810696. Epub Mar. 18, 2009. Erratum in: N Engl J Med. Apr. 23, 2009;360(17):1797.
Babst et al., Mammalian tumor susceptibility gene 101 (TSG101) and the yeast homologue, Vps23p, both function in late endosomal trafficking. Traffic. Mar. 2000;1(3):248-58.
Babst, A protein's final ESCRT. Traffic. Jan. 2005;6(1):2-9.
Baccile et al., Modular synthesis of photocleavable peptides using click chemistry. Tetrahedron Lett. Apr. 11, 2012;53(15):1933-5.
Bache et al., Hrs regulates multivesicular body formation via ESCRT recruitment to endosomes. J Cell Biol. Aug. 4, 2003;162(3):435-42.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Beltri, Mechanisms controlling the secretion and composition of exosomes. Doctoral Thesis, Universidad Autónoma de Madrid. Dec. 2016. 208 pages.
Bieniasz, The cell biology of HIV-1 virion genesis. Cell Host Microbe. Jun. 18, 2009;5(6):550-8. doi: 10.1016/j.chom.2009.05.015.
Bigbee et al., Tumor markers and immunodiagnosis. Chapter 13. Cancer Medicine. 6th Edition. BC Decker Inc., Eds. 2003. pp. 209-220.
Biomarkers Definitions Working Group, Biomarkers and Surrogate Endpoints: Preferred Definitions and Conceptual Framework. Clin Pharmacol Ther. Mar. 2001;69(3):89-95. doi: 10.1067/mcp.2001.113989.
Bork et al., The WW domain: a signaling site in dystrophin? Trends Biochem Sci. Dec. 1994;19(12):531-3.
Brown et al., Serine recombinases as tools for genome engineering. Methods. Apr. 2011;53(4):372-9. doi: 10.1016/j.ymeth.2010.12.031. Epub Dec. 30, 2010.
Buchwald, Long-term, continuous intravenous heparin administration by an implantable infusion pump in ambulatory patients with recurrent venous thrombosis. Surgery. Oct. 1980;88(4):507-16.
Buys et al., Effect of screening on ovarian cancer mortality: the Prostate, Lung, Colorectal and Ovarian (PLCO) Cancer Screening Randomized Controlled Trial. JAMA. Jun. 8, 2011;305(22):2295-303. doi: 10.1001/jama.2011.766.
Cai et al., Solution structure of P22 transcriptional antitermination N peptide-boxB RNA complex. Nat Struct Biol. Mar. 1998;5(3):203-12.
Carillo et al., The multiple sequence alignment problem in biology. SIAM J Appl Math. 1988;48:1073-1082.
Carroll, Progress and prospects: zinc-finger nucleases as gene therapy agents. Gene Ther. Nov. 2008; 5(22):1463-8. doi: 10.1038/gt.2008.145. Epub Sep. 11, 2008.
Chang et al., Human immunodeficiency virus type 1 subtype E envelope recombinant peptides containing naturally immunogenic epitopes. J Infect Dis. Aug. 2000;182(2):442-50. doi: 10.1086/315730. Epub Jul. 21, 2000.
Chantry, WWP2 ubiquitin ligase and its isoforms: new biological insight and promising disease targets. Cell Cycle. Aug. 1, 2011;10(15):2437-9. Epub Aug. 1, 2011.
Chavez et al., Therapeutic applications of the ΦC31 integrase system. Curr Gene Ther. Oct. 2011;11(5):375-81.
Chen et al., Design of an in vivo cleavable disulfide linker in recombinant fusion proteins. Biotechniques. Jul. 2010;49(1):513-8. doi: 10.2144/000113450.
Chen et al., Fusion protein linkers: property, design and functionality. Adv Drug Deliv Rev. Oct. 2013;65(10):1357-69. doi: 10.1016/j.addr.2012.09.039. Epub Sep. 29, 2012.
Chesnoy et al., Structure and function of lipid-DNA complexes for gene delivery. Annu Rev Biophys Biomol Struct. 2000;29:27-47.
Choi et al., Protease-activated drug development. Theranostics. 2012;2(2):156-78. doi: 10.7150/thno.4068. Epub Feb. 8, 2012.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Cilley et al., Structural mimicry in the phage ϕ21 N peptide-boxB RNA complex. RNA. Jun. 2003;9(6):663-76.
Cochrane et al., The human immunodeficiency virus rev protein is a nuclear phosphoprotein. Virology. Jul. 1989;171(1):264-6.
Colletier et al., Protein encapsulation in liposomes: efficiency depends on interactions between protein and phospholipid bilayer. BMC Biotechnol. May 10, 2002;2:9.
Cong et al., Multiplex genome engineering using CRISPR/Cas systems. Science. Feb. 15, 2013;339(6121):819-23. doi: 10.1126/science.1231143. Epub Jan. 3, 2013.
Cook et al., Characterization of HIV-1 Rev protein: binding stoichiometry and minimal RNA substrate. Nucleic Acids Res. Apr. 11, 1991;19(7):1577-83.
Cordingley et al., Sequence-specific interaction of Tat protein and Tat peptides with the transactivation-responsive sequence element of human immunodeficiency virus type 1 in vitro. Proc Natl Acad Sci U S A. Nov. 1990;87(22):8985-9.
Cramer et al., Ovarian cancer biomarker performance in prostate, lung, colorectal, and ovarian cancer screening trial specimens. Cancer Prev Res (Phila). Mar. 2011;4(3):365-74. doi: 10.1158/1940-6207.CAPR-10-0195.
Cronican et al., A class of human proteins that deliver functional proteins into mammalian cells in vitro and in vivo. Chem Biol. Jul. 29, 2011;18(7):833-8. doi: 10.1016/j.chembiol.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Deltcheva et al., CRISPR RNA maturation by trans-encoded small RNA and host factor RNase III. Nature. Mar. 31, 2011;471(7340):602-7. doi: 10.1038/nature09886.
Demirov et al., Overexpression of the N-terminal domain of TSG101 inhibits HIV-1 budding by blocking late domain function. Proc Natl Acad Sci U S A. Jan. 22, 2002;99(2):955-60.
Demirov et al., Retrovirus budding. Virus Res. Dec. 2004;106(2):87-102.
Denzer et al., Exosome: from internal vesicle of the multivesicular body to intercellular signaling device. J Cell Sci. Oct. 2000;113 Pt 19:3365-74.
Devereux et al., A comprehensive set of sequence analysis programs for the VAX. Nucleic Acids Res. Jan. 11, 1984;12(1 Pt 1):387-95.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.

(56) References Cited

OTHER PUBLICATIONS

Dingwall et al., Human immunodeficiency virus 1 tat protein binds trans-activation- responsive region (TAR) RNA in vitro. Proc Natl Acad Sci U S A. Sep. 1989;86(18):6925-9.
Dingwall et al., The nucleoplasmin nuclear location sequence is larger and more complex than that of SV-40 large T antigen. J Cell Biol. Sep. 1988;107(3):841-9.
Dowdy, Overcoming cellular barriers for RNA therapeutics. Nat Biotechnol. Mar. 2017;35(3):222-229. doi: 10.1038/nbt.3802. Epub Feb. 27, 2017.
Draheim et al., ARRDC3 suppresses breast cancer progression by negatively regulating integrin beta4. Oncogene. Sep. 9, 2010;29(36):5032-47. doi: 10.1038/onc.2010.250. Epub Jul. 5, 2010.
During et al., Controlled release of dopamine from a polymeric brain implant: in vivo characterization. Ann Neurol. Apr. 1989;25(4):351-6.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.
Esvelt et al., Genome-scale engineering for systems and synthetic biology. Mol Syst Biol. 2013;9:641. doi: 10.1038/msb.2012.66.
Fernandes et al., The HIV-1 Rev response element: an RNA scaffold that directs the cooperative assembly of a homo-oligomeric ribonucleoprotein complex. RNA Biol. Jan. 2012;9(1):6-11. doi: 10.4161/rna.9.1.18178. Epub Jan. 1, 2012.
Ferretti et al., Complete genome sequence of an M1 strain of Streptococcus pyogenes. Proc Natl Acad Sci U S A Apr. 10, 2001;98(8):4658-63.
Freed et al., The cell biology of HIV-1 and other retroviruses. Retrovirology. Nov. 3, 2006;3:77.
Fuchs et al., Polyarginine as a multifunctional fusion tag. Protein Sci. Jun. 2005;14(6):1538-44.
Fujii et al., Beyond Tsg101: the role of Alix in 'ESCRTing' HIV-1. Nat Rev Microbiol. Dec. 2007;5(12):912-6.
Garrus et al., Tsg101 and the vacuolar protein sorting pathway are essential for HIV-1 budding. Cell. Oct. 5, 2001;107(1):55-65.
Gatignol et al., Characterization of a human TAR RNA-binding protein that activates the HIV-1 LTR. Science. Mar. 29, 1991;251(5001):1597-600.
Gatignol et al., Identification of cellular proteins that bind to the human immunodeficiency virus type 1 trans-activation-responsive TAR element RNA. Proc Natl Acad Sci U S A. Oct. 1989;86(20):7828-32.
Gaynor et al., Specific binding of a HeLa cell nuclear protein to RNA sequences in the human immunodeficiency virus transactivating region. Proc Natl Acad Sci U S A. Jul. 1989;86(13):4858-62.
GENBANK Submission, NIH/NCBI, Accession No. NP_848495.2 arrestin domain-containing protein 1 isoform b [Mus musculus], Sundberg et al., Feb. 23, 2019. 2 pages.
GENBANK Submission; NIH/NCBI, Accession No. NC_ 021284.1 Spiroplasma syrphidicola EA-1, complete genome, Ku et al., Aug. 26, 2019. 2 pages.
GENBANK Submission; NIH/NCBI, Accession No. NC_015683. Trost et al., Jul. 6, 2013.
GENBANK Submission; NIH/NCBI, Accession No. NC_015683.1 Corynebacterium ulcerans BR-AD22, complete genome, Trost et al., Aug. 26, 2019. 2 pages.
GENBANK Submission; NIH/NCBI, Accession No. NC_016782. Trost et al., Jun. 11, 2013.
GENBANK Submission; NIH/NCBI, Accession No. NC_016782.1 Corynebacterium diphtheriae 241, complete genome, Trost et al., Aug. 26, 2019. 2 pages.
GENBANK Submission; NIH/NCBI, Accession No. NC_016786. Trost et al., Aug. 28, 2013.
GENBANK Submission; NIH/NCBI, Accession No. NC_016786.1 Corynebacterium diphtheriae HC01, complete genome, Trost et al., Aug. 26, 2019. 2 pages.
GENBANK Submission; NIH/NCBI, Accession No. NC_017053. Fittipaldi et al., Jul. 6, 2013.
GENBANK Submission; NIH/NCBI, Accession No. NC_017053.1 *Streptococcus pyogenes* MBAS1882, complete genome, Fittipaldi et al., Mar. 22, 2017. 2 pages.
GENBANK Submission; NIH/NCBI, Accession No. NC_017317. Trost et al., Jun. 11, 2013.
GENBANK Submission; NIH/NCBI, Accession No. NC_017317.1 Corynebacterium ulcerans 809, complete genome, Trost et al., Mar. 30, 2017. 2 pages.
GENBANK Submission; NIH/NCBI, Accession No. NC_017861. Heidelberg et al., Jun. 11, 2013.
GENBANK Submission; NIH/NCBI, Accession No. NC_017861.1 Prevotella intermedia 17 chromosome II, complete sequence, Heidelberg et al., Mar. 30, 2017. 2 pages.
GENBANK Submission; NIH/NCBI, Accession No. NC_018010. Lucas et al., Jun. 11, 2013.
GENBANK Submission; NIH/NCBI, Accession No. NC_018010.1 Belliella baltica DSM 15883, complete genome, Lucas et al., May 18, 2017. 3 pages.
GENBANK Submission; NIH/NCBI, Accession No. NC_018721. Feng et al., Jun. 11, 2013.
GENBANK Submission; NIH/NCBI, Accession No. NC_018721.1 Psychroflexus torquis ATCC 700755, complete genome, Feng et al., May 19, 2017. 2 pages.
GENBANK Submission; NIH/NCBI, Accession No. NC_021284. Ku et al., Jul. 12, 2013.
GENBANK Submission; NIH/NCBI, Accession No. NC_021314. Zhang et al., Jul. 15, 2013.
GENBANK Submission; NIH/NCBI, Accession No. NC_021846. Lo et al., Jul. 22, 2013.
GENBANK Submission; NIH/NCBI, Accession No. NC_021846.1 Spiroplasma Taiwanese CT-1, complete genome, Lo et al., Aug. 26, 2019. 2 pages.
GENBANK Submission; NIH/NCBI, Accession No. NC_023414.1 *Streptococcus iniae* SF1, complete genome, Zhang et al., Dec. 18, 2014. 1 page.
GENBANK Submission; NIH/NCBI, Accession No. NM_015277. 5. Wilkars et al., Aug. 16, 2014. 9 pages.
GENBANK Submission; NIH/NCBI, Accession No. NM_015277.6 *Homo sapiens* NEDD4 like E3 ubiquitin protein ligase (NEDD4L), transcript variant d, mRNA, Todaro et al., Sep. 22, 2019. 8 pages.
GENBANK Submission; NIH/NCBI, Accession No. NP_001155957. Skarnes et al., Feb. 26, 2014.
GENBANK Submission; NIH/NCBI, Accession No. NP_001155957.1 arrestin domain-containing protein 1 isoform a [Mus musculus], Sundberg et al., Feb. 22, 2019. 2 pages.
GENBANK Submission; NIH/NCBI, Accession No. NP_006283. Rush et al., May 4, 2014.
GENBANK Submission; NIH/NCBI, Accession No. NP_056092.2 E3 ubiquitin-protein ligase NEDD4-like isoform 3 [*Homo sapiens*], Todaro et al., Sep. 22, 2019. 3 pages.
GENBANK Submission; NIH/NCBI, Accession No. NP_056092.2. Wilkars et al., Aug. 16, 2014. 3 pages.
GENBANK Submission; NIH/NCBI, Accession No. NP_068684. Gunn et al., Feb. 26, 2014.
GENBANK Submission; NIH/NCBI, Accession No. NP_472073. Glaser et al., Jun. 27, 2013.
GENBANK Submission; NIH/NCBI, Accession No. NP_472073.1 Hypothetical protein lin2744 [Listeria innocua Clip11262], Glaser et al., Dec. 17, 2014. 2 pages.
GENBANK Submission; NIH/NCBI, Accession No. NP_689498. Puca et al., Mar. 22, 2014.
GENBANK Submission; NIH/NCBI, Accession No. NP_689498.1 arrestin domain-containing protein 1 isoform 1 [*Homo sapiens*], Mackenzie et al., May 2, 2019. 3 pages.
GENBANK Submission; NIH/NCBI, Accession No. NP_848495. Skarnes et al., Feb. 26, 2014.
GENBANK Submission; NIH/NCBI, Accession No. NP_853659. Leithe et al., Aug. 10, 2014.
GENBANK Submission; NIH/NCBI, Accession No. YP_002342100. Bernardini et al., Jun. 10, 2013.
GENBANK Submission; NIH/NCBI, Accession No. YP_002342100.1 Hypothetical protein NMA0631 [Neisseria meningitidis Z2491], Bernardini et al., Dec. 19, 2014. 2 pages.

(56) References Cited

OTHER PUBLICATIONS

GENBANK Submission; NIH/NCBI, Accession No. YP_002344900. Gundogdu et al., Jul. 11, 2013.
GENBANK Submission; NIH/NCBI, Accession No. YP_002344900.1 CRISPR-associated protein [*Campylobacter jejuni* subsp. *jejuni* Nctc 11168=ATCC 700819], Gundogdu et al., Aug. 3, 2016. 2 pages.
GENBANK Submission; NIH/NCBI, Accession No. YP_820832. Makarova et al., Aug. 27, 2013.
GENBANK Submission; NIH/NCBI, Accession No. YP_820832.1 CRISPR-system-like protein [*Streptococcus thermophilus* LMD-9], Makarova et al., Dec. 16, 2014. 2 pages.
Gordley et al., Synthesis of programmable integrases. Proc Natl Acad Sci U S A. Mar. 31, 2009;106(13):5053-8. doi: 10.1073/pnas.0812502106. Epub Mar. 12, 2009.
Gottlinger et al., Effect of mutations affecting the p6 gag protein on human immunodeficiency virus particle release. Proc Natl Acad Sci U S A. Apr. 15, 1991;88(8):3195-9.
Grate et al., Role REVersal: understanding how RRE RNA binds its peptide ligand. Structure. Jan. 15, 1997;5(1):7-11.
Groth et al., Phage integrases: biology and applications. J Mol Biol. Jan. 16, 2004;335(3):667-78.
Hall et al., Delivery of Therapeutic Proteins via Extracellular Vesicles: Review and Potential Treatments for Parkinson's Disease, Glioma, and Schwannoma. Cell Mol Neurobiol. Apr. 2016;36(3):417-27. doi: 10.1007/s10571-015-0309-0. Epub Mar. 26, 2016.
Hammarstedt et al., Passive and active inclusion of host proteins in human immunodeficiency virus type 1 gag particles during budding at the plasma membrane. J Virol. Jun. 2004;78(11):5686-97.
Hartung et al., Correction of metabolic, craniofacial, and neurologic abnormalities in MPS I mice treated at birth with adeno-associated virus vector transducing the human alpha-L-*Iduronidase* gene. Mol Ther. Jun. 2004;9(6):866-75.
Hatahet et al., Disruption of reducing pathways is not essential for efficient disulfide bond formation in the cytoplasm of *E. coli*. Microb Cell Fact. Sep. 13, 2010;9:67. doi: 10.1186/1475-2859-9-67.
Heaphy et al., HIV-1 regulator of virion expression (Rev) protein binds to an RNA stem-loop structure located within the Rev response element region. Cell. Feb. 23, 1990;60(4):685-93.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.
Henne et al., The ESCRT pathway. Dev Cell. Jul. 19, 2011;21(1):77-91. doi: 10.1016/j.devcel.2011.05.015.
Hirano et al., Site-specific recombinases as tools for heterologous gene integration. Appl Microbiol Biotechnol. Oct. 2011;92(2):227-39. doi: 10.1007/s00253-011-3519-5. Epub Aug. 7, 2011.
Hockemeyer et al., Efficient targeting of expressed and silent genes in human ESCs and iPSCs using zinc-finger nucleases. Nat Biotechnol. Sep. 2009;27(9):851-7. doi: 10.1038/nbt.1562. Epub Aug. 13, 2009.
Howard et al., Intracerebral drug delivery in rats with lesion-induced memory deficits. J Neurosurg. Jul. 1989;71(1):105-12.
Huang et al., p6Gag is required for particle production from full-length human immunodeficiency virus type 1 molecular clones expressing protease. J Virol. Nov. 1995;69(11):6810-8.
Hurley et al., Membrane budding. Cell. Dec. 10, 2010;143(6):875-87. doi: 10.1016/j.cell.2010.11.030.
Hurley et al., Molecular mechanisms of ubiquitin-dependent membrane traffic. Annu Rev Biophys. 2011;40:119-42. doi: 10.1146/annurev-biophys-042910-155404.
Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.
Ikediobi et al., Mutation analysis of 24 known cancer genes in the NCI-60 cell line set. Mol Cancer Ther. Nov. 2006;5(11):2606-12. doi: 10.1158/1535-7163.MCT-06-0433. Epub Nov. 6, 2006.
Ingham et al., WW domains provide a platform for the assembly of multiprotein networks. Mol Cell Biol. Aug. 2005;25(16):7092-106. doi: 10.1128/MCB.25.16.7092-7106.2005.
Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.
Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.
Jinek et al., RNA-programmed genome editing in human cells. Elife. Jan. 29, 2013;2:e00471. doi: 10.7554/eLife.00471.
Kakiyama et al., A peptide release system using a photo-cleavable linker in a cell array format for cell-toxicity analysis. Polymer Journal. Feb. 27, 2013;45:535-9.
Kalderon et al., A short amino acid sequence able to specify nuclear location. Cell. Dec. 1984;39(3 Pt 2):499-509.
Kamine et al., Mapping of HIV-1 Tat protein sequences required for binding to Tar RNA. Virology. Jun. 1991;182(2):570-7.
Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.
Karpenshif et al., From yeast to mammals: recent advances in genetic control of homologous recombination. DNA Repair (Amst). Oct. 1, 2012;11(10):781-8. doi: 10.1016/j.dnarep.2012.07.001. Epub Aug. 11, 2012.
Katzmann et al., Receptor downregulation and multivesicular-body sorting. Nat Rev Mol Cell Biol. Dec. 2002;3(12):893-905.
Keryer-Bibens et al., Tethering of proteins to RNAs by bacteriophage proteins. Biol Cell. Feb. 2008;100(2):125-38. doi: 10.1042/BC20070067.
Kim et al., Highly efficient RNA-guided genome editing in human cells via delivery of purified Cas9 ribonucleoproteins. Genome Res. Jun. 2014;24(6):1012-9. doi: 10.1101/gr.171322.113. Epub Apr. 2, 2014.
Kim et al., Targeted genome editing in human cells with zinc finger nucleases constructed via modular assembly. Genome Res. Jul. 2009;19(7):1279-88. doi: 10.1101/gr.089417.108. Epub May 21, 2009.
Kole et al., RNA therapeutics: beyond RNA interference and antisense oligonucleotides. Nat Rev Drug Discov. Jan. 20, 2012;11(2):125-40. doi: 10.1038/nrd3625.
Komada et al., Hrs, a FYVE finger protein localized to early endosomes, is implicated in vesicular traffic and required for ventral folding morphogenesis. Genes Dev. Jun. 1, 1999;13(11):1475-85.
Kosaka et al., Secretory mechanisms and intercellular transfer of microRNAs in living cells. J Biol Chem. Jun. 4, 2010;285(23):17442-52.
Kosugi et al., Six classes of nuclear localization signals specific to different binding grooves of importin α. J Biol Chem. Jan. 2, 2009;284(1):478-85. doi: 10.1074/jbc.M807017200. Epub Nov. 10, 2008.
Kuo et al., ARRDC1 as a mediator of microvesicle budding. PNAS. Mar. 2012;109(11):4025-4026.
Lake, A human alpha-arrestin protein with a potential role in cargo protein trafficking within the endocytic system. PhD thesis, University of Nottingham. Jul. 2012. 238 pages.
Langer et al., Chemical and physical structure of polymers as carriers for controlled release of bioactive agents: A review. J Macromol Sci C. 1983;23(1):61-126. doi: 10.1080/07366578308079439. Epub Dec. 19, 2006.
Langer, New methods of drug delivery. Science. Sep. 28, 1990;249(4976):1527-33.
Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.
Lawrence et al., Supercharging proteins can impart unusual resilience. J Am Chem Soc. Aug. 22, 2007;129(33):10110-2. Epub Aug. 1, 2007.
Lee et al., PIK3CA gene is frequently mutated in breast carcinomas and hepatocellular carcinomas. Oncogene. Feb. 17, 2005;24(8):1477-80. doi: 10.1038/sj.onc.1208304.
Lefkowitz et al., Transduction of receptor signals by beta-arrestins. Science. Apr. 22, 2005;308(5721):512-7. doi: 10.1126/science.1109237.

(56) References Cited

OTHER PUBLICATIONS

Legault et al., NMR structure of the bacteriophage lambda N peptide/boxB RNA complex: recognition of a GNRA fold by an arginine-rich motif. Cell. Apr. 17, 1998;93(2):289-99.
Levary et al., Protein-protein fusion catalyzed by sortase A. PLoS One. Apr. 6, 2011;6(4):e18342. doi: 10.1371/journal.pone.0018342.
Levy et al., Inhibition of calcification of bioprosthetic heart valves by local controlled-release diphosphonate. Science. Apr. 12, 1985;228(4696):190-2.
Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.
Liu et al., Design strategies and application progress of therapeutic exosomes. Theranostics. 2019;9(4):1015-1028. doi: 10.7150/thno.30853.
Loh et al., The Oct4 and Nanog transcription network regulates pluripotency in mouse embryonic stem cells. Nat Genet. Apr. 2006;38(4):431-40. Epub Mar. 5, 2006.
Lombardo et al., Gene editing in human stem cells using zinc finger nucleases and integrase-defective lentiviral vector delivery. Nat Biotechnol. Nov. 2007;25(11):1298-306. Epub Oct. 28, 2007.
Lu et al., TSG101 interaction with HRS mediates endosomal trafficking and receptor down-regulation. PNAS. Jun. 24, 2003;100(13):7626-31. Epub Jun. 11, 2003.
Maeder et al., Robust, synergistic regulation of human gene expression using TALE activators. Nat Methods. Mar. 2013;10(3):243-5. doi: 10.1038/nmeth.2366. Epub Feb. 10, 2013.
Maeder et al., Targeted DNA demethylation and activation of endogenous genes using programmable TALE-TET1 fusion proteins. Nat Biotechnol. Dec. 2013;31(12):1137-42. doi: 10.1038/nbt.2726. Epub Oct. 9, 2013.
Mak et al., The crystal structure of TAL effector PthXol bound to its DNA target. Science. Feb. 10, 2012;335(6069):716-9. doi: 10.1126/science.1216211. Epub Jan. 5, 2012.
Makkerh et al., Comparative mutagenesis of nuclear localization signals reveals the importance of neutral and acidic amino acids. Curr Biol. Aug. 1, 1996;6(8):1025-7.
Mali et al., RNA-guided human genome engineering via Cas9. Science. Feb. 15, 2013;339(6121):823-6. doi: 10.1126/science.1232033. Epub Jan. 3, 2013.
Mani et al., Design, engineering, and characterization of zinc finger nucleases. Biochem Biophys Res Commun. Sep. 23, 2005;335(2):447-57.
Marciniak et al., HIV-1 Tat protein trans-activates transcription in vitro. Cell. Nov. 16, 1990;63(4):791-802. doi: 10.1016/0092-8674(90)90145-5.
Marciniak et al., Identification and characterization of a HeLa nuclear protein that specifically binds to the trans-activation-response (TAR) element of human immunodeficiency virus. Proc Natl Acad Sci U S A. May 1990;87(9):3624-8.
Martin-Serrano et al., HIV-1 and Ebola virus encode small peptide motifs that recruit Tsg101 to sites of particle assembly to facilitate egress. Nat Med. Dec. 2001;7(12):1313-9.
Martin-Serrano et al., Host factors involved in retroviral budding and release. Nat Rev Microbiol. Jun. 16, 2011;9(7):519-31. doi: 10.1038/nrmicro2596.
Martin-Serrano et al., Role of ESCRT-I in retroviral budding. J Virol. Apr. 2003;77(8):4794-804.
Mathivanan et al., Proteomics analysis of A33 immunoaffinity-purified exosomes released from the human colon tumor cell line LIM1215 reveals a tissue-specific protein signature. Mol Cell Proteomics. Feb. 2010;9(2):197-208. doi: 10.1074/mcp.M900152-MCP200. Epub Oct. 16, 2009.
McElroy et al., The use of alveolar epithelial type I cell-selective markers to investigate lung injury and repair. Eur Respir J. Oct. 2004;24(4):664-73.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Morita et al., Retrovirus budding. Annu Rev Cell Dev Biol. 2004;20:395-425.
Morris et al., A peptide carrier for the delivery of biologically active proteins into mammalian cells. Nat Biotechnol. Dec. 2001;19(12):1173-6.
Muesing et al., Regulation of mRNA accumulation by a human immunodeficiency virus trans-activator protein. Cell. Feb. 27, 1987;48(4):691-701.
Murphy, Phage recombinases and their applications. Adv Virus Res. 2012;83:367-414. doi: 10.1016/B978-0-12-394438-2.00008-6.
Myers et al., Optimal alignments in linear space. Comput Appl Biosci. 1988;4(1):11-17. doi: 10.1093/bioinformatics/4.1.11.
Nabhan et al., Arrestin domain-containing protein 3 recruits the NEDD4 E3 ligase to mediate ubiquitination of the beta2-adrenergic receptor. EMBO Rep. Aug. 2010;11(8):605-11. doi: 10.1038/embor.2010.80. Epub Jun. 18, 2010.
Nabhan et al., Formation and release of arrestin domain-containing protein 1-mediated microvesicles (ARMMs) at plasma membrane by recruitment of TSG101 protein. Proc Natl Acad Sci U S A. Mar. 13, 2012;109(11):4146-51. doi: 10.1073/pnas.1200448109. Epub Feb. 6, 2012.
Nichols et al., Formation of pluripotent stem cells in the mammalian embryo depends on the POU transcription factor Oct. 4. Cell. Oct. 30, 1998;95(3):379-91.
Nimjee et al., Aptamers: an emerging class of therapeutics. Annu Rev Med. 2005;56:555-83.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Olejnik et al., Photocleavable biotin phosphoramidite for 5'-end-labeling, affinity purification and phosphorylation of synthetic oligonucleotides. Nucleic Acids Res. Jan. 15, 1996;24(2):361-6.
Ono et al., Cell-type-dependent targeting of human immunodeficiency virus type 1 assembly to the plasma membrane and the multivesicular body. J Virol. Feb. 2004;78(3):1552-63.
Ono et al., Relationship between human immunodeficiency virus type 1 Gag multimerization and membrane binding. J Virol. Jun. 2000;74(11):5142-50.
Parrott et al., RNA aptamers for the MS2 bacteriophage coat protein and the wild-type RNA operator have similar solution behaviour. Nucleic Acids Res. Jan. 15, 2000;28(2):489-97.
Patel, Adaptive recognition in RNA complexes with peptides and proteinmodules. Curr Opin Struct Biol. Feb. 1999;9(1):74-87.
Pennisi, The CRISPR craze. Science. Aug. 23, 2013;341(6148):833-6. doi: 10.1126/science.341.6148.833.
Perez et al., Establishment of HIV-1 resistance in CD4+ T cells by genome editing using zinc-finger nucleases. Nat Biotechnol. Jul. 2008;26(7):808-16. doi: 10.1038/nbt1410. Epub Jun. 29, 2008.
Perrin et al., Role of the HIV-1 envelope transmembrane domain in intracellular sorting. BMC Cell Biol. Mar. 15, 2018;19(1):3. doi: 10.1186/s12860-018-0153-4.
Pisitkun et al., Identification and proteomic profiling of exosomes in human urine. Proc Natl Acad Sci U S A. Sep. 7, 2004;101(36):13368-73. Epub Aug. 23, 2004.
Pornillos et al., HIV Gag mimics the Tsg101-recruiting activity of the human Hrs protein. J Cell Biol. Aug. 4, 2003;162(3):425-34.
Pornillos et al., Structure and functional interactions of the Tsg101 UEV domain. EMBO J. May 15, 2002;21(10):2397-406.
Pornillos et al., Structure of the Tsg101 UEV domain in complex with the PTAP motif of the HIV-1 p6 protein. Nat Struct Biol. Nov. 2002;9(11):812-7.
Potti et al., Regulatable aptamers in medicine: focus on antithrombotic strategies. Expert Opin Biol Ther. Oct. 2004;4(10):1641-7.
Properzi et al., Exosomes: the future of biomarkers in medicine. Biomark Med. Oct. 2013;7(5):769-78.

(56) References Cited

OTHER PUBLICATIONS

Qi et al., Repurposing CRISPR as an RNA-guided platform for sequence-specific control of gene expression. Cell. Feb. 28, 2013;152(5):1173-83. doi: 10.1016/j.cell.2013.02.022.
Rauch et al., Multiple interactions between the ESCRT machinery and arrestin-related proteins: implications for PPXY-dependent budding. J Virol. Apr. 2011;85(7):3546-56. doi: 10.1128/JVI.02045-10. Epub Dec. 29, 2010.
Ray et al., Quantitative tracking of protein trafficking to the nucleus using cytosolic protein delivery by nanoparticle-stabilized nanocapsules. Bioconjug Chem. Jun. 17, 2015;26(6):1004-7. doi: 10.1021/acs.bioconjchem.5b00141. Epub Jun. 2, 2015.
Razi et al., Distinct roles for Tsg101 and Hrs in multivesicular body formation and inward vesiculation. Mol Biol Cell. Aug. 2006;17(8):3469-83. Epub May 17, 2006.
Rotin et al., Physiological functions of the HECT family of ubiquitin ligases. Nat Rev Mol Cell Biol. Jun. 2009;10(6):398-409. doi: 10.1038/nrm2690. Epub May 13, 2009.
Rouet et al., Engineering CRISPR-Cas9 RNA—Protein Complexes for Improved Function and Delivery. CRISPR J. Dec. 2018;1(6):367-378. doi: 10.1089/crispr.2018.0037.
Roy et al., A bulge structure in HIV-1 TAR RNA is required for Tat binding and Tat-mediated trans-activation. Genes Dev. Aug. 1990;4(8):1365-73.
Roy et al., Candidate prognostic markers in breast cancer: focus on extracellular proteases and their inhibitors. Breast Cancer (Dove Med Press). Jul. 3, 2014;6:81-91. doi: 10.2147/BCTT.S46020.
Roy et al., Control of the interferon-induced 68-kilodalton protein kinase by the HIV-1 tat gene product. Science. Mar. 9, 1990;247(4947):1216-9.
Saudek et al., A preliminary trial of the programmable implantable medication system for insulin delivery. N Engl J Med. Aug. 31, 1989;321(9):574-9.
Schorey et al., Exosome function: from tumor immunology to pathogen biology. Traffic. Jun. 2008;9(6):871-81. doi: 10.1111/j.1600-0854.2008.00734.x. Epub Mar. 6, 2008.
Schröder et al., Screening and prostate-cancer mortality in a randomized European study. N Engl J Med. Mar. 26, 2009;360(13):1320-8. doi: 10.1056/NEJMoa0810084. Epub Mar. 18, 2009.
Scott et al., Structural and mechanistic studies of VPS4 proteins. EMBO J. Oct. 19, 2005;24(20):3658-69. Epub Sep. 29, 2005.
Sefton, Implantable pumps. Crit Rev Biomed Eng. 1987;14(3):201-40.
Sells et al., Delivery of protein into cells using polycationic liposomes. Biotechniques. Jul. 1995;19(1):72-6, 78.
Sen et al., Cellular unfolded protein response against viruses used in gene therapy. Front Microbiol. May 26, 2014;5:250. doi: 10.3389/fmicb.2014.00250. eCollection 2014.
Shui et al., RNA aptamers that functionally interact with green fluorescent protein and its derivatives. Nucleic Acids Res. Mar. 2012;40(5):e39. doi: 10.1093/nar/gkr1264. Epub Dec. 20, 2011.
Skog et al., Glioblastoma microvesicles transport RNA and proteins that promote tumour growth and provide diagnostic biomarkers. Nat Cell Biol. Dec. 2008;10(12):1470-6. doi: 10.1038/ncb1800. Epub Nov. 16, 2008.
Srisawat et al., Streptavidin aptamers: affinity tags for the study of RNAs and ribonucleoproteins. RNA. Apr. 2001;7(4):632-41.
Stockley et al., Probing sequence-specific RNA recognition by the bacteriophage MS2 coat protein. Nucleic Acids Res. Jul. 11, 1995;23(13):2512-8.
Sundquist et al., Ubiquitin recognition by the human TSG101 protein. Mol Cell. Mar. 26, 2004;13(6):783-9.
Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Thery et al., Exosomes: composition, biogenesis and function. Nat Rev Immunol. Aug. 2002;2(8):569-79.
Thery et al., Membrane vesicles as conveyors of immune responses. Nat Rev Immunol. Aug. 2009;9(8):581-93. doi: 10.1038/nri2567. Epub Jun. 5, 2009.
Tuerk et al., Systematic evolution of ligands by exponential enrichment: RNA ligands to bacteriophage T4 DNA polymerase. Science. Aug. 3, 1990;249(4968):505-10.
Turan et al., Site-specific recombinases: from tag-and-target-to tag-and-exchange-based genomic modifications. FASEB J. Dec. 2011;25(12):4088-107. doi: 10.1096/fj.11-186940. Epub Sep. 2, 2011.
Tykodi, PD-1 as an emerging therapeutic target in renal cell carcinoma: current evidence. Onco Targets Ther. Jul. 25, 2014;7:1349-59. doi: 10.2147/OTT.S48443.
Ulrich et al., DNA and RNA aptamers: from tools for basic research towards therapeutic applications. Comb Chem High Throughput Screen. Sep. 2006;9(8):619-32.
UniProt Submission; UniProt, Accession No. O00308. Last modified Oct. 29, 2014, version 141.
UniProt Submission; UniProt, Accession No. P46934. Last modified Oct. 29, 2014, version 152.
UniProt Submission; UniProt, Accession No. Q76N89. Last modified Oct. 29, 2014, version 95.
UniProt Submission; UniProt, Accession No. Q96J02. Last modified Oct. 29, 2014, version 129.
UniProt Submission; UniProt, Accession No. Q9H0M0. Last modified Oct. 29, 2014, version 136.
UniProt Submission; UniProt, Accession No. Q9HAU4. Last modified Oct. 29, 2014, version 143.
UniProt Submission; UniProt, Accession No. Q9HCE7.Last modified Oct. 29, 2014, version 136.
UniProt Submission; UniProt, Accession No. Q9P2P5. Last modified Oct. 29, 2014, version 105.
Urnov et al., Highly efficient endogenous human gene correction using designed zinc-finger nucleases. Nature. Jun. 2, 2005;435(7042):646-51. Epub Apr. 3, 2005.
Valadi et al., Exosome-mediated transfer of mRNAs and microRNAs is a novel mechanism of genetic exchange between cells. Nat Cell Biol. Jun. 2007;9(6):654-9. Epub May 7, 2007.
Venken et al., Genome-wide manipulations of *Drosophila melanogaster* with transposons, Flp recombinase, and ΦC31 integrase. Methods Mol Biol. 2012;859:203-28. doi: 10.1007/978-1-61779-603-6_12.
Verplank et al., Tsg101, a homologue of ubiquitin-conjugating (E2) enzymes, binds the L domain in HIV type 1 Pr55(Gag). Proc Natl Acad Sci U S A. Jul. 3, 2001;98(14):7724-9. Epub Jun. 26, 2001.
Von Schwedler et al., The protein network of HIV budding. Cell. Sep. 19, 2003;114(6):701-13.
Wang et al., ARMMs as a versatile platform for intracellular delivery of macromolecules. Nat Commun. Mar. 6, 2018;9(1):960. doi: 10.1038/s41467-018-03390-x.
Weeks et al., Fragments of the HIV-1 Tat protein specifically bind TAR RNA. Science. Sep. 14, 1990;249(4974):1281-5.
Weeks et al., RNA binding assays for Tat-derived peptides: implications for specificity. Biochemistry. Oct. 27, 1992;31(42):10281-7.
Weeks et al., RNA recognition by Tat-derived peptides: Interaction in the major groove? Cell. Aug. 9, 1991;66(3):577-88. doi: 10.1016/0092-8674(81)90020-9.
Wehman et al., The P4-ATPase TAT-5 inhibits the budding of extracellular vesicles in C. elegans embryos. Curr Biol. Dec. 6, 2011;21(23):1951-9. doi: 10.1016/j.cub.2011.10.040. Epub Nov. 17, 2011.
Weiss, RNA-mediated signaling in transcription. Nat Struct Biol. May 1998;5(5):329-33.
Welton et al., Proteomics analysis of bladder cancer exosomes. Mol Cell Proteomics. Jun. 2010;9(6):1324-38. doi: 10.1074/mcp.M000063-MCP201. Epub Mar. 11, 2010.
Witherell et al., Specific interaction between RNA phage coat proteins and RNA. Prog Nucleic Acid Res Mol Biol. 1991;40:185-220.
Xu et al., Extracellular vesicle isolation and characterization: toward clinical application. J Clin Invest. Apr. 1, 2016;126(4):1152-62. doi: 10.1172/JCI81129. Epub Apr. 1, 2016.
Zelphati et al., Intracellular delivery of proteins with a new lipid-mediated delivery system. J Biol Chem. Sep. 14, 2001;276(37):35103-10. Epub Jul. 10, 2001.

(56) References Cited

OTHER PUBLICATIONS

Zhang et al., Conditional gene manipulation: Cre-ating a new biological era. J Zhejiang Univ Sci B. Jul. 2012;13(7):511-24. doi: 10.1631/jzus.B1200042.
Zhang et al., Stabilized plasmid-lipid particles for regional gene therapy: formulation and transfection properties. Gene Ther. Aug. 1999;6(8):1438-47.

Sequences of full-length and minimal ARRDC1 proteins

Full length ARRDC1: 433 amino acids (italicized segments are deleted in the shorter ARRDC1)

MGRVQLFEISLSHGRVVYSPGEPLAGTVRVRLGAPLPFRAIRVTCIGSCGVSNKANDTAW
VVEEGYFNSSLSLADKGSLPAGEHSFPFQFLLPATAPTSFEGPFGKIVHQVRAAIHTPRF
SKDHKCSLVFYILSPLNLNSIPDIEQPNVASATKKFSYKLVKTGSVVLTASTDLRGYVVG
QALQLHADVENQSGKDTSPVVASLLQKVSYKAKRWIHDVRTIAEVEGAGVKAWRRAQWHE
QILVPALPQSALPGCSLIHIDYYLQVSLKAPEATVTLPVFIGNIAVNHAPVSPRPGLGLP
PGAPPLVVPSAPPQEEAE*AEAAAGGPHFLDPVFLSTKSHSQRQPLLATLSSVPGAPEPCP*
*QDGSPASHPLHPPLCISTGATVPYFAEGSGGPVPTTSTLIL*PPEY*SSWGY*PYEAPPSY*EQ*
*SCGGVEPSLTPES* SEQ ID NO: 116

Minimal ARRDC1: 330 amino acids

MGRVQLFEISLSHGRVVYSPGEPLAGTVRVRLGAPLPFRAIRVTCIGSCGVSNKANDTAW
VVEEGYFNSSLSLADKGSLPAGEHSFPFQFLLPATAPTSFEGPFGKIVHQVRAAIHTPRF
SKDHKCSLVFYILSPLNLNSIPDIEQPNVASATKKFSYKLVKTGSVVLTASTDLRGYVVG
QALQLHADVENQSGKDTSPVVASLLQKVSYKAKRWIHDVRTIAEVEGAGVKAWRRAQWHE
QILVPALPQSALPGCSLIHIDYYLQVSLKAPEATVTLPVFIGNIAVNHAPVSPRPGLGLP
PGAPPLVVPSAPPQEEAEPPEYPYEAPPSY SEQ ID NO: 1

FIG. 5

MINIMAL ARRESTIN DOMAIN CONTAINING PROTEIN 1(ARRDC1) CONSTRUCTS

RELATED APPLICATIONS

This application is a national stage filing under 35 U.S.C. § 371 of International PCT Application No. PCT/US2020/052784, filed Sep. 25, 2020, which claims priority under 35 U.S.C. § 119(e) to U.S. Provisional Application, U.S. Ser. No. 62/906,685, filed Sep. 26, 2019, each of which is incorporated herein by reference.

REFERENCE TO A SEQUENCE LISTING SUBMITTED AS A TEXT FILE VIA EFS-WEB

This application contains a Sequence Listing which has been submitted in ASCII format via EFS-Web and is hereby incorporated by reference in its entirety. Said ASCII copy, created on Mar. 23, 2022, is named H082470331US01-SEQ-AZW and is 282,100 bytes in size.

BACKGROUND OF THE INVENTION

Arrestin domain containing protein 1 (ARRDC1) drives the formation of extracellular vesicles known as ARRDC1-mediated microvesicles (ARMMs), and these vesicles can be harnessed to package and deliver a variety of molecular cargos, such as small molecules, proteins, and nucleic acids.

SUMMARY OF THE INVENTION

The arrestin domain containing protein 1 (ARRDC1) drives the formation of extracellular vesicles, known as ARMMs (Nabhan J et al., PNAS 2012) and these vesicles can be harnessed to package and deliver a variety of cargos, such as proteins, nucleic acids, and small molecules (Wang Q and Lu Q, Nat Commun 2018). Full-length ARRDC1 protein (433 amino acids at ~46 kD) has been used to recruit the molecular cargos into the vesicles, either through a direct fusion with the molecular cargo or via a protein-protein interaction. As ARRDC1 protein itself is packaged into ARMMs, and because the size of the vesicles is limited (~80-100 nm), a smaller ARRDC1 protein that can still function in driving budding would potentially increase the number of cargos that can be packaged into the vesicles. Moreover, a smaller ARRDC1 may allow the recruitment of relatively large molecular cargos.

Disclosed herein are minimal ARRDC1 proteins sufficient to drive ARMM budding. The ARMM delivery system, described herein, addresses many limitations of current delivery systems that prevent the safe and efficient delivery of molecular cargos, such as small molecules, proteins, and nucleic acids to cells. As ARMMS are derived from an endogenous budding pathway, they are unlikely to elicit a strong immune response, unlike viral delivery systems, which are known to trigger inflammatory responses (Sen D. et al., "Cellular unfolded protein response against viruses used in gene therapy", *Front Microbiology.* 2014; 5:250, 1-16.). Additionally, ARMMs allow for the specific packaging of any cargo protein of interest (e.g., a targeted endonuclease such as a Cas9 protein, or Cas9 variant, with a guide RNA (gRNA)). These cargos can then be delivered by fusion or uptake by specific recipient cells/tissues by incorporating antibodies or other types of molecules in ARMMs that recognize tissue-specific markers. In some aspects, targeted endonucleases such Cas9-gRNAs and their variants can be loaded into ARMMs for delivery to a target cell. ARMMs are microvesicles that are distinct from exosomes and, like budding viruses, are produced by direct plasma membrane budding (DPMB). DPMB is driven by a specific interaction of TSG101 with the tetrapeptide PSAP (SEQ ID NO: 122) or PTAP (SEQ ID NO: 123) motif of the arrestin-domain-containing protein ARRDC1 accessory protein, which is localized to the plasma membrane through its arrestin domain. ARMMS have been described in detail, for example, in PCT application number PCT/US2013/024839, filed Feb. 6, 2013 (published as WO 2013/119602 A1) by Lu Q. et al., and entitled "Arrdc1-mediated microvesicles (ARMMs) and uses thereof," the entire contents of which are incorporated herein by reference; U.S. application Ser. No. 14/929,177, filed Oct. 30, 2015 (published as US 20160206566 A1) by Lu Q. et al., entitled "Delivery of Cas9 via ARRDC1-Mediated Microvesicles (ARMMs)," the entire contents of which are incorporated herein by reference; and in PCT application number PCT/US2017/054912, filed Oct. 3, 2017 (published as WO 2018/067546 A1) by Lu Q. et al., and entitled "Delivery of Therapeutic RNAs via ARRDC1-Medicated Microvesicles," the entire contents of which are incorporated herein by reference. The ARRDC1/TSG101 interaction results in relocation of TSG101 from endosomes to the plasma membrane and mediates the release of microvesicles that contain TSG101, ARRDC1, and other cellular components.

Accordingly, in some embodiments, the present disclosure provides a minimal arrestin domain-containing protein 1 (ARRDC1) comprising an arrestin domain, at least one PSAP (SEQ ID NO: 122) or PTAP (SEQ ID NO: 123) motif, and at least one PPXY motif, wherein the minimal ARRDC1 is shorter than full-length ARRDC1 protein. In some embodiments, the minimal ARRDC1 comprises at least two PPXY motifs. In some embodiments, the minimal ARRDC1 is less than 400 amino acids in length. In some embodiments, one or more of the PPXY motifs is PPEY (SEQ ID NO: 124). In some embodiments, one or more of the PPXY motifs is PPSY (SEQ ID NO: 115). In some embodiments, at least two PPXY motifs are PPEY (SEQ ID NO: 124) and PPSY(SEQ ID NO: 115). In some embodiments, the minimal ARRDC1 comprises the amino acid sequence set forth in SEQ ID NO: 1.

Aspects of the present disclosure provide arrestin domain-containing protein 1 (ARRDC1)-mediated microvesicles (ARMM) comprising a lipid bilayer and a minimal ARRDC1 protein or variant thereof. In some embodiments, the minimal ARRDC1 protein comprises at least one PSAP (SEQ ID NO: 122) or PTAP (SEQ ID NO: 123) motif and at least one PPXY motif, and wherein the minimal ARRDC1 protein is shorter than full-length ARRDC1 protein. In some embodiments, the minimal ARRDC1 protein comprises the amino acid sequence set forth in SEQ ID NO: 1. In some embodiments, the microvesicle further comprises an cargo, for example, a nucleic acid, a protein, and/or a small molecule.

In some embodiments, the microvesicle further comprises a TSG101 protein or fragment thereof. In some embodiments, the TSG101 protein fragment comprises a TSG101 UEV domain. In some embodiments, the cargo to be delivered is conjugated to the minimal ARRDC1 protein, the minimal ARRDC1 fragment, the TSG101 protein, or the TSG101 fragment. In some embodiments, the microvesicle further comprises an integrin, a receptor tyrosine kinase, a G-protein coupled receptor, or a membrane-bound immunoglobulin.

In some embodiments, the microvesicle comprises an agent selected from the group consisting of Cas9 protein or Cas9 protein variant, Oct4, Sox2, c-Myc, KLF4 reprogramming factor, p53, Rb (retinoblastoma protein), BRCA1, BRCA2, PTEN, APC, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre recombinase, Dre recombinase, FLP recombinase, Hin, Gin, Tn3, β-six, CinH, ParA, γδ, Bxb1, ϕC31, TP901, TG1, φBT1, R4, φRV1, φFC1, MR11, A118, U153, gp29, Cre, FLP, R, Lambda, HK101, HK022, pSAM2, CAS9 nuclease or other Cas9-like targeted endonucleases such as Cpf1, CasX, CasY, or Geo), Sp1, NF1, CCAAT, GATA, HNF, PIT-1, MyoD, Myf5, Hox, Winged Helix, SREBP, p53, CREB, AP-1, Mef2, STAT, R-SMAD, NF-κB, Notch, TUBBY, NFAT, α1β1 integrin, α2β1 integrin, α4β1 integrin, α5β1 integrin, α6β1 integrin, αLβ2 integrin, αMβ2 integrin, αIIbβ3 integrin, αVβ3 integrin, αVβ5 integrin, αVβ6 integrin, α6β4 integrin, EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, MuSK receptor, rhodopsin-like receptor, the secretin receptor, metabotropic glutamate/pheromone receptor, cyclic AMP receptor, frizzled/smoothened receptor, CXCR4, CCR5, beta-adrenergic receptor, CA19-9, c-met, PD-1, CTLA-4, ALK, AFP, EGFR, Estrogen receptor (ER), Progesterone receptor (PR), HER2/neu, KIT, B-RAF, S100, MAGE, Thyroglobulin, MUC-1, and PSMA.

In some embodiments, the agent (payload or cargo) to be delivered is a nucleic acid. In some embodiments, the nucleic acid comprises an RNA. In certain embodiments, the RNA is an RNAi agent. The RNA could be a coding RNA, a non-coding RNA, an antisense RNA, an mRNA, a guide RNA, a small RNA, an siRNA, an shRNA, a microRNA, an snRNA, a snoRNA, a lincRNA, or a structural RNA, or an rRNA or ribozyme.

In some embodiments, the nucleic acid comprises a DNA. In some embodiments, the DNA comprises a retrotransposon sequence, a LINE sequence, a SINE sequence, a composite SINE sequence, or an LTR-retrotransposon sequence.

In some embodiments, the nucleic acid agent encodes a protein. In some embodiments, the agent comprises a detectable label.

In some embodiments, the agent comprises a therapeutic agent.

In some embodiments, the agent is selected from the group consisting of enzymes, antibodies, a Fab, a Fab', a F(ab')2, a Fd, a scFv, a Fv, a dsFv, diabodies, and affibodies. In some embodiments, the agent comprises a cytotoxic agent.

In some embodiments, the agent comprises a protein. In some embodiments, the agent comprises a transcription factor, a transcriptional repressor, a fluorescent protein, a kinase, a phosphatase, a protease, a ligase, or a recombinase.

In some embodiments the agent comprises a lipid, or a lipoprotein, or a glycoprotein, or a polysaccharide, or a lipopolysaccharide.

In some embodiments, the agent is covalently bound to the ARRDC1 protein or fragment thereof, or the TSG101 protein or fragment thereof. In some embodiments, the agent is conjugated to the ARRDC1 protein or fragment thereof or the TSG101 protein or fragment thereof via a linker. In some embodiments, the linker is a cleavable linker. In some embodiments, the linker comprises a protease recognition site or a UV-cleavable moiety, a photocleavable linker, or other linker cleavable by a biological mechanism, chemical degradation of a covalent bond, dissociation of a non-covalent association, a thermally labile link, or pH labile link.

In some embodiments, the agent to be delivered is fused to at least one WW domain or variant thereof. In some embodiments, the agent comprises two, three, four or five WW domains or variants thereof. In some embodiments, the WW domain is derived from a WW domain of the ubiquitin ligase WWP1, WWP2, Nedd4-1, Nedd4-2, Smurf1, Smurf2, ITCH, NEDL1, or NEDL2. In some embodiments, the WW domain comprises a sequence selected from the group consisting of SEQ ID NO: 6-14.

In some embodiments, the agent is a protein. In some embodiments, the agent comprises a Cas9 protein. In some embodiments, the Cas9 protein or variant thereof comprises at least one nuclear localization sequence (NLS). In some embodiments, the microvesicle further comprises a guide RNA (gRNA). In some embodiments, the WW domain is fused to the N-terminus of the protein. In some embodiments, the WW domain is fused to the C-terminus of the protein. In some embodiments, the microvesicle does not include an exosomal biomarker. In some embodiments, the microvesicle is negative for an exosomal biomarker.

In some embodiments, the exosomal biomarker is chosen from the group consisting of CD63, Lamp-1, Lamp-2, CD9, HSPA8, GAPDH, CD81, SDCBP, PDCD6IP, ENO1, ANXA2, ACTB, YWHAZ, HSP90AA129, ANXA5, EEF1A1, YWHAE, PPIA, MSN, CFL1, ALDOA, PGK1, EEF2, ANXA1, PKM2, HLA-DRA, and YWHAB. In some embodiments, the microvesicle does not include or is negative for Lamp-1. In some embodiments, the microvesicle diameter is from about 30 nm to about 500 nm.

Aspects of the present disclosure disclose an arrestin domain-containing protein 1 (ARRDC1)-mediated microvesicle (ARMM) as described above, further comprising a Cas9 cargo protein. The Cas9 cargo protein may be linked to the minimal ARRDC1 protein. The ARRDC1 protein can be covalently linked to the Cas9 cargo protein. In some embodiments, the minimal ARRDC1 protein is linked to the Cas9 protein via a cleavable linker. The linker may be a UV-cleavable linker, and could include a protease recognition site or other linker cleavable by a biological mechanism, chemical degradation of a covalent bond, dissociation of a non-covalent association, a thermally labile link, or pH labile link.

In some aspects, the present disclosure provides an arrestin domain-containing protein 1 (ARRDC1)-mediated microvesicle (ARMM) comprising a minimal ARRDC1 protein or variant thereof, and a cargo protein, wherein the cargo protein is linked to the TSG101 protein or variant thereof. In some aspects the cargo protein is linked to the TSG101 protein or variant by expression as a cargo-TSG101 fusion protein.

In some aspects, the present disclosure provides an arrestin domain-containing protein 1 (ARRDC1)-mediated microvesicle (ARMM) comprising a minimal ARRDC1 protein or variant thereof, and a targeted endonuclease, wherein the targeted endonuclease is linked to the TSG101 protein or variant thereof.

In some aspects, the present disclosure provides an arrestin domain-containing protein 1 (ARRDC1)-mediated microvesicle (ARMM) comprising a minimal ARRDC1 protein or variant thereof, and a Cas9 cargo protein, wherein the Cas9 cargo protein is linked to the TSG101 protein or variant thereof.

Some aspects of the present disclosure relate to minimal ARRDC1 fusion proteins. In some embodiments, the minimal ARRDC1 fusion protein comprises a minimal ARRDC1 protein or a variant thereof, wherein the minimal ARRDC1 protein comprises an arrestin domain, at least one PSAP (SEQ ID NO: 122) motif, at least one PPXY motif, and a Cas9 protein or variant thereof.

In some aspects, the present disclosure provides microvesicle-producing cells comprising a recombinant expression construct encoding a minimal ARRDC1 protein under the control of a heterologous promoter. In some embodiments, the microvesicle-producing cells further comprise a recombinant expression construct encoding a cargo protein under the control of a heterologous promoter. The cargo protein can be fused to at least one WW domain or variant thereof. The cargo protein can be expressed as a fusion protein with the minimal ARRDC1. The cargo protein can be expressed as a fusion protein with TSG101. In some embodiments, the microvesicle-producing cells further comprise a recombinant expression construct encoding a cargo nucleic acid produced under the control of a heterologous promoter.

In some aspects, the present disclosure includes a microvesicle-producing cell comprising a recombinant expression construct encoding a minimal ARRDC1 protein under the control of a heterologous promoter, wherein the minimal ARRDC1 protein comprises an arrestin domain, at least one PSAP (SEQ ID NO: 122) motif or PTAP (SEQ ID NO: 123) motif, and at least one PPXY motif, and wherein the minimal ARRDC1 protein is shorter than full-length ARRDC1 protein; and wherein the minimal ARRDC1 protein is linked to a Cas9 cargo protein or variant thereof. In some embodiments, the microvesicle producing cell comprises minimal ARRDC1 including at least two PPXY motifs.

Aspects of the present disclosure include methods of delivering a cargo to a target cell by contacting the target cell with any of the microvesicles or microvesicle-producing cells disclosed herein. Some aspects of the present disclosure provide methods of gene editing comprising contacting the target cell with any of the microvesicles or microvesicle-producing cells disclosed herein.

Other advantages, features, and uses of the invention will be apparent from the detailed description of certain exemplary, non-limiting embodiments; the drawings; the non-limiting working examples; and the claims.

BRIEF DESCRIPTION OF THE DRAWINGS

FIG. 2B shows an image of a Western Blot. The constructs (all fused to the GFP protein) were transfected into HEK293T cells. 48 hours post transfection, extracellular vesicles (EVs) were isolated via ultracentrifugation and used for anti-GFP Western blotting. Whole cell lysates of transfected cells were included. FIG. 2C is a graph showing the number of EVs in cultured media from transfected cells (as in FIG. 2B) as measured by a Nanosight NS300 instrument.

FIG. 3B shows the results of anti-Flag Western blotting. Cas9, ARRDC1-Cas9, and mini-ARRDC1-Cas9 (all with a Flag tag at the C-terminus) were transfected into HEK293T cells. 48 hours post transfection, EVs were isolated via ultracentrifugation and used for anti-Flag Western blotting. Whole cell lysates of transfected cells were included. FIG. 3C is a graph showing the gRNA ratio (ARMMs/cell) for Cas9/GFP-gRNA, a minimal ARRDC1-Cas9/GFP-gRNA, and a control. Cas9 and mini-ARRDC1-Cas9 along with a guide RNA (gRNA) that targets the GFP gene were transfected into donor HEK293T cells. 48 hours post transfection, EVs were isolated via ultracentrifugation. gRNA amount in ARMMs was measured by qRT-PCR and normalized against the cellular gRNA.

FIG. 5 shows the protein sequence of full-length ARRDC1 and an example of a minimal ARRDC1.

DEFINITIONS

Figure 1:
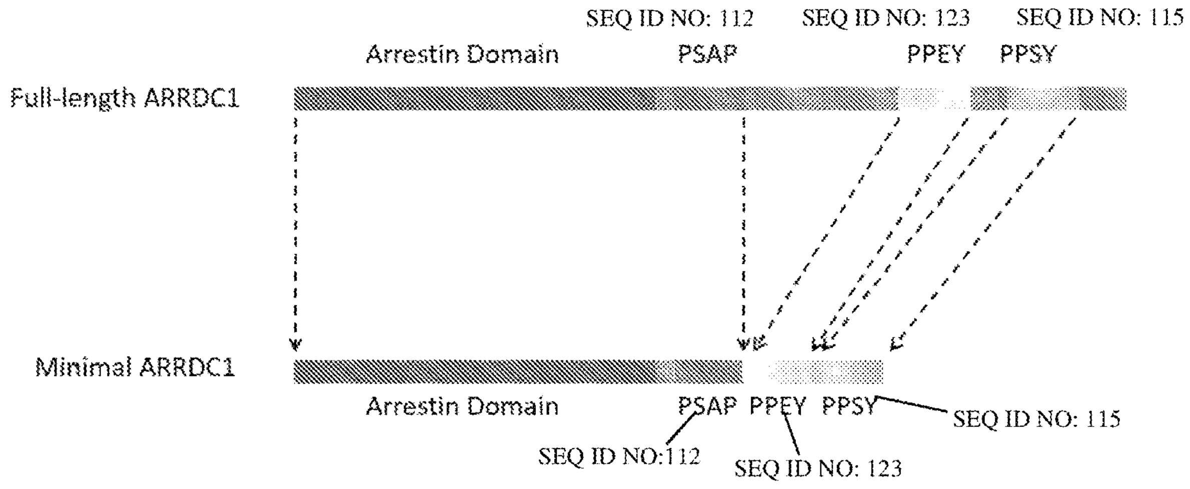
FIG. 1 is a schematic showing the domain/motifs in full-length ARRDC1 protein and an example of a minimal ARRDC1.

ARRDC1: ARRDC1 is a protein that comprises a PSAP (SEQ ID NO: 122) and a PPXY motif, also referred to herein as a PSAP (SEQ ID NO: 122) and PPXY motif, respectively, in its C-terminus, and interacts with TSG101 as shown herein. Exemplary, non-limiting ARRDC1 protein sequences are provided herein, and additional, suitable ARRDC1 protein variants according to aspects of this invention are known in the art. In addition, exemplary, non-limiting minimal ARRDC1 protein sequences are provided herein. It will be appreciated by those of skill in the art that this invention is not limited in this respect. Exemplary ARRDC1 sequences include the following (PSAP (SEQ ID NO: 122) and PPXY motifs are marked):

>gi|22748653|ref|NP_689498.1| arrestin domain-containing protein 1 [*Homo sapiens*]

(SEQ ID NO: 15)

MGRVQLFEISLSHGRVVYSPGEPLAGTVRVRLGAPLPFRAIRVTCIGSCGVSNKANDT

AWVVEEGYFNSSLSLADKGSLPAGEHSFPFQFLLPATAPTSFEGPFGKIVHQVRAAIH

TPRFSKDHKCSLVFYILSPLNLNSIPDIEQPNVASATKKFSYKLVKTGSVVLTASTDLR

GYVVGQALQLHADVENQSGKDTSPVVASLLQKVSYKAKRWIHDVRTIAEVEGAGV

KAWRRAQWHEQILVPALPQSALPGCSLIHIDYYLQVSLKAPEATVTLPVFIGNIAVNH

-continued

APVSPRPGLGLPPGAPPLVVPSAPPQEEAEAEAAAGGPHFLDPVFLSTKSHSQRQPLL

ATLSSVPGAPEPCPQDGSPASHPLHPPLCISTGATVPYFAEGSGGPVPTTSTLILPPEYS

SWGYPYEAPPSYEQSCGGVEPSLTPES

>gi|244798004|ref|NP_001155957.1| arrestin domain-containing protein 1 isoform a [*Mus musculus*]
(SEQ ID NO: 16)

MGRVQLFEIRLSQGRVVYGPGEPLAGTVHLRLGAPLPFRAIRVTCMGSCGVSTKAND

GAWVVEESYFNSSLSLADKGSLPAGEHNFPFQFLLPATAPTSFEGPFGKIVHQVRASI

DTPRFSKDHKCSLVFYILSPLNLNSIPDIEQPNVASTTKKFSYKLVKTGNVVLTASTDL

RGYVVGQVLRLQADIENQSGKDTSPVVASLLQKVSYKAKRWIYDVRTIAEVEGTGV

KAWRRAQWQEQILVPALPQSALPGCSLIHIDYYLQVSMKAPEATVTLPLFVGNIAVN

QTPLSPCPGRESSPGTLSLVVPSAPPQEEAEAVASGPHFSDPVSLSTKSHSQQQPLSAP

LGSVSVTTTEPWVQVGSPARHSLHPPLCISIGATVPYFAEGSAGPVPTTSALILPPEYS

SWGYPYEAPPSYEQSCGAAGTDLGLIPGS

>gi|244798112|ref|NP_848495.2| arrestin domain-containing protein 1 isoform b [*Mus musculus*]
(SEQ ID NO: 17)

MGRVQLFEIRLSQGRVVYGPGEPLAGTVHLRLGAPLPFRAIRVTCMGSCGVSTKAND

GAWVVEESYFNSSLSLADKGSLPAGEHNFPFQFLLPATAPTSFEGPFGKIVHQVRASI

DTPRFSKDHKCSLVFYILSPLNLNSIPDIEQPNVASTTKKFSYKLVKTGNVVLTASTDL

RGYVVGQVLRLQADIENQSGKDTSPVVASLLQVSYKAKRWIYDVRTIAEVEGTGVK

AWRRAQWQEQILVPALPQSALPGCSLIHIDYYLQVSMKAPEATVTLPLFVGNIAVNQ

TPLSPCPGRESSPGTLSLVVPSAPPQEEAEAVASGPHFSDPVSLSTKSHSQQQPLSAPL

GSVSVTTTEPWVQVGSPARHSLHPPLCISIGATVPYFAEGSAGPVPTTSALILPPEYSS

WGYPYEAPPSYEQSCGAAGTDLGLIPGS

The term "ARMM," as used herein, refers to a microvesicle comprising an ARRDC1 protein or variant thereof, and/or TSG101 protein or variant thereof. In some embodiments, the ARRDC1 protein or variant thereof is a minimal ARRDC1 protein or variant thereof. In some embodiments, the ARMM is shed from a cell, and comprises a molecule, for example, a nucleic acid, protein, or small molecule, present in the cytoplasm or associated with the membrane of the cell. In some embodiments, the ARMM is shed from a transgenic cell comprising a recombinant expression construct that includes the transgene, and the ARMM comprises a gene product, for example, a transcript or a protein (e.g., a cargo protein) encoded by the expression construct. In some embodiments, the protein encoded by the expression construct is a Cas9 fusion protein, or Cas9 cargo protein fused to at least one WW domain, or variant thereof, which may associate with the minimal ARRDC1 protein to facilitate loading of the Cas9 cargo protein into the ARMM. In some embodiments, the ARMM is produced synthetically, for example, by contacting a lipid bilayer within ARRDC1 protein, or variant thereof, in a cell-free system in the presence of TSG101, or a variant thereof. In other embodiments, the ARMM is synthetically produced by further contacting a lipid bilayer with HECT domain ligase, and VPS4a. In some embodiments, an ARMM lacks a late endosomal marker. Some ARMMs as provided herein do not include, or are negative for, one or more exosomal biomarker. Exosomal biomarkers are known to those of skill in the art and include, but are not limited to, CD63, Lamp-1, Lamp-2, CD9, HSPA8, GAPDH, CD81, SDCBP, PDCD6IP, ENO1, ANXA2, ACTB, YWHAZ, HSP90AA1, ANXA5, EEF1A1, YWHAE, PPIA, MSN, CFL1, ALDOA, PGK1, EEF2, ANXA1, PKM2, HLA-DRA, and YWHAB. For example, some ARMMs provided herein lack CD63, some ARMMs lack LAMP1, some ARMMs lack CD9, some ARMMs lack CD81, some ARMMs lack CD63 and Lamp-1, some ARMMs lack CD63, Lamp-1, and CD9, some ARMMs lack CD63, Lamp-1, CD81, and CD9, and so forth. Certain ARMMs provided herein may include an exosomal biomarker. Accordingly, some ARMMs may be negative for one or more exosomal biomarkers but positive for one or more other exosomal biomarkers. For example, such an ARMM may be negative for CD63 and Lamp-1, but may include PGK1 or GAPDH; or may be negative for CD63, Lamp-1, CD9, and CD81, but may be positive for HLA-DRA. In some embodiments, ARMMs include an exosomal biomarker, but at a lower level than those typically found in exosomes. For example, some ARMMs include one or more exosomal biomarkers at a level of less than about 1%, less than about 5%, less than about 10%, less than about 20%, less than about 30%, less than about 40%, or less than about 50% of the level of that biomarker found in exosomes. To give a non-limiting example, in some embodiments, an ARMM may be negative for CD63 and Lamp-1, include CD9 at a level of less than about 5% of the level of CD9 typically found in exosomes, and be positive for ACTB. Exosomal biomarkers in addition to those listed above are known to those of skill in the art, and the invention is not limited in this regard.

Agent and agent to be delivered: As used herein, the term "agent" refers to a substance that can be incorporated in an ARMM, for example, into the liquid phase of the ARMM or into the lipid bilayer of the ARMM. The term "agent to be delivered" refers to any substance that can be delivered to a subject, organ, tissue, or cell. In some embodiments, the agent is an agent to be delivered to a target cell. In some embodiments, the agent to be delivered is a biologically active agent, i.e., it has activity in a cell, biological system, and/or subject. For instance, a substance that, when administered to a subject, has a biological effect on that subject, is considered to be biologically active. In some embodiments, an agent to be delivered is a therapeutic agent. As used herein, the term "therapeutic agent" refers to any agent that, when administered to a subject, has a beneficial effect. The term "therapeutic agent" refers to any agent that, when administered to a subject, has a therapeutic, diagnostic, and/or prophylactic effect and/or elicits a desired biological and/or pharmacological effect. As used herein, the term "therapeutic agent" may be a nucleic acid that is delivered to a cell via its association with or inclusion into an ARMM. In certain embodiments, the agent to be delivered is a nucleic acid. In certain embodiments, the agent to be delivered is DNA. In certain embodiments, the agent to be delivered is RNA. In certain embodiments, the agent to be delivered is a peptide or protein. In some embodiments, the functional protein or peptide to be delivered into a cell is a transcription factor, a tumor suppressor, a developmental regulator, a reprograming factor, a growth factor, a metastasis suppressor, a pro-apoptotic protein, a zinc-finger nuclease, transcription activator-like effector nuclease, Cas9 protein, or a recombinase. In some embodiments, the protein to be delivered is p53, Rb (retinoblastoma protein), BRCA1, BRCA2, PTEN, APC, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre, Dre, or FLP recombinase. In certain embodiments, the agent to be delivered is a small molecule. In some embodiments, the small molecule is an FDA-approved drug. In some embodiments, the agent to be delivered is a diagnostic agent. In some embodiments, the agent to be delivered is useful as an imaging agent. In some of these embodiments, the diagnostic or imaging agent is, and in others it is not, biologically active.

Animal: As used herein, the term "animal" refers to any member of the animal kingdom. In some embodiments, "animal" refers to humans of either sex at any stage of development. In some embodiments, "animal" refers to non-human animals at any stage of development. In certain embodiments, the non-human animal is a mammal (e.g., a rodent, a mouse, a rat, a rabbit, a monkey, a dog, a cat, a sheep, cattle, a primate, or a pig). In some embodiments, animals include, but are not limited to, mammals, birds, reptiles, amphibians, fish, and worms. In some embodiments, the animal is a transgenic animal, genetically-engineered animal, or a clone. In some embodiments, the animal is a transgenic non-human animal, genetically-engineered non-human animal, or a non-human clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Associated with: As used herein, the terms "associated with," "conjugated," "linked," "attached," and "tethered," when used with respect to two or more entities, for example, moieties, molecules, and/or ARMMs, means that the entities are physically associated or connected with one another, either directly or via one or more additional moieties that serve as a linker, to form a structure that is sufficiently stable so that the entities remain physically associated under the conditions in which the structure is used, e.g., physiological conditions.

An ARMM is typically associated with an agent, for example, a nucleic acid, protein, or small molecule, by a mechanism that involves a covalent or non-covalent association. In certain embodiments, the agent to be delivered is covalently bound to a molecule that is part of the ARMM, for example, an ARRCD1 protein or fragment thereof, a TSG101 protein or fragment thereof, or a lipid or protein that forms part of the lipid bilayer of the ARMM. In some embodiments, a peptide or protein is associated with an ARRCD1 protein or fragment thereof, a TSG101 protein or fragment thereof, or a lipid bilayer-associated protein by a covalent bond (e.g., an amide bond). In some embodiments, the association is via a linker, for example, a cleavable linker. In some embodiments, an entity is associated with an ARMM by inclusion in the ARMM, for example, by encapsulation of an entity (e.g., an agent) within the ARMM. For example, in some embodiments, an agent present in the cytoplasm of an ARMM-producing cell is associated with an ARMM by encapsulation of agent-comprising cytoplasm in the ARMM upon ARMM budding. Similarly, a membrane protein, or other molecule associated with the cell membrane of an ARMM producing cell may be associated with an ARMM produced by the cell by inclusion into the ARMM membrane upon budding. In certain embodiments, the agent to be delivered comprises a WW domain that effects binding to proline containing or proline rich domains in a molecule that is part of the ARMM.

Biologically active: As used herein, the phrase "biologically active" refers to a characteristic of any substance that has activity in a biological system and/or organism. For instance, a substance that, when administered to an organism, has a biological effect on that organism, is considered to be biologically active. In particular embodiments, where a nucleic acid is biologically active, a portion of that nucleic acid that shares at least one biological activity of the whole nucleic acid is typically referred to as a "biologically active" portion. As one example, a nuclease cargo protein may be considered biologically active if it increases or decreases the expression of a gene product when administered to a subject.

Biomarker: The term "biomarker", as used herein, in the context of ARMM-based diagnostics, refers to a detectable molecule (e.g., a protein, a peptide, a proteoglycan, a glycoprotein, a lipoprotein, a carbohydrate, a lipid, a nucleic acid (e.g., DNA, such as cDNA or amplified DNA, or RNA, such as mRNA), an organic or inorganic chemical compound, a small molecule (e.g., second messenger, a metabolite), or a discriminating molecule or discriminating fragment of any of the foregoing), that is present in or derived from a biological sample containing ARMMs, or any ratio of such molecules, or any other characteristic that is objectively measured and evaluated as an indicator of a specific biological feature or process, for example, of cell or vesicle identity, of a normal or a pathogenic processes, or a pharmacologic response to a therapeutic intervention, or an indication thereof. See Atkinson, A. J., et al., Biomarkers and Surrogate Endpoints: Preferred Definitions and Conceptual Framework, *Clinical Pharm. & Therapeutics,* 2001 March; 69(3): 89-95. In this context, the term "derived from" refers to a compound that, when detected, is indicative of a particular molecule being present in the biological sample. For example, detection of a particular cDNA can be indicative of the presence of a particular RNA transcript or protein in the biological sample. As another example, detection of or binding to a particular antibody can be indicative of the presence of a particular antigen (e.g., protein) in the biological sample. In some embodiments, a discriminating molecule or fragment is a molecule or fragment that, when detected, indicates presence or abundance of the compound of which its presence is indicative. A biomarker can, for example, be isolated from an ARMM, directly measured as part of an ARMM, or detected in or determined to be included in an ARMM. In some embodiments, the amount of ARMMs detected in a sample from a subject or in a cell population derived from a sample obtained from a subject, or the rate of ARMM generation within a sample or cell population obtained from a subject serves as a biomarker. Methods for the detection of biomarkers are known to those of skill in the art and include nucleic acid detection methods, protein detection methods, carbohydrate detection methods, antigen detection methods, small molecule detection methods, and other suitable methods.

Biomarker profile: A "biomarker profile" comprises one or more biomarkers (e.g., an mRNA molecule, a cDNA molecule, a protein, and/or a carbohydrate, or an indication thereof). The biomarkers of the biomarker profile can be in the same or different classes, such as, for example, a nucleic acid, a carbohydrate, a metabolite, and a protein. A biomarker profile may comprise at least 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or more biomarkers. In some embodiments, a biomarker profile comprises hundreds, or even thousands, of biomarkers. A biomarker profile can further comprise one or more controls or internal standards. In some embodiments, the biomarker profile comprises at least one biomarker that serves as an internal standard. In some embodiments, the presence or level of ARRDC1 or TSG101 in a sample or cell population is used as an internal standard. Biomarker profiles for several conditions, diseases, and pathologies, and also for normal states are known to those of skill in the art, and the invention is not limited to any particular biomarker profile. In some embodiments, the biomarker profile used in the context of ARMM-based diagnostic methods as described herein is a biomarker profile that has been described to be useful for exosome-based diagnostics. Exosomal biomarker profiles are known to those of skill in the art and biomarker profiles useful for the diagnosis of various disease, including different cancers, stroke, autism, and other diseases, have been described, for example, in U.S. patent application U.S. Ser. No. 13/009,285, filed on Jan. 19, 2011 (published as US 2011/0151460 A1) by Kaas et al., and entitled Methods And Systems Of Using Exosomes For Determining Phenotypes, the entire contents of which are incorporated herein by reference.

Cas9 or Cas9 Protein: The term "Cas9" or "Cas9 protein" refers to an RNA-guided nuclease comprising a Cas9 protein, or a variant thereof (e.g., a protein comprising an active, inactive, or altered DNA cleavage domain of Cas9, and/or the gRNA binding domain of Cas9). A Cas9 nuclease is also referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand not complementary to crRNA is first cut endonucleolytically, then trimmed 3'-5' exonucleolytically. In nature, DNA-binding and cleavage typically requires protein and both RNAs. However, single guide RNAs ("sgRNA", or simply "gNRA") can be engineered so as to incorporate aspects of both the crRNA and tracrRNA into a single RNA species. See, e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti et al., J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L., White J., Yuan X., Clifton S. W., Roe B. A., McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference). Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) *RNA Biology* 10:5, 726-737; the entire contents of which are incorporated herein by reference. In some embodiments, a Cas9 nuclease has an inactive (e.g., an inactivated) DNA cleavage domain.

A nuclease-inactivated Cas9 protein may interchangeably be referred to as a "dCas9" protein (for nuclease-"dead"

Cas9). Methods for generating a Cas9 protein (or a variant thereof) having an inactive DNA cleavage domain are known (See, e.g., Jinek et al., *Science*. 337:816-821(2012); Qi et al., "Repurposing CRISPR as an RNA-Guided Platform for Sequence-Specific Control of Gene Expression" (2013) Cell. 28; 152(5):1173-83, the entire contents of each of which are incorporated herein by reference). For example, the DNA cleavage domain of Cas9 is known to include two subdomains, the HNH nuclease subdomain and the RuvC1 subdomain. The HNH subdomain cleaves the strand complementary to the gRNA, whereas the RuvC1 subdomain cleaves the non-complementary strand. Mutations within these subdomains can silence the nuclease activity of Cas9. For example, the mutations D10A and H841A completely inactivate the nuclease activity of *S. pyogenes* Cas9 (Jinek et al., *Science*. 337:816-821(2012); Qi et al., Cell. 28; 152(5):1173-83 (2013). In some embodiments, proteins comprising variants of Cas9 are provided. For example, in some embodiments, a protein comprises one of two Cas9 domains: (1) the gRNA binding domain of Cas9; or (2) the DNA cleavage domain of Cas9. In some embodiments, proteins comprising Cas9 or variants thereof are referred to as "Cas9 variants." A Cas9 variant shares homology to Cas9, or a variant thereof. For example, a Cas9 variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to wild type Cas9. In some embodiments, the Cas9 variant comprises a variant of Cas9 (e.g., a gRNA binding domain or a DNA-cleavage domain), such that the variant is at least about 70% identical, at least about 80% identical, at least about 90% identical, at least about 95% identical, at least about 96% identical, at least about 97% identical, at least about 98% identical, at least about 99% identical, at least about 99.5% identical, or at least about 99.9% to the corresponding variant of wild type Cas9. In some embodiments, wild type Cas9 corresponds to Cas9 from *Streptococcus pyogenes* (NCBI Reference Sequence:

NC_017053.1, SEQ ID NO: 108(nucleotide); SEQ ID NO: 2 (amino acid)).

(SEQ ID NO: 1)

```
ATGGATAAGAAATACTCAATAGGCTTAGATATCGGCACAAATAGCGTCGGATGGGCGGTGATCACTGATGATTAT

AAGGTTCCGTCTAAAAAGTTCAAGGTTCTGGGAAATACAGACCGCCACAGTATCAAAAAAAATCTTATAGGGGCT

CTTTTATTTGGCAGTGGAGAGACAGCGGAAGCGACTCGTCTCAAACGGACAGCTCGTAGAAGGTATACACGTCGG

AAGAATCGTATTTGTTATCTACAGGAGATTTTTTCAAATGAGATGGCGAAAGTAGATGATAGTTTCTTTCATCGA

CTTGAAGAGTCTTTTTTGGTGGAAGAAGACAAGAAGCATGAACGTCATCCTATTTTTGGAAATATAGTAGATGAA

GTTGCTTATCATGAGAAATATCCAACTATCTATCATCTGCGAAAAAAATTGGCAGATTCTACTGATAAAGCGGAT

TTGCGCTTAATCTATTTGGCCTTAGCGCATATGATTAAGTTTCGTGGTCATTTTTTGATTGAGGGAGATTTAAAT

CCTGATAATAGTGATGTGGACAAACTATTTATCCAGTTGGTACAAATCTACAATCAATTATTTGAAGAAAACCCT

ATTAACGCAAGTAGAGTAGATGCTAAAGCGATTCTTTCTGCACGATTGAGTAAATCAAGACGATTAGAAAATCTC

ATTGCTCAGCTCCCCGGTGAGAAGAGAAATGGCTTGTTTGGGAATCTCATTGCTTTGTCATTGGGATTGACCCCT

AATTTTAAATCAAATTTTGATTTGGCAGAAGATGCTAAATTACAGCTTTCAAAAGATACTTACGATGATGATTTA

GATAATTTATTGGCGCAAATTGGAGATCAATATGCTGATTTGTTTTTGGCAGCTAAGAATTTATCAGATGCTATT

TTACTTTCAGATATCCTAAGAGTAAATAGTGAAATAACTAAGGCTCCCCTATCAGCTTCAATGATTAAGCGCTAC

GATGAACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATAAATTT

ATCAAACCAATTTTAGAAAAAATGGATGGTACTGAGGAATTATTGGTGAAACTAAATCGTGAAGATTTGCTGCGC

AAGCAACGGACCTTTGACAACGGCTCTATTCCCCATCAAATTCACTTGGGTGAGCTGCATGCTATTTTGAGAAGA

CAAGAAGACTTTTATCCATTTTTAAAAGACAATCGTGAGAAGATTGAAAAAATCTTGACTTTTCGAATTCCTTAT

TATGTTGGTCCATTGGCGCGTGGCAATAGTCGTTTTGCATGGATGACTCGGAAGTCTGAAGAAACAATTACCCCA

TGGAATTTTGAAGAAGTTGTCGATAAAGGTGCTTCAGCTCAATCATTTATTGAACGCATGACAAACTTTGATAAA

AATCTTCCAAATGAAAAAGTACTACCAAAACATAGTTTGCTTTATGAGTATTTTACGGTTTATAACGAATTGACA

AAGGTCAAATATGTTACTGAGGGAATGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGATTATTTCAAAAAAATAGAATGTTTT

GATAGTGTTGAAATTTCAGGAGTTGAAGATAGATTTAATGCTTCATTAGGCGCCTACCATGATTTGCTAAAAATT

ATTAAAGATAAAGATTTTTTGGATAATGAAGAAAATGAAGATATCTTAGAGGATATTGTTTTAACATTGACCTTA

TTTGAAGATAGGGGGATGATTGAGGAAAGACTTAAAACATATGCTCACCTCTTTGATGATAAGGTGATGAAACAG

CTTAAACGTCGCCGTTATACTGGTTGGGGACGTTTGTCTCGAAAATTGATTAATGGTATTAGGGATAAGCAATCT
```

-continued

GGCAAAACAATATTAGATTTTTTGAAATCAGATGGTTTTGCCAATCGCAATTTTATGCAGCTGATCCATGATGAT
AGTTTGACATTTAAAGAAGATATTCAAAAAGCACAGGTGTCTGGACAAGGCCATAGTTTACATGAACAGATTGCT
AACTTAGCTGGCAGTCCTGCTATTAAAAAAGGTATTTTACAGACTGTAAAAATTGTTGATGAACTGGTCAAAGTA
ATGGGGCATAAGCCAGAAAATATCGTTATTGAAATGGCACGTGAAAATCAGACAACTCAAAAGGGCCAGAAAAAT
TCGCGAGAGCGTATGAAACGAATCGAAGAAGGTATCAAAGAATTAGGAAGTCAGATTCTTAAAGAGCATCCTGTT
GAAAATACTCAATTGCAAAATGAAAAGCTCTATCTCTATTATCTACAAAATGGAAGAGACATGTATGTGGACCAA
GAATTAGATATTAATCGTTTAAGTGATTATGATGTCGATCACATTGTTCCACAAAGTTTCATTAAAGACGATTCA
ATAGACAATAAGGTACTAACGCGTTCTGATAAAAATCGTGGTAAATCGGATAACGTTCCAAGTGAAGAAGTAGTC
AAAAAGATGAAAAACTATTGGAGACAACTTCTAAACGCCAAGTTAATCACTCAACGTAAGTTTGATAATTTAACG
AAAGCTGAACGTGGAGGTTTGAGTGAACTTGATAAAGCTGGTTTTATCAAACGCCAATTGGTTGAAACTCGCCAA
ATCACTAAGCATGTGGCACAAATTTTGGATAGTCGCATGAATACTAAATACGATGAAAATGATAAACTTATTCGA
GAGGTTAAAGTGATTACCTTAAAATCTAAATTAGTTTCTGACTTCCGAAAAGATTTCCAATTCTATAAAGTACGT
GAGATTAACAATTACCATCATGCCCATGATGCGTATCTAAATGCCGTCGTTGGAACTGCTTTGATTAAGAAATAT
CCAAAACTTGAATCGGAGTTTGTCTATGGTGATTATAAAGTTTATGATGTTCGTAAAATGATTGCTAAGTCTGAG
CAAGAAATAGGCAAAGCAACCGCAAAATATTTCTTTTACTCTAATATCATGAACTTCTTCAAAACAGAAATTACA
CTTGCAAATGGAGAGATTCGCAAACGCCCTCTAATCGAAACTAATGGGGAAACTGGAGAAATTGTCTGGGATAAA
GGGCGAGATTTTGCCACAGTGCGCAAAGTATTGTCCATGCCCCAAGTCAATATTGTCAAGAAAACAGAAGTACAG
ACAGGCGGATTCTCCAAGGAGTCAATTTTACCAAAAAGAAATTCGGACAAGCTTATTGCTCGTAAAAAAGACTGG
GATCCAAAAAAATATGGTGGTTTTGATAGTCCAACGGTAGCTTATTCAGTCCTAGTGGTTGCTAAGGTGGAAAAA
GGGAAATCGAAGAAGTTAAAATCCGTTAAAGAGTTACTAGGGATCACAATTATGGAAAGAAGTTCCTTTGAAAAA
AATCCGATTGACTTTTTAGAAGCTAAAGGATATAAGGAAGTTAAAAAAGACTTAATCATTAAACTACCTAAATAT
AGTCTTTTTGAGTTAGAAAACGGTCGTAAACGGATGCTGGCTAGTGCCGGAGAATTACAAAAAGGAAATGAGCTG
GCTCTGCCAAGCAAATATGTGAATTTTTTATATTTAGCTAGTCATTATGAAAAGTTGAAGGGTAGTCCAGAAGAT
AACGAACAAAAACAATTGTTTGTGGAGCAGCATAAGCATTATTTAGATGAGATTATTGAGCAAATCAGTGAATTT
TCTAAGCGTGTTATTTTAGCAGATGCCAATTTAGATAAAGTTCTTAGTGCATATAACAAACATAGAGACAAACCA
ATACGTGAACAAGCAGAAAATATTATTCATTTATTTACGTTGACGAATCTTGGAGCTCCCGCTGCTTTTAAATAT
TTTGATACAACAATTGATCGTAAACGATATACGTCTACAAAAGAAGTTTTAGATGCCACTCTTATCCATCAATCC
ATCACTGGTCTTTATGAAACACGCATTGATTTGAGTCAGCTAGGAGGTGACTGA (SEQ ID NO: 2)

MDKKYSIGLDIGTNSVGWAVITDDYKVPSKKFKVLGNTDRHSIKKNLIGALLFGSGETAEATRLKRTARRRYTRR
KNRICYLQEIFSNEMAKVDDSFFHRLEESFLVEEDKKHERHPIFGNIVDEVAYHEKYPTIYHLRKKLADSTDKAD
LRLIYLALAHMIKFRGHFLIEGDLNPDNSDVDKLFIQLVQIYNQLFEENPINASRVDAKAILSARLSKSRRLENL
IAQLPGEKRNGLFGNLIALSLGLTPNFKSNFDLAEDAKLQLSKDTYDDDLDNLLAQIGDQYADLFLAAKNLSDAI
LLSDILRVNSEITKAPLSASMIKRYDEHHQDLTLLKALVRQQLPEKYKEIFFDQSKNGYAGYIDGGASQEEFYKF
IKPILEKMDGTEELLVKLNREDLLRKQRTFDNGSIPHQIHLGELHAILRRQEDFYPFLKDNREKIEKILTFRIPY
YVGPLARGNSRFAWMTRKSEETITPWNFEEVVDKGASAQSFIERMTNFDKNLPNEKVLPKHSLLYEYFTVYNELT
KVKYVTEGMRKPAFLSGEQKKAIVDLLFKTNRKVTVKQLKEDYFKKIECFDSVEISGVEDRFNASLGAYHDLLKI
IKDKDFLDNEENEDILEDIVLTLTLFEDRGMIEERLKTYAHLFDDKVMKQLKRRRYTGWGRLSRKLINGIRDKQS
GKTILDFLKSDGFANRNFMQLIHDDSLTFKEDIQKAQVSGQGHSLHEQIANLAGSPAIKKGILQTVKIVDELVKV
MGHKPENIVIEMARENQTTQKGQKNSRERMKRIEEGIKELGSQILKEHPVENTQLQNEKLYLYYLQNGRDMYVDQ
ELDINRLSDYDVDHIVPQSFIKDDSIDNKVLTRSDKNRGKSDNVPSEEVVKKMKNYWRQLLNAKLITQRKFDNLT

-continued

KAERGGLSELDKAGFIKRQLVETRQITKHVAQILDSRMNTKYDENDKLIREVKVITLKSKLVSDFRKDFQFYKVR

EINNYHHAHDAYLNAVVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESILPKRNSDKLIARKKDW

DPKKYGGFDSPTVAYSVLVVAKVEKGKSKKLKSVKELLGITIMERSSFEKNPIDFLEAKGYKEVKKDLIIKLPKY

SLFELENGRKRMLASAGELQKGNELALPSKYVNFLYLASHYEKLKGSPEDNEQKQLFVEQHKHYLDEIIEQISEF

SKRVILADANLDKVLSAYNKHRDKPIREQAENIIHLFTLTNLGAPAAFKYFDTTIDRKRYTSTKEVLDATLIHQS

ITGLYETRIDLSQLGGD
(single underline: HNH domain; double underline: RuvC domain)

In some embodiments, wild type (*S. pyogenes*) Cas9 corresponds to, or comprises SEQ ID NO: 3 (nucleotide) and/or SEQ ID NO: 4 (amino acid):

(SEQ ID NO: 3)
ATGGATAAAAAGTATTCTATTGGTTTAGACATCGGCACTAATTCCGTTGGATGGGCTGTCATAACCGATGAATAC

AAAGTACCTTCAAAGAAATTTAAGGTGTTGGGGAACACAGACCGTCATTCGATTAAAAAGAATCTTATCGGTGCC

CTCCTATTCGATAGTGGCGAAACGGCAGAGGCGACTCGCCTGAAACGAACCGCTCGGAGAAGGTATACACGTCGC

AAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAG

GTGGCATATCATGAAAAGTACCCAACGATTTATCACCTCAGAAAAAAGCTAGTTGACTCAACTGATAAAGCGGAC

CTGAGGTTAATCTACTTGGCTCTTGCCCATATGATAAAGTTCCGTGGGCACTTTCTCATTGAGGGTGATCTAAAT

CCGGACAACTCGGATGTCGACAAACTGTTCATCCAGTTAGTACAAACCTATAATCAGTTGTTTGAAGAGAACCCT

ATAAATGCAAGTGGCGTGGATGCGAAGGCTATTCTTAGCGCCCGCCTCTCTAAATCCCGACGGCTAGAAAACCTG

ATCGCACAATTACCCGGAGAGAAGAAAAATGGGTTGTTCGGTAACCTTATAGCGCTCTCACTAGGCCTGACACCA

AATTTTAAGTCGAACTTCGACTTAGCTGAAGATGCCAAATTGCAGCTTAGTAAGGACACGTACGATGACGATCTC

GACAATCTACTGGCACAAATTGGAGATCAGTATGCGGACTTATTTTTGGCTGCCAAAAACCTTAGCGATGCAATC

CTCCTATCTGACATACTGAGAGTTAATACTGAGATTACCAAGGCGCCGTTATCCGCTTCAATGATCAAAAGGTAC

GATGAACATCACCAAGACTTGACACTTCTCAAGGCCCTAGTCCGTCAGCAACTGCCTGAGAAATATAAGGAAATA

TTCTTTGATCAGTCGAAAAACGGGTACGCAGGTTATATTGACGGCGGAGCGAGTCAAGAGGAATTCTACAAGTTT

ATCAAACCCATATTAGAGAAGATGGATGGGACGGAAGAGTTGCTTGTAAAACTCAATCGCGAAGATCTACTGCGA

AAGCAGCGGACTTTCGACAACGGTAGCATTCCACATCAAATCCACTTAGGCGAATTGCATGCTATACTTAGAAGG

CAGGAGGATTTTTATCCGTTCCTCAAAGACAATCGTGAAAAGATTGAGAAAATCCTAACCTTTCGCATACCTTAC

TATGTGGGACCCCTGGCCCGAGGGAACTCTCGGTTCGCATGGATGACAAGAAAGTCCGAAGAAACGATTACTCCA

TGGAATTTTGAGGAAGTTGTCGATAAAGGTGCGTCAGCTCAATCGTTCATCGAGAGGATGACCAACTTTGACAAG

AATTTACCGAACGAAAAAGTATTGCCTAAGCACAGTTTACTTTACGAGTATTTCACAGTGTACAATGAACTCACG

AAAGTTAAGTATGTCACTGAGGGCATGCGTAAACCCGCCTTTCTAAGCGGAGAACAGAAGAAAGCAATAGTAGAT

CTGTTATTCAAGACCAACCGCAAAGTGACAGTTAAGCAATTGAAAGAGGACTACTTTAAGAAAATTGAATGCTTC

GATTCTGTCGAGATCTCCGGGGTAGAAGATCGATTTAATGCGTCACTTGGTACGTATCATGACCTCCTAAAGATA

ATTAAAGATAAGGACTTCCTGGATAACGAAGAGAATGAAGATATCTTAGAAGATATAGTGTTGACTCTTACCCTC

TTTGAAGATCGGGAAATGATTGAGGAAAGACTAAAAACATACGCTCACCTGTTCGACGATAAGGTTATGAAACAG

TTAAAGAGGCGTCGCTATACGGGCTGGGGACGATTGTCGCGGAAACTTATCAACGGGATAAGAGACAAGCAAAGT

GGTAAAACTATTCTCGATTTTCTAAAGAGCGACGGCTTCGCCAATAGGAACTTTATGCAGCTGATCCATGATGAC

TCTTTAACCTTCAAAGAGGATATACAAAAGGCACAGGTTTCCGGACAAGGGGACTCATTGCACGAACATATTGCG

-continued

AATCTTGCTGGTTCGCCAGCCATCAAAAAGGGCATACTCCAGACAGTCAAAGTAGTGGATGAGCTAGTTAAGGTC

ATGGGACGTCACAAACCGGAAAACATTGTAATCGAGATGGCACGCGAAAATCAAACGACTCAGAAGGGGCAAAAA

AACAGTCGAGAGCGGATGAAGAGAATAGAAGAGGGTATTAAAGAACTGGGCAGCCAGATCTTAAAGGAGCATCCT

GTGGAAAATACCCAATTGCAGAACGAGAAACTTTACCTCTATTACCTACAAAATGGAAGGGACATGTATGTTGAT

CAGGAACTGGACATAAACCGTTTATCTGATTACGACGTCGATCACATTGTACCCCAATCCTTTTTGAAGGACGAT

TCAATCGACAATAAAGTGCTTACACGCTCGGATAAGAACCGAGGGAAAAGTGACAATGTTCCAAGCGAGGAAGTC

GTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGC

CAAATCACAAAGCATGTTGCACAGATACTAGATTCCCGAATGAATACGAAATACGACGAGAACGATAAGCTGATT

CGGGAAGTCAAAGTAATCACTTTAAAGTCAAAATTGGTGTCGGACTTCAGAAAGGATTTTCAATTCTATAAAGTT

AGGGAGATAAATAACTACCACCATGCGCACGACGCTTATCTTAATGCCGTCGTAGGGACCGCACTCATTAAGAAA

TACCCGAAGCTAGAAAGTGAGTTTGTGTATGGTGATTACAAAGTTTATGACGTCCGTAAGATGATCGCGAAAAGC

GAACAGGAGATAGGCAAGGCTACAGCCAAATACTTCTTTTATTCTAACATTATGAATTTCTTTAAGACGGAAATC

ACTCTGGCAAACGGAGAGATACGCAAACGACCTTTAATTGAAACCAATGGGGAGACAGGTGAAATCGTATGGGAT

AAGGGCCGGGACTTCGCGACGGTGAGAAAAGTTTTGTCCATGCCCCAAGTCAACATAGTAAAGAAAACTGAGGTG

CAGACCGGAGGGTTTTCAAAGGAATCGATTCTTCCAAAAAGGAATAGTGATAAGCTCATCGCTCGTAAAAAGGAC

TGGGACCCGAAAAAGTACGGTGGCTTCGATAGCCCTACAGTTGCCTATTCTGTCCTAGTAGTGGCAAAAGTTGAG

AAGGGAAAATCCAAGAAACTGAAGTCAGTCAAAGAATTATTGGGGATAACGATTATGGAGCGCTCGTCTTTTGAA

AAGAACCCCATCGACTTCCTTGAGGCGAAAGGTTACAAGGAAGTAAAAAAGGATCTCATAATTAAACTACCAAAG

TATAGTCTGTTTGAGTTAGAAAATGGCCGAAAACGGATGTTGGCTAGCGCCGGAGAGCTTCAAAAGGGGAACGAA

CTCGCACTACCGTCTAAATACGTGAATTTCCTGTATTTAGCGTCCCATTACGAGAAGTTGAAAGGTTCACCTGAA

GATAACGAACAGAAGCAACTTTTTGTTGAGCAGCACAAACATTATCTCGACGAAATCATAGAGCAAATTTCGGAA

TTCAGTAAGAGAGTCATCCTAGCTGATGCCAATCTGGACAAAGTATTAAGCGCATACAACAAGCACAGGGATAAA

CCCATACGTGAGCAGGCGGAAAATATTATCCATTTGTTTACTCTTACCAACCTCGGCGCTCCAGCCGCATTCAAG

TATTTTGACACAACGATAGATCGCAAACGATACACTTCTACCAAGGAGGTGCTAGACGCGACACTGATTCACCAA

TCCATCACGGGATTATATGAAACTCGGATAGATTTGTCACAGCTTGGGGGTGACGGATCCCCCAAGAAGAAGAGG

AAAGTCTCGAGCGACTACAAAGACCATGACGGTGATTATAAAGATCATGACATCGATTACAAGGATGACGATGAC

AAGGCTGCAGGA (SEQ ID NO: 4)

MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDHIVPQSFLKDDSIDNKVLTRSDKNRGKSDNVPSEEVVKKMKNYWRQLLNAKLITQRKFDNL

-continued

```
TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
(single underline: HNH domain; double underline: RuvC domain)
```

In some embodiments, dCas9 corresponds to, or comprises in part or in whole, a Cas9 amino acid sequence having one or more mutations that inactivate the Cas9 nuclease activity. For example, in some embodiments, a dCas9 domain comprises D10A and/or H820A mutation.

```
dCas9 (D10A and H840A):
                                                              (SEQ ID NO: 5)
MDKKYSIGLAIGTNSVGWAVITDEYKVPSKKFKVLGNTDRHSIKKNLIGALLFDSGETAEATRLKRTARRRYTRR

KNRICYLQEIFSNEMAKVDDSFFHRLEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENPINASGVDAKAILSARLSKSRRLENL

IAQLPGEKKNGLFGNLIALSLGLTPNFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEIFFDQSKNGYAGYIDGGASQEEFYKF

IKPILEKMDGTEELLVKLNREDLLRKQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDKNLPNEKVLPKHSLLYEYFTVYNELT

KVKYVTEGMRKPAFLSGEQKKAIVDLLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQLKRRRYTGWGRLSRKLINGIRDKQS

GKTILDFLKSDGFANRNFMQLIHDDSLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHPVENTQLQNEKLYLYYLQNGRDMYVD

QELDINRLSDYDVDAIVPQSFLKDDSIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLIREVKVITLKSKLVSDFRKDFQFYKV

REINNYHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLIARKKD

WDPKKYGGFDSPTVAYSVLVVAKVEKGKSKKLKSVKELLGITIMERSSFEKNPIDFLEAKGYKEVKKDLIIKLPK

YSLFELENGRKRMLASAGELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRKRYTSTKEVLDATLIHQ

SITGLYETRIDLSQLGGD
(single underline: HNH domain; double underline: RuvC domain)
```

In other embodiments, dCas9 variants having mutations other than D10A and H820A are provided, which e.g., result in nuclease inactivated Cas9 (dCas9). Such mutations, by way of example, include other amino acid substitutions at D10 and H820, or other substitutions within the nuclease domains of Cas9 (e.g., substitutions in the HNH nuclease subdomain and/or the RuvC1 subdomain). In some embodiments, variants or homologues of dCas9 (e.g., variants of SEQ ID NO: 5) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:5. In some embodiments, variants of dCas9 (e.g., variants of SEQ ID NO: 5) are provided having amino acid sequences which are shorter, or longer than SEQ ID NO: 5, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more.

In some embodiments, Cas9 fusion proteins as provided herein comprise the full-length amino acid of a Cas9 protein, e.g., one of the sequences provided above. In other embodiments, however, fusion proteins as provided herein do not comprise a full-length Cas9 sequence, but only a fragment thereof. For example, in some embodiments, a Cas9 fusion protein provided herein comprises a Cas9 fragment, wherein the fragment binds crRNA and tracrRNA or sgRNA, but does not comprise a functional nuclease domain, e.g., in that it comprises only a truncated version of a nuclease domain or no nuclease domain at all. Exemplary amino acid sequences of suitable Cas9 domains and Cas9 fragments are provided herein, and additional suitable sequences of Cas9 domains and fragments will be apparent to those of skill in the art.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The teaching herein with respect to the delivery of Cas9 or Cas9-like molecules as the payload in the ARRMs comprising minimal-ARRDC1 is provided by way of a non-limiting example. Those skilled in art will recognize that the disclosure provides a means to load other payloads including but not limited to other targeted endonucleases, including other RNA guided DNA-nucleases such as are known in the art that are in need of intracellular delivery.

The term "deaminase" refers to an enzyme that catalyzes a deamination reaction. In some embodiments, the deaminase is a cytidine deaminase, catalyzing the hydrolytic deamination of cytosine to uracil.

Cargo protein: The term "cargo protein", as used herein, refers to a protein that may be incorporated in an ARMM, for example, into the liquid phase of the ARMM or into the lipid bilayer of an ARMM. The term "cargo protein to be delivered" refers to any protein that can be delivered via its association with or inclusion in an ARMM to a subject, organ, tissue, or cell. In some embodiments, the cargo protein is to be delivered to a target cell in vitro, in vivo, or ex vivo. In some embodiments, the cargo protein to be delivered is a biologically active agent, i.e., it has activity in a cell, organ, tissue, and/or subject. For instance, a protein that, when administered to a subject, has a biological effect on that subject, is considered to be biologically active. In certain embodiments the cargo protein is a nuclease, deaminase, recombinase, or variant thereof (e.g., a Cas9 protein or variant thereof). In certain embodiments, the nuclease may be a Cas9 nuclease, a TALE nuclease, a zinc finger nuclease, or any variant thereof. Nucleases, including Cas9 proteins and their variants, are described in more detail elsewhere herein. In some embodiments, the Cas9 protein or variant thereof is associated with a nucleic acid. For example, the cargo protein may be a Cas9 protein associated with a gRNA. In some embodiments, a cargo protein to be delivered is a therapeutic agent. As used herein, the term "therapeutic agent" refers to any agent that, when administered to a subject, has a beneficial effect. In some embodiments, the cargo protein to be delivered to a cell is a transcription factor, a tumor suppressor, a developmental regulator, a growth factor, a metastasis suppressor, a pro-apoptotic protein, a nuclease, a immunoglobulin or fragment thereof, a receptor, a T-cell receptor, a cytokine, an enzyme or a recombinase. In some embodiments, the protein to be delivered is p53, Rb (retinoblastoma protein), BRCA1, BRCA2, PTEN, APC, CD95, ST7, ST14, a BCL-2 family protein, a caspase, BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre recombinase, Dre recombinase, or FLP recombinase. In some embodiments, the cargo protein is associated with a small molecule. In some embodiments, the cargo protein to be delivered is a diagnostic agent. In some embodiments, the cargo protein to be delivered is a prophylactic agent. In some embodiments, the cargo protein to be delivered is useful as an imaging agent. In some of these embodiments, the diagnostic or imaging agent is, and in others it is not, biologically active.

Conserved: As used herein, the term "conserved" refers to nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. In some embodiments, two or more sequences are said to be "completely conserved" if they are 100% identical to one another. In some embodiments, two or more sequences are said to be "highly conserved" if they are at least 70% identical, at least 80% identical, at least 90% identical, or at least 95% identical to one another. In some embodiments, two or more sequences are said to be "highly conserved" if they are about 70% identical, about 80% identical, about 90% identical, about 95% identical, about 98% identical, or about 99% identical to one another. In some embodiments, two or more sequences are said to be "conserved" if they are at least 60% identical, at least 70% identical, at least 80% identical, at least 90% identical, or at least 95% identical to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

Engineered: The term "engineered," as used herein, refers to a protein, nucleic acid, complex, substance, or entity that has been designed, produced, prepared, synthesized, and/or manufactured by a human. Accordingly, an engineered product is a product that does not occur in nature. In some embodiments, an engineered protein or nucleic acid is a protein or nucleic acid that has been designed to meet particular requirements or to have particular design features. For example, a Cas9 cargo protein may be engineered to associate with the minimal ARRDC1 by fusing one or more WW domains to the Cas9 protein to facilitate loading of the Cas9 cargo protein into an ARMM. As another example, a guide RNA (gRNA) may be engineered to target the delivery of a Cas9 cargo protein to a specific genomic sequence.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

Functional: As used herein, a "functional" biological molecule is a biological molecule in a form in which it exhibits a property and/or activity by which it is characterized or useful.

Fusion protein: As used herein, a "fusion protein" includes a first protein moiety, e.g., an ARRCD1 protein or fragment thereof, or a TSG101 protein or fragment thereof, having a peptide linkage with a second protein moiety, for example, a protein to be delivered to a target cell. In certain embodiments, the fusion protein is encoded by a single fusion gene.

Gene: As used herein, the term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules, such as gRNAs, RNAi agents, ribozymes, tRNAs, rRNAs, etc. For the purpose of clarity, it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein-coding expression units but rather to clarify that, in most cases, the term as used herein refers to a protein-coding nucleic acid.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Green fluorescent protein: As used herein, the term "green fluorescent protein" (GFP) refers to a protein originally isolated from the jellyfish *Aequorea victoria* that fluoresces green when exposed to blue light or a derivative of such a protein (e.g., an enhanced or wavelength-shifted version of the protein). The amino acid sequence of wild type GFP is as follows:

```
                                        (SEQ ID NO: 35)
MSKGEELFTG VVPILVELDG DVNGHKFSVS GEGEGDATYG

KLTLKFICTT GKLPVPWPTL VTTFSYGVQC FSRYPDHMKQ

HDFFKSAMPE GYVQERTIFF KDDGNYKTRA EVKFEGDTLV

NRIELKGIDF KEDGNILGHK LEYNYNSHNV YIMADKQKNG

IKVNFKIRHN IEDGSVQLAD HYQQNTPIGD GPVLLPDNHY

LSTQSALSKD PNEKRDHMVL LEFVTAAGIT HGMDELYK
```

Proteins that are at least 70%, at least 75%, at least 80%, at least 85%, at least 90%, at least 95%, at least 98%, or at least 99% identical are also considered to be green fluorescent proteins.

Homology: As used herein, the term "homology" refers to the overall relatedness between polymeric molecules, e.g., between nucleic acid molecules (e.g. DNA molecules and/or RNA molecules) and/or between polypeptide molecules. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. In some embodiments, polymeric molecules are considered to be "homologous" to one another if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% similar. The term "homologous" necessarily refers to a comparison between at least two sequences (nucleotides sequences or amino acid sequences). In accordance with the invention, two nucleotide sequences are considered to be homologous if the polypeptides they encode are at least about 50% identical, at least about 60% identical, at least about 70% identical, at least about 80% identical, or at least about 90% identical for at least one stretch of at least about 20 amino acids. In some embodiments, homologous nucleotide sequences are characterized by the ability to encode a stretch of at least 4-5 uniquely specified amino acids. Both the identity and the approximate spacing of these amino acids relative to one another must be considered for nucleotide sequences to be considered homologous. For nucleotide sequences less than 60 nucleotides in length, homology is determined by the ability to encode a stretch of at least 4-5 uniquely specified amino acids. In accordance with the invention, two protein sequences are considered to be homologous if the proteins are at least about 50% identical, at least about 60% identical, at least about 70% identical, at least about 80% identical, or at least about 90% identical for at least one stretch of at least about 20 amino acids.

Identity: As used herein, the term "identity" refers to the overall relatedness between polymeric molecules, e.g., between nucleic acid molecules (e.g. DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using methods such as those described in Computational Molecular Biology, Lesk, A. M., ed., Oxford University Press, New York, 1988; Biocomputing: Informatics and Genome Projects, Smith, D. W., ed., Academic Press, New York, 1993; Sequence Analysis in Molecular Biology, von Heinje, G., Academic Press, 1987; Computer Analysis of Sequence Data, PART I, Griffin, A. M., and Griffin, H. G., eds., Humana Press, New Jersey, 1994; and SEQUENCE ANALYSIS PRIMER, Gribskov, M. and Devereux, J., eds., M Stockton Press, New York, 1991; each of which is incorporated herein by reference. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix. Methods commonly employed to determine percent identity between sequences include, but are not limited to those disclosed in Carillo, H., and Lipman, D., SIAM J Applied Math., 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984)), BLASTP, BLASTN, and FASTA Atschul, S. F. et al., *J. Molec. Biol.,* 215, 403 (1990)).

Inhibit expression of a gene: As used herein, the phrase "inhibit expression of a gene" means to cause a reduction in the amount of an expression product of the gene. The expression product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of gene expression may be determined using standard techniques for measuring mRNA and/or protein levels.

In vitro: As used herein, the term "in vitro" refers to events that occur in an artificial environment, e.g., in a test tube or reaction vessel, in cell culture, in a Petri dish, etc., rather than within an organism (e.g., animal, plant, or microbe).

In vivo: As used herein, the term "in vivo" refers to events that occur within an organism (e.g., animal, plant, or microbe).

Isolated: As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated substances are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

Linker: The term "linker," as used herein, refers to a chemical moiety linking two molecules or moieties, e.g., a minimal ARRDC1 protein and a target, such as a Cas9 nuclease. Typically, the linker is positioned between, or flanked by, two groups, molecules, or other moieties and connected to each one via a covalent bond, thus connecting the two. In some embodiments, the linker comprises an amino acid or a plurality of amino acids (e.g., a peptide or protein). In some embodiments, the linker is an organic molecule, group, polymer, or other chemical moiety. In some embodiments, the linker is a cleavable linker, e.g., the linker comprises a bond that can be cleaved upon exposure to, for example, UV light or a hydrolytic enzyme, such as a protease or esterase. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In other embodiments, the linker is a chemical bond (e.g., a covalent bond).

microRNA (miRNA): As used herein, the term "microRNA" or "miRNA" refers to an RNAi agent that is approximately 21 nucleotides (nt)-23 nt in length. miRNAs can range between 18 nt-26 nt in length. Typically, miRNAs are single-stranded. However, in some embodiments, miRNAs may be at least partially double-stranded. In certain embodiments, miRNAs may comprise an RNA duplex (referred to herein as a "duplex region") and may optionally further comprises one to three single-stranded overhangs. In some embodiments, an RNAi agent comprises a duplex region ranging from 15 bp to 29 bp in length and optionally further comprising one or two single-stranded overhangs. An miRNA may be formed from two RNA molecules that hybridize together, or may alternatively be generated from a single RNA molecule that includes a self-hybridizing portion. In general, free 5' ends of miRNA molecules have phosphate groups, and free 3' ends have hydroxyl groups. The duplex portion of an miRNA usually, but does not necessarily, comprise one or more bulges consisting of one or more unpaired nucleotides. One strand of an miRNA includes a portion that hybridizes with a target RNA. In certain embodiments, one strand of the miRNA is not precisely complementary with a region of the target RNA, meaning that the miRNA hybridizes to the target RNA with one or more mismatches. In some embodiments, one strand of the miRNA is precisely complementary with a region of the target RNA, meaning that the miRNA hybridizes to the target RNA with no mismatches. Typically, miRNAs are thought to mediate inhibition of gene expression by inhibiting translation of target transcripts. However, in some embodiments, miRNAs may mediate inhibition of gene expression by causing degradation of target transcripts.

The term "microvesicle," as used herein, refers to a droplet of liquid surrounded by a lipid bilayer. In some embodiments, a microvesicle has a diameter of about 10 nm to about 1000 nm. In some embodiments, a microvesicle has a diameter of at least about 10 nm, at least about 20 nm, at least about 30 nm, at least about 40 nm, at least about 50 nm, at least about 60 nm, at least about 70 nm, at least about 80 nm, at least about 90 nm, at least about 100 nm, at least about 125 nm, at least about 150 nm, at least about 175 nm, at least about 200 nm, at least about 250 nm, at least about 300 nm, at least about 400 nm, or at least about 500 nm. In some embodiments, a microvesicle has a diameter of less than about 1000 nm, less than about 900 nm, less than about 800 nm, less than about 700 nm, less than about 600 nm, lesson about 500 nm, less than about 400 nm, less than about 300 nm, less than about 250 nm, less than about 200 nm, lesson about 150 nm, less than about 100 nm, less than about 90 nm, less than about 80 nm, lesson about 70 nm, lesson about 60 nm, or less than about 50 nm. The term microvesicle includes microvesicle shed from cells as well as synthetically produced microvesicles. Microvesicles shed from cells typically comprise the antigenic content of the cells from which they originate. Microvesicles shed from cells also typically comprise an asymmetric distribution of phospholipids, reflecting the phospholipid distribution of the cells from which they originate. In some embodiments, the inner membrane of microvesicles provided herein, e.g., of some ARMMs, comprises the majority of aminophospholipids, phosphatidylserine, and/or phosphatidylethanolamine within the lipid bilayer.

Minimal ARRDC1: As used herein, the term "minimal ARRDC1" refers to a ARRDC1 protein that is shorter than the full-length ARRDC1 protein, and comprises, at least, a portion of an arrestin domain, at least one PSAP (SEQ ID NO: 122) or PTAP (SEQ ID NO: 123) motif, and at least one PPXY motif. An exemplary minimal ARRDC1 is provided in SEQ ID NO: 1.

```
                                        (SEQ ID NO: 1)
MGRVQLFEISLSHGRVVYSPGEPLAGTVRVRLGAPLPFRAIRVTCIGSC

GVSNKANDTAWVVEEGYFNSSLSLADKGSLPAGEHSFPFQFLLPATAPT

SFEGPFGKIVHQVRAAIHTPRFSKDHKCSLVFYILSPLNLNSIPDIEQP

NVASATKKFSYKLVKTGSVVLTASTDLRGYVVGQALQLHADVENQSGKD

TSPVVASLLQKVSYKAKRWIHDVRTIAEVEGAGVKAWRRAQWHEQILVP

ALPQSALPGCSLIHIDYYLQVSLKAPEATVTLPVFIGNIAVNHAPVSPR

PGLGLPPGAPPLVVPSAPPQEEAEPPEYPYEAPPSY.
```

Nucleic acid: As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably to refer to a polymer of nucleotides (e.g., a string of at least two nucleotides). In some embodiments, "nucleic acid" encompasses RNA as well as single and/or double-stranded DNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Protein: The term "protein" is used herein interchangeably with the terms polypeptide and peptide, and refers to a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., addition of a chemical entity such as a carbohydrate group, a phosphate group, a farnesyl group, an isofarnesyl group, a fatty acid group, an amide group, a terminal acetyl group, a linker for conjugation, functionalization, or other modification (e.g., alpha amidation), etc. In certain embodiments, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide. In certain embodiments, the modifications of the peptide lead to a more biologically active peptide. In some embodiments, polypeptides may comprise natural amino acids, non-natural amino acids, synthetic amino acids, amino acid analogs, and combinations thereof.

Recombinase: The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." Methods. 2011; 53(4):372-9; Hirano et al., "Site-specific recombinases as tools for heterologous gene integration." Appl. Microbiol. Biotechnol. 2011; 92(2):227-39; Chavez and Calos, "Therapeutic applications of the ΦC31 integrase system." Curr.

Gene Ther. 2011; 11(5):375-81; Turan and Bode, "Site-specific recombinases: from tag-and-target- to tag-and-exchange-based genomic modifications." FASEB J. 2011; 25(12):4088-107; Venken and Bellen, "Genome-wide manipulations of Drosophila melanogaster with transposons, Flp recombinase, and ΦC31 integrase." Methods Mol. Biol. 2012; 859:203-28; Murphy, "Phage recombinases and their applications." Adv. Virus Res. 2012; 83:367-414; Zhang et al., "Conditional gene manipulation: Cre-ating a new biological era." J. Zhejiang Univ. Sci. B. 2012; 13(7): 511-24; Karpenshif and Bernstein, "From yeast to mammals: recent advances in genetic control of homologous recombination." DNA Repair (Amst). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." J. Mol. Biol. 2004; 335, 667-678; Gordley et al., "Synthesis of programmable integrases." Proc. Natl. Acad. Sci. USA. 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, a recombinase (or catalytic domain thereof) is fused to a Cas9 protein (e.g., dCas9).

Recombine: The term "recombine" or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules.

Reprogramming factor: As used herein, the term "reprogramming factor" refers to a factor that, alone or in combination with other factors, can change the state of a cell from a somatic, differentiated state into a pluripotent stem cell state. Non-limiting examples of reprogramming factors include a protein (e.g., a transcription factor), a peptide, a nucleic acid, or a small molecule. Known reprogramming factors that are useful for cell reprogramming include, but are not limited to Oct4, Sox2, Klf4, and c-myc. Similarly, a programming factor may be used to modulate cell differentiation or de-differentiation, for example, to facilitate or induce cell differentiation towards a desired lineage.

RNA interference (RNAi): As used herein, the term "RNA interference" or "RNAi" refers to sequence-specific inhibition of gene expression and/or reduction in target RNA levels mediated by an RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression.

RNAi agent: As used herein, the term "RNAi agent" or "RNAi" refers to an RNA, optionally including one or more nucleotide analogs or modifications, having a structure characteristic of molecules that can mediate inhibition of gene expression through an RNAi mechanism. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include siRNA, shRNA, and/or miRNA. In some embodiments, RNAi agents may be composed entirely of natural RNA nucleotides (i.e., adenine, guanine, cytosine, and uracil). In some embodiments, RNAi agents may include one or more non-natural RNA nucleotides (e.g., nucleotide analogs, DNA nucleotides, etc.). Inclusion of non-natural RNA nucleic acid residues may be used to make the RNAi agent more resistant to cellular degradation than RNA. In some embodiments, the term "RNAi agent" may refer to any RNA, RNA derivative, and/or nucleic acid encoding an RNA that induces an RNAi effect (e.g., degradation of target RNA and/or inhibition of translation). In some embodiments, an RNAi agent may comprise a blunt-ended (i.e., without overhangs) dsRNA that can act as a Dicer substrate. For example, such an RNAi agent may comprise a blunt-ended dsRNA which is >25 base pairs length, which may optionally be chemically modified to abrogate an immune response.

RNAi-inducing agent: As used herein, the term "RNAi-inducing agent" encompasses any entity that delivers, regulates, and/or modifies the activity of an RNAi agent. In some embodiments, RNAi-inducing agents may include vectors (other than naturally occurring molecules not modified by the hand of man) whose presence within a cell results in RNAi and leads to reduced expression of a transcript to which the RNAi-inducing agent is targeted. In some embodiments, RNAi-inducing agents are RNAi-inducing vectors. In some embodiments, RNAi-inducing agents are compositions comprising RNAi agents and one or more pharmaceutically acceptable excipients and/or carriers. In some embodiments, an RNAi-inducing agent is an "RNAi-inducing vector," which refers to a vector whose presence within a cell results in production of one or more RNAs that self-hybridize or hybridize to each other to form an RNAi agent (e.g. siRNA, shRNA, and/or miRNA). In various embodiments, this term encompasses plasmids, e.g., DNA vectors (whose sequence may comprise sequence elements derived from a virus), or viruses (other than naturally occurring viruses or plasmids that have not been modified by the hand of man), whose presence within a cell results in production of one or more RNAs that self-hybridize or hybridize to each other to form an RNAi agent. In general, the vector comprises a nucleic acid operably linked to expression signal(s) so that one or more RNAs that hybridize or self-hybridize to form an RNAi agent are transcribed when the vector is present within a cell. Thus the vector provides a template for intracellular synthesis of the RNA or RNAs or precursors thereof. For purposes of inducing RNAi, presence of a viral genome in a cell (e.g., following fusion of the viral envelope with the cell membrane) is considered sufficient to constitute presence of the virus within the cell. In addition, for purposes of inducing RNAi, a vector is considered to be present within a cell if it is introduced into the cell, enters the cell, or is inherited from a parental cell, regardless of whether it is subsequently modified or processed within the cell. An RNAi-inducing vector is considered to be targeted to a transcript if presence of the vector within a cell results in production of one or more RNAs that hybridize to each other or self-hybridize to form an RNAi agent that is targeted to the transcript, i.e., if presence of the vector within a cell results in production of one or more RNAi agents targeted to the transcript.

RNA-programmable nuclease: The terms "RNA-programmable nuclease" and "RNA-guided nuclease" are used interchangeably herein and refer to a nuclease that forms a complex with (e.g., binds or associates with) one or more RNA molecule that is not a target for cleavage. In some embodiments, an RNA-programmable nuclease, when in a complex with an RNA, may be referred to as a nuclease: RNA complex. RNA-programmable nucleases include Cas9 nucleases. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as two or more molecules. Typically, gRNAs that exist as single RNA species comprise two domains: (1) a domain that shares homology to a target nucleic acid (e.g., and directs binding of a Cas9 complex to the target); and (2) a domain that binds an endonuclease enzyme (e.g., Cas9 protein). The gRNA comprises a nucleotide sequence that complements a target site, which mediates binding of the nuclease/RNA complex to said target site and providing the sequence specificity of the nuclease:RNA complex.

Short, interfering RNA (siRNA): As used herein, the term "short, interfering RNA" or "siRNA" refers to an RNAi agent comprising an RNA duplex (referred to herein as a "duplex region") that is approximately 19 base pairs (bp) in length and optionally further comprises one to three single-stranded overhangs. In some embodiments, an RNAi agent comprises a duplex region ranging from 15 bp to 29 bp in length and optionally further comprising one or two single-stranded overhangs. An siRNA may be formed from two RNA molecules that hybridize together, or may alternatively be generated from a single RNA molecule that includes a self-hybridizing portion. In general, free 5'-ends of siRNA molecules have phosphate groups, and free 3'-ends have hydroxyl groups. The duplex portion of an siRNA may, but typically does not, comprise one or more bulges consisting of one or more unpaired nucleotides. One strand of an siRNA includes a portion that hybridizes with a target transcript. In certain embodiments, one strand of the siRNA is precisely complementary with a region of the target transcript, meaning that the siRNA hybridizes to the target transcript without a single mismatch. In some embodiments, one or more mismatches between the siRNA and the targeted portion of the target transcript may exist. In some embodiments in which perfect complementarity is not achieved, any mismatches are generally located at or near the siRNA termini. In some embodiments, siRNAs mediate inhibition of gene expression by causing degradation of target transcripts.

Short hairpin RNA (shRNA): As used herein, the term "short hairpin RNA" or "shRNA" refers to an RNAi agent comprising an RNA having at least two complementary portions hybridized or capable of hybridizing to form a double-stranded (duplex) structure sufficiently long to mediate RNAi (typically at least approximately 19 bp in length), and at least one single-stranded portion, typically ranging between approximately 1 nucleotide (nt) and approximately 10 nt in length that forms a loop. In some embodiments, an shRNA comprises a duplex portion ranging from 15 bp to 29 bp in length and at least one single-stranded portion, typically ranging between approximately 1 nt and approximately 10 nt in length that forms a loop. The duplex portion may, but typically does not, comprise one or more bulges consisting of one or more unpaired nucleotides. In some embodiments, siRNAs mediate inhibition of gene expression by causing degradation of target transcripts. shRNAs are thought to be processed into siRNAs by the conserved cellular RNAi machinery. Thus, shRNAs may be precursors of siRNAs. Regardless, siRNAs in general are capable of inhibiting expression of a target RNA, similar to siRNAs.

Small molecule: In general, a "small molecule" refers to a substantially non-peptidic, non-oligomeric organic compound either prepared in the laboratory or found in nature. Small molecules, as used herein, can refer to compounds that are "natural product-like," however, the term "small molecule" is not limited to "natural product-like" compounds. Rather, a small molecule is typically characterized in that it contains several carbon-carbon bonds, and has a molecular weight of less than 2000 g/mol, less than 1500 g/mol, less than 1250 g/mol, less than 1000 g/mol, less than 750 g/mol, less than 500 g/mol, or less than 250 g/mol, although this characterization is not intended to be limiting for the purposes of the present invention. In certain other embodiments, natural-product-like small molecules are utilized.

Similarity: As used herein, the term "similarity" refers to the overall relatedness between polymeric molecules, e.g., between nucleic acid molecules (e.g. DNA molecules and/or RNA molecules) and/or between polypeptide molecules. Calculation of percent similarity of polymeric molecules to one another can be performed in the same manner as a calculation of percent identity, except that calculation of percent similarity takes into account conservative substitutions as is understood in the art.

Subject: As used herein, the term "subject" or "patient" refers to any organism to which a composition in accordance with the invention may be administered, e.g., for experimental, diagnostic, prophylactic, and/or therapeutic purposes. Typical subjects include animals (e.g., mammals, such as mice, rats, rabbits, non-human primates, and humans) and/or plants.

Therapeutically effective amount: As used herein, the term "therapeutically effective amount" means an amount of an agent to be delivered (e.g., nucleic acid, drug, therapeutic agent, diagnostic agent, prophylactic agent, etc.) that is sufficient, when administered to a subject suffering from or susceptible to a disease, disorder, and/or condition, to treat, improve symptoms of, diagnose, prevent, and/or delay the onset of the disease, disorder, and/or condition.

Transcription factor: As used herein, the term "transcription factor" refers to a DNA-binding protein that regulates transcription of DNA into RNA, for example, by activation or repression of transcription. Some transcription factors effect regulation of transcription alone, while others act in concert with other proteins. Some transcription factor can both activate and repress transcription under certain conditions. In general, transcription factors bind a specific target sequence or sequences highly similar to a specific consensus sequence in a regulatory region of a target gene. Transcription factors may regulate transcription of a target gene alone or in a complex with other molecules. Examples of transcription factors include, but are not limited to, Sp1, NF1, CCAAT, GATA, HNF, PIT-1, MyoD, Myf5, Hox, Winged Helix, SREBP, p53, CREB, AP-1, Mef2, STAT, R-SMAD, NF-κB, Notch, TUBBY, and NFAT.

Treating: As used herein, the term "treating" refers to partially or completely alleviating, ameliorating, improving, relieving, delaying onset of, inhibiting progression of, reducing severity of, and/or reducing incidence of one or more symptoms or features of a particular disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

Vector: As used herein, "vector" refers to a nucleic acid molecule which can transport another nucleic acid to which it has been linked. In some embodiment, vectors can achieve extra-chromosomal replication and/or expression of nucleic acids to which they are linked in a host cell such as a eukaryotic and/or prokaryotic cell. Vectors capable of directing the expression of operatively linked genes are referred to herein as "expression vectors."

WW Domain: The term "WW domain," as described herein, is a protein domain having two basic residues at the C-terminus that mediates protein-protein interactions with short proline-rich or proline-containing motifs. The WW domain possessing the two basic C-terminal amino acid residues may have the ability to associate with short proline-rich or proline-containing motifs (i.e., a PPXY motif). WW domains bind a variety of distinct peptide ligands including motifs with core proline-rich sequences, such as PPXY, which is found in AARDC1. A WW domain may be a 30-40 amino acid protein interaction domain with two signature tryptophan residues spaced by 20-22 amino acids. The three-dimensional structure of WW domains shows that they generally fold into a three-stranded, antiparallel β sheet with two ligand-binding grooves.

WW domains are found in many eukaryotes and are present in approximately 50 human proteins (Bork, P. & Sudol, M. The WW domain: a signaling site in dystrophin? Trends Biochem Sci 19, 531-533 (1994)). WW domains may be present together with several other interaction domains, including membrane targeting domains, such as C2 in the NEDD4 family proteins, the phosphotyrosine-binding (PTB) domain in FE65 protein, FF domains in CA150 and FBPII, and pleckstrin homology (PH) domains in PLEKHA5. WW domains are also linked to a variety of catalytic domains, including HECT E3 protein-ubiquitin ligase domains in NEDD4 family proteins, rotomerase or peptidyl prolyisomerase domains in Pinl, and Rho GAP domains in ArhGAP9 and ArhGAP12.

In the instant disclosure, the WW domain may be a WW domain that naturally possesses two basic amino acids at the C-terminus, for example a WW domain or WW domain variant may be from the human ubiquitin ligase WWP1, WWP2, Nedd4-1, Nedd4-2, Smurf1, Smurf2, ITCH, NEDL1, or NEDL2. Exemplary amino acid sequences of WW domain containing proteins (WW domains underlined) are listed below. It should be appreciated that any of the WW domains or WW domain variants of the exemplary proteins may be used in the invention, described herein, and are not meant to be limiting.

Human WWP1 amino acid sequence (uniprot.org/uniprot/Q9H0M0). The four underlined WW domains correspond to amino acids 349-382 (WW1), 381-414 (WW2), 456-489 (WW3), and 496-529 (WW4).

```
                                                  (SEQ ID NO: 6)
MATASPRSDT SNNHSGRLQL QVTVSSAKLK RKKNWFGTAI YTEVVVDGEI    50
TKTAKSSSSS NPKWDEQLTV NVTPQTTLEF QVWSHRTLKA DALLGKATID   100
LKQALLIHNR KLERVKEQLK LSLENKNGIA QTGELTVVLD GLVIEQENIT   150
NCSSSPTIEI QENGDALHEN GEPSARTTAR LAVEGTNGID NHVPTSTLVQ   200
NSCCSYWNGD DNTPSSPSQV AARPKNTPAP KPLASEPADD TVNGESSSFA   250
PTDNASVTGT PVVSEENALS PNCTSTTVED PPVQEILTSS ENNECIPSTS   300
ALLESEARSI LEPDISNSRS SSAFEAAKSR QPDGCMDPVR QQSGNANTET   350
LPSGWEQRKD PHGRTYYVDH NIRIILWERP QPLPPGWERR VDDRRRVYYV   400
DHNTRTTTWQ RPTMESVRNF EQWQSQRNQL QGAMQQFNQR YLYSASMLAA   450
ENDPYGPLPP GWEKRVDSTD RVYFVNHNTK TTQWEDPRTQ GLQNEEPLPE   500
GWEIRYIREG VRYFVDHNTR TTTFKDPRNG KSSVTKGGPQ IAYERGFRWK   550
LAHFRYLCOS NALPSHVRIN VSRQTLFEDS FQQIMALKPY DLRRRLYVIE   600
RGEEGLDYGG LAREWFFLLS HEVLNPMYCL FEYAGKNNYC LQINPASTIN   650
PDHLSYFCFI GRFIAMALFH GKFIDTGFSL PFYKRMLSKK LTIKDLESID   700
TEFYNSLIWI RDNNIEECGL EMYFSVDMEI LGKVTSHDLK LGGSNILVTE   750
ENKDEYIGLM TEWRFSRGVQ EQTKAFLDGF NEVVPLQWLQ YFDEKELEVM   800
LCGMQEVDLA DWQRNTVYRH YTRNSKQIIW FWQFVKETDN EVRMRLLQFV   850
TGTCRLPLGG FAELMGSNGP QKECIEKVGK DTWLPRSHTC FNRLDLPPYK   900
SYEQLKEKLL FAIEETEGFG QE                                 922
```

-continued

WW1 (349-382):

(SEQ ID NO: 36)

ETLPSGWEQRKDPHGRTYYVDHNTRTTTWERPQP.

WW2 (381-414):

(SEQ ID NO: 37)

QPLPPGWERRVDDRRRVYYVDHNTRTTTWQRPTM.

WW3 (456-489):

(SEQ ID NO: 38)

ENDPYGPLPPGWEKRVDSTDRVYFVNHNTKTTQWEDPRT.

WW4 (496-529):

EPLPEGWEIRYTREGVRYFVDHNTRTTTFKDPRN.

Human WWP2 amino acid sequence (uniprot.org/uniprot/O00308). The four underlined WW domains correspond to amino acids 300-333 (WW1), 330-363 (WW2), 405-437 (WW3), and 444-547 (WW4).

(SEQ ID NO: 7)

```
MASASSSRAG VALPFEKSQL TLKVVSAKPK VHNRQPRINS YVEVAVDGLP  50
SETKKTGKRI GSSELLWNEI IILNVTAQSH LDLKVWSCHT LRNELLGTAS 100
VNLSNVLKNN GGKMENMQLT LNLQTENKGS VVSGGELTIF LDGPTVDLGN 150
VPNGSALTDG SQLPSRDSSG TAVAPENRHQ PPSTNCFGGR SRTHRHSGAS 200
ARTTPATGEQ SPGARSRHRQ PVKNSGHSGL ANGTVNDEPT TATDPEEPSV 250
VGVTSPPAAP LSVTPNPNTT SLPAPATPAE GEEPSTSGTQ QLPAAAQAPD 300
ALPAGWEQRE LPNGRVYYVD ANTKTTTWER PLPPGWEKRT DPRGRFYYVD 350
HNTRTTTWQR PTAEYVRNYE QWQSQRNQLQ GAMQHFSQRF LYQSSSASTD 400
HDPLGPLPPG WEKRQDNGRV YYVNHNTRTT QWEDPRTQGM IQEPALPPGW 450
EMKYTSEGVR YFVDHNTRTT TFKDPRPGFE SGTKQGSPGA YDRSFRWKYH 500
QFRFLCHSNA LPSHVKISVS RQTLFEDSFQ QIMNMKPYDL RRRLYIIMRG 550
EEGLDYGGIA REWFFLLSHE VLNPMYCLFE YAGKNNYCLQ INPASSINPD 600
HLTYFRFIGR FIAMALYHGK FIDTGFTLPF YKRMLNKRPT LKDLESIDPE 650
FYNSIVWIKE NNLEECGLEL YFIQDMEILG KVTTHELKEG GESIRVTEEN 700
KEEYIMLLTD WRFTRGVEEQ TKAFLDGFNE VAPLEWLRYF DEKELELMLC 750
GMQEIDMSDW QKSTIYRHYT KNSKQIQWFW QVVKEMDNEK RIRLLQFVTG 800
TCRLPVGGFA ELIGSNGPQK FCIDKVGKET WLPRSHTCFN RLDLPPYKSY 850
EQLREKLLYA IEETEGFGQE                                 870
```

WW1 (300-333):

(SEQ ID NO: 40)

DALPAGWEQRELPNGRVYYVDHNTKTTTWERPLP.

WW2 (330-363):

(SEQ ID NO: 41)

PLPPGWEKRT DPRGRFYYVDHNTRTTTWQRPTA.

WW3 (405-437):

(SEQ ID NO: 42)

HDPLGPLPPGWEKRQDNGRVYYVNHNTRTTQWEDPRT

WW4 (444-477):

(SEQ ID NO: 43)

PALPPGWEMKYTSEGVRYFVDHNTRTTTFKDPRP.

Human Nedd4-1 amino acid sequence (uniprot.org/uniprot/P46934). The four underlined WW domains correspond to amino acids 610-643 (WW1), 767-800 (WW2), 840-873 (WW3), and 892-925 (WW4).

(SEQ ID NO: 8)

```
MAQSLRLHFA ARRSNTYPLS ETSGDDLDSH VHMCFKRPTR ISTSNVVQMK   50
LTPRQTALAP LIKENVQSQE RSSVPSSENV NKKSSCLQIS LQPTRYSGYL  100
QSSNVLADSD DASFTCILKD GIYSSAVVDN ELNAVNDGHL VSSPAICSGS  150
LSNFSTSDNG SYSSNGSDFG SCASITSGGS YTNSVISDSS SYTFPPSDDT  200
FLGGNLPSDS TSNRSVPNRN TTPCEIFSRS TSTDPFVQDD LEHGLEIMKL  250
PVSRNTKIPL KRYSSLVIFP RSPSTTRPTS PTSLCTLLSK GSYQTSHQFI  300
ISPSEIAHNE DGTSAKGFLS TAVNGLRLSK TICTPGEVRD IRPLHRKGSL  350
QKKIVLSNNT PRQTVCEKSS EGYSCVSVHF TQRKAATLDC ETTNGDCKPE  400
MSEIKLNSDS EYIKLMHRTS ACLPSSQNVD CQININGELE RPHSQMNKNH  450
GILRRSISLG GAYPNISCLS SLKHNCSKGG PSQLLIKFAS GNEGKVDNLS  500
RDSNRDCTNE LSNSCKTRDD FLGQVDVPLY PLPTENPRLE RPYTFKDFVL  550
HPRSHKSRVK GYLRLKMTYL PKTSGSEDDN AEQAEELEPG WVVLDQPDAA  600
CHLQQQQEPS PLPPGWEERQ DILGRTYYVN HESRRTQWKR PTPQDNLTDA  650
ENGNIQLQAQ RAFTTRRQIS EETESVDNRE SSENWEIIRE DEATMYSNQA  700
FPSPPPSSNL DVPTHLAEEI NARLTIFGNS AVSQPASSSN HSSRRGSLQA  750
YTFEEQPTLP VLLPTSSGLP PGWEEKQDER GRSYYVDHNS RTTTWTKPTV  800
QATVETSQLT SSQSSAGPQS QASTSDSGQQ VTQPSEIEQG FLPKGWEVRH  850
APNGRPFFID HNTKTTTWED PRLKIPAHLR GKTSLDTSND LGPLPPGWEE  900
RTHTDGRIFY INHNIKRTQW EDPRLENVAI TGPAVPYSRD YKRKYEFFRR  950
KLKKQNDIPN KFEMKLRRAT VLEDSYRRIM GVKRADFLKA RLWIEFDGEK 1000
GLDYGGVARE WFFLISKEMF NPYYGLFEYS ATDNYTLQIN PNSGLCNEDH 1050
LSYFKFIGRV AGMAVYHGKL LDGFFIRPFY KMMLHKPITL HDMESVDSEY 1100
YNSLRWILEN DPTELDLRFI IDEELFGQTH QHELKNGGSE IVVTNKNKKE 1150
YIYLVIQWRF VNRIQKQMAA FKEGFFELIP QDLIKIFDEN ELELLMCGLG 1200
DVDVNDWREH TKYKNGYSAN HQVIQWFWKA VLMMDSEKRI RLLQFVTGTS 1250
RVPMNGFAEL YGSNGPQSFT VEQWGTPEKL PRAHTCFNRL DLPPYESFEE 1300
LWDKLQMAIE NTQGFDGVD                                  1319
```

WW1 (610-643):

(SEQ ID NO: 44)

SPLPPGWEERQDILGRTYYVNHESRRTQWKRPTP.

WW2 (767-800):

(SEQ ID NO: 45)

SGLPPGWEEKQDERGRSYYVDHNSRTTTWTKPTV.

WW3 (840-873):

(SEQ ID NO: 46)

GFLPKGWEVRHAPNGRPFFIDHNTKTTTWEDPRL.

WW4 (892-925):

(SEQ ID NO: 47)

GPLPPGWEERTHTDGRIFYINHNIKRTQWEDPRL.

Human Nedd4-2 amino acid sequence (>gi|21361472|ref|NP_056092.2|E3 ubiquitin-protein ligase NEDD4-like isoform 3 [*Homo sapiens*]). The four underlined WW domains correspond to amino acids 198-224 (WW1), 368-396 (WW2), 480-510 (WW3), and 531-561 (WW4).

(SEQ ID NO: 9)

MATGLGEPVYGLSEDEGESRILRVKVVSGIDLAKKDIFGASDPYVKLSLY

VADENRELALVQTKTIKKTLNPKWNEEFYFRVNPSNHRLLFEVFDENRLT

RDDFLGQVDVPLSHLPTEDPTMERPYTFKDFLLRPRSHKSRVKGFLRLKM

AYMPKNGGQDEENSDQRDDMEHGWEVVDSNDSASQHQEELPPPPLPPGWE

EKVDNLGRTYYVNHNNRTTQWHRPSLMDVSSESDNNIRQINQEAAHRRFR

SRRHISEDLEPEPSEGGDVPEPWETISEEVNIAGDSLGLALPPPPASPGS

RTSPQELSEELSRRLQITPDSNGEQFSSLIQREPSSRLRSCSVTDAVAEQ

GHLPPPSVAYVHTTPGLPSGWEERKDAKGRTYYVNHNNRTTTWTRPIMQL

AEDGASGSATNSNNHLIEPQIRRPRSLSSPTVTLSAPLEGAKDSPVRRAV

KDTLSNPQSPQPSPYNSPKPQHKVTQSFLPPGWEMRIAPNGRPFFIDHNT

KTTTWEDPRLKFPVHMRSKTSLNPNDLGPLPPGWEERIHLDGRTFYIDHN

SKITQWEDPRLQNPAITGPAVPYSREFKQKYDYFRKKLKKPADIPNRFEM

KLHRNNIFEESYRRIMSVKRPDVLKARLWIEFESEKGLDYGGVAREWFFL

-continued

LSKEMFNPYYGLFEYSATDNYTLQINPNSGLCNEDHLSYFTFIGRVAGLA

VFHGKLLDGFFIRPFYKMMLGKQITLNDMESVDSEYYNSLKWILENDPTE

LDLMFCIDEENFGQTYQVDLKPNGSEIMVTNENKREYIDLVIQWRFVNRV

QKQMNAFLEGFTELLPIDLIKIFDENELELLMCGLGDVDVNDWRQHSIYK

NGYCPNHPVIQWFWKAVLLMDAEKRIRLLQFVTGTSRVPMNGFAELYGSN

GPQLFTIEQWGSPEKLPRAHTCFNRLDLPPYETFEDLREKLLMAVENAQG

FEGVD

WW1(198-224):

(SEQ ID NO: 61)

GWEEKVDNLGRTYYVNHNNRTTQWHRP.

WW2 (368 - 396):

(SEQ ID NO: 62)

PSGWEERKDAKGRTYYVNHNNRTTTWTRP.

WW3 (480-510):

(SEQ ID NO: 63)

PPGWEMRIAPNGRPFFIDHNTKTTTWEDPRL.

WW4 (531 -561):

(SEQ ID NO: 64)

PPGWEERIHLDGRTFYIDHNSKITQWEDPRL.

Human Smurf1 amino acid sequence (uniprot.org/uniprot/Q9HCE7). The two underlined WW domains correspond to amino acids 234-267 (WW1), and 306-339 (WW2).

(SEQ ID NO: 10)

```
MSNPGTRRNG SSIKIRLTVL CAKNLAKKDF FRLPDPFAKI VVDGSGQCHS   50
TDTVKNTLDP KWNQHYDLYV GKTDSITISV WNHKKIHKKQ GAGFLGCVRL  100
LSNAISRLKD TGYQRLDLCK LNPSDTDAVR GQIVVSLQTR DRIGTGGSVV  150
DCRGLLENEG TVYEDSGPGR PLSCFMEEPA PYTDSTGAAA GGGNCRFVES  200
PSQDQRLQAQ RLRNPDVRGS LQTPQNRPAG HQSPELPEGY EQRTTVQGQV  250
YFLHTQTGVS TWHDPRIPSP SGTIPGGDAA FLYEFLLQGH TSEPRDLNSV  300
NCDELGPLPP GWEVRSTVSG RIYFVDHNNR TTQFTDPRLH HIMNHQCQLK  350
EPSQPLPLPS EGSLEDEELP AQRYERDLVQ KLKVLRHELS LQQPQAGHCR  400
IEVSREEIFE ESYRQIMKMR PKDLKKRLMV KFRGEEGLDY GGVAREWLYL  450
LCHEMLNPYY GLFQYSTDNI YMLQINPDSS INPDHLSYFH FVGRIMGLAV  500
FHGHYINGGF TVPFYKQLLG KPIQLSDLES VDPELHKSLV WILENDITPV  550
LDHTFCVEHN AFGRILQHEL KPNGRNVPVT EENKKEYVRL YVNWRFMRGI  600
EAQFLALQKG FNELIPQHLL KPFDQKELEL IIGGLDKIDL NDWKSNTRLK  650
HCVADSNIVR WFWQAVETFD EERRARLLQF VIGSTRVPLQ GFKALQGSTG  700
AAGPRLFTIH LIDANTDNLP KAHTCFNRID IPPYESYEKL YEKLLTAVEE  750
TCGFAVE                                                 757
```

WW1 (234-267):

(SEQ ID NO: 48)

PELPEGYEQRTTVQGQVYFLHTQTGVSTWHDPRI

W2 (306-339):

(SEQ ID NO: 49)

GPLPPGWEVRSTVSGRIYFVDHNNRTTQFTDPRL.

Human Smurf2 amino acid sequence (uniprot.org/uniprot/Q9HAU4). The three underlined WW domains correspond to amino acids 157-190 (WW1), 251-284 (WW2), and 297-330 (WW3).

```
                                                    (SEQ ID NO: 11)
MSNPGGRRNG PVKLRLTVLC AKNLVKKDFF RLPDPFAKVV VDGSGQCHST     50

DTVKNTLDPK WNQHYDLYIG KSDSVTISVW NHKKIHKKQG AGFLGCVRLL    100

SNAINRLKDT GYQRLDLCKL GPNDNDTVRG QIVVSLQSRD RIGTGGQVVD    150

CSRLFDNDLP DGWEERRTAS GRIQYLNHIT RTTQWERPTR PASEYSSPGR    200

PLSCFVDENT PISGTNGATC GQSSDPRLAE RRVRSQRHRN YMSRTHLHTP    250

PDLPEGYEQR TTQQGQVYFL HTQTGVSTWH DPRVPRDLSN INCEELGPLP    300

PGWEIRNTAT GRVYFVDHNN RTTQFTDPRL SANLHLVLNR QNQLKDQQQQ    350

QVVSLCPDDT ECLTVPRYKR DLVQKLKILR QELSQQQPQA GHCRIEVSRE    400

EIFEESYRQV MKMRPKDLWK RLMIKFRGEE GLDYGGVARE WLYLLSHEML    450

NPYYGLFQYS RDDIYTLQIN PDSAVNPEHL SYFHFVGRIM GMAVFHGHYI    500

DGGFTLPFYK QLLGKSITLD DMELVDPDLH NSLVWILEND ITGVLDHTFC    550

VEHNAYGEII QHELKPNGKS IPVNEENKKE YVRLYVNWRF LRGIEAQFLA    600

LQKGFNEVIP QHLLKTFDEK ELELIICGLG KIDVNDWKVN TRLKHCTPDS    650

NIVKWFWKAV EFFDEERRAR LLQFVTGSSR VPLQGFKALQ GAAGPRLFTI    700

HQIDACTNNL PKAHTCFNRI DIPPYESYEK LYEKLLTAIE ETCGFAVE      748

WW1 (157-190):
                                                    (SEQ ID NO: 50)
NDLPDGWEERRTASGRIQYLNHITRTTQWERPTR.

W2 (251-284):
                                                    (SEQ ID NO: 51)
PDLPEGYEQRTTQQGQVYFLHTQTGVSTWHDPRV.

WW3 (297-330):
                                                    (SEQ ID NO: 52)
GPLPPGWEIRNTATGRVYFVDHNNRTTQFTDPRL.
```

Human ITCH amino acid sequence (uniprot.org/uniprot/Q96J02). The four underlined WW domains correspond to amino acids 326-359 (WW1), 358-391 (WW2), 438-471 (WW3), and 478-511 (WW4).

```
                                                    (SEQ ID NO: 12)
MSDSGSQLGS MGSLTMKSQL QITVISAKLK ENKKNWFGPS PYVEVTVDGQ     50

SKKTEKCNNT NSPKWKQPLT VIVTPVSKLH FRVWSHQTLK SDVLLGTAAL    100

DIYETLKSNN MKLEEVVVTL QLGGDKEPTE TIGDLSICLD GLQLESEVVT    150

NGETTCSENG VSLCLPRLEC NSAISAHCNL CLPGLSDSPI SASRVAGFTG    200

ASQNDDGSRS KDETRVSTNG SDDPEDAGAG ENRRVSGNNS PSLSNGGFKP    250

SRPPRPSRPP PPTPRRPASV NGSPSATSES DGSSTGSLPP TNTNTNTSEG    300

ATSGLIIPLT ISGGSGPRPL NPVTQAPLPP GWEQRVDQHG RVYYVDHVEK    350

RTTWDRPEPL PPGWERRVDN MGRIYYVDHF TRTTTWQRPT LESVRNYEQW    400

QLQRSQLQGA MQQFNQRFIY GNQDLFATSQ SKEFDPLGPL PPGWEKRTDS    450

NGRVYFVNHN TRITQWEDPR SQGQLNEKPL PEGWEMRFTV DGIPYFVDHN    500

RRTTTYIDPR TGKSALDNGP QIAYVRDFKA KVQYFRFWCQ QLAMPQHIKI    550

TVTRKTLFED SFQQIMSFSP QDLRRRLWVI FPGEEGLDYG GVAREWFFLL    600
```

-continued

```
SHEVLNPMYC LFEYAGKDNY CLQINPASYI NPDHLKYFRF IGRFIAMALF    650

HGKFIDTGFS LPFYKRILNK PVGLKDLESI DPEFYNSLIW VKENNIEECD    700

LEMYFSVDKE ILGEIKSHDL KPNGGNILVT EENKEEYIRM VAEWRLSRGV    750

EEQTQAFFEG FNEILPQQYL QYFDAKELEV LLCGMQEIDL NDWQRHAIYR    800

HYARTSKQIM WFWQFVKEID NEKRMRLLQF VTGTCRLPVG GFADLMGSNG    850

PQKFCIEKVG KENWLPRSHT CFNRLDLPPY KSYEQLKEKL LFAIEETEGF    900

GQE                                                       903
```

ITCH WW1 (326-359):

(SEQ ID NO: 53)

APLPPGWEQRVDQHGRVYYVDHVEKRTTWDRPEP

ITCH WW2 (358-391):

(SEQ ID NO: 54)

EPLPPGWERRVDNMGRIYYVDHFTRTTTWQRPTL.

ITCH WW3 (438-471):

(SEQ ID NO: 55)

GPLPPGWEKRTDSNGRVYFVNHNTRITQWEDPRS.

ITCH WW4 (478-511):

(SEQ ID NO: 56)

KPLPEGWEMRFTVDGIPYFVDHNRRTTTYIDPRT.

Human NEDL1 amino acid sequence (uniprot.org/uniprot/Q76N89). The two underlined WW domains correspond to amino acids 829-862 (WW1), and 1018-1051 (WW2).

(SEQ ID NO: 13)

```
MLLHLCSVKN LYQNRFLGLA AMASPSRNSQ SRRRCKEPER YSYNPDQFHN     50

MDLRGGPHDG VTIPRSTSDT DLVTSDSRST LMVSSSYYSI GHSQDLVIHW    100

DIKEEVDAGD WIGMYLIDEV LSENFLDYKN RGVNGSHRGQ IIWKIDASSY    150

FVEPETKICF KYYHGVSGAL RATTPSVTVK NSAAPIFKSI GADETVQGQG    200

SRRLISFSLS DFQAMGLKKG MFFNPDPYLK ISIQPGKHSI FPALPHHGQE    250

RRSKIIGNTV NPIWQAEQFS FVSLPTDVLE IEVKDKFAKS RPIIKRFLGK    300

LSMPVQRLLE RHAIGDRVVS YTLGRRLPTD HVSGQLQFRF EITSSIHPDD    350

EEISLSTEPE SAQIQDSPMN NLMESGSGEP RSEAPESSES WKPEQLGEGS    400

VPDGPGNQSI ELSRPAEEAA VITEAGDQGM VSVGPEGAGE LLAQVQKDIQ    450

PAPSAEELAE QLDLGEEASA LLLEDGEAPA STKEEPLEEE ATTQSRAGRE    500

EEEKEQEEEG DVSTLEQGEG RLQLRASVKR KSRPCSLPVS ELETVIASAC    590

GDPETPRTHY IRIHTLLHSM PSAQGGSAAE EEDGAEEEST LKDSSEKDGL    600

SEVDTVAADP SALEEDREEP EGATPGTAHP GHSGGHFPSL ANGAAQDGDT    650

HPSTGSESDS SPRQGGDHSC EGCDASCCSP SCYSSSCYST SCYSSSCYSA    700

SCYSPSCYNG NRFASHTRFS SVDSAKISES TVFSSQDDEE EENSAFESVP    750

DSMQSPELDP ESTNGAGPWQ DELAAPSGHV ERSPEGLESP VAGPSNRREG    800

ECPILHNSQP VSQLPSLRPE HHHYPTIDEP LPPNWEARID SHGRVFYVDH    850

VNRTTTWQRP TAAATPDGMR RSGSIQQMEQ LNRRYQNIQR TIATERSEED    900

SGSQSCEQAP AGGGGGGGSD SEAESSQSSL DLRREGSLSP VNSQKITLLL    950

QSPAVKFITN PEFFTVLHAN YSAYRVFTSS TCLKHMILKV RRDARNFERY   1000

QHNRDLVNFI NMFADTRLEL PRGWEIKTDQ QGKSFFVDHN SRATTFIDPR   1050
```

-continued

```
IPLQNGRLPN HLTHRQHLQR LRSYSAGEAS EVSRNRGASL LARPGHSLVA    1100

AIRSQHQHES LPLAYNDKIV AFLRQPNIFE MLQERQPSLA RNHTLREKIH    1150

YIRTEGNHGL EKLSCDADLV ILLSLFEEEI MSYVPLQAAF HPGYSFSPRC    1200

SPCSSPQNSP GLQRASARAP SPYRRDFEAK LRNFYRKLEA KGFGQGPGKI    1250

KLIIRRDHLL EGTFNQVMAY SRKELQRNKL YVTFVGEEGL DYSGPSREFF    1300

FLLSQELFNP YYGLFEYSAN DTYTVQISPM SAFVENHLEW FRFSGRILGL    1350

ALIHQYLLDA FFTRPFYKAL LRLPCDLSDL EYLDEEFHQS LQWMKDNNIT    1400

DILDLTFTVN EEVFGQVTER ELKSGGANTQ VTEKNKKEYI ERMVKWRVER    1450

GVVQQTEALV RGFYEVVDSR LVSVFDAREL ELVIAGTAEI DLNDWRNNTE    1500

YRGGYHDGHL VIRWFWAAVE RFNNEQRLRL LQFVTGTSSV PYEGFAALRG    1550

SNGLRRFCIE KWGKITSLPR AHTCFNRLDL PPYPSYSMLY EKLLTAVEET    1600

STFGLE                                                     1606

WW1 (829-862):
                                               (SEQ ID NO: 57)
PLPPNWEARIDSHGRVFYVDHVNRTTTWQRPTA.

WW2 (1018-1051):
                                               (SEQ ID NO: 58)
LELPRGWEIKTDQQGKSFFVDHNSRATTFIDPRI.
```

Human NEDL2 amino acid sequence (uniprot.org/uniprot/Q9P2P5). The two underlined WW domains correspond to amino acids 807-840 (WW1), and 985-1018 (WW2).

```
                                               (SEQ ID NO: 14)
MASSAREHLL FVRRRNPQMR YTLSPENLQS LAAQSSMPEN MTLQRANSDT      50

DLVTSESRSS LTASMYEYTL GQAQNLIIFW DIKEEVDPSD WIGLYHIDEN     100

SPANFWDSKN RGVTGTQKGQ IVWRIEPGPY FMEPEIKICF KYYHGISGAL     150

RATTPCITVK NPAVMMGAEG MEGGASGNLH SRKLVSFTLS DLRAVGLKKG     200

MFFNPDPYLK MSIQPGKKSS FPTCAHHGQE RRSTIISNTT NPIWHREKYS     250

FFALLTDVLE IEIKDKFAKS RPIIKRFLGK LTIPVQRLLE RQAIGDQMLS     300

YNLGRRLPAD HVSGYLQFKV EVTSSVHEDA SPEAVGTILG VNSVNGDLGS     350

PSDDEDMPGS HHDSQVCSNG PVSEDSAADG TPKHSFRTSS TLEIDTEELT     400

STSSRTSPPR GRQDSLNDYL DAIEHNGHSR PGTATCSERS MGASPKLRSS     450

FPTDTRLNAM LHIDSDEEDH EFQQDLGYPS SLEEEGGLIM FSRASRADDG     500

SLTSQTKLED NPVENEEAST HEAASFEDKP ENLPELAESS LPAGPAPEEG     550

EGGPEPQPSA DQGSAELCGS QEVDQPTSGA DTGTSDASGG SRRAVSETES     600

LDQGSEPSQV SSETEPSDPA RTESVSEAST RPEGESDLEC ADSSCNESVT     650

TQLSSVDTRC SSLESARFPE TPAFSSQEEE DGACAAEPTS SGPAEGSQES     700

VCTAGSLPVV QCPSGEDEGP GAESATVPDQ EELGEVWQRR GSLEGAAAAA     750

ESPPQEEGSA GEAQGTCEGA TAQEEGATGG SQANGHQPLR SLPSVRQDVS     800

RYQRVDEALP PNWEARIDSH GRIFYVDHVN RTTTWQRPTA PPAPQVLQRS     850

NSIQQMEQLN RRYQSIRRTM TNERPEENTN AIDGAGEEAD FHQASADFRR     900

ENILPHSTSR SRITLLLQSP PVKFLISPEF FTVLHSNPSA YRMFTNNTCL     950

KHMITKVRRD THHFERYQHN RDLVGFLNMF ANKQLELPRG WEMKHDHQGK    1000

AFFVDHNSRT TTFIDPRLPL QSSRPTSALV HRQHLTRQRS HSAGEVGEDS    1050
```

-continued

```
RHAGPPVLPR PSSTFNTVSR PQYQDMVPVA YNDKIVAFLR QPNIFEILQE    1100

RQPDLTRNHS LREKIQFIRT EGTPGLVRLS SDADLVMLLS LFEEEIMSYV    1150

PPHALLHPSY CQSPRGSPVS SPQNSPGTQR ANARAPAPYK RDFEAKLRNF    1200

YRKLETKGYG QGPGKLKLII RRDHLLEDAF NQIMGYSRKD LQRNKLYVTF    1250

VGEEGLDYSG PSREFFFLVS RELFNPYYGI FEYSANDTYT VQISPMSAFV    1300

DNHHEWFRFS GRILGLALIH QYLLDAFFTR PFYKALLRIL CDLSDLEYLD    1350

EEFHQSLQWM KDNDIHDILD LTFTVNEEVF GQITERELKP GGANIPVTEK    1400

NKKEYIERMV KWRIERGVVQ QTESLVRGFY EVVDARLVSV FDARELELVI    1450

AGTAEIDLSD WRNNTEYRGG YHDNHIVIRW FWAAVERFNN EQRLRLLQFV    1500

TGTSSIPYEG FASLRGSNGP RRFCVEKWGK ITALPRAHTC FNRLDLPPYP    1550

SFSMLYEKLL TAVEETSTFG LE                                  1572

WW1 (807-840):
                                              (SEQ ID NO: 59)
EALPPNWEARIDSHGRIFYVDHVNRTTTWQRPTA.

W2 (985-1018):
                                              (SEQ ID NO: 60)
LELPRGWEMKHDHQGKAFFVDHNSRTTTFIDPRL.
```

In some embodiments, the WW domain comprises a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In other embodiments, the WW domain consists of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In another embodiment, the WW domain consists essentially of a WW domain or WW domain variant from the amino acid sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). Consists essentially of means that a domain, peptide or polypeptide consists essentially of an amino acid sequence when such an amino acid sequence is present with only a few additional amino acid residues, for example, from about 1 to about 10 or so additional residues, typically from 1 to about 5 additional residues in the domain, peptide or polypeptide.

Alternatively, the WW domain may be a WW domain that has been modified to include two basic amino acids at the C-terminus of the domain. Techniques are known in the art and are described in the art, for example, in Sambrook et al. ((2001) *Molecular Cloning: a Laboratory Manual,* 3rd ed., Cold Spring Harbour Laboratory Press). Thus, a skilled person could readily modify an existing WW domain that does not normally have two C-terminal basic residues so as to include two basic residues at the C-terminus.

Basic amino acids are amino acids that possess a side-chain functional group that has a pKa of greater than 7 and include lysine, arginine, and histidine, as well as basic amino acids that are not included in the twenty α-amino acids commonly included in proteins. The two basic amino acids at the C-terminus of the WW domain may be the same basic amino acid or may be different basic amino acids. In one embodiment, the two basic amino acids are two arginines.

The term WW domain also includes variants of a WW domain provided that any such variant possesses two basic amino acids at its C-terminus and maintains the ability of the WW domain to associate with the PPXY motif. A variant of such a WW domain refers to a WW domain which retains the ability to associate with the PPXY motif (i.e., the PPXY motif of minimal ARRDC1) and that has been mutated at one or more amino acids, including point, insertion or deletion mutations, but still retains the ability to associate with the PPXY motif. A variant or derivative therefore includes deletions, including truncations and fragments; insertions and additions, for example, conservative substitutions, site-directed mutants and allelic variants; and modifications, including one or more non-amino acyl groups (e.g., sugar, lipid, etc.) covalently linked to the peptide and post-translational modifications. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing.

The WW domain may be part of a longer protein. Thus, the protein, in various different embodiments, comprises the WW domain, consists of the WW domain or consists essentially of the WW domain, as defined herein. The polypeptide may be a protein that includes a WW domain as a functional domain within the protein sequence. In some embodiments, the polypeptide is an endonuclease. In some embodiments, the endonuclease is Cas9 protein or a Cas9 protein variant. In other embodiments, the polypeptide comprises the sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), consists of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14), or consists essentially of (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14).

The term "target site," as used herein in the context of functional effector proteins that bind a nucleic acid molecule, such as nucleases, deaminases, and transcriptional activators or repressors, refers to a sequence within a nucleic acid molecule that is bound and acted upon by the effector protein, e.g., cleaved by the nuclease or transcriptionally activated or repressed by the transcriptional activator or repressor, respectively. A target site may be single-stranded or double-stranded. In the context of RNA-guided (e.g., RNA-programmable) nucleases (e.g., a protein dimer comprising a Cas9 gRNA binding domain and an active Cas9 DNA cleavage domain), a target site typically comprises a nucleotide sequence that is complementary to the gRNA of the RNA-programmable nuclease, and a protospacer adjacent motif (PAM) at the 3' end adjacent to the gRNA-complementary sequence. For the RNA-guided nuclease Cas9, the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW (SEQ ID NO: 121) and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [NZ]-[PAM], where each N is, independently, any nucleotide, and Z is an integer between 1 and 50, inclusive. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA, however because the DNA cleavage site is inactivated, the target site is not cleaved by the particular protein. However, such proteins as described herein are typically associated with another protein (e.g., a nuclease or transcription factor) or molecule that mediates cleavage of the nucleic acid molecule. In some embodiments, the sequence actually cleaved will depend on the protein (e.g., nuclease) or molecule that mediates cleavage of the nucleic acid molecule, and in some cases, for example, will relate to the proximity or distance from which the inactivated Cas9 protein(s) is/are bound.

DETAILED DESCRIPTION OF CERTAIN EMBODIMENTS OF THE INVENTION

The instant disclosure relates to the discovery that a minimal ARRDC1 protein can efficiently package cargos. Overexpression of a minimal ARRDC1 can produce larger amounts of functional ARRDC1 than overexpression of full length ARRDC1, while still achieving packaging of cargos into ARMMs. Minimal ARRDC1 constructs may reduce the volume of ARRDC1 in ARMMs, thus increasing the loading capacity of an ARMM. Reducing the size of the ARRDC1 required to achieve packaging of cargo also increases the practical limit of cargos that can be expressed with minimal ARRDC1 as a direct fusion or linked to the minimal ARRDC1 molecule post-translationally. Motifs in the minimal ARRDC1 protein yield efficient ARMM budding: the arrestin domain directs the protein to the plasma membrane; the tetrapeptide PSAP (SEQ ID NO: 122) or PTAP (SEQ ID NO: 123) interacts with and recruits TSG101 and ESCRT I complex proteins to the plasma membrane; and the PPXY motif(s) interact with the WW domains of NEDD4 E3 ligases to enhance ARMM budding (Nabhan et al., 2012).

Aspects of the present disclosure provide a minimal ARRDC1 that is shorter than the full-length ARRDC1 protein, yet maintains its same function with respect to microvesicle formation. In some embodiments, the minimal ARRDC1 comprises at least a portion of an arrestin domain, at least one PSAP (SEQ ID NO: 122) or PTAP (SEQ ID NO: 123) motif, and at least one PPXY motif, wherein the minimal ARRDC1 is shorter than the full-length ARRDC1 protein. A non-limiting example of a minimal ARRDC1 is provided in SEQ ID NO: 1.

(SEQ ID NO: 1)

MGRVQLFEISLSHGRVVYSPGEPLAGTVRVRLGAPLPFRAIRVTCIGSCG

VSNKANDTAWVVEEGYFNSSLSLADKGSLPAGEHSFPFQFLLPATAPTSF

EGPFGKIVHQVRAAIHTPRFSKDHKCSLVFYILSPLNLNSIPDIEQPNVA

SATKKFSYKLVKTGSVVLTASTDLRGYVVGQALQLHADVENQSGKDTSPV

VASLLQKVSYKAKRWIHDVRTIAEVEGAGVKAWRRAQWHEQILVPALPQS

ALPGCSLIHIDYYLQVSLKAPEATVTLPVFIGNIAVNHAPVSPRPGLGLP

PGAPPLVVPSAPPQEEAEPPEYPYEAPPSY.

Another non-limiting example of a minimal ARRDC1 is provided in SEQ ID NO: 125:

(SEQ ID NO: 125)

MGRVQLFEISLSHGRVVYSPGEPLAGTVRVRLGAPLPFRAIRVTCIGSCG

VSNKANDTAWVVEEGYFNSSLSLADKGSLPAGEHSFPFQFLLPATAPTSF

EGPFGKIVHQVRAAIHTPRFSKDHKCSLVFYILSPLNLNSIPDIEQPNVA

SATKKFSYKLVKTGSVVLTASTDLRGYVVGQALQLHADVENQSGKDTSPV

VASLLQKVSYKAKRWIHDVRTIAEVEGAGVKAWRRAQWHEQILVPALPQS

ALPGCSLIHIDYYLQVSLKAPEATVTLPVFIGNIAVNHAPVSPRPGLGLP

PGAPPLVVPTAPPQEEAEPPEYPYEAPPSY.

A non-limiting example of a nucleic acid sequence encoding a minimal ARRDC1 is provided in SEQ ID NO: 126:

(SEQ ID NO: 126)

Atggggcgagtgcagctcttcgagatcagcctgagccacggccgcgtcgt ctacagccccggggagccgttggctgggaccgtgcgcgtgcgcctgggg caccgctgccgttccgagccatccgggtgacctgcataggttcctgcggg -continued

```
gtctccaacaaggctaatgacacagcgtgggtagtggaggagggttactt
caacagttccctgtcgctggcagacaaggggagcctgcccgctggagagc
acagcttccccttccagttcctgcttcctgccactgcacccacgtccttt
gagggtcctttcgggaagatcgtgcaccaggtgagggccgccatccacac
gccacggttttccaaggatcacaagtgcagcctcgtgttctatatcttga
gccccttgaacctgaacagcatcccagacattgagcaacccaacgtggcc
tctgccaccaagaagttctcctacaagctggtgaagacgggcagcgtggt
cctcacagccagcactgatctccgcggctatgtggtggggcaggcactgc
agctgcatgccgacgttgagaaccagtcaggcaaggacaccagccctgtg
gtggccagtctgctgcagaaagtgtcctataaggccaagcgctggatcca
cgacgtacggaccattgcggaggtggagggtgcgggcgtcaaggcctggc
ggcgggcgcagtggcacgagcagatcctggtgcctgccttgccccagtcg
gccctgccgggctgcagcctcatccacatcgactactacttacaggtctc
tctgaaggcgccggaagctactgtgaccctcccggtcttcattggcaata
ttgctgtgaaccatgccccagtgagcccccggccaggcctggggctgcct
cctggggccccacccctggtggtgccttccgcaccaccccaggaggaggc
tgagccctatgaggccccaccgtcttat
```

A minimal ARRDC1 may comprise an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO: 1. In some embodiments, the minimal ARRDC1 comprises SEQ ID NO: 1. In some embodiments, the minimal ARRDC1 consists of SEQ ID NO: 1.

A minimal ARRDC1, as provided herein, may comprise any length amino acid sequence that is fewer amino acids than full-length ARRDC1. In some embodiments, the minimal ARRDC1 comprises between 100-400 amino acids. In some embodiments, the minimal ARRDC1 comprises between 100-350 amino acids, between 100-300 amino acids, between 100-250 amino acids, between 100-200 amino acids, or between 100-150 amino acids. In some embodiments, the minimal ARRDC1 comprises between 150-350 amino acids, between 200-350 amino acids, between 250-350 amino acids, or between 300-350 amino acids.

In some embodiments, the minimal ARRDC1 comprises up to 400 amino acids, up 375 amino acids, up to 350 amino acids, up to 325 amino acids, up to 300 amino acids, up to 275 amino acids, up to 250 amino acids, up to 225 amino acids, up to 200 amino acids, up to 200 amino acids, up to 175 amino acids, up to 150 amino acids, up to 125 amino acids, or up to 100 amino acids.

In some embodiments, the minimal ARRDC1 comprises about 400 amino acids, about 375 amino acids, about 350 amino acids, about 325 amino acids, about 300 amino acids, about 275 amino acids, about 250 amino acids, about 225 amino acids, about 200 amino acids, about 175 amino acids, about 150 amino acids, about 125 amino acids, or about 100 amino acids.

In some embodiments, the minimal ARRDC1 comprises at least a portion of an arrestin domain. In some embodiments, the portion of the arrestin domain comprises amino acids 1-308 of SEQ ID NO: 116.

Minimal ARRDC1 as provided herein may comprise any number of PSAP (SEQ ID NO: 122) motifs and/or PTAP (SEQ ID NO: 123) motifs. In some embodiments, the minimal ARRDC1 comprises at least one PSAP (SEQ ID NO: 122) motif or at least one PTAP (SEQ ID NO: 123) motif. In some embodiments, the minimal ARRDC1 comprises at least one PSAP (SEQ ID NO: 122) motif. In some embodiments, the minimal ARRDC1 comprises at least one PTAP (SEQ ID NO: 123) motif. In some embodiments, the minimal ARRDC1 comprises at least one PSAP (SEQ ID NO: 122) motif and at least one PTAP (SEQ ID NO: 123) motif.

Minimal ARRDC1 as provided herein may comprise any number of PPXY motifs. In some embodiments, the minimal ARRDC1 comprises at least one PPXY motif. In some embodiments, the minimal ARRDC1 comprises at least two PPXY motifs. In some embodiments, the minimal ARRDC1 comprises at least three PPXY motifs.

The minimal ARRDC1, in some embodiments, encompasses functional variants. A functional variant may contain one or more mutations outside the functional domain(s) of the minimal ARRDC1, for example, a mutation outside the arrestin domain, or a mutation within the arrestin domain which does not affect its function. Mutations outside the functional domain(s) would not be expected to affect the biological activity of the protein. For example, mutation outside the functional domain would not be expected to substantially affect the formation or budding of microvesicles. In some embodiments, a functional variant may comprise an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identity to SEQ ID NO: 1.

Alternatively or in addition, the functional mutation may contain a conservative at mutation(s) at one or more positions in the minimal ARRDC1. For example, the fictional variant may contain a conservative mutation at up to 20 positions, up to 15 positions, up to 10 positions, up to 5 positions, up to 4 positions, up to 3 positions, up to 2 positions, or only at 1 position.

Microvesicles with WW-Domain-Containing-Cargos

Some aspects of this invention provide arrestin domain-containing protein 1 (ARRDC1)-mediated microvesicles (ARMMs) containing a cargo that is fused to a WW domain. Such ARMMs typically include a lipid bilayer and a minimal ARRDC1 protein or variant thereof. In some embodiments, the cargo is fused to a WW domain that associates with the PPXY (where x is any amino acid) domain of minimal ARRDC1 which may facilitate loading of the cargo into an ARMM. In some embodiments, the cargo is a protein, nucleic acid, or small molecule. In some embodiments, the cargo is a Cas9 protein or Cas9 variant. In some embodiments the Cas9 protein or variant is a fusion protein. For example, the Cas9 protein or Cas9 variant may be fused to one or more WW domains to facilitate loading into an ARMM. In some embodiments, the Cas9 fusion protein or Cas9 variant is fused to one or more nuclear localization sequences (NLSs) to facilitate translocation of the Cas9 fusion protein into the nucleus of a target cell. In certain embodiments the Cas9 variant is a Cas9 protein or Cas9 protein variant comprising an active or inactive DNA cleavage domain of Cas9 or a partially inactive DNA cleavage domain (e.g., a Cas9 “nickase”), and/or the gRNA binding domain of Cas9. It should be appreciated that any number of proteins, nucleic acids, or small molecules known in the art can be fused to one or more WW domains to generate a cargo that can be loaded into an ARMM, for example, a reprogramming factor (e.g., Oct4, Sox2, c-Myc, or KLF4) may be fused to one or more WW domains to facilitate loading of one or more reprogramming factors into an ARMM. In some embodiments, the cargo protein is a therapeutic protein (e.g., a transcription factor, a tumor suppressor, a developmental regulator, a growth factor, a metastasis suppressor, a pro-apoptotic protein, a zinc finger nuclease, or a recombinase) that is fused to one or more WW domains. In other embodiments, an ARMM further includes a non-cargo protein, such as a TSG101 protein or variant thereof to facilitate the release of ARMMs. The TSG101 protein interacts with ARRDC1, which results in relocation of TSG101 from endosomes to the plasma membrane and mediates the release of microvesicles that contain TSG101, ARRDC1, and other cellular components, including, for example, cargo proteins, nucleic acids (i.e., gRNAs), and small molecules.

In some embodiments, microvesicle, e.g., ARMMs, are provided that comprise a minimal ARRDC1 protein fragment, and/or a TSG101 protein fragment. In some embodiments, fusion proteins are provided that comprise a minimal ARRDC1 protein fragment and/or a TSG101 protein fragment. In some embodiments, expression constructs are provided that encode a minimal ARRDC1 protein fragment and/or a TSG101 protein fragment. In some embodiments, the minimal ARRDC1 protein fragment is a C-terminal minimal ARRDC1 protein fragment. In some embodiments, the ARRDC1 protein fragment comprises the PSAP (SEQ ID NO: 122) motif and at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the minimal ARRCD1 sequence. In some embodiments, the TSG101 protein fragment comprises a TSG101 UEV domain. In some embodiments, the TSG101 protein fragment comprises the UEV domain and comprises at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

In some embodiments, the inventive microvesicles, e.g., ARMMs comprising a minimal ARRDC1, further comprise a cell surface protein, for example, an integrin, a receptor tyrosine kinase, a G-protein coupled receptor, or a membrane-bound immunoglobulin. Other cell surface proteins may also be included in an ARMM. Integrins, receptor tyrosine kinases, G-protein coupled receptors, and a membrane-bound immunoglobulins suitable for use with embodiments of this invention will be apparent to those of skill in the art and the invention is not limited in this respect. For example, in some embodiments, the integrin is an all, α2β1, α4β1, α5β1, α6β1, αLβ2, αMβ2, αIIbβ, αVβ3, αVβ5, αVβ6, or α6β4 integrin. In some embodiments, the receptor tyrosine kinase is a an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, or MuSK receptor. In some embodiments, the G-protein coupled receptor is a rhodopsin-like receptor, the secretin receptor, metabotropic glutamate/pheromone receptor, cyclic AMP receptor, frizzled/smoothened receptor, CXCR4 receptor, CCR5 receptor, or beta-adrenergic receptor.

Some aspects of this invention relate to the recognition that ARMMs are taken up by target cells, and ARMM uptake results in the release of the contents of the ARMM into the cytoplasm of the target cells. Some aspects of this invention relate to the recognition that this can be used to deliver an agent in ARMMs to the target cell or a population of target cells, for example, by contacting the target cell with ARMMs comprising the agent to be delivered. Accordingly, some aspects of this invention provide ARMMs that comprise an agent, for example, a recombinant nucleic acid, a recombinant protein, or a synthetic small molecule.

In some embodiments, the agent is an agent that effects a desired change in the target cell, for example, a change in cell survival, proliferation rate, a change in differentiation stage, a change in a cell identity, a change in chromatin state, a change in the transcription rate of one or more genes, a change in the transcriptional profile, or a post-transcriptional change in gene compression of the target cell. It will be understood by those of skill in the art, that the agent to be delivered will be chosen according to the desired effect in the target cell. For example, to effect a change in the differentiation stage of a target cell, for example, to reprogram a differentiated target cell into an embryonic stem cell-like stage, the cell is contacted, in some embodiments, with ARMMs with reprogramming factors, for example, Oct4, Sox2, c-Myc, and/or KLF4. Similarly, to effect the change in the chromatin state of a target cell, the cell is contacted, in some embodiments, with ARMMs containing a chromatin modulator, for example, a DNA methyltransferase or a histone deacetylase. For another example, if survival of the target cell is to be diminished, the target cell, in some embodiments, is contacted with ARMMs comprising a cytotoxic agent, for example, a chemotherapeutic drug. Additional agents suitable for inclusion into ARMMs and for a ARMM-mediated delivery to a target cell or target cell population will be apparent to those skilled in the art, and the invention is not limited in this respect.

In some embodiments, the agent is included in the ARMMs by contacting cells producing the ARMMs with the agent. For example, if the agent is a small molecule, for example a therapeutic drug to be delivered to a target cell population within the body of a subject, ARMMs containing the drug are produced by contacting cells expressing minimal ARRDC1 with the drug in an amount and for a time sufficient to generate ARMMs containing the drug. For another example, if the agent is a nucleic acid or a protein, ARMMs containing nucleic acid or the protein are produced by expressing the nucleic acid or the protein in cells expressing minimal ARRDC1 and TSG101, for example, from a recombinant expression construct.

In some embodiments, the agent is conjugated to the minimal ARRDC1 protein, the minimal ARRDC1 fragment, the TSG101 protein, or the TSG101 fragment. In some embodiments, where the agent is a protein, the protein may be conjugated to the ARRDC protein, the minimal ARRDC1 fragment, the TSG101 protein, or the TSG101 fragment, by expressing the protein agent as a fusion with the ARRDC1 protein, the ARRDC1 fragment, the TSG101 protein, or the TSG101 fragment.

In some embodiments, ARMMs comprising a minimal ARRDC1 are provided that include a recombinant or a synthetic nucleic acid. Such ARMMs can be used to deliver the recombinant or synthetic nucleic acids to a target cell or target cell population. In some embodiments, the recombinant nucleic acid comprises an RNA, for example, an RNA encoding a protein (e.g., an mRNA), or a non-coding RNA. In some embodiments, the nucleic acid comprises an RNAi agent, for example, an antisense RNA, a small interfering RNA (siRNA), a small hairpin RNA (shRNA), a microRNA (miRNA), a small nuclear RNA (snRNA), a small nucleolar RNA (snoRNA), or a long intergenic non-coding RNA (lincRNA), or a precursor thereof. Some embodiments, ARMMs are provided that include a recombinant structural RNA, a ribozyme, or a precursor thereof.

Coding RNAs, RNAi agents, structural RNAs, and ribozymes, as well as precursors thereof, are well known to those skilled in the art and suitable RNAs and RNAi agents according to aspects of this invention will be apparent to the skilled artisan. It will be appreciated that the invention is not limited in this respect. ARMMs including RNA can be used to express the RNA function in a target cell without the need for genetic manipulation of the target cell. For example, ARMMs including protein-encoding nucleic acids can be used to express the encoded protein in a target cell or cell population upon ARMMs uptake without the need to genetically manipulate the target cell or cell population. For another example, ARMMs including an RNAi agent can be used to knock down a gene of interest in the target cell or the target cell population without the need to genetically amended claims department cell or cell population. For a third example, ARMMs including a ribozyme can be used to modulate the expression of a target nucleic acid, or to edit a target mRNA and a target cell without the need for genetic manipulation.

In some embodiments, ARMMs comprising a minimal ARRDC1 are provided that include a DNA, for example, a vector including an expression construct, a LINE sequence, a SINE sequence, a composite SINE sequence, or an LTR-retrotransposon sequence. ARMMs containing DNA allow for the transfer of genes or DNA elements from cell to cell, or, in some embodiments, for the targeted insertion of genes or DNA elements into a target cell or target cell type, for example a pathological target cell type in a subject. In some embodiments, ARMMs are provided that include a DNA encoding a protein. In some embodiments, ARMMs are provided that include a DNA encoding a non-coding RNA, for example, an antisense RNA, a small interfering RNA (siRNA), a small hairpin RNA (shRNA), a microRNA (miRNA), a small nuclear RNA (snRNA), a small nucleolar RNA (snoRNA), or a long intergenic non-coding RNA (lincRNA), or a precursor thereof. In some embodiments, the use of ARMMs containing a DNA has the advantage that a higher level of expression or a more sustained expression of the encoded protein or RNA can be achieved in a target cell as compared to direct delivery of the protein or RNA. In some embodiments, the DNA included in the ARMMs comprises a cell type specific promoter controlling the conscription of the encoded protein or RNA. The use of a cell type specific promoter allows for the targeted expression of the proteins were RNA encoded by the ARMM-delivered DNA, which can be used, for example in some therapeutic embodiments, to minimize the effect on subpopulations that are not targeted but may take up ARMMs.

In some embodiments, ARMMs comprising a minimal ARRDC1 are provided that include a detectable label. Such ARMMs allow for the labeling of a target cell without genetic manipulation. Detectable labels suitable for direct delivery to target cells are known in the art, and include, but are not limited to, fluorescent proteins, fluorescent dyes, membrane-bound dyes, and enzymes, for example, membrane-bound enzymes, catalyzing the reaction resulting in a detectable reaction product. Detectable labels suitable according to some aspects of this invention further include membrane-bound antigens, for example, membrane-bound ligands that can be detected with commonly available antibodies or antigen binding agents.

In some embodiments, ARMMs are provided that comprise a therapeutic agent. It will be appreciated, that any therapeutic agent that can be introduced into a cell shedding ARMMs or that can be packaged into synthetic ARMMs is suitable for inclusion into ARMMs according to some aspects of this invention. Suitable therapeutic agents include, but are not limited to, small organic molecules, also referred to as small molecules, or small compounds, and biologics, for example, therapeutic proteins, or protein fragments. Some non-limiting examples of therapeutic agents suitable for inclusion in ARMMs include antibacterial agents, antifungal antibiotics, antimyobacterials, neuraminidase inhibitors, antineoplastic agents, cytotoxic agents, cholinergic agents, parasympathomimetics, anticholinergic agents, antidepressants, antipsychotics, respiratory and cerebral stimulants, proton pump inhibitors, hormones and synthetic substitutes, receptor ligands, kinase inhibitors, chemotherapeutic agents, signaling molecules, kinases, phosphatases, proteases, RNA editing enzymes, nucleases, and zinc finger proteins.

In some embodiments, ARMMs are provided that comprise a protein to be delivered to a target cell. In some embodiments, the protein is or comprises a transcription factor, a transcriptional repressor, a fluorescent protein, a kinase, a phosphatase, a protease, a ligase, a chromatin modulator, or a recombinase. In some embodiments, the protein is a therapeutic protein. In some embodiments the protein is a protein that effects a change in the state or identity of a target cell. For example, in some embodiments, the protein is a reprogramming factor. Suitable transcription factors, transcriptional repressors, fluorescent proteins, kinases, phosphatases, proteases, ligases, chromatin modulators, recombinases, and reprogramming factors are known to those skilled in the art, and the invention is not limited in this respect.

In some embodiments, ARMMs are provided that comprise an agent, for example, a small molecule, a nucleic acid, or a protein, that is covalently or non-covalently bound, or conjugated, to a minimal ARRDC1 protein or fragment thereof, or a TSG101 protein or fragment thereof. In some embodiments, agent is conjugated to the minimal ARRDC1 protein or fragment thereof, or the TSG101 protein or fragment thereof, via a linker. The linker may be cleavable or uncleavable. In some embodiments, the linker comprises an amide, ester, ether, carbon-carbon, or disulfide bond, although any covalent bond in the chemical art may be used. In some embodiments, the linker comprises a labile bond, cleavage of which results in separation of the supercharged protein from the peptide or protein to be delivered. In some embodiments, the linker is cleaved under conditions found in the target cell (e.g., a specific pH, a reductive environment, or the presence of a cellular enzyme). In some embodiments, the linker is cleaved by an enzyme, for example, a cellular enzyme. In some embodiments, the enzyme is a cellular protease or a cellular esterase. In some embodiments, the cellular protease is a cytoplasmic protease, an endosomal protease, or an endosomal esterase. In some embodiments, the cellular enzyme is specifically expressed in a target cell or cell type, resulting in preferential or specific release of the functional protein or peptide in the target cell or cell type. The target sequence of the protease may be engineered into the linker between the agent to be delivered and the minimal ARRDC1 protein or the TSG101 protein or fragment thereof. In some embodiments, the target cell or cell type is a cancer cell or cancer cell type, a cell or cell type of the immune system, or a pathologic or diseased cell or cell type, and the linker is cleaved by an enzyme or based on a characteristic specific for the target cell. In some embodiments, the linker comprises an amino acid sequence chosen from the group including AGVF (SEQ ID NO: 114), GFLG (SEQ ID NO: 117), FK, AL, ALAL (SEQ ID NO: 118), or ALALA (SEQ ID NO: 119). Other suitable linkers will be apparent to those of skill in the art. In some embodiments, the linker is a cleavable linker. In some embodiments, the linker comprises a protease recognition site. In certain embodiments, the linker is a UV-cleavable moiety. Suitable linkers, for example, linkers comprising a protease recognition site, or linkers comprising a UV cleavable moiety are known to those of skill in the art. In some embodiments, the agent is conjugated to the minimal ARRDC1 protein or fragment thereof via a sortase reaction, and the linker comprises an LPXTG (SEQ ID NO: 120) motif. Methods and reagents for conjugating agents according to some aspects of this invention to proteins are known to those of skill in the art. Accordingly, suitable method for conjugating and agents to be included in an ARMM to an minimal ARRDC1 protein or fragment thereof, or a TSG101 protein or fragment thereof will be apparent to those of skill in the art based on this disclosure.

Methods for isolating ARMMs are also provided herein. One exemplary method includes collecting the culture medium, or supernatant, of a cell culture comprising microvesicle-producing cells. In some embodiments, the cell culture comprises cells obtained from a subject, for example, cells suspected to exhibit a pathological phenotype, e.g., a hyperproliferative phenotype. In some embodiments, the cell culture comprises genetically engineered cells producing ARMMs, for example, cells expressing a recombinant ARMM protein, for example, a recombinant minimal ARRDC1 or TSG101 protein, such as a minimal ARRDC1 or TSG101 fusion protein. In some embodiments, the supernatant is pre-cleared of cellular debris by centrifugation, for example, by two consecutive centrifugations of increasing G value (e.g., 500G and 2000G). In some embodiments, the method comprises passing the supernatant through a 0.2 μm filter, eliminating all large pieces of cell debris and whole cells. In some embodiments, the supernatant is subjected to ultracentrifugation, for example, at 120,000 g for 2 h, depending on the volume of centrifugate. The pellet obtained comprises microvesicles. In some embodiments, exosomes are depleted from the microvesicle pellet by staining and/or sorting (e.g., by FACS or MACS) using an exosome marker as described herein. Isolated or enriched ARMMs can be suspended in culture media or a suitable buffer, as described herein.

WW Domain Containing Cargos

Figure 2A:
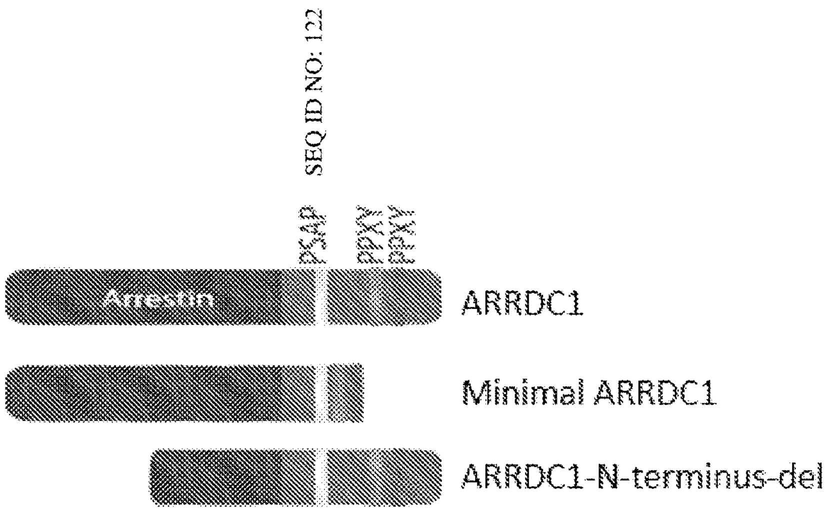
FIGS. 2A-2C—FIG. 2A is a schematic showing the domain/motifs in full-length ARRDC1, an example of a minimal ARRDC1, and an ARRDC1 with a short N-terminus.

Aspects of the disclosure relate to ARMMs comprising a cargo associated with at least one WW domain. In some aspects, fusion proteins are provided that comprise a cargo protein with at least one WW domain. In some aspects, expression constructs are provided that encode a cargo protein associated with at least one WW domain. The WW domain of a cargo protein may associate with the PPXY motif of ARRDC1, or variant thereof, to facilitate association with or inclusion of the cargo protein into an ARMM. A schematic representation of a Cas9 cargo protein fused to a WW domain that associates with the PPXY motif of ARRDC1 can be seen in FIG. 2. In some embodiments, the cargo protein is fused to at least one, at least two, at least three, at least four, at least five, at least six, at least seven, at least eight, at least nine, at least ten, or more WW domains. The WW domain may be derived from a WW domain of the ubiquitin ligase WWP1, WWP2, Nedd4-1, Nedd4-2, Smurf1, Smurf2, ITCH, NEDL1, or NEDL2 (FIG. 1). For example, the WW domain may comprise a WW domain or WW domain variant from the amino acid sequence set forth in (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); or (SEQ ID NO: 14). In certain embodiments, the cargo proteins may comprise two WW domains or WW domain variants from the human ITCH protein having the amino acid sequence:

```
                                                  (SEQ ID NO: 18)
PLPPGWEQRVDQHGRVYYVDHVEKRTTWDRPEPLPPGWERRVDNMGRIYY

VDHFTRTTTWQRPTL.
```

In other embodiments, the cargo proteins may comprise four WW domains or WW domain variants from the human ITCH protein having the amino acid sequence:

```
                                                  (SEQ ID NO: 19)
PLPPGWEQRVDQHGRVYYVDHVEKRTTWDRPEPLPPGWERRVDNMGRIYY

VDHFTRTTTWQRPTLESVRNYEQWQLQRSQLQGAMQQFNQRFIYGNQDLF

ATSQSKEFDPLGPLPPGWEKRTDSNGRVYFVNHNTRITQWEDPRSQGQLN

EKPLPEGWEMRFTVDGIPYFVDHNRRTTTYIDPRT.
```

The cargo proteins, described herein, that are fused to at least one WW domain or WW domain variant are non-naturally occurring, that is, they do not exist in nature.

In some embodiments, one or more WW domains may be fused to the N-terminus of a cargo protein. In other embodiments, one or more WW domains may be fused to the C-terminus or the N-terminus of a cargo protein. In yet other embodiments, one or more WW domains may be inserted into a cargo protein. It should be appreciated that the WW domains may be configured in any number of ways to maintain function of the cargo protein, which can be tested by methods known to one of ordinary skill in the art.

The cargo protein of the inventive microvesicles may be a protein comprising at least one WW domain. For example, the cargo protein may be a WW domain containing protein or a protein fused to at least one WW domain. In some embodiments, the cargo protein may be a Cas9 protein or Cas9 variant fused to at least one WW domain. In some embodiments, the cargo protein may be a recombinant cargo protein. For example the recombinant cargo protein may be a Cas9 protein, or Cas9 variant, fused to at least one nuclear localization sequence (NLS). A NLS, as referred to herein, is an amino acid sequence that facilitates the import of a protein into the cell nucleus by nuclear transport. In some embodiments, a NLS is fused to the N-terminus of a Cas9 protein, or Cas9 variant. In some embodiments, a NLS is fused to the C-terminus of Cas9 protein, or Cas9 variant. In some embodiments, Cas9 is fused to at least one, at least two, at least three, at least four, at least five, at least six, at least seven, at least eight, at least nine, at least ten, or more nuclear localization sequences (NLSs). In certain embodiments, one NLS is fused to the N-terminus, and one NLS is fused to the C-terminus of the Cas9 protein to create a recombinant NLS:Cas9:NLS fusion protein. In certain embodiments, the Cas9 protein, or Cas9 variant, fused to at least one NLS may also be fused to at least one WW domain. It should be appreciated that, as described above, the WW domains may be configured in any number of ways such that the Cas9 protein or Cas9 variant may be loaded into an ARMM for delivery to a target cell and translocate into the nucleus of the target cell to perform its nuclease function. In certain embodiments, one or more WW domains are fused to the N-terminus of a recombinant NLS:Cas9:NLS fusion protein. In certain embodiments, one or more WW domains are fused to the C-terminus of a recombinant NLS:Cas9: NLS fusion protein. In certain embodiments, the cargo protein comprises the sequence (SEQ ID NO: 109) or (SEQ ID NO: 110). In certain embodiments, the cargo protein consists of the sequence (SEQ ID NO: 109) or (SEQ ID NO: 110). In certain embodiments, the cargo protein consists essentially of (SEQ ID NO: 109) or (SEQ ID NO: 110).

The following amino acid sequences are exemplary Cas9 cargo protein sequences that have either 2 WW domains (SEQ ID NO: 109) or 4 WW domains (SEQ ID NO: 110), which were cloned into the AgeI site of the pX330 plasmid (Addgene).

(SEQ ID NO: 109)

MPLPPGWEQRVDQHGRVYYVDHVEKRTTWDRPEPLPPGWERRVDNMGRIY

YVDHFTRTTTWQRPTLTGATMDYKDHDGDYKDHDIDYKDDDDKMAPKKKR

KVGIHGVPAADKKYSIGLDIGTNSVGWAVITDEYKVPSKKFKVLGNTDRH

SIKKNLIGALLFDSGETAEATRLKRTARRRYTRRKNRICYLQEIFSNEMA

KVDDSFFHRLEESFLVEEDKKHERHPIFGNIVDEVAYHEKYPTIYHLRKK

LVDSTDKADLRLIYLALAHMIKFRGHFLIEGDLNPDNSDVDKLFIQLVQT

YNQLFEENPINASGVDAKAILSARLSKSRRLENLIAQLPGEKKNGLFGNL

IALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQ

QLPEKYKEIFFDQSKNGYAGYIDGGASQEEFYKFIKPILEKMDGTEELLV

KLNREDLLRKQRTFDNGSIPHQIHLGELHAILRRQEDFYPFLKDNREKIE

KILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFLS

GEQKKAIVDLLFKTNRKVTVKQLKEDYFKKIECFDSVEISGVEDRFNASL

GTYHDLLKIIKDKDFLDNEENEDILEDIVLTLTLFEDREMIEERLKTYAH

LFDDKVMKQLKRRRYTGWGRLSRKLINGIRDKQSGKTILDFLKSDGFANR

NFMQLIHDDSLTEKEDIQKAQVSGQGDSLHEHIANLAGSPAIKKGILQTV

KVVDELVKVMGRHKPENIVIEMARENQTTQKGQKNSRERMKRIEEGIKEL

GSQILKEHPVENTQLQNEKLYLYYLQNGRDMYVDQELDINRLSDYDVDHI

VPQSFLKDDSIDNKVLTRSDKNRGKSDNVPSEEVVKKMKNYWRQLLNAKL

ITQRKFDNLTKAERGGLSELDKAGFIKRQLVETRQITKHVAQILDSRMNT

KYDENDKLIREVKVITLKSKLVSDFRKDFQFYKVREINNYHHAHDAYLNA

VVGTALIKKYPKLESEFVYGDYKVYDVRKMIAKSEQEIGKATAKYFFYSN

IMNFFKTEITLANGEIRKRPLIETNGETGEIVWDKGRDFATVRKVLSMPQ

VNIVKKTEVQTGGFSKESILPKRNSDKLIARKKDWDPKKYGGFDSPTVAY

SVLVVAKVEKGKSKKLKSVKELLGITIMERSSFEKNPIDFLEAKGYKEVK

-continued

KDLIIKLPKYSLFELENGRKRMLASAGELQKGNELALPSKYVNFLYLASH

YEKLKGSPEDNEQKQLFVEQHKHYLDEIIEQISEFSKRVILADANLDKVL

SAYNKHRDKPIREQAENIIHLFTLTNLGAPAAFKYFDTTIDRKRYTSTKE

VLDATLIHQSITGLYETRIDLSQLGGDKRPAATKKAGQAKKKK (SEQ ID NO: 119)

MPLPPGWEQRVDQHGRVYYVDHVEKRTTWDRPEPLPPGWERRVDNMGRIY

YVDHFTRTTTWQRPTLESVRNYEQWQLQRSQLQGAMQQFNQRFIYGNQDL

FATSQSKEFDPLGPLPPGWEKRTDSNGRVYFVNHNTRITQWEDPRSQGQL

NEKPLPEGWEMRFTVDGIPYFVDHNRRTTTYIDPRTGGGTGATMDYKDHD

GDYKDHDIDYKDDDDKMAPKKKRKVGIHGVPAADKKYSIGLDIGTNSVGW

AVITDEYKVPSKKFKVLGNTDRHSIKKNLIGALLFDSGETAEATRLKRTA

RRRYTRRKNRICYLQEIFSNEMAKVDDSFFHRLEESFLVEEDKKHERHPI

FGNIVDEVAYHEKYPTIYHLRKKLVDSTDKADLRLIYLALAHMIKFRGHF

LIEGDLNPDNSDVDKLFIQLVQTYNQLFEENPINASGVDAKAILSARLSK

SRRLENLIAQLPGEKKNGLFGNLIALSLGLTPNFKSNFDLAEDAKLQLSK

DTYDDDLDNLLAQIGDQYADLFLAAKNLSDAILLSDILRVNTEITKAPLS

ASMIKRYDEHHQDLTLLKALVRQQLPEKYKEIFFDQSKNGYAGYIDGGAS

QEEFYKFIKPILEKMDGTEELLVKLNREDLLRKQRTFDNGSIPHQIHLGE

LHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYF

TVYNELTKVKYVTEGMRKPAFLSGEQKKAIVDLLFKTNRKVTVKQLKEDY

FKKIECFDSVEISGVEDRFNASLGTYHDLLKIIKDKDFLDNEENEDILED

IVLTLTLFEDREMIEERLKTYAHLFDDKVMKQLKRRRYTGWGRLSRKLIN

GIRDKQSGKTILDFLKSDGFANRNFMQLIHDDSLTFKEDIQKAQVSGQGD

SLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQN

GRDMYVDQELDINRLSDYDVDHIVPQSFLKDDSIDNKVLTRSDKNRGKSD

NVPSEEVVKKMKNYWRQLLNAKLITQRKFDNLTKAERGGLSELDKAGFIK

RQLVETRQITKHVAQILDSRMNTKYDENDKLIREVKVITLKSKLVSDFRK

DFQFYKVREINNYHHAHDAYLNAVVGTALIKKYPKLESEFVYGDYKVYDV

RKMIAKSEQEIGKATAKYFFYSNIMNFFKTEITLANGEIRKRPLIETNGE

TGEIVWDKGRDFATVRKVLSMPQVNIVKKTEVQTGGFSKESILPKRNSDK

LIARKKDWDPKKYGGFDSPTVAYSVLVVAKVEKGKSKKLKSVKELLGITI

MERSSFEKNPIDFLEAKGYKEVKKDLIIKLPKYSLFELENGRKRMLASAG

ELQKGNELALPSKYVNFLYLASHYEKLKGSPEDNEQKQLFVEQHKHYLDE

IIEQISEFSKRVILADANLDKVLSAYNKHRDKPIREQAENIIHLFTLTNL

GAPAAFKYFDTTIDRKRYTSTKEVLDATLIHQSITGLYETRIDLSQLGGD

KRPAATKKAGQAKKKK

The microvesicles described herein may further comprise a nucleic acid. In some embodiments, the microvesicles may comprise at least one guide RNA (gRNA), which may be associated, for example, with a nuclease or a nickase. As one example, a gRNA may be associated with a Cas9 cargo protein or Cas9 variant cargo protein. The gRNA may comprise a nucleotide sequence that complements a target site, which mediates binding of the nuclease/RNA complex to said target site and providing the sequence specificity of the nuclease:RNA complex. In certain embodiments, the gRNA comprises a nucleotide sequence that is complementary to any target known in the art. For example, the gRNA may comprise a nucleotide sequence that is complementary to a therapeutic target (e.g., APOC3, alpha 1 antitrypsin, HBV, or HIV). In certain embodiments the gRNA comprises the sequence complementary to enhanced green fluorescent protein (EGFP). For example, the gRNA sequence may be encoded by the nucleic acid sequence set forth in SEQ ID NO: 113.

The following is an exemplary nucleic acid sequence that encodes a guide RNA (gRNA) that targets EGFP. The EGFP target sequence is underlined below.

(SEQ ID NO: 113)

ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAG

TSG101

In certain embodiments, the inventive microvesicles further comprise TSG101. Tumor susceptibility gene 101, also referred to herein as TSG101, is a protein encoded by this gene belongs to a group of apparently inactive homologs of ubiquitin-conjugating enzymes. The protein contains a coiled-coil domain that interacts with stathmin, a cytosolic phosphoprotein implicated in tumorigenesis. TSG101 is a protein that comprises a UEV domain, and interacts with ARRDC1. Exemplary, non-limiting TSG101 protein sequences are provided herein, and additional, suitable TSG101 protein sequences, isoforms, and variants according to aspects of this invention are known in the art. It will be appreciated by those of skill in the art that this invention is not limited in this respect. Exemplary TSG101 sequences include the following:

>gi|5454140|ref|NP_006283.1| tumor susceptibility gene 101 protein [*Homo sapiens*]

(SEQ ID NO: 20)

MAVSESQLKKMVSKYKYRDLTVRETVNVITLYKDLKPVLDSYVFNDGSSR

ELMNLTGTIPVPYRGNTYNIPICLWLLDTYPYNPPICFVKPTSSMTIKTG

-continued

KHVDANGKIYLPYLHEWKHPQSDLLGLIQVMIVVFGDEPPVFSRPISASY

PPYQATGPPNTSYMPGMPGGISPYPSGYPPNPSGYPGCPYPPGGPYPATT

SSQYPSQPPVTTVGPSRDGTISEDTIRASLISAVSDKLRWRMKEEMDRAQ

AELNALKRTEEDLKKGHQKLEEMVTRLDQEVAEVDKNIELLKKKDEELSS

ALEKMENQSENNDIDEVIIPTAPLYKQILNLYAEENAIEDTIFYLGEALR

RGVIDLDVFLKHVRLLSRKQFQLRALMQKARKTAGLSDLY

>gi|11230780|ref|NP_068684.1| tumor susceptibility gene 101 protein [*Mus musculus*]

(SEQ ID NO: 21)

MAVSESQLKKMMSKYKYRDLTVRQTVNVIAMYKDLKPVLDSYVFNDGSSR

ELVNLTGTIPVRYRGNIYNIPICLWLLDTYPYNPPICFVKPTSSMTIKTG

KHVDANGKIYLPYLHDWKHPRSELLELIQIMIVIFGEEPPVFSRPTVSAS

YPPYTATGPPNTSYMPGMPSGISAYPSGYPPNPSGYPGCPYPPAGPYPAT

TSSQYPSQPPVTTVGPSRDGTISEDTIRASLISAVSDKLRWRMKEEMDGA

QAELNALKRTEEDLKKGHQKLEEMVTRLDQEVAEVDKNIELLKKKDEELS

SALEKMENQSENNDIDEVIIPTAPLYKQILNLYAEENAIEDTIFYLGEAL

RRGVIDLDVFLKHVRLLSRKQFQLRALMQKARKTAGLSDLY

>gi|48374087|ref|NP_853659.2| tumor susceptibility gene 101 protein [*Rattus norvegicus*]

(SEQ ID NO: 22)

MAVSESQLKKMMSKYKYRDLTVRQTVNVIAMYKDLKPVLDSYVFNDGSSR

ELVNLTGTIPVRYRGNIYNIPICLWLLDTYPYNPPICFVKPTSSMTIKTG

KHVDANGKIYLPYLHDWKHPRSELLELIQIMIVIFGEEPPVFSRPTVSAS

YPPYTAAGPPNTSYLPSMPSGISAYPSGYPPNPSGYPGCPYPPAGPYPAT

TSSQYPSQPPVTTAGPSRDGTISEDTIRASLISAVSDKLRWRMKEEMDGA

QAELNALKRTEEDLKKGHQKLEEMVTRLDQEVAEVDKNIELLKKKDEELS

SALEKMENQSENNDIDEVIIPTAPLYKQILNLYAEENAIEDTIFYLGEAL

RRGVIDLDVFLKHVRLLSRKQFQLRALMQKARKTAGLSDLY

The UEV domain in these sequences includes amino acids 1-145 (underlined in the sequences above). The structure of UEV domains is known to those of skill in the art (see, e.g., Owen Pornillos et al., Structure and functional interactions of the Tsg101 UEV domain, *EMBO J.* 2002 May 15; 21(10): 2397-2406, the entire contents of which are incorporated herein by reference).

Cas9 Cargo Proteins Fused to Minimal ARRDC1

In some aspects, microvesicles, e.g., ARMMs, are provided that comprise a minimal ARRDC1 protein, or variant thereof, fused to a Cas9 protein or Cas9 variant. In some aspects, fusion proteins are provided that comprise a minimal ARRDC1 protein, or variant thereof, fused to a Cas9 protein and/or a TSG101 protein, or variant thereof, fused to a Cas9 protein. In some aspects, expression constructs are provided that encode a minimal ARRDC1 protein, or variant thereof, fused to a Cas9 cargo protein and/or a TSG101 protein, or variant thereof, fused to a Cas9 cargo protein. In some embodiments, the minimal ARRDC1 protein variant is a C-terminal minimal ARRDC1 protein variant. In some embodiments, the TSG101 protein variant comprises a TSG101 UEV domain. In some embodiments, the TSG101 protein variant comprises the UEV domain and comprises at least 150, at least 160, at least 170, at least 180, at least 190, at least 200, at least 210, at least 220, at least 230, at least 240, at least 250, at least 260, at least 270, at least 280, at least 290, or at least 300 contiguous amino acids of the TSG101 sequence.

Some aspects of this invention provide ARRDC1 fusion proteins that comprise a minimal ARRDC1 protein or a variant thereof, and an endonuclease, (e.g., a Cas9 protein, or Cas9 variant), associated with the minimal ARRDC1 protein or variant thereof. In some embodiments the endonuclease is covalently linked to the minimal ARRDC1 protein, or variant thereof. The endonuclease, for example, may be covalently linked to the N-terminus, the C-terminus, or within the amino acid sequence of the minimal ARRDC1 protein.

In certain embodiments, the endonuclease (e.g., Cas9 protein or Cas9 variant) is fused to the C-terminus of the minimal ARRDC1 protein or protein variant, or to the C-terminus of the TSG101 protein or protein variant. The Cas9 protein or Cas9 variant may also be fused to the N terminus of the minimal ARRDC1 protein or protein variant, or to the N terminus of the TSG101 protein or protein variant. In some embodiments, the Cas9 protein or Cas9 variant may be within the minimal ARRDC1 or TSG101 protein or variants thereof.

In certain embodiments, the Cas9 protein is associated with a minimal ARRDC1 protein, a minimal ARRDC1 variant, a TSG101 protein, or a TSG101 variant via a covalent bond. In some embodiments, the Cas9 protein is associated with the minimal ARRDC1 protein, the minimal ARRDC1 protein variant, the TSG101 protein, or the TSG101 protein variant via a linker. In some embodiments, the linker is a cleavable linker, for example, the linker may contain a protease recognition site. The protease recognition site of the linker may be recognized by a protease expressed in a target cell, resulting in the Cas9 protein fused to the minimal ARRDC1 protein or variant thereof or the TSG101 protein variant thereof being released into the cytoplasm of the target cell upon uptake of the ARMM. A person skilled in the art would appreciate that any number of linkers may be used to fuse the Cas9 protein or Cas9 variant to the minimal ARRDC1 protein or variant thereof or the TSG101 protein or variant thereof.

The Cas9 protein or Cas9 variant associated with a minimal ARRDC1 protein, a minimal ARRDC1 protein variant, a TSG101 protein, or a TSG101 protein variant, may further include a nuclear localization sequence (NLS). In some embodiments, the Cas9 fusion protein is fused to at least one NLS. In some embodiments, one or more nuclear localization sequences (NLSs) are fused to the N-terminus of Cas9. In some embodiments, one or more NLSs are fused to the C-terminus of Cas9. In some embodiments, Cas9 is fused to at least one, at least two, at least three, at least four, at least five, at least six, at least seven, at least eight, at least nine, at least ten, or more NLSs. It should be appreciated that one or more NLSs may be fused to Cas9 to allow translocation of Cas9 fusion protein into the nucleus of a target cell. In some embodiments, the Cas9 protein fused to at least one NLS is associated with ARRDC1, a minimal ARRDC1 protein variant, a TSG101 protein, or a TSG101 protein variant via a linker. In some embodiments, the linker contains a protease recognition site. In other embodiments, the linker contains a UV-cleavable moiety. In some embodiments, the protease recognition site is recognized by a protease expressed in a target cell, resulting in the Cas9 protein fused to at least one NLS being released from the minimal ARRDC1 protein or variant thereof or the TSG101 protein or variant thereof into the cytoplasm, where it may translocate into the nucleus upon uptake of the ARMM.

RNA Binding Proteins

Some aspects of the disclosure relate to proteins that bind to RNA. In some embodiments, the RNA binding protein is a naturally-occurring protein, or non-naturally-occurring variant thereof, or a non-naturally occurring protein that binds to an RNA, for example, an RNA with a specific sequence or structure.

In certain embodiments, the RNA binding protein is a trans-activator of transcription (Tat) protein that specifically binds a trans-activating response element (TAR element). An exemplary Tat protein comprises the amino acid sequence as set forth in SEQ ID NO: 65 (Table 1). Exemplary amino acid sequences of Tat proteins, as well as Tat protein fragments that bind TAR elements, are shown in Table 1. In some embodiments, the RNA binding protein is at least 60%, 65%, 70%, 75%, 80%, 85%, 90%, 95%, 98%, or 99% identical to the amino acid sequence of any one of SEQ ID NOs: 65-84, and binds a TAR element. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, at least 120, at least 125, or at least 130 identical contiguous amino acids of any one of SEQ ID NOs: 65-84, and binds a TAR element. In some embodiments, the RNA binding protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 65-84, and binds a TAR element. In some embodiments, the RNA binding protein comprises any one of the amino acid sequences set forth in SEQ ID NOs: 65-84. In some embodiments, the Tat protein comprises an amino acid sequence as set forth in any one of SEQ ID NOs: 65-84. The RNA binding protein may also be a variant of a Tat protein that is capable of associating with a TAR element. Tat proteins, as well as variants of Tat proteins that bind to a TAR element, are known in the art and have been described previously, for example, in Kamine et al., "Mapping of HIV-1 Tat Protein Sequences Required for Binding to Tar RNA", *Virology* 182, 570-577 (1991); and Patel, "Adaptive recognition in RNA complexes with peptides and protein modules" *Curr Opin Struct Biol.* 1999 February; 9(1):74-87; the entire contents of each of which are incorporated herein by reference. In some embodiments, the Tat protein is an HIV-1 Tat protein, or variant thereof. In some embodiments, the Tat protein is bovine immunodeficiency virus (BIV) Tat protein, or variant thereof.

A Tat protein is a nuclear transcriptional activator of viral gene expression that is essential for viral transcription from the LTR promoter and replication; it acts as a sequence-specific molecular adapter, directing components of the cellular transcription machinery to the viral RNA to promote processive transcription elongation by the RNA polymerase II (RNA pol II) complex, thereby increasing the level of full-length transcripts. Tat binds to a hairpin structure at the 5'-end of all nascent viral mRNAs referred to as the transactivation responsive RNA element (TAR RNA) in a CCNT1-independent mode.

The Tat protein consists of several domains, one is a short lysine and arginine rich region important for nuclear localization. The nine amino acid basic region of HIV-1 Tat is found at positions 49-57 of SEQ ID NO: 65, and is capable of binding a TAR element. In some embodiments, the Tat sequence comprises the nine amino acid basic region of Tat (SEQ ID NO: 73). In some embodiments the RNA binding protein comprises any one of the amino acid sequences as set forth in SEQ ID NOs: 65-67, 69, 70, or 73-84. In some embodiments, the Tat proteins are fusion proteins.

TABLE 1

| Tat Sequences | | |
|---|---|---|
| Tat (Residue NOs) | Sequence | SEQ ID NO |
| HIV-1 Tat (1-101) | MEPVDPRLEPWKHPGSQPRT PCTTCYCKKC CFHCQVCFTT KALGISYGRK KRRQRRRPPQ GSQTHQVSLS KQPSSQPRGD QTGPKESKKK VERETEADPKP | 65 |
| HIV-1 Tat (1-86) | MEPVDPRLEP WKHPGSQPRT PCTTCYCKKC CFHCQVCFTT KALGISYGRK KRRQRRRPPQ GSQTHQVSLS KQPSSQPRGD QTGPKE | 66 |
| HIV-1 Tat (37-72) | CFTT KALGISYGRK KRRQRRRPPQ GSQTHQVSLS KQ | 67 |
| HIV-1 Tat (1-45) | MEPVDPRLEP WKHPGSQPRT PCTTCYCKKC CFHCQVCFTT KALGI | 68 |
| HIV-1 Tat (49-86) | RK KRRQRRRPPQ GSQTHQVSLS KQPSSQPRGD QTGPKE | 69 |
| HIV-1 Tat (52-86) | RRQRRRPPQ GSQTHQVSLS KQPSSQPRGD QTGPKE | 70 |
| HIV-1 Tat (55-86) | RRRPPQ GSQTHQVSLS KQPSSQPRGD QTGPKE | 71 |
| HIV-1 Tat (58-86) | PPQ GSQTHQVSLS KQPSSQPRGD QTGPKE | 72 |
| HIV-1 Tat (49-57) | RK KRRQRRR | 73 |
| HIV-1 Tat (49-59) | RK KRRQRRRPP | 74 |
| HIV-1 Tat (49-61) | RK KRRQRRRPPQ G | 75 |
| HIV-1 Tat (49-63) | RK KRRQRRRPPQ GSQ | 76 |
| HIV-1 Tat (49-65) | RK KRRQRRRPPQ GSQTH | 77 |
| HIV-1 Tat (37-57) | CFTT KALGISYGRK KRRQRRR | 78 |
| HIV-1 Tat (38-62) | CFTT KALGISYGRK KRRQRRRPPQ GSQ | 79 |
| HIV-1 Tat (47-58) | GRRK KRRQRRRP | 80 |
| HIV-1 Tat (46-65) | SYGRK KRRQRRRPPQ GSQTH | 81 |
| HIV-2 Tat (1-130) | METPLKAPEG SLGSYNEPSS CTSEQDAAAQ GLVSPGDEIL YQLYQPLEAC DNKCYCKKCC YHCQMCFLNK GLGIWYERKG RRRRTPKKTK AHSSSASDKS ISTRTGNSQP EKKQKKTLET ALETIGGPGR | 82 |
| BIV Tat | MPGPWVAMIM LPQPKESFGG KPIGWLFWNT CKGPRRDCPH CCCPICSWHC QLCFLQKNLG INYGSGPRRR GTRGKGRRIR RTASGGDQRR EADSQRSFTN MDQ | 83 |
| BIV Tat | SGPRPRGTRGKGRRIRR | 84 |

In some embodiments, the RNA binding protein is a regulator of virion expression (Rev) protein (e.g., Rev from HIV-1), or variant thereof, that binds to a Rev response element (RRE). Rev proteins are known in the art and are known to the skilled artisan. For example, Rev proteins have been described in Fernandes et al., "The HIV-1 Rev response element: An RNA scaffold that directs the cooperative assembly of a homo-oligomeric ribonucleoprotein complex" *RNA Biology* 9:1, 6-11; January 2012; Cochrane et al., "The human immunodeficiency virus Rev protein is a nuclear phosphoprotein" *Virology* 171 (1):264-266, 1989; Grate et al., "Role REVersal: understanding how RRE RNA binds its peptide ligand" *Structure.* 1997 Jan. 15; 5(1):7-11; and Patel, "Adaptive recognition in RNA complexes with peptides and protein modules" *Curr Opin Struct Biol.* 1999 February; 9(1):74-87; the entire contents of each of which are incorporated herein by reference in their entirety. An exemplary Rev protein comprises the amino acid sequence as set forth in SEQ ID NOs: 93-95 (Table 3). In some embodiments, the RNA binding protein is at least 60%, 65%, 70%, 75%, 80%, 85%, 90%, 95%, 98%, or 99% identical to the amino acid sequence of any one of SEQ ID NOs: 93-95, and binds a Rev response element. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115 identical contiguous amino acids of any one of SEQ ID NOs: 93-95, and binds a Rev response element. In some embodiments, the RNA binding protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to any one of the amino acid sequences set forth in SEQ ID NOs: 93-95, and binds a Rev response element. In some embodiments, the RNA binding protein comprises any one of the amino acid sequences set forth in SEQ ID NOs: 93-95. In some embodiments, the RNA binding protein comprises a variant of any one of the amino acid sequences as set forth in SEQ ID NOs: 93-95 that are capable of binding an RRE. Such variants would be apparent to the skilled artisan based on this disclosure and knowledge in the art and may be tested (e.g. for binding to an RRE) using routine methods known in the art.

In some embodiments, the RNA binding protein is a coat protein of an MS2 bacteriophage that specifically binds to an MS2 RNA. MS2 bacteriophage coat proteins that specifically bind MS2 RNAs are known in the art. For example MS2 phage coat proteins have been described in Parrott et al., "RNA aptamers for the MS2 bacteriophage coat protein and the wild-type RNA operator have similar solution behavior" Nucl. Acids Res. 28(2):489-497 (2000); Keryer-Bibens et al., "Tethering of proteins to RNAs by bacteriophage proteins" Biol. Cell. 100(2): 125-38 (2008); and Patel, "Adaptive recognition in RNA complexes with peptides and protein modules" Curr Opin Struct Biol. 1999 February; 9(1):74-87; the entire contents of each are hereby incorporated by reference in their entirety. An exemplary MS2 phage coat protein comprises the amino acid sequence as set forth in SEQ ID NO: 99 (Table 4). In some embodiments, the RNA binding protein is at least 60%, 65%, 70%, 75%, 80%, 85%, 90%, 95%, 98%, or 99% identical to the amino acid sequence of SEQ ID NO: 99, and binds an MS2 RNA. In some embodiments, the RNA binding protein has at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or at least 115 identical contiguous amino acids of SEQ ID NO: 99, and binds an MS2 RNA. In some embodiments, the RNA binding protein has 1, 2, 3, 4, 5, 6, 7, 8, 9, 10, 11, 12, 13, 14, 15, 16, 17, 18, 19, 20, 21, 22, 21, 24, 25, 26, 27, 28, 29, 30, 31, 32, 33, 34, 35, 36, 37, 38, 39, 40, 41, 42, 43, 44, 45, 46, 47, 48, 49, 50 or more mutations compared to SEQ ID NO: 99, and binds an MS2 RNA. In some embodiments, the RNA binding protein comprises the amino acid sequence set forth in SEQ ID NO: 99. In some embodiments, the RNA binding protein comprises a fragment or variant of SEQ ID NO: 99 that is capable of binding to an MS2 RNA. Methods for testing whether variants or fragments of MS2 phage coat proteins bind to MS2 RNAs (e.g., SEQ ID NO: 99) can be performed using routine experimentation and would be apparent to the skilled artisan.

In some embodiments, the RNA binding protein is a P22 N protein (e.g., P22 N from bacteriophage), or variant thereof, that binds to a P22 boxB RNA. P22 N proteins are known in the art and would be apparent to the skilled artisan. For example, P22 N proteins have been described in Cai et al., "Solution structure of P22 transcriptional antitermination N peptide-boxB RNA complex" Nat Struct Biol. 1998 March; 5(3):203-12; and Patel, "Adaptive recognition in RNA complexes with peptides and protein modules" Curr Opin Struct Biol. 1999 February; 9(1):74-87; the entire contents of each are incorporated by reference herein. An exemplary P22 N that specifically binds to a protein P22 boxB RNA comprises the amino acid sequence NAKTRRHERRRKLAIERDTI (SEQ ID NO: 100).

In some embodiments, the RNA binding protein is a λ N protein (e.g., λ N from bacteriophage), or variant thereof, that binds to a λ boxB RNA. λ N proteins are known in the art and would be apparent to the skilled artisan. For example, λ N proteins have been described in Keryer-Bibens et al., "Tethering of proteins to RNAs by bacteriophage proteins" Biol Cell. 2008 February; 100(2):125-38; Legault et al., "NMR structure of the bacteriophage lambda N peptide/boxB RNA complex: recognition of a GNRA fold by an arginine-rich motif" Cell. 1998 Apr. 17; 93(2):289-99; and Patel, "Adaptive recognition in RNA complexes with peptides and protein modules" Curr Opin Struct Biol. 1999 February; 9(1):74-87; the entire contents of each are incorporated by reference herein. An exemplary λ N protein that specifically binds to a λ boxB comprises the amino acid sequence GSMDAQTRRRERRAEKQAQWKAAN (SEQ ID NO: 101).

In some embodiments, the RNA binding protein is a φ21 N protein (e.g., φ21 N from bacteriophage), or variant thereof, that binds to a φ21 boxB RNA. φ21 N proteins are known in the art and would be apparent to the skilled artisan. For example, φ21 proteins have been described in Cilley et al. "Structural mimicry in the phage φ21 N peptide-boxB RNA complex." RNA. 2003; 9(6):663-676; and Patel, "Adaptive recognition in RNA complexes with peptides and protein modules" Curr Opin Struct Biol. 1999 February; 9(1):74-87; the entire contents of each are incorporated by reference herein. An exemplary φ21 N protein that specifically binds to a φ21 boxB RNA comprises amino acid sequence GTAKSRYKARRAELIAERR (SEQ ID NO: 102). The N peptide binds as an α-helix and interacts predominately with the major groove side of the 5' half of the boxB RNA stem-loop. This binding interface is defined by surface complementarity of polar and nonpolar interactions. The N peptide complexed with the exposed face of the φ21 boxB loop is similar to the GNRA tetraloop-like folds of the related λ and P22 bacteriophage N peptide-boxB RNA complexes.

In some embodiments, the RNA binding protein is a HIV-1 nucleocapsid (e.g., nucleocapsid from HIV-1), or variant thereof, that binds to a SL3 ψ RNA. HIV-1 nucleocapsid proteins are known in the art and would be apparent to the skilled artisan. For example, HIV-1 nucleocapsid proteins have been described in Patel, "Adaptive recognition in RNA complexes with peptides and protein modules" Curr Opin Struct Biol. 1999 February; 9(1):74-87; the entire contents of which is incorporated by reference herein. An exemplary HIV-1 nucleocapsid that specifically binds to a SL3 Y RNA comprises amino acid sequence:

```
                                           (SEQ ID NO: 103)
MQKGNFRNQRKTVKCFNCGKEGHIAKNCRAPRKKGCWKCGKEGHQMKDCT

ERQAN.
```

Binding RNAs

Some aspects of the disclosure relate to RNA molecules that bind proteins. In some embodiments, the binding RNA is a naturally occurring RNA, or non-naturally occurring variant thereof, or a non-naturally occurring RNA, that binds to a protein having a specific amino acid sequence or structure.

In certain embodiments, the binding RNA is a trans-activating response element (TAR element), which is an RNA stem-loop structure that is found at the 5' ends of nascent human immunodeficiency virus-1 (HIV-1) transcripts and specifically bind to a trans-activator of transcription (Tat) protein. In some embodiments, the TAR element is a bovine immunodeficiency virus (BIV) TAR. An exemplary TAR element comprises the nucleic acid sequence as set forth in SEQ ID NO: 84. Further exemplary TAR sequences can be found in Table 2; however, these sequences are not meant to be limiting and additional TAR element sequences that bind to a Tat protein, or variant thereof, are also within the scope of this disclosure. The binding RNA may also be a variant of a TAR element that is capable of associating with the RNA binding protein, trans-activator of transcription (Tat protein), which is a regulatory protein that is involved in transcription of the viral genome. Variants of TAR elements that are capable of associating with Tat proteins would be apparent to the skilled artisan based on this disclosure and knowledge in the art, and are within the scope of this disclosure. Further, the association between a TAR variant and a Tat protein, or Tat protein variant, may be tested using routine methods. TAR elements and variants of TAR elements that bind to Tat proteins are known in the art and have been described previously, for example in Kamine et al., "Mapping of HIV-1 Tat Protein Sequences Required for Binding to Tar RNA" Virology 182, 570-577 (1991); and Patel, "Adaptive recognition in RNA complexes with peptides and protein modules" Curr Opin Struct Biol. 1999 February; 9(1):74-87; the entire contents of each are incorporated by reference herein. In some embodiments, the binding RNA comprises the nucleic acid sequence as set forth in SEQ ID NOs: 85-90. In some embodiments, the binding RNA comprises a variant of any of the nucleic acid sequences set forth in SEQ ID NOs: 85-90 that are capable of binding to a Tat protein or variant thereof.

Without wishing to be bound by any particular theory, a TAR element is capable of forming a stable stem-loop structure (Muesing et al., 1987) in the native viral RNA. On the stem of TAR, a three nucleotide bulge, has been demonstrated to play a role in high-affinity binding of the Tat protein to the TAR element (Roy et al., 1990; Cordingley et al., 1990; Dingwall et al., 1989; Weeks et al., 1990). In the TAR element, the integrity of the stem and the initial U22 of the bulge may contribute to Tat protein binding (Roy et al., 1990b). Other sequences that may not affect the binding of the Tat protein to the TAR site play a role in trans-activation of transcription in vivo. One such region is the sequence at the loop, which is required for the binding of cellular factors that may interact with the Tat protein to mediate transactivation (Gatignol et al., 1989; Gaynor et al., 1989; Marciniak et al., 1990a; Gatignol et al., 1991).

TABLE 2

TAR Sequences

| TAR | Sequence | SEQ ID NO |
|---|---|---|
| HIV-1 TAR RNA +1-59 | gggucucucugguuagaccagaucugagccugggagcucucuggcuaacuagggaacccacug | 85 |
| Δ TAR | gggucucucugguuagaccagaucugagccugggcucuggcuaacuagggaacccacug | 86 |
| HIV-1TAR (shown in FIG. 2) | gggucucucugguuagaccagaucugagccugggagcucucuggcuaacuagggaacc | 87 |
| HIV-1 TAR | agaucugagccugggagcucucu | 88 |
| Hybrid TAR | gcucguugagcucugggaagcuccgagc | 89 |
| BIV TAR | ucguguagcucauuagcuccga | 90 |

In some embodiments, the binding RNA is a Rev response element (RRE), or variant thereof, that binds to a Rev protein (e.g., Rev from HIV-1). Rev response elements are known in the art and would be apparent to the skilled artisan for use in the present invention. For example, Rev response elements have been described in Fernandes et al., "The HIV-1 Rev response element: An RNA scaffold that directs the cooperative assembly of a homo-oligomeric ribonucleoprotein complex." RNA Biology 9:1, 6-11, January 2012; Cook et al., "Characterization of HIV-1 REV protein: binding stoichiometry and minimal RNA substrate." Nucleic Acids Res. April 11; 19(7):1577-1583, 1991; Grate et al., "Role REVersal: understanding how RRE RNA binds its peptide ligand" Structure. 1997 Jan. 15; 5(1):7-11; and Patel, "Adaptive recognition in RNA complexes with peptides and protein modules" Curr Opin Struct Biol. 1999 February; 9(1):74-87; the entire contents of each are incorporated herein by reference. Any of the RRE nucleic acid sequences or any of the fragments of RRE nucleic acid sequences described in the above references may be used as binding RNAs in accordance with this disclosure. Exemplary RRE nucleic acid sequences that bind Rev include, without limitation, those nucleic acid sequences set forth in SEQ ID NOs: 91 and 92 (Table 3).

In some embodiments, the Rev peptide may adopt a particular structure and several amino acids, rather than a single arginine, may participate in sequence-specific RNA interactions. Without wishing to be bound by any particular theory, Rev recognition of the RRE, like Tat recognition of TAR, is due to direct binding. Binding can be tight (Kd=1-3 nM) and highly specific for the RRE. As the concentration of Rev increases, progressively larger complexes with RRE RNA are formed, whereas Tat forms one-to-one complexes with TAR RNA.

Generally, a Rev protein may bind initially to a high affinity site and subsequently additional Rev molecules occupy lower affinity sites. RNAs that bind Rev have been described in Heaphy et al., "HIV-1 regulator of virion expression (Rev) protein binds to an RNA stem-loop structure located within the Rev-response element region" Cell, 1990. 60, 685-693; the entire contents of which is incorporated by reference herein.

TABLE 3

RRE/Rev Sequences

| | Sequence | SEQ ID NO |
|---|---|---|
| HIV-1 RRE | ggucugggcgcagcgcaagcugacgguacaggcc | 91 |
| HIV-1 RRE aptamer | ggcuggacucguacuucgguacuggagaaacagcc | 92 |
| HIV-1 Rev | MAGRSGDSDEELIRTVRLIKLLYQSNPPPNPEGTRQARRNRRRRWRERQRQIHSISERILGTYLGRSAEPVPLQLPPLERLTLDCNEDCGTSGTQGVGSPQILVESPTVLESGTKE | 93 |
| HIV-1 Rev peptide | TRQARRNRRRRWRERQR | 94 |
| Evolved HIV-1 RRE-binding peptide | RDRRRRGSRPSGAERRRRRAAAA | 95 |

In some embodiments, the binding RNA is an MS2 RNA that specifically binds to a MS2 phage coat protein. Typically, the coat protein of the RNA bacteriophage MS2 binds a specific stem-loop structure in viral RNA (e.g., MS2 RNA) to accomplish encapsidation of the genome and translational repression of replicase synthesis. RNAs that specifically bind MS2 phage coat proteins are known in the art and would be apparent the skilled artisan. For example RNAs that bind MS2 phage coat proteins have been described in Parrott et al., "RNA aptamers for the MS2 bacteriophage coat protein and the wild-type RNA operator have similar solution behavior." Nucl. Acids Res. 28(2): 489-497 (2000); Witherell et al., "Specific interaction between RNA phage coat proteins and RNA." Prog Nucleic Acid Res Mol Biol. 1991; 40:185-220; Stockley et al., "Probing sequence-specific RNA recognition by the bacteriophage MS2 coat protein." Nucleic Acids Res. 1995 Jul. 11; 23(13):2512-8; Keryer-Bibens C., et al., "Tethering of proteins to RNAs by bacteriophage proteins." Biol. Cell. 100(2): 125-38 (2008); and Patel. "Adaptive recognition in RNA complexes with peptides and protein modules." Curr Opin Struct Biol. 1999 February; 9(1):74-87; the entire contents of each are hereby incorporated by reference in their entirety. In some embodiments, an exemplary MS2 RNA that specifically binds to a MS2 phage coat protein comprises a nucleic acid sequence as set forth in any one of SEQ ID NOs: 96-98 (Table 4). In some embodiments, the binding RNA comprises the nucleic acid sequence of any one of SEQ ID NOs: 96, 97, or 98.

TABLE 4

MS2 Sequences

| MS2 | Sequence | SEQ ID NO |
|---|---|---|
| Bacteriophage MS2 RNA | acaugaggauuacccaugu | 96 |
| MS2 RNA | ccggaggaucaccacggg | 97 |
| MS2 RNA | ccacagucacuggg | 98 |
| Bacteriophage MS2 Coat Protein | ASNFTQFVLVDNGGTGDVTVAPSNFANGVAE WISSNSRSQAYKVTCSVRQSSAQNRKYTIKV EVPKVAT QTVGGVELPVAAWRSYLNMELTIPIFATNSD CELIVKAMQ GLLKDGNPIP SAIAANSGIY | 99 |

In some embodiments, the binding RNA is an RNA that specifically binds to a P22 N protein (e.g., P22 N from bacteriophage), or variant thereof. P22 N proteins are known in the art and would be apparent to the skilled artisan. For example, P22 N proteins have been described in Cai et al., "Solution structure of P22 transcriptional antitermination N peptide-boxB RNA complex" Nat Struct Biol. 1998 March; 5(3):203-12; Weiss, "RNA-mediated signaling in transcription" Nat Struct Biol. 1998 May; 5(5):329-33; and Patel, "Adaptive recognition in RNA complexes with peptides and protein modules" Curr Opin Struct Biol. 1999 February; 9(1):74-87; the entire contents of each are incorporated by reference herein. An exemplary P22 boxB RNA that specifically binds to a P22 N protein comprises a nucleic acid sequence as set forth in gcgcugacaaagcgc (SEQ ID NO: 104).

In some embodiments, the binding RNA is an RNA that specifically binds to a λ N protein (e.g., λ N from bacteriophage), or variant thereof. λ N proteins are known in the art and would be apparent to the skilled artisan. For example, λ N proteins have been described in Keryer-Bibens et al., "Tethering of proteins to RNAs by bacteriophage proteins." Biol Cell. 2008 February; 100(2):125-38; Weiss. "RNA-mediated signaling in transcription." Nat Struct Biol. 1998 May; 5(5):329-33; Legault et al., "NMR structure of the bacteriophage lambda N peptide/boxB RNA complex: recognition of a GNRA fold by an arginine-rich motif." Cell. 1998 Apr. 17; 93(2):289-99; and Patel, "Adaptive recognition in RNA complexes with peptides and protein modules." Curr Opin Struct Biol. 1999 February; 9(1):74-87; the entire contents of each are incorporated by reference herein. An exemplary λ boxB RNA that specifically binds to a λ N protein comprises a nucleic acid sequence as set forth in gggcccugaagaagggccc (SEQ ID NO: 105).

In some embodiments, the binding RNA is an RNA that specifically binds to a φ21 N protein (e.g., φ21 N from bacteriophage), or variant thereof. φ21 N proteins are known in the art and would be apparent to the skilled artisan. For example, φ21 proteins have been described in Cilley et al. "Structural mimicry in the phage φ21 N peptide-boxB RNA complex." RNA. 2003; 9(6):663-676; and Patel, "Adaptive recognition in RNA complexes with peptides and protein modules." Curr Opin Struct Biol. 1999 February; 9(1):74-87; the entire contents of each are incorporated by reference herein. An exemplary φ21 boxB RNA that specifically binds to a φ21 N protein comprises a nucleic acid sequence as set forth in ucucaaccuaaccguugaga (SEQ ID NO: 106).

In some embodiments, the binding RNA is an RNA that specifically binds to an HIV-1 nucleocapsid protein (e.g., nucleocapsid from HIV-1) or variant thereof. HIV-1 nucleocapsid proteins are known in the art and would be apparent to the skilled artisan. For example, HIV-1 nucleocapsid proteins have been described in Patel, "Adaptive recognition in RNA complexes with peptides and protein modules." Curr Opin Struct Biol. 1999 February; 9(1):74-87; the entire contents of which is incorporated by reference herein. An exemplary SL3 ψ RNA that specifically binds to a HIV-1 nucleocapsid comprises a nucleic acid sequence as set forth in ggacuagcggaggcuagucc (SEQ ID NO: 107).

It should be appreciated that the binding RNAs of the present disclosure need not be limited to naturally-occurring RNAs or non-naturally-occurring variants thereof, that have recognized protein binding partners. In some embodiments, the binding RNA may also be a synthetically produced RNA, for example an RNA that is designed to specifically bind to a protein (e.g., an RNA binding protein). In some embodiments, the binding RNA is designed to specifically bind to any protein of interest, for example ARRDC1. In some embodiments, the binding RNA is an RNA produced by the systematic evolution of ligands by exponential enrichment (SELEX). SELEX methodology would be apparent to the skilled artisan and has been described previously, for example in U.S. Pat. Nos. 5,270,163; 5,817,785; 5,595,887; 5,496,938; 5,475,096; 5,861,254; 5,958,691; 5,962,219; 6,013,443; 6,030,776; 6,083,696; 6,110,900; 6,127,119; and 6,147,204; U.S. Appln 20030175703 and 20030083294, Potti et al., Expert Opin. Biol. Ther. 4:1641-1647 (2004), and Nimjee et al., Annu. Rev. Med. 56:555-83 (2005). The technique of SELEX has been used to evolve aptamers to have extremely high binding affinity to a variety of target proteins. See, for example, Trujillo U. H., et al., "DNA and RNA aptamers: from tools for basic research towards therapeutic applications". Comb Chem High Throughput Screen 9 (8): 619-32 (2006) for its disclosure of using SELEX to design aptamers that bind vascular endothelial growth factor (VEGF). In some embodiments, the binding RNA is an aptamer that specifically binds a target protein, for example, a protein found in an ARMM (e.g., ARRDC1 or TSG101).

Cargo RNAs

Some aspects of the disclosure provide RNAs that are associated with, for example, incorporated into the liquid phase of, an ARMM. In some embodiments, a cargo RNAis an RNA molecule that can be delivered via its association with or inclusion in an ARMM to a subject, organ, tissue, or cell. In some embodiments, the cargo RNA is to be delivered to a target cell in vitro, in vivo, or ex vivo. In some embodiments, the cargo RNA to be delivered is a biologically active agent, i.e., it has activity in a cell, organ, tissue, and/or subject. For instance, an RNA that, when administered to a subject, has a biological effect on that subject, or is considered to be biologically active. In certain embodiments, the cargo RNA is a messenger RNA or an RNA that expresses a protein in a cell. In certain embodiments, the cargo RNA is a small interfering RNA (siRNA) that inhibits the expression of one or more genes in a cell. In some embodiments, a cargo RNA to be delivered is a therapeutic agent, for example, an agent that has a beneficial effect on a subject when administered to a subject. In some embodiments, the cargo RNA to be delivered to a cell is an RNA that expresses a transcription factor, a tumor suppressor, a developmental regulator, a growth factor, a metastasis suppressor, a pro-apoptotic protein, a nuclease, or a recombinase. In some embodiments, the cargo RNA to be delivered is an RNA that expresses p53, Rb (retinoblastoma protein), a BIM protein, BRCA1, BRCA2, PTEN, adenomatous polyposis coli (APC), CDKN1B, cyclin-dependent kinase inhibitor 1C, HEPACAM, INK4, Mir-145, p16, p63, p73, SDHB, SDHD, secreted frizzled-related protein 1, TCF21, TIG1, TP53, tuberous sclerosis complex tumor suppressors, Von Hippel-Lindau (VHL) tumor suppressor, CD95, ST7, ST14, a BCL-2 family protein, a caspase; BRMS1, CRSP3, DRG1, KAI1, KISS1, NM23, a TIMP-family protein, a BMP-family growth factor, EGF, EPO, FGF, G-CSF, GM-CSF, a GDF-family growth factor, HGF, HDGF, IGF, PDGF, TPO, TGF-α, TGF-β, VEGF; a zinc finger nuclease, Cre, Dre, or FLP recombinase.

In some embodiments, the cargo RNA may be an RNA that inhibits expression of one or more genes in a cell. For example, in some embodiments, the cargo RNA is a microRNA (miRNA), a small interfering RNA (siRNA), or an antisense RNA (asRNA).

In some embodiments, the cargo RNA to be delivered comprises a messenger RNA (mRNA), a ribosomal RNA (rRNA), a signal recognition particle RNA (SRP RNA), or a transfer RNA (tRNA). In some embodiments, the cargo RNA to be delivered comprises a small nuclear RNA (snRNA), a small nucleolar (snoRNA), a SmY RNA (smY), a guide RNA (gRNA), a ribonuclease P (RNase P), a ribonuclease MRP (RNase MRP), a Y RNA, a telomerase RNA component (TERC), or a spliced leader RNA (SL RNA). In some embodiments, the cargo RNA to be delivered comprises an antisense RNA (asRNA), a cis-natural antisense sequence (cis-NAT), a CRISPR RNA (crRNA), a long noncoding RNA (lncRNA), a microRNA (miRNA), a piwi-interacting RNA (piRNA), a small interfering RNA (siRNA), or a trans-acting siRNA (tasiRNA).

In some embodiments, the cargo RNA to be delivered is a diagnostic agent. In some embodiments, the cargo RNA to be delivered is a prophylactic agent. In some embodiments, the cargo RNA to be delivered is useful as an imaging agent. In some of these embodiments, the diagnostic or imaging agent is, and in others it is not, biologically active.

In some embodiments, any of the cargo RNAs provided herein are associated with a binding RNA. In some embodiments, the cargo RNA is covalently associated with the binding RNA. In some embodiments, the cargo RNA and the binding RNA are part of the same RNA molecule, (e.g., an RNA from a single transcript). In some embodiments, the cargo RNA and the binding RNA are covalently associated via a linker. In some embodiments, the linker comprises a nucleotide or nucleic acid (e.g., DNA or RNA). In some embodiments, the linker comprises RNA. In some embodiments, the linker comprises at least 1, at least 2, at least 3, at least 4, at least 5, at least 6, at least 7, at least 8, at least 9, at least 10, at least 15, at least 20, at least 25, at least 30, at least 40, at least 50, at least 100, at least 150, at least 200, at least 250, at least 300, at least 400, or at least 500 nucleotides (e.g., DNA or RNA).

In other embodiments, the cargo RNA is non-covalently associated with the binding RNA. For example, the cargo RNA may associate with the binding RNA via complementary base pairing. In some embodiments, the cargo RNA is bound to the binding RNA via at least 2, at least 3, at least 4, at least 5, at least 6, at least 7, at least 8, at least 9, at least 10, at least 15, at least 20, at least 25, at least 30, at least 40, at least 50, complementary base pairs, which may be contiguous or non-contiguous. In some embodiments, the cargo RNA is bound to the binding RNA via at least 2, at least 3, at least 4, at least 5, at least 6, at least 7, at least 8, at least 9, at least 10, at least 15, at least 20, at least 25, at least 30, at least 40, at least 50 contiguous complementary base pairs.

It should be appreciated that any of the RNAs provided herein (e.g., binding RNAs, cargo RNAs, and/or binding RNAs fused to cargo RNAs) may comprise one or more modified oligonucleotides. In some embodiments, any of the RNAs described herein may be modified, e.g., comprise a modified sugar moiety, a modified internucleoside linkage, a modified nucleotide and/or combinations thereof. In some embodiments, RNA oligonucleotides of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification. In some embodiments, the nucleic acids are "locked," i.e., comprise nucleic acid analogues in which the ribose ring is "locked" by a methylene bridge connecting the 2'-O atom and the 4'-C atom.

Any of the modified chemistries or formats of RNA oligonucleotides described herein can be combined with each other, and that one, two, three, four, five, or more different types of modifications can be included within the same molecule.

In some embodiments, the RNA oligonucleotide may comprise at least one bridged nucleotide. In some embodiments, the oligonucleotide may comprise a bridged nucleotide, such as a locked nucleic acid (LNA) nucleotide, a constrained ethyl (cEt) nucleotide, or an ethylene bridged nucleic acid (ENA) nucleotide. Examples of such nucleotides are disclosed herein and known in the art. In some embodiments, the oligonucleotide comprises a nucleotide analog disclosed in one of the following United States Patent or Patent Application Publications: U.S. Pat. Nos. 7,399,845, 7,741,457, 8,022,193, 7,569,686, 7,335,765, 7,314,923, 7,335,765, and 7,816,333, US 20110009471, the entire contents of each of which are incorporated herein by reference for all purposes. The oligonucleotide may have one or more 2' O-methyl nucleotides. The oligonucleotide may consist entirely of 2' O-methyl nucleotides.

Expression Constructs

Some aspects of this invention provide expression constructs that encode any of the minimal ARRDC1 fusion proteins, TSG101 fusion proteins, or cargo fusion proteins described herein. In some embodiments, the expression constructs described herein may further encode a guide RNA (gRNA). It should be appreciated that the gRNA may be expressed under the control of the same promoter sequence or a different promoter sequence as any of the fusion proteins described herein. In some embodiments, an expression construct encoding a gRNA may be co-expressed with any of the expression constructs described herein.

In some embodiments, the expression constructs described herein may further encode a gene product or gene products that induce or facilitate the generation of ARMMs in cells harboring such a construct. In some embodiments, the expression constructs encode a minimal ARRDC1 protein, or variant thereof, and/or a TSG101 protein, or variant thereof. In some embodiments, overexpression of either or both of these gene products in a cell increase the production of ARMMs in the cell, thus turning the cell into a microvesicle producing cell. In some embodiments, such an expression construct comprises at least one restriction or recombination site that allows in-frame cloning of a Cas9 sequence to be fused, either at the C-terminus, or at the N-terminus of the encoded minimal ARRDC1 and/or TSG101 protein or variant thereof.

In some embodiments, the expression construct comprises (a) a nucleotide sequence encoding a minimal ARRDC1 protein, or variant thereof, operably linked to a heterologous promoter, and (b) a restriction site or a recombination site positioned adjacent to the minimal ARRDC1-encoding nucleotide sequence allowing for the insertion of a nucleotide sequence encoding an additional polypeptide in frame with the ARRDC1-encoding nucleotide sequence. In some embodiments, the expression construct comprises (a) a nucleotide sequence encoding a minimal ARRDC1 protein, or variant thereof, operably linked to a heterologous promoter, and (b) a restriction site or a recombination site positioned adjacent to the minimal ARRDC1-encoding nucleotide sequence allowing for the insertion of a Cas9 or Cas9 variant sequence in frame with the minimal ARRDC1-encoding nucleotide sequence. Some aspects of this invention provide an expression construct comprising (a) a nucleotide sequence encoding a TSG101 protein, or variant thereof, operably linked to a heterologous promoter, and (b) a restriction site or a recombination site positioned adjacent to the TSG101-encoding nucleotide sequence allowing for the insertion of a Cas9 or Cas9 variant sequence in frame with the TSG101-encoding nucleotide sequence.

The expression constructs may encode a cargo protein fused to at least one WW domain. In some embodiments, the expression constructs encode a Cas9 protein, or variant thereof, fused to at least one WW domain, or variant thereof. Any of the expression constructs, described herein, may encode any WW domain or variant thereof. For example, the expression constructs may comprise any nucleotide sequence capable of encoding a WW domain or variant thereof from the poly peptide sequence (SEQ ID NO: 6); (SEQ ID NO: 7); (SEQ ID NO: 8); (SEQ ID NO: 9); (SEQ ID NO: 10); (SEQ ID NO: 11); (SEQ ID NO: 12); (SEQ ID NO: 13); (SEQ ID NO: 14); (SEQ ID NO: 18) or (SEQ ID NO: 19).

The expression constructs, described herein, may comprise any nucleic acid sequence capable of encoding a WW domain or variant thereof. For example, a nucleic acid sequence encoding a WW domain or WW domain variant may be from the human ubiquitin ligase WWP1, WWP2, Nedd4-1, Nedd4-2, Smurf1, Smurf2, ITCH, NEDL1, or NEDL2. Exemplary nucleic acid sequences of WW domain containing proteins are listed below. It should be appreciated that any of the nucleic acids encoding WW domains or WW domain variants of the exemplary proteins may be used in the invention, described herein, and are not meant to be limiting.

Human WWP1 nucleic acid sequence (uniprot.org/uniprot/Q9H0M0).
(SEQ ID NO: 23)

GAATTCGCGGCCGCGTCGACCGCTTCTGTGGCCACGGCAGATGAAACAGAAAGGCTAAAG

AGGGCTGGAGTCAGGGGACTTCTCTTCCACCAGCTTCACGGTGATGATATGGCATCTGCC

AGCTCTAGCCGGGCAGGAGTGGCCCTGCCTTTTGAGAAGTCTCAGCTCACTTTGAAAGTG

GTGTCCGCAAAGCCCAAGGTGCATAATCGTCAACCTCGAATTAACTCCTACGTGGAGGTG

GCGGTGGATGGACTCCCCAGTGAGACCAAGAAGACTGGGAAGCGCATTGGGAGCTCTGAG

CTTCTCTGGAATGAGATCATCATTTTGAATGTCACGGCACAGAGTCATTTAGATTTAAAG

GTCTGGAGCTGCCATACCTTGAGAAATGAACTGCTAGGCACCGCATCTGTCAACCTCTCC

AACGTCTTGAAGAACAATGGGGGCAAAATGGAGAACATGCAGCTGACCCTGAACCTGCAG

ACGGAGAACAAAGGCAGCGTTGTCTCAGGCGGAAAACTGACAATTTTCCTGGACGGGCCA

ACTGTTGATCTGGGAAATGTGCCTAATGGCAGTGCCCTGACAGATGGATCACAGCTGCCT

TCGAGAGACTCCAGTGGAACAGCAGTAGCTCCAGAGAACCGGCACCAGCCCCCCAGCACA

AACTGCTTTGGTGGAAGATCCCGGACGCACAGACATTCGGGTGCTTCAGCCAGAACAACC

CCAGCAACCGGCGAGCAAAGCCCCGGTGCTCGGAGCCGGCACCGCCAGCCCGTCAAGAAC

TCAGGCCACAGTGGCTTGGCCAATGGCACAGTGAATGATGAACCCACAACAGCCACTGAT

CCCGAAGAACCTTCCGTTGTTGGTGTGACGTCCCCACCTGCTGCACCCTTGAGTGTGACC

-continued

CCGAATCCCAACACGACTTCTCTCCCTGCCCCAGCCACACCGGCTGAAGGAGAGGAACCC

AGCACTTCGGGTACACAGCAGCTCCCAGCGGCTGCCCAGGCCCCCGACGCTCTGCCTGCT

GGATGGGAACAGCGAGAGCTGCCCAACGGACGTGTCTATTATGTTGACCACAATACCAAG

ACCACCACCTGGGAGCGGCCCCTTCCTCCAGGCTGGGAAAAACGCACAGATCCCCGAGGC

AGGTTTTACTATGTGGATCACAATACTCGGACCACCACCTGGCAGCGTCCGACCGCGGAG

TACGTGCGCAACTATGAGCAGTGGCAGTCGCAGCGGAATCAGCTCCAGGGGGCCATGCAG

CACTTCAGCCAAAGATTCCTATACCAGTTTTGGAGTGCTTCGACTGACCATGATCCCCTG

GGCCCCCTCCCTCCTGGTTGGGAGAAAAGACAGGACAATGGACGGGTGTATTACGTGAAC

CATAACACTCGCACGACCCAGTGGGAGGATCCCCGGACCCAGGGGATGATCCAGGAACCA

GCTTTGCCCCCAGGATGGGAGATGAAATACACCAGCGAGGGGGTGCGATACTTTGTGGAC

CACAATACCCGCACCACCACCTTTAAGGATCCTCGCCCGGGGTTTGAGTCGGGGACGAAG

CAAGGTTCCCCTGGTGCTTATGACCGCAGTTTTCGGTGGAAGTATCACCAGTTCCGTTTC

CTCTGCCATTCAAATGCCCTACCTAGCCACGTGAAGATCAGCGTTTCCAGGCAGACGCTT

TTCGAAGATTCCTTCCAACAGATCATGAACATGAAACCCTATGACCTGCGCCGCCGGCTT

TACATCATCATGCGTGGCGAGGAGGGCCTGGACTATGGGGGCATCGCCAGAGAGTGGTTT

TTCCTCCTGTCTCACGAGGTGCTCAACCCTATGTATTGTTTATTTGAATATGCCGGAAAG

AACAATTACTGCCTGCAGATCAACCCCGCCTCCTCCATCAACCCGGACCACCTCACCTAC

TTTCGCTTTATAGGCAGATTCATCGCCATGGCGCTGTACCATGGAAAGTTCATCGACACG

GGCTTCACCCTCCCTTTCTACAAGCGGATGCTCAATAAGAGACCAACCCTGAAAGACCTG

GAGTCCATTGACCCTGAGTTCTACAACTCCATTGTCTGGATCAAAGAGAACAACCTGGAA

GAATGTGGCCTGGAGCTGTACTTCATCCAGGACATGGAGATACTGGGCAAGGTGACGACC

CACGAGCTGAAGGAGGGCGGCGAGAGCATCCGGGTCACGGAGGAGAACAAGGAAGAGTAC

ATCATGCTGCTGACTGACTGGCGTTTCACCCGAGGCGTGGAAGAGCAGACCAAAGCCTTC

CTGGATGGCTTCAACGAGGTGGCCCCGCTGGAGTGGCTGCGCTACTTTGACGAGAAAGAG

CTGGAGCTGATGCTGTGCGGCATGCAGGAGATAGACATGAGCGACTGGCAGAAGAGCACC

ATCTACCGGCACTACACCAAGAACAGCAAGCAGATCCAGTGGTTCTGGCAGGTGGTGAAG

GAGATGGACAACGAGAAGAGGATCCGGCTGCTGCAGTTTGTCACCGGTACCTGCCGCCTG

CCCGTCGGGGGATTTGCCGAACTCATCGGTAGCAACGGACCACAGAAGTTTTGCATTGAC

AAAGTTGGCAAGGAAACCTGGCTGCCCAGAAGCCACACCTGCTTCAACCGTCTGGATCTT

CCACCCTACAAGAGCTACGAACAGCTGAGAGAGAAGCTGCTGTATGCCATTGAGGAGACC

GAGGGCTTTGGACAGGAGTAACCGAGGCCGCCCCTCCCACGCCCCCCAGCGCACATGTAG

TCCTGAGTCCTCCCTGCCTGAGAGGCCACTGGCCCCGCAGCCCTTGGGAGGCCCCCGTGG

ATGTGGCCCTGTGTGGGACCACACTGTCATCTCGCTGCTGGCAGAAAAGCCTGATCCCAG

GAGGCCCTGCAGTTCCCCCGACCCGCGGATGGCAGTCTGGAATAAAGCCCCCTAGTTGCC

TTTGGCCCCACCTTTGCAAAGTTCCAGAGGGCTGACCCTCTCTGCAAAACTCTCCCCTGT

CCTCTAGACCCCACCCTGGGTGTATGTGAGTGTGCAAGGGAAGGTGTTGCATCCCCAGGG

GCTGCCGCAGAGGCCGGAGACCTCCTGGACTAGTTCGGCGAGGAGACTGGCCACTGGGGG

TGGCTGTTCGGGACTGAGAGCGCCAAGGGTCTTTGCCAGCAAAGGAGGTTCTGCCTGTAA

TTGAGCCTCTCTGATGATGGAGATGAAGTGAAGGTCTGAGGGACGGGCCCTGGGGCTAGG

CCATCTCTGCCTGCCTCCCTAGCAGGCGCCAGCGGTGGAGGCTGAGTCGCAGGACACATG

-continued

CCGGCCAGTTAATTCATTCTCAGCAAATGAAGGTTTGTCTAAGCTGCCTGGGTATCCACG

GGACAAAAACAGCAAACTCCCTCCAGACTTTGTCCATGTTATAAACTTGAAAGTTGGTTG

TTGTTTGTTAGGTTTGCCAGGTTTTTTTGTTTACGCCTGCTGTCACTTTCCTGTC

Human WWP2 nucleic acid sequence (uniprot.org/uniprot/O00308).

(SEQ ID NO: 24)

GAATTCGCGGCCGCGTCGACCGCTTCTGTGGCCACGGCAGATGAAACAGAAAGGCTAAAG

AGGGCTGGAGTCAGGGGACTTCTCTTCCACCAGCTTCACGGTGATGATATGGCATCTGCC

AGCTCTAGCCGGGCAGGAGTGGCCCTGCCTTTTGAGAAGTCTCAGCTCACTTTGAAAGTG

GTGTCCGCAAAGCCCAAGGTGCATAATCGTCAACCTCGAATTAACTCCTACGTGGAGGTG

GCGGTGGATGGACTCCCCAGTGAGACCAAGAAGACTGGGAAGCGCATTGGGAGCTCTGAG

CTTCTCTGGAATGAGATCATCATTTTGAATGTCACGGCACAGAGTCATTTAGATTTAAAG

GTCTGGAGCTGCCATACCTTGAGAAATGAACTGCTAGGCACCGCATCTGTCAACCTCTCC

AACGTCTTGAAGAACAATGGGGGCAAAATGGAGAACATGCAGCTGACCCTGAACCTGCAG

ACGGAGAACAAAGGCAGCGTTGTCTCAGGCGGAAAACTGACAATTTTCCTGGACGGGCCA

ACTGTTGATCTGGGAAATGTGCCTAATGGCAGTGCCCTGACAGATGGATCACAGCTGCCT

TCGAGAGACTCCAGTGGAACAGCAGTAGCTCCAGAGAACCGGCACCAGCCCCCCAGCACA

AACTGCTTTGGTGGAAGATCCCGGACGCACAGACATTCGGGTGCTTCAGCCAGAACAACC

CCAGCAACCGGCGAGCAAAGCCCCGGTGCTCGGAGCCGGCACCGCCAGCCCGTCAAGAAC

TCAGGCCACAGTGGCTTGGCCAATGGCACAGTGAATGATGAACCCACAACAGCCACTGAT

CCCGAAGAACCTTCCGTTGTTGGTGTGACGTCCCCACCTGCTGCACCCTTGAGTGTGACC

CCGAATCCCAACACGACTTCTCTCCCTGCCCCAGCCACACCGGCTGAAGGAGAGGAACCC

AGCACTTCGGGTACACAGCAGCTCCCAGCGGCTGCCCAGGCCCCCGACGCTCTGCCTGCT

GGATGGGAACAGCGAGAGCTGCCCAACGGACGTGTCTATTATGTTGACCACAATACCAAG

ACCACCACCTGGGAGCGGCCCCTTCCTCCAGGCTGGGAAAAACGCACAGATCCCCGAGGC

AGGTTTTACTATGTGGATCACAATACTCGGACCACCACCTGGCAGCGTCCGACCGCGGAG

TACGTGCGCAACTATGAGCAGTGGCAGTCGCAGCGGAATCAGCTCCAGGGGGCCATGCAG

CACTTCAGCCAAAGATTCCTATACCAGTTTTGGAGTGCTTCGACTGACCATGATCCCCTG

GGCCCCCTCCCTCCTGGTTGGGAGAAAAGACAGGACAATGGACGGGTGTATTACGTGAAC

CATAACACTCGCACGACCCAGTGGGAGGATCCCCGGACCCAGGGGATGATCCAGGAACCA

GCTTTGCCCCCAGGATGGGAGATGAAATACACCAGCGAGGGGGTGCGATACTTTGTGGAC

CACAATACCCGCACCACCACCTTTAAGGATCCTCGCCCGGGGTTTGAGTCGGGGACGAAG

CAAGGTTCCCCTGGTGCTTATGACCGCAGTTTTCGGTGGAAGTATCACCAGTTCCGTTTC

CTCTGCCATTCAAATGCCCTACCTAGCCACGTGAAGATCAGCGTTTCCAGGCAGACGCTT

TTCGAAGATTCCTTCCAACAGATCATGAACATGAAACCCTATGACCTGCGCCGCCGGCTT

TACATCATCATGCGTGGCGAGGAGGGCCTGGACTATGGGGGCATCGCCAGAGAGTGGTTT

TTCCTCCTGTCTCACGAGGTGCTCAACCCTATGTATTGTTTATTTGAATATGCCGGAAAG

AACAATTACTGCCTGCAGATCAACCCCGCCTCCTCCATCAACCCGGACCACCTCACCTAC

TTTCGCTTTATAGGCAGATTCATCGCCATGGCGCTGTACCATGGAAAGTTCATCGACACG

GGCTTCACCCTCCCTTTCTACAAGCGGATGCTCAATAAGAGACCAACCCTGAAAGACCTG

GAGTCCATTGACCCTGAGTTCTACAACTCCATTGTCTGGATCAAAGAGAACAACCTGGAA

GAATGTGGCCTGGAGCTGTACTTCATCCAGGACATGGAGATACTGGGCAAGGTGACGACC

CACGAGCTGAAGGAGGGCGGCGAGAGCATCCGGGTCACGGAGGAGAACAAGGAAGAGTAC

-continued

ATCATGCTGCTGACTGACTGGCGTTTCACCCGAGGCGTGGAAGAGCAGACCAAAGCCTTC

CTGGATGGCTTCAACGAGGTGGCCCCGCTGGAGTGGCTGCGCTACTTTGACGAGAAAGAG

CTGGAGCTGATGCTGTGCGGCATGCAGGAGATAGACATGAGCGACTGGCAGAAGAGCACC

ATCTACCGGCACTACACCAAGAACAGCAAGCAGATCCAGTGGTTCTGGCAGGTGGTGAAG

GAGATGGACAACGAGAAGAGGATCCGGCTGCTGCAGTTTGTCACCGGTACCTGCCGCCTG

CCCGTCGGGGGATTTGCCGAACTCATCGGTAGCAACGGACCACAGAAGTTTTGCATTGAC

AAAGTTGGCAAGGAAACCTGGCTGCCCAGAAGCCACACCTGCTTCAACCGTCTGGATCTT

CCACCCTACAAGAGCTACGAACAGCTGAGAGAGAAGCTGCTGTATGCCATTGAGGAGACC

GAGGGCTTTGGACAGGAGTAACCGAGGCCGCCCCTCCCACGCCCCCCAGCGCACATGTAG

TCCTGAGTCCTCCCTGCCTGAGAGGCCACTGGCCCCGCAGCCCTTGGGAGGCCCCCGTGG

ATGTGGCCCTGTGTGGGACCACACTGTCATCTCGCTGCTGGCAGAAAAGCCTGATCCCAG

GAGGCCCTGCAGTTCCCCCGACCCGCGGATGGCAGTCTGGAATAAAGCCCCCTAGTTGCC

TTTGGCCCCACCTTTGCAAAGTTCCAGAGGGCTGACCCTCTCTGCAAAACTCTCCCCTGT

CCTCTAGACCCCACCCTGGGTGTATGTGAGTGTGCAAGGGAAGGTGTTGCATCCCCAGGG

GCTGCCGCAGAGGCCGGAGACCTCCTGGACTAGTTCGGCGAGGAGACTGGCCACTGGGGG

TGGCTGTTCGGGACTGAGAGCGCCAAGGGTCTTTGCCAGCAAAGGAGGTTCTGCCTGTAA

TTGAGCCTCTCTGATGATGGAGATGAAGTGAAGGTCTGAGGGACGGGCCCTGGGGCTAGG

CCATCTCTGCCTGCCTCCCTAGCAGGCGCCAGCGGTGGAGGCTGAGTCGCAGGACACATG

CCGGCCAGTTAATTCATTCTCAGCAAATGAAGGTTTGTCTAAGCTGCCTGGGTATCCACG

GGACAAAAACAGCAAACTCCCTCCAGACTTTGTCCATGTTATAAACTTGAAAGTTGGTTG

TTGTTTGTTAGGTTTGCCAGGTTTTTTTGTTTACGCCTGCTGTCACTTTCCTGTC

Human Nedd4-1 nucleic acid sequence (uniprot.org/uniprot/P46934).
(SEQ ID NO: 25)

ACAGTTGCCTGCCCTGGGCGGGGGCGAGCGCGTCCGGTTTGCTGGAAGCGTTCGGAAATG

GCAACTTGCGCGGTGGAGGTGTTCGGGCTCCTGGAGGACGAGGAAAATTCACGAATTGTG

AGAGTAAGAGTTATAGCCGGAATAGGCCTTGCCAAGAAGGATATATTGGGAGCTAGTGAT

CCTTACGTGAGAGTGACGTTATATGACCCAATGAATGGAGTTCTTACAAGTGTGCAAACA

AAAACCATTAAAAAGAGTTTGAATCCAAAGTGGAATGAAGAAATATTATTCAGAGTTCAT

CCTCAGCAGCACCGGCTTCTTTTTGAAGTGTTTGACGAAAACCGATTGACAAGAGATGAT

TTCCTAGGTCAAGTGGATGTTCCACTTTATCCATTACCGACAGAAAATCCAAGATTGGAG

AGACCATATACATTTAAGGATTTTGTTCTTCATCCAAGAAGTCACAAATCAAGAGTTAAA

GGTTATCTGAGACTAAAAATGACTTATTTACCTAAAACCAGTGGCTCAGAAGATGATAAT

GCAGAACAGGCTGAGGAATTAGAGCCTGGCTGGGTTGTTTTGGACCAACCAGATGCTGCT

TGCCATTTGCAGCAACAACAAGAACCTTCTCCTCTACCTCCAGGGTGGGAAGAGAGGCAG

GATATCCTTGGAAGGACCTATTATGTAAACCATGAATCTAGAAGAACACAGTGGAAAAGA

CCAACCCCTCAGGACAACCTAACAGATGCTGAGAATGGCAACATTCAACTGCAAGCACAA

CGTGCATTTACCACCAGGCGGCAGATATCCGAGGAAACAGAAAGTGTTGACAACCAAGAG

TCTTCCGAGAACTGGGAAATTATAAGAGAAGATGAAGCCACCATGTATAGCAGCCAGGCC

TTCCCATCACCTCCACCGTCAAGTAACTTGGATGTTCCAACTCATCTTGCAGAAGAATTG

AATGCCAGACTCACCATTTTTGGAAATTCAGCCGTGAGCCAGCCAGCATCGAGCTCAAAT

CATTCCAGCAGAAGAGGCAGCTTACAAGCCTATACTTTTGAGGAACAACCTACACTTCCT

-continued

GTGCTTTTGCCTACTTCATCTGGATTACCACCAGGTTGGGAAGAAAAACAAGATGAAAGA

GGAAGATCATATTATGTAGATCACAATTCCAGAACGACTACTTGGACAAAGCCCACTGTA

CAGGCCACAGTGGAGACCAGTCAGCTGACCTCAAGCCAGAGTTCTGCAGGCCCTCAATCA

CAAGCCTCCACCAGTGATTCAGGCCAGCAGGTGACCCAGCCATCTGAAATTGAGCAAGGA

TTCCTTCCTAAAGGCTGGGAAGTCCGGCATGCACCAAATGGGAGGCCTTTCTTTATTGAC

CACAACACTAAAACCACCACCTGGGAAGATCCAAGATTGAAAATTCCAGCCCATCTGAGA

GGAAAGACATCACTTGATACTTCCAATGATCTAGGGCCTTTACCTCCAGGATGGGAAGAG

AGAACTCACACAGATGGAAGAATCTTCTACATAAATCACAATATAAAAAGAACACAATGG

GAAGATCCTCGGTTGGAGAATGTAGCAATAACTGGACCAGCAGTGCCCTACTCCAGGGAT

TACAAAAGAAAGTATGAGTTCTTCCGAAGAAAGTTGAAGAAGCAGAATGACATTCCAAAC

AAATTTGAAATGAAACTTCGCCGAGCAACTGTTCTTGAAGACTCTTACCGGAGAATTATG

GGTGTCAAGAGAGCAGACTTCCTGAAGGCTCGACTGTGGATTGAGTTTGATGGTGAAAAG

GGATTGGATTATGGAGGAGTTGCCAGAGAATGGTTCTTCCTGATCTCAAAGGAAATGTTT

AACCCTTATTATGGGTTGTTTGAATATTCTGCTACGGACAATTATACCCTACAGATAAAT

CCAAACTCTGGATTGTGTAACGAAGATCACCTCTCTTACTTCAAGTTTATTGGTCGGGTA

GCTGGAATGGCAGTTTATCATGGCAAACTGTTGGATGGTTTTTTCATCCGCCCATTTTAC

AAGATGATGCTTCACAAACCAATAACCCTTCATGATATGGAATCTGTGGATAGTGAATAT

TACAATTCCCTAAGATGGATTCTTGAAAATGACCCAACAGAATTGGACCTCAGGTTTATC

ATAGATGAAGAACTTTTTGGACAGACACATCAACATGAGCTGAAAAATGGTGGATCAGAA

ATAGTTGTCACCAATAAGAACAAAAAGGAATATATTTATCTTGTAATACAATGGCGATTT

GTAAACCGAATCCAGAAGCAAATGGCTGCTTTTAAAGAGGGATTCTTTGAACTAATACCA

CAGGATCTCATCAAAATTTTTGATGAAAATGAACTAGAGCTTCTTATGTGTGGACCGGGA

GATGTTGATGTGAATGACTGGAGGGAACATACAAAGTATAAAAATGGCTACAGTGCAAAT

CATCAGGTTATACAGTGGTTTTGGAAGGCTGTTTTAATGATGGATTCAGAAAAAAGAATA

AGATTACTTCAGTTTGTCACTGGCACATCTCGGGTGCCTATGAATGGATTTGCTGAACTA

TACGGTTCAAATGGACCACAGTCATTTACAGTTGAACAGTGGGGTACTCCTGAAAAGCTG

CCAAGAGCTCATACCTGTTTTAATCGCCTGGACTTGCCACCTTATGAATCATTTGAAGAA

TTATGGGATAAACTTCAGATGGCAATTGAAAACACCCAGGGCTTTGATGGAGTTGATTAG

ATTACAAATAACAATCTGTAGTGTTTTTACTGCCATAGTTTTATAACCAAAATCTTGACT

TAAAATTTTCCGGGGAACTACTAAAATGTGGCCACTGAGTCTTCCCAGATCTTGAAGAAA

ATCATATAAAAAGCATTTGAAGAAATAGTACGAC

Human Nedd4-2 nucleic acid sequence (>gi|345478679|ref|NM_015277.5| *Homo sapiens* neural precursor cell expressed, developmentally down-regulated 4-like, E3 ubiquitin protein ligase (NEDD4L), transcript variant d, mRNA).

(SEQ ID NO: 26)

ATGGCGACCGGGCTCGGGGAGCCGGTCTATGGACTTTCCGAAGACGAGGGAGAGTCCCGTATTCTCA

GAGTAAAAGTTGTTTCTGGAATTGATCTCGCCAAAAAGGACATCTTTGGAGCCAGTGATCCGTATGTGAA

ACTTTCATTGTACGTAGCGGATGAGAATAGAGAACTTGCTTTGGTCCAGACAAAAACAATTAAAAAGACA

CTGAACCCAAAATGGAATGAAGAATTTTATTTCAGGGTAAACCCATCTAATCACAGACTCCTATTTGAAG

TATTTGACGAAAATAGACTGACACGAGACGACTTCCTGGGCCAGGTGGACGTGCCCCTTAGTCACCTTCC

GACAGAAGATCCAACCATGGAGCGACCCTATACATTTAAGGACTTTCTCCTCAGACCAAGAAGTCATAAG

TCTCGAGTTAAGGGATTTTTGCGATTGAAAATGGCCTATATGCCAAAAAATGGAGGTCAAGATGAAGAAA

-continued

ACAGTGACCAGAGGGATGACATGGAGCATGGATGGGAAGTTGTTGACTCAAATGACTCGGCTTCTCAGCA

CCAAGAGGAACTTCCTCCTCCTCCTCTGCCTCCCGGGTGGGAAGAAAAAGTGGACAATTTAGGCCGAACT

TACTATGTCAACCACAACAACCGGACCACTCAGTGGCACAGACCAAGCCTGATGGACGTGTCCTCGGAGT

CGGACAATAACATCAGACAGATCAACCAGGAGGCAGCACACCGGCGCTTCCGCTCCCGCAGGCACATCAG

CGAAGACTTGGAGCCCGAGCCCTCGGAGGGCGGGGATGTCCCCGAGCCTTGGGAGACCATTTCAGAGGAA

GTGAATATCGCTGGAGACTCTCTCGGTCTGGCTCTGCCCCCACCACCGGCCTCCCCAGGATCTCGGACCA

GCCCTCAGGAGCTGTCAGAGGAACTAAGCAGAAGGCTTCAGATCACTCCAGACTCCAATGGGGAACAGTT

CAGCTCTTTGATTCAAAGAGAACCCTCCTCAAGGTTGAGGTCATGCAGTGTCACCGACGCAGTTGCAGAA

CAGGGCCATCTACCACCGCCATCAGTGGCCTATGTACATACCACGCCGGGTCTGCCTTCAGGCTGGGAAG

AAAGAAAAGATGCTAAGGGGCGCACATACTATGTCAATCATAACAATCGAACCACAACTTGGACTCGACC

TATCATGCAGCTTGCAGAAGATGGTGCGTCCGGATCAGCCACAAACAGTAACAACCATCTAATCGAGCCT

CAGATCCGCCGGCCTCGTAGCCTCAGCTCGCCAACAGTAACTTTATCTGCCCCGCTGGAGGGTGCCAAGG

ACTCACCCGTACGTCGGGCTGTGAAAGACACCCTTTCCAACCCACAGTCCCCACAGCCATCACCTTACAA

CTCCCCCAAACCACAACACAAAGTCACACAGAGCTTCTTGCCACCCGGCTGGGAAATGAGGATAGCGCCA

AACGGCCGGCCCTTCTTCATTGATCATAACACAAAGACTACAACCTGGGAAGATCCACGTTTGAAATTTC

CAGTACATATGCGGTCAAAGACATCTTTAAACCCCAATGACCTTGGCCCCCTTCCTCCTGGCTGGGAAGA

AAGAATTCACTTGGATGGCCGAACGTTTTATATTGATCATAATAGCAAAATTACTCAGTGGGAAGACCCA

AGACTGCAGAACCCAGCTATTACTGGTCCGGCTGTCCCTTACTCCAGAGAATTTAAGCAGAAATATGACT

ACTTCAGGAAGAAATTAAAGAAACCTGCTGATATCCCCAATAGGTTTGAAATGAAACTTCACAGAAATAA

CATATTTGAAGAGTCCTATCGGAGAATTATGTCCGTGAAAAGACCAGATGTCCTAAAAGCTAGACTGTGG

ATTGAGTTTGAATCAGAGAAAGGTCTTGACTATGGGGGTGTGGCCAGAGAATGGTTCTTCTTACTGTCCA

AAGAGATGTTCAACCCCTACTACGGCCTCTTTGAGTACTCTGCCACGGACAACTACACCCTTCAGATCAA

CCCTAATTCAGGCCTCTGTAATGAGGATCATTTGTCCTACTTCACTTTTATTGGAAGAGTTGCTGGTCTG

GCCGTATTTCATGGGAAGCTCTTAGATGGTTTCTTCATTAGACCATTTTACAAGATGATGTTGGGAAAGC

AGATAACCCTGAATGACATGGAATCTGTGGATAGTGAATATTACAACTCTTTGAAATGGATCCTGGAGAA

TGACCCTACTGAGCTGGACCTCATGTTCTGCATAGACGAAGAAAACTTTGGACAGACATATCAAGTGGAT

TTGAAGCCCAATGGGTCAGAAATAATGGTCACAAATGAAAACAAAAGGGAATATATCGACTTAGTCATCC

AGTGGAGATTTGTGAACAGGGTCCAGAAGCAGATGAACGCCTTCTTGGAGGGATTCACAGAACTACTTCC

TATTGATTTGATTAAAATTTTTGATGAAAATGAGCTGGAGTTGCTCATGTGCGGCCTCGGTGATGTGGAT

GTGAATGACTGGAGACAGCATTCTATTTACAAGAACGGCTACTGCCCAAACCACCCCGTCATTCAGTGGT

TCTGGAAGGCTGTGCTACTCATGGACGCCGAAAAGCGTATCCGGTTACTGCAGTTTGTCACAGGGACATC

GCGAGTACCTATGAATGGATTTGCCGAACTTTATGGTTCCAATGGTCCTCAGCTGTTTACAATAGAGCAA

TGGGGCAGTCCTGAGAAACTGCCCAGAGCTCACACATGCTTTAATCGCCTTGACTTACCTCCATATGAAA

CCTTTGAAGATTTACGAGAGAAACTTCTCATGGCCGTGGAAAATGCTCAAGGATTTGAAGGGGTGGATTA

A

Human Smurf1 nucleic acid sequence (uniprot.org/uniprot/Q9HCE7).
(SEQ ID NO: 27)

ATGTCGAACCCCGGGACACGCAGGAACGGCTCCAGCATCAAGATCCGTCTGACAGTGTTA

TGTGCCAAGAACCTTGCAAAGAAAGACTTCTTCAGGCTCCCTGACCCTTTTGCAAAGATT

GTCGTGGATGGGTCTGGGCAGTGCCACTCAACCGACACTGTGAAAAACACATTGGACCCA

AAGTGGAACCAGCACTATGATCTATATGTTGGGAAAACGGATTCGATAACCATTAGCGTG

TGGAACCATAAGAAAATTCACAAGAAACAGGGAGCTGGCTTCCTGGGCTGTGTGCGGCTG

-continued

CTCTCCAATGCCATCAGCAGATTAAAAGATACCGGATACCAGCGTTTGGATCTATGCAAA

CTAAACCCCTCAGATACTGATGCAGTTCGTGGCCAGATAGTGGTCAGTTTACAGACACGA

GACAGAATAGGAACCGGCGGCTCGGTGGTGGACTGCAGAGGACTGTTAGAAAATGAAGGA

ACGGTGTATGAAGACTCCGGGCCTGGGAGGCCGCTCAGCTGCTTCATGGAGGAACCAGCC

CCTTACACAGATAGCACCGGTGCTGCTGCTGGAGGAGGGAATTGCAGGTTCGTGGAGTCC

CCAAGTCAAGATCAAAGACTTCAGGCACAGCGGCTTCGAAACCCTGATGTGCGAGGTTCA

CTACAGACGCCCCAGAACCGACCACACGGCCACCAGTCCCCGGAACTGCCCGAAGGCTAC

GAACAAAGAACAACAGTCCAGGGCCAAGTTTACTTTTTGCATACACAGACTGGAGTTAGC

ACGTGGCACGACCCCAGGATACCAAGTCCCTCGGGGACCATTCCTGGGGGAGATGCAGCT

TTTCTATACGAATTCCTTCTACAAGGCCATACATCTGAGCCCAGAGACCTTAACAGTGTG

AACTGTGATGAACTTGGACCACTGCCGCCAGGCTGGGAAGTCAGAAGTACAGTTTCTGGG

AGGATATATTTTGTAGATCATAATAACCGAACAACCCAGTTTACAGACCCAAGGTTACAC

CACATCATGAATCACCAGTGCCAACTCAAGGAGCCCAGCCAGCCGCTGCCACTGCCCAGT

GAGGGCTCTCTGGAGGACGAGGAGCTTCCTGCCCAGAGATACGAAAGAGATCTAGTCCAG

AAGCTGAAAGTCCTCAGACACGAACTGTCGCTTCAGCAGCCCCAAGCTGGTCATTGCCGC

ATCGAAGTGTCCAGAGAAGAAATCTTTGAGGAGTCTTACCGCCAGATAATGAAGATGCGA

CCGAAAGACTTGAAAAAACGGCTGATGGTGAAATTCCGTGGGGAAGAAGGTTTGGATTAC

GGTGGTGTGGCCAGGGAGTGGCTTTACTTGCTGTGCCATGAAATGCTGAATCCTTATTAC

GGGCTCTTCCAGTATTCTACGGACAATATTTACATGTTGCAAATAAATCCGGATTCTTCA

ATCAACCCCGACCACTTGTCTTATTTCCACTTTGTGGGGCGGATCATGGGGCTGGCTGTG

TTCCATGGACACTACATCAACGGGGGCTTCACAGTGCCCTTCTACAAGCAGCTGCTGGGG

AAGCCCATCCAGCTCTCAGATCTGGAATCTGTGGACCCAGAGCTGCATAAGAGCTTGGTG

TGGATCCTAGAGAACGACATCACGCCTGTACTGGACCACACCTTCTGCGTGGAACACAAC

GCCTTCGGGCGGATCCTGCAGCATGAACTGAAACCCAATGGCAGAAATGTGCCAGTCACA

GAGGAGAATAAGAAAGAATACGTCCGGTTGTATGTAAACTGGAGGTTTATGAGAGGAATC

GAAGCCCAGTTCTTAGCTCTGCAGAAGGGGTTCAATGAGCTCATCCCTCAACATCTGCTG

AAGCCTTTTGACCAGAAGGAACTGGAGCTGATCATAGGCGGCCTGGATAAAATAGACTTG

AACGACTGGAAGTCGAACACGCGGCTGAAGCACTGTGTGGCCGACAGCAACATCGTGCGG

TGGTTCTGGCAAGCGGTGGAGACGTTCGATGAAGAAAGGAGGGCCAGGCTCCTGCAGTTT

GTGACTGGGTCCACGCGAGTCCCGCTCCAAGGCTTCAAGGCTTTGCAAGGTTCTACAGGC

GCGGCAGGGCCCCGGCTGTTCACCATCCACCTGATAGACGCGAACACAGACAACCTTCCG

AAGGCCCATACCTGCTTTAACCGGATCGACATTCCACCATATGAGTCCTATGAGAAGCTC

TACGAGAAGCTGCTGACAGCCGTGGAGGAGACCTGCGGGTTTGCTGTGGAGTGA

Human Smurf2 nucleic acid sequence (uniprot.org/uniprot/Q9HAU4).
(SEQ ID NO: 28)

ATGTCTAACCCCGGACGCCGGAGGAACGGGCCCGTCAAGCTGCGCCTGACAGTACTCTGT

GCAAAAAACCTGGTGAAAAAGGATTTTTTCCGACTTCCTGATCCATTTGCTAAGGTGGTG

GTTGATGGATCTGGGCAATGCCATTCTACAGATACTGTGAAGAATACGCTTGATCCAAAG

TGGAATCAGCATTATGACCTGTATATTGGAAAGTCTGATTCAGTTACGATCAGTGTATGG

AATCACAAGAAGATCCATAAGAAACAAGGTGCTGGATTTCTCGGTTGTGTTCGTCTTCTT

TCCAATGCCATCAACCGCCTCAAAGACACTGGTTATCAGAGGTTGGATTTATGCAAACTC

-continued

GGGCCAAATGACAATGATACAGTTAGAGGACAGATAGTAGTAAGTCTTCAGTCCAGAGAC

CGAATAGGCACAGGAGGACAAGTTGTGGACTGCAGTCGTTTATTTGATAACGATTTACCA

GACGGCTGGGAAGAAAGGAGAACCGCCTCTGGAAGAATCCAGTATCTAAACCATATAACA

AGAACTACGCAATGGGAGCGCCCAACACGACCGGCATCCGAATATTCTAGCCCTGGCAGA

CCTCTTAGCTGCTTTGTTGATGAGAACACTCCAATTAGTGGAACAAATGGTGCAACATGT

GGACAGTCTTCAGATCCCAGGCTGGCAGAGAGGAGAGTCAGGTCACAACGACATAGAAAT

TACATGAGCAGAACACATTTACATACTCCTCCAGACCTACCAGAAGGCTATGAACAGAGG

ACAACGCAACAAGGCCAGGTGTATTTCTTACATACACAGACTGGTGTGAGCACATGGCAT

GATCCAAGAGTGCCCAGGGATCTTAGCAACATCAATTGTGAAGAGCTTGGTCCATTGCCT

CCTGGATGGGAGATCCGTAATACGGCAACAGGCAGAGTTTATTTCGTTGACCATAACAAC

AGAACAACACAATTTACAGATCCTCGGCTGTCTGCTAACTTGCATTTAGTTTTAAATCGG

CAGAACCAATTGAAAGACCAACAGCAACAGCAAGTGGTATCGTTATGTCCTGATGACACA

GAATGCCTGACAGTCCCAAGGTACAAGCGAGACCTGGTTCAGAAACTAAAAATTTTGCGG

CAAGAACTTTCCCAACAACAGCCTCAGGCAGGTCATTGCCGCATTGAGGTTTCCAGGGAA

GAGATTTTTGAGGAATCATATCGACAGGTCATGAAAATGAGACCAAAAGATCTCTGGAAG

CGATTAATGATAAAATTTCGTGGAGAAGAAGGCCTTGACTATGGAGGCGTTGCCAGGGAA

TGGTTGTATCTCTTGTCACATGAAATGTTGAATCCATACTATGGCCTCTTCCAGTATTCA

AGAGATGATATTTATACATTGCAGATCAATCCTGATTCTGCAGTTAATCCGGAACATTTA

TCCTATTTCCACTTTGTTGGACGAATAATGGGAATGGCTGTGTTTCATGGACATTATATT

GATGGTGGTTTCACATTGCCTTTTTATAAGCAATTGCTTGGGAAGTCAATTACCTTGGAT

GACATGGAGTTAGTAGATCCGGATCTTCACAACAGTTTAGTGTGGATACTTGAGAATGAT

ATTACAGGTGTTTTGGACCATACCTTCTGTGTTGAACATAATGCATATGGTGAAATTATT

CAGCATGAACTTAAACCAAATGGCAAAAGTATCCCTGTTAATGAAGAAAATAAAAAAGAA

TATGTCAGGCTCTATGTGAACTGGAGATTTTTACGAGGCATTGAGGCTCAATTCTTGGCT

CTGCAGAAAGGATTTAATGAAGTAATTCCACAACATCTGCTGAAGACATTTGATGAGAAG

GAGTTAGAGCTCATTATTTGTGGACTTGGAAAGATAGATGTTAATGACTGGAAGGTAAAC

ACCCGGTTAAAACACTGTACACCAGACAGCAACATTGTCAAATGGTTCTGGAAAGCTGTG

GAGTTTTTTGATGAAGAGCGACGAGCAAGATTGCTTCAGTTTGTGACAGGATCCTCTCGA

GTGCCTCTGCAGGGCTTCAAAGCATTGCAAGGTGCTGCAGGCCCGAGACTCTTTACCATA

CACCAGATTGATGCCTGCACTAACAACCTGCCGAAAGCCCACACTTGCTTCAATCGAATA

GACATTCCACCCTATGAAAGCTATGAAAAGCTATATGAAAAGCTGCTAACAGCCATTGAA

GAAACATGTGGATTTGCTGTGGAATGA

Human ITCH nucleic acid sequence (uniprot.org/uniprot/Q96J02).

(SEQ ID NO: 29)

GGAGTCGCCGCCGCCCCGAGTTCCGGTACCATGCATTTCACGGTGGCCTTGTGGAGACAA

CGCCTTAACCCAAGGAAGTGACTCAAACTGTGAGAACTCCAGGTTTTCCAACCTATTGGT

GGTATGTCTGACAGTGGATCACAACTTGGTTCAATGGGTAGCCTCACCATGAAATCACAG

CTTCAGATCACTGTCATCTCAGCAAAACTTAAGGAAAATAAGAAGAATTGGTTTGGACCA

AGTCCTTACGTAGAGGTCACAGTAGATGGACAGTCAAAGAAGACAGAAAAATGCAACAAC

ACAAACAGTCCCAAGTGGAAGCAACCCCTTACAGTTATCGTTACCCCTGTGAGTAAATTA

CATTTTCGTGTGTGGAGTCACCAGACACTGAAATCTGATGTTTTGTTGGGAACTGCTGCA

TTAGATATTTATGAAACATTAAAGTCAAACAATATGAAACTTGAAGAAGTAGTTGTGACT

-continued

TTGCAGCTTGGAGGTGACAAAGAGCCAACAGAGACAATAGGAGACTTGTCAATTTGTCTT
GATGGGCTACAGTTAGAGTCTGAAGTTGTTACCAATGGTGAAACTACATGTTCAGAAAGT
GCTTCTCAGAATGATGATGGCTCCAGATCCAAGGATGAAACAAGAGTGAGCACAAATGGA
TCAGATGACCCTGAAGATGCAGGAGCTGGTGAAAATAGGAGAGTCAGTGGGAATAATTCT
CCATCACTCTCAAATGGTGGTTTTAAACCTTCTAGACCTCCAAGACCTTCACGACCACCA
CCACCCACCCCACGTAGACCAGCATCTGTCAATGGTTCACCATCTGCCACTTCTGAAAGT
GATGGGTCTAGTACAGGCTCTCTGCCGCCGACAAATACAAATACAAATACATCTGAAGGA
GCAACATCTGGATTAATAATTCCTCTTACTATATCTGGAGGCTCAGGCCCTAGGCCATTA
AATCCTGTAACTCAAGCTCCCTTGCCACCTGGTTGGGAGCAGAGAGTGGACCAGCACGGG
CGAGTTTACTATGTAGATCATGTTGAGAAAAGAACAACATGGGATAGACCAGAACCTCTA
CCTCCTGGCTGGGAACGGCGGGTTGACAACATGGGACGTATTTATTATGTTGACCATTTC
ACAAGAACAACAACGTGGCAGAGGCCAACACTGGAATCCGTCCGGAACTATGAACAATGG
CAGCTACAGCGTAGTCAGCTTCAAGGAGCAATGCAGCAGTTTAACCAGAGATTCATTTAT
GGGAATCAAGATTTATTTGCTACATCACAAAGTAAAGAATTTGATCCTCTTGGTCCATTG
CCACCTGGATGGGAGAAGAGAACAGACAGCAATGGCAGAGTATATTTCGTCAACCACAAC
ACACGAATTACACAATGGGAAGACCCCAGAAGTCAAGGTCAATTAAATGAAAAGCCCTTA
CCTGAAGGTTGGGAAATGAGATTCACAGTGGATGGAATTCCATATTTTGTGGACCACAAT
AGAAGAACTACCACCTATATAGATCCCCGCACAGGAAAATCTGCCCTAGACAATGGACCT
CAGATAGCCTATGTTCGGGACTTCAAAGCAAAGGTTCAGTATTTCCGGTTCTGGTGTCAG
CAACTGGCCATGCCACAGCACATAAAGATTACAGTGACAAGAAAAACATTGTTTGAGGAT
TCCTTTCAACAGATAATGAGCTTCAGTCCCCAAGATCTGCGAAGACGTTTGTGGGTGATT
TTTCCAGGAGAAGAAGGTTTAGATTATGGAGGTGTAGCAAGAGAATGGTTCTTTCTTTTG
TCACATGAAGTGTTGAACCCAATGTATTGCCTGTTTGAATATGCAGGGAAGGATAACTAC
TGCTTGCAGATAAACCCCGCTTCTTACATCAATCCAGATCACCTGAAATATTTTCGTTTT
ATTGGCAGATTTATTGCCATGGCTCTGTTCCATGGGAAATTCATAGACACGGGTTTTTCT
TTACCATTCTATAAGCGTATCTTGAACAAACCAGTTGGACTCAAGGATTTAGAATCTATT
GATCCAGAATTTTACAATTCTCTCATCTGGGTTAAGGAAAACAATATTGAGGAATGTGAT
TTGGAAATGTACTTCTCCGTTGACAAAGAAATTCTAGGTGAAATTAAGAGTCATGATCTG
AAACCTAATGGTGGCAATATTCTTGTAACAGAAGAAAATAAAGAGGAATACATCAGAATG
GTAGCTGAGTGGAGGTTGTCTCGAGGTGTTGAAGAACAGACACAAGCTTTCTTTGAAGGC
TTTAATGAAATTCTTCCCCAGCAATATTTGCAATACTTTGATGCAAAGGAATTAGAGGTC
CTTTTATGTGGAATGCAAGAGATTGATTTGAATGACTGGCAAAGACATGCCATCTACCGT
CATTATGCAAGGACCAGCAAACAAATCATGTGGTTTTGGCAGTTTGTTAAAGAAATTGAT
AATGAGAAGAGAATGAGACTTCTGCAGTTTGTTACTGGAACCTGCCGATTGCCAGTAGGA
GGATTTGCTGATCTCATGGGGAGCAATGGACCACAGAAATTCTGCATTGAAAAAGTTGGG
AAAGAAAATTGGCTACCCAGAAGTCATACCTGTTTTAATCGCCTGGACCTGCCACCATAC
AAGAGCTATGAGCAACTGAAGGAAAAGCTGTTGTTTGCCATAGAAGAAACAGAAGGATTT
GGACAAGAGTAACTTCTGAGAACTTGCACCATGAATGGGCAAGAACTTATTTGCAATGTT
TGTCCTTCTCTGCCTGTTGCACATCTTGTAAAATTGGACAATGGCTCTTTAGAGAGTTAT
CTGAGTGTAAGTAAATTAATGTTCTCATTTAAAAAAAAAAAAAAAAAAA

-continued

Human NEDL1 nucleic acid sequence (uniprot.org/uniprot/Q76N89).

(SEQ ID NO: 30)

GCGCATCAGGUGCTGTTGTTGGAGUUGGAACACCGTGCGACTCLGACCGAACCGGCCCCC

TCCTCGCGCACACACTCGCCGAGCCGCGCGCGCCCCTCCGCCGTGACAGTGGCCGTGGGG

TCCGCTCTCTCGGGGCACCCGGCAGCCAGAGCGCAGCGAGAGCGGGCGGTCGCCAGGGTC

CCCTCCCCAGCCAGTCCCAGGCGCCCGGTGCACTATGCGGGGCACGTGCGCCCCCCAGCT

CTAATCTGCGCGCTGACAGGAGCATGATCTGTGCCCAGGCCAGGGCTGCCAAGGAATTGA

TGCGCGTACACGTGGTGGGTCATTATGCTGCTACACCTGTGTAGTGTGAAGAATCTGTAC

CAGAACAGGTTTTTAGGCCTGGCCGCCATGGCGTCTCCTTCTAGAAACTCCCAGAGCCGA

CGCCGGTGCAAGGAGCCGCTCCGATACAGCTACAACCCCGACCAGTTCCACAACATGGAC

CTCAGGGGCGGCCCCCACGATGGCGTCACCATTCCCCGCTCCACCAGCGACACTGACCTG

GTCACCTCGGACAGCCGCTCCACGCTCATGGTCAGCAGCTCCTACTATTCCATCGGGCAC

TCTCAGGACCTGGTCATCCACTGGGACATAAAGGAGGAAGTGGACGCTGGGGACTGGATT

GGCATGTACCTCATTGATGAGGTCTTGTCCGAAAACTTTCTGGACTATAAAAACCGTGGA

GTCAATGGTTCTCATCGGGGCCAGATCATCTGGAAGATCGATGCCAGCTCGTACTTTGTG

GAACCTGAAACTAAGATCTGCTTCAAATACTACCATGGAGTGAGTGGGGCCCTGCGAGCA

ACCACCCCCAGTGTCACGGTCAAAAACTCGGCAGCTCCTATTTTTAAAAGCATTGGTGCT

GATGAGACCGTCCAAGGACAAGGAAGTCGGAGGCTGATCAGCTTCTCTCTCTCAGATTTC

CAAGCCATGGGGTTGAAGAAAGGGATGTTTTTCAACCCAGACCCTTATCTGAAGATTTCC

ATTCAGCCTGGGAAACACAGCATCTTCCCCGCCCTCCCTCACCATGGACAGGAGAGGAGA

TCCAAGATCATAGGCAACACCGTGAACCCCATCTGGCAGGCCGAGCAATTCAGTTTTGTG

TCCTTGCCCACTGACGTGCTGGAAATTGAGGTGAAGGACAAGTTTGCCAAGAGCCGCCCC

ATCATCAAGCGCTTCTTGGGAAAGCTGTCGATGCCCGTTCAAAGACTCCTGGAGAGACAC

GCCATAGGGGATAGGGTGGTCAGCTACACACTTGGCCGCAGGCTTCCAACAGATCATGTG

AGTGGACAGCTGCAATTCCGATTTGAGATCACTTCCTCCATCCACCCAGATGATGAGGAG

ATTTCCCTGAGTACCGAGCCTGAGTCAGCCCAAATTCAGGACAGCCCCATGAACAACCTG

ATGGAAAGCGGCAGTGCGGAAGGTCGGTGTGAGGGACGAGAGTCCTGTGAGAGGTGGAAG

CCAGAGCAGCTGGGTGAGGGCAGTGTCCCCGATGGTCCAGGGAACCAAAGCATAGAGCTT

TCCAGACCAGCTGAGGAAGCAGCAGTCATCACGGAGGCAGGAGACCAGGGCATGGTCTCT

GTGGGACCTGAAGGGGCTGGGGAGCTCCTGGCCCAGGTGCAAAAGGACATCCAGCCTGCC

CCCAGTGCAGAAGAGCTGGCCGAGCAGCTGGACCTGGGTGAGGAGGCATCAGCACTGCTG

CTGGAAGACGGTGAAGCCCCAGCCAGCACCAAGGAGGAGCCCTTGGAGGAGGAAGCAACG

ACCCAGAGCCGGGCTGGAAGGGAAGAAGAGGAGAAGGAGCAGGAGGAGGAGGGAGATGTG

TCTACCCTGGAGCAGGGAGAGGGCAGGCTGCAGCTGCGGGCCTCGGTGAAGAGAAAAAGC

AGGCCCTGCTCCTTGCCTGTGTCCGAGCTGGAGACGGTGATCGCGTCAGCCTGCGGGGAC

CCCGAGACCCCGCGGACACACTACATCCGCATCCACACCCTGCTGCACAGCATGCCCTCC

GCCCAGGGCGGCAGCGCGGCAGAGGAGGAGGACGGCGCGGAGGAGGAGTCCACCCTCAAG

GACTCCTCGGAGAAGGATGGGCTCAGCGAGGTGGACACGGTGGCCGCTGACCCGTCTGCC

CTGGAAGAGGACAGAGAAGAGCCCGAGGGGGCTACTCCAGGCACGGCGCACCCTGGCCAC

TCCGGGGGCCACTTCCCCAGCCTGGCCAATGGCGCGGCCCAGGATGGCGACACGCACCCC

AGCACCGGGAGCGAGAGCGACTCCAGCCCCAGGCAAGGCGGGGACCACAGTTGCGAGGGC

TGTGACGCGTCCTGCTGCAGCCCCTCGTGCTACAGCTCCTCGTGCTACAGCACGTCCTGC

-continued

TACAGCAGCTCGTGCTACAGCGCCTCGTGCTACAGCCCCTCCTGCTACAACGGCAACAGG

TTCGCCAGCCACACGCGCTTCTCCTCCGTGGACAGCGCCAAGATCTCCGAGAGCACGGTC

TTCTCCTCGCAAGACGACGAGGAGGAGGAGAACAGCGCGTTCGAGTCGGTACCCGACTCC

ATGCAGAGCCCTGAGCTGGACCCGGAGTCCACGAACGGCGCTGGGCCGTGGCAAGACGAG

CTGGCCGCCCCTAGCGGGCACGTGGAAAGAAGCCCGGAAGGTCTGGAATCCCCCGTGGCA

GGTCCAAGCAATCGGAGAGAAGACTGGGAAGCTCGAATTGACAGCCACGGGCGGGTCTTT

TATGTGGACCACGTGAACCGCACAACCACCTGGCAGCGTCCGACGGCAGCAGCCACCCCG

GATGGCATGCGGAGATCGGGGTCCATCCAGCAGATGGAGCAACTCAACAGGCGGTATCAA

AACATTCAGCGAACCATTGCAACAGAGAGGTCCGAAGAAGATTCTGGCAGCCAAAGCTGC

GAGCAAGCCCCAGCAGGAGGAGGCGGAGGTGGAGGGAGTGACTCAGAAGCCGAATCTTCC

CAGTCCAGCTTAGATCTAAGGAGAGAGGGGTCACTTTCTCCAGTGAACTCACAAAAAATC

ACCTTGCTGCTGCAGTCCCCAGCGGTCAAGTTCATCACCAACCCCGAGTTCTTCACTGTG

CTACACGCCAATTATAGTGCCTACCGAGTCTTCACCAGTAGCACCTGCTTAAAGCACATG

ATTCTGAAAGTCCGACGGGATGCTCGCAATTTTGAACGCTACCAGCACAACCGGGACTTG

GTGAATTTCATCAACATGTTCGCAGACACTCGGCTGGAACTGCCCCGGGGCTGGGAGATC

AAAACGGACCAGCAGGGAAAGTCTTTTTTCGTGGACCACAACAGTCGAGCTACCACTTTC

ATTGACCCCCGAATCCCTCTTCAGAACGGTCGTCTTCCCAATCATCTAACTCACCGACAG

CACCTCCAGAGGCTCCGAAGTTACAGCGCCGGAGAGGCCTCAGAAGTTTCTAGAAACAGA

GGAGCCTCTTTACTGGCCAGGCCAGGACACAGCTTAGTAGCTGCTATTCGAAGCCAACAT

CAACATGAGTCATTGCCACTGGCATATAATGACAAGATTGTGGCATTTCTTCGCCAGCCA

AACATTTTTGAAATGCTGCAAGAGCGTCAGCCAAGCTTAGCAAGAAACCACACACTCAGG

GAGAAAATCCATTACATTCGGACTGAGGGTAATCACGGGCTTGAGAAGTTGTCCTGTGAT

GCGGATCTGGTCATTTTGCTGAGTCTCTTTGAAGAAGAGATTATGTCCTACGTCCCCCTG

CAGGCTGCCTTCCACCCTGGGTATAGCTTCTCTCCCCGATGTTCACCCTGTTCTTCACCT

CAGAACTCCCCAGGTTTACAGAGAGCCAGTGCAAGAGCCCCTTCCCCCTACCGAAGAGAC

TTTGAGGCCAAGCTCCGCAATTTCTACAGAAAACTGGAAGCCAAAGGATTTGGTCAGGGT

CCGGGGAAAATTAAGCTCATTATTCGCCGGGATCATTTGTTGGAGGGAACCTTCAATCAG

GTGATGGCCTATTCGCGGAAAGAGCTCCAGCGAAACAAGCTCTACGTCACCTTTGTTGGA

GAGGAGGGCCTGGACTACAGTGGCCCCTCGCGGGAGTTCTTCTTCCTTCTGTCTCAGGAG

CTCTTCAACCCTTACTATGGACTCTTTGAGTACTCGGCAAATGATACTTACACGGTGCAG

ATCAGCCCCATGTCCGCATTTGTAGAAAACCATCTTGAGTGGTTCAGGTTTAGCGGTCGC

ATCCTGGGTCTGGCTCTGATCCATCAGTACCTTCTTGACGCTTTCTTCACGAGGCCCTTC

TACAAGGCACTCCTGAGACTGCCCTGTGATTTGAGTGACCTGGAATATTTGGATGAGGAA

TTCCACCAGAGTTTGCAGTGGATGAAGGACAACAACATCACAGACATCTTAGACCTCACT

TTCACTGTTAATGAAGAGGTTTTTGGACAGGTCACGGAAAGGGAGTTGAAGTCTGGAGGA

GCCAACACACAGGTGACGGAGAAAAACAAGAAGGAGTACATCGAGCGCATGGTGAAGTGG

CGGGTGGAGCGCGGCGTGGTACAGCAGACCGAGGCGCTGGTGCGCGGCTTCTACGAGGTT

GTAGACTCGAGGCTGGTGTCCGTGTTTGATGCCAGGGAGCTGGAGCTGGTGATAGCTGGC

ACCGCGGAAATCGACCTAAATGACTGGCGGAATAACACTGAGTACCGGGGAGGTTACCAC

GATGGGCATCTTGTGATCCGCTGGTTCTGGGCTGCGGTGGAGCGCTTCAATAATGAGCAG

-continued

AGGCTGAGATTACTGCAGTTTGTCACGGGAACATCCAGCGTGCCCTACGAAGGCTTCGCA

GCCCTCCGTGGGAGCAATGGGCTTCGGCGCTTATAAATAGAGAAATAGGAGAAAATTAAT

TCTCTCCCCAGGGCACACACATGCTTCAACCGACTGGATCTTCCACCGTATCCCTCGTAC

TCCATGTTGTATGAAAAGCTGTTAACAGCAGTAGAGGAAACCAGCACCTTTGGACTTGAG

TGAGGACATGGAACCTCGCCTGACATTTTCCTGGCCAGTGACATCACCCTTCCTGGGATG

ATCCCCTTTTCCCTTTCCCTTAATCAACTCTCCTTTGATTTTGGTATTCCATGATTTTTA

TTTTCAAAC

Human NEDL2 nucleic acid sequence (uniprot.org/uniprot/Q9P2P5).

(SEQ ID NO: 31)

AGAGTTCCATCAGAGCCTGCAGTGGATGAAAGACAATGATATCCATGACATCCTAGACCT

CACGTTCACTGTGAACGAAGAAGTATTTGGGCAGATAACTGAACGAGAATTAAAGCCAGG

GGGTGCCAATATCCCAGTTACAGAGAAGAACAAGAAGGAGTACATCGAGAGGATGGTGAA

GTGGAGGATTGAGAGGGGTGTTGTACAGCAAACAGAGAGCTTAGTGCGTGGCTTCTATGA

GGTGGTGGATGCCAGGCTGGTATCTGTTTTTGATGCAAGAGAACTGGAATTGGTCATCGC

AGGCACAGCTGAAATAGACCTAAGTGATTGGAGAAACAACACAGAATATAGAGGAGGATA

CCATGACAATCATATTGTAATTCGGTGGTTCTGGGCTGCAGTGGAAAGATTCAACAATGA

ACAACGACTAAGGTTGTTACAGTTTGTTACAGGCACATCCAGCATTCCCTATGAAGGATT

TGCTTCACTCCGAGGGAGTAACGGCCCAAGAAGATTCTGTGTGGAGAAATGGGGGAAAAT

CACTGCTCTTCCCAGAGCGCATACATGTTTTAACCGTCTGGATCTGCCTCCCTACCCATC

CTTTTCCATGCTTTATGAAAAACTGTTGACAGCAGTTGAAGAAACCAGTACTTTTGGACT

TGAGTGACCTGGAAGCTGAATGCCCATCTCTGTGGACAGGCAGTTTCAGAAGCTGCCTTC

TAGAAGAATGATTGAACATTGGAAGTTTCAAGAGGATGCTTCCTTTAGGATAAAGCTACG

TGCTGTTGTTTTCCAGGAACAAGTGCTCTGTCACATTTGGGGACTGGAGATGAGTCCTCT

TGGAAGGATTTGGGTGAGCTTGATGCCCAGGGAACAACCCAACCGTCTTTCAATCAACAG

TTCTTGACTGCCAAACTTTTTCCATTTGTTATGTTCCAAGACAAAGATGAACCCATACAT

GATCAGCTCCACGGTAATTTTTAGGGACTCAGGAGAATCTTGAAACTTACCCTTGAACGT

GGTTCAAGCCAAACTGGCAGCATTTGGCCCAATCTCCAAATTAGAGCAAGTTAAATAATA

TAATAAAAGTAAATATATTTCCTGAAAGTACATTCATTTAAGCCCTAAGTTATAACAGAA

TATTCATTTCTTGCTTATGAGTGCCTGCATGGTGTGCACCATAGGTTTCCGCTTTCATGG

GACATGAGTGAAAATGAAACCAAGTCAATATGAGGTACCTTTACAGATTTGCAATAAGAT

GGTCTGTGACAATGTATATGCAAGTGGTATGTGTGTAATTATGGCTAAAGACAAACCATT

ATTCAGTGAATTACTAATGACAGATTTTATGCTTTATAATGCATGAAAACAATTTTAAAA

TAACTAGCAATTAATCACAGCATATCAGGAAAAAGTACACAGTGAGTTCTGTTTATTTTT

TGTAGGCTCATTATGTTTATGTTCTTTAAGATGTATATAAGAACCTACTTATCATGCTGT

ATGTATCACTCATTCCATTTTCATGTTCCATGCATACTCGGGCATCATGCTAATATGTAT

CCTTTTAAGCACTCTCAAGGAAACAAAAGGGCCTTTTATTTTTATAAAGGTAAAAAAAAT

TCCCCAAATATTTTGCACTGAATGTACCAAAGGTGAAGGGACATTACAATATGACTAACA

GCAACTCCATCACTTGAGAAGTATAATAGAAAATAGCTTCTAAATCAAACTTCCTTCACA

GTGCCGTGTCTACCACTACAAGGACTGTGCATCTAAGTAATAATTTTTTAAGATTCACTA

TATGTGATAGTATGATATGCATTTATTTAAAATGCATTAGACTCTCTTCCATCCATCAAA

TACTTTACAGGATGGCATTTAATACAGATATTTCGTATTTCCCCCACTGCTTTTTATTTG

TACAGCATCATTAAACACTAAGCTCAGTTAAGGAGCCATCAGCAACACTGAAGAGATCAG

-continued

```
TAGTAAGAATTCCATTTTCCCTCATCAGTGAAGACACCACAAATTGAAACTCAGAACTAT

ATTTCTAAGCCTGCATTTTCACTGATGCATAATTTTCTTATTAATATTAAGAGACAGTTT

TTCTATGGCATCTCCAAAACTGCATGACATCACTAGTCTTACTTCTGCTTAATTTTATGA

GAAGGTATTCTTCATTTTAATTGCTTTTGGGATTACTCCACATCTTTGTTTATTTCTTGA

CTAATCAGATTTTCAATAGAGTGAAGTTAAATTGGGGGTCATAAAAGCATTGGATTGACA

TATGGTTTGCCAGCCTATGGGTTTACAGGCATTGCCCAAACATTTCTTTGAGATCTATAT

TTATAAGCAGCCATGGAATTCCTATTATGGGATGTTGGCAATCTTACATTTTATAGAGGT

CATATGCATAGTTTTCATAGGTGTTTTGTAAGAACTGATTGCTCTCCTGTGAGTTAAGCT

ATGTTTACTACTGGGACCCTCAAGAGGAATACCACTTATGTTACACTCCTGCACTAAAGG

CACGTACTGCAGTGTGAAGAAATGTTCTGAAAAAGGGTTATAGAAATCTGGAAATAAGAA

AGGAAGAGCTCTCTGTATTCTATAATTGGAAGAGAAAAAAAGAAAAACTTTTAACTGGAA

ATGTTAGTTTGTACTTATTGATCATGAATACAAGTATATATTTAATTTTGCAAAAAAAAA

AAAAAAAAAAAAAAG
```

In certain embodiments, the nucleic acids may encode cargo proteins having two WW domains or WW domain variants from the human ITCH protein having the nucleic acid sequence: CCCTTGCCACCTGGTTGG-GAGCAGAGAGTGGACCAGCACGGGCGAGTTTAC-TAT GTAGATCATGTTGAGAAAAGAACAACATGG-GATAGACCAGAACCTCTACCTCCT GGCTGGGAACGGCGGGTTGACAACATGGGACGT-ATTTATTATGTTGACCATTTCA CAAGAACAACAACGTGGCAGAGGCCAACACTG (SEQ ID NO: 32). In other embodiments, the nucleic acids may encode cargo proteins having four WW domains or WW domain variants from the human ITCH protein having the nucleic acid sequence: CCCTTGCCACCTGGTTGG-GAGCAGAGAGTGGACCAGCACGGGCGAGTTTAC-TAT GTAGATCATGTTGAGAAAAGAACAACATGG-GATAGACCAGAACCTCTACCTCCT GGCTGGGAACGGCGGGTTGACAACATGGGACGT-ATTTATTATGTTGACCATTTCA CAAGAACAACAACGTGGCAGAGGCCAACACTG-GAATCCGTCCGGAACTATGAAC AATGGCAGCTA-CAGCGTAGTCAGCTT-CAAGGAGCAATGCAGCAGTTTAACCAGA GATTCATTTATGGGAATCAAGATTTATTTGCTACAT-CACAAAGTAAAGAATTTGA TCCTCTTGGTCCAT-TGCCACCTGGATGGGAGAAGAGAACA-GACAGCAATGGCAG AGTATATTTCGTCAACCACAACACACGAATTA-CACAATGGGAAGACCCCAGAAG TCAAGGTCAAT-TAAATGAAAAGCCCTTACCTGAAGGTTGGGAAAT-GAGATTCAC AGTGGATGGAATTCCATATTTTGTGGAC-CACAATAGAAGAACTACCACCTATATA GATCCCCGCACA (SEQ ID NO: 33). The nucleic acid constructs that encode the cargo proteins, described herein, that are fused to at least one WW domain or WW domain variant are non-naturally occurring, that is, they do not exist in nature.

In some embodiments the expression constructs comprise a nucleic acid sequence encoding a WW domain, or variant thereof from the nucleic acid sequence (SEQ ID NO: 23); (SEQ ID NO: 24); (SEQ ID NO: 25); (SEQ ID NO: 26); (SEQ ID NO: 27); (SEQ ID NO: 28); (SEQ ID NO: 29); (SEQ ID NO: 30); (SEQ ID NO: 31); (SEQ ID NO: 32) or (SEQ ID NO: 33). In certain embodiments, the expression constructs encode a fusion protein comprising a WW domain or multiple WW domains, a nuclear localization sequence (NLS), and a Cas9 protein or variant thereof. In certain embodiments, the expression constructs comprise the nucleic acid sequence (SEQ ID NO: 111) or (SEQ ID NO:112). In certain embodiments, the expression constructs consist of the nucleic acid sequence (SEQ ID NO: 111) or (SEQ ID NO: 112). In certain embodiments, the expression constructs consist essentially of the nucleic acid sequence (SEQ ID NO: 111) or (SEQ ID NO: 112).

The following nucleic acid sequences encode exemplary Cas9 cargo protein sequences that have either 2 WW domains (SEQ ID NO: 109) or 4 WW domains (SEQ ID NO: 110), which were cloned into the AgeI site of the pX330 plasmid (Addgene).

```
(SEQ ID NO: 111)
ATGCCCTTGCCACCTGGTTGGGAGCAGAGAGTGGACCAGCACGGGCGAGTTTAC

TATGTAGATCATGTTGAGAAAAGAACAACATGGGATAGACCAGAACCTCTACCT

CCTGGCTGGGAACGGCGGGTTGACAACATGGGACGTATTTATTATGTTGACCATT

TCACAAGAACAACAACGTGGCAGAGGCCAACACTGACCGGTGCCACCATGGACT

ATAAGGACCACGACGGAGACTACAAGGATCATGATATTGATTACAAAGACGATG

ACGATAAGATGGCCCCAAAGAAGAAGCGGAAGGTCGGTATCCACGGAGTCCCAG
```

-continued
CAGCCGACAAGAAGTACAGCATCGGCCTGGACATCGGCACCAACTCTGTGGGCT
GGGCCGTGATCACCGACGAGTACAAGGTGCCCAGCAAGAAATTCAAGGTGCTGG
GCAACACCGACCGGCACAGCATCAAGAAGAACCTGATCGGAGCCCTGCTGTTCG
ACAGCGGCGAAACAGCCGAGGCCACCCGGCTGAAGAGAACCGCCAGAAGAAGA
TACACCAGACGGAAGAACCGGATCTGCTATCTGCAAGAGATCTTCAGCAACGAG
ATGGCCAAGGTGGACGACAGCTTCTTCCACAGACTGGAAGAGTCCTTCCTGGTGG
AAGAGGATAAGAAGCACGAGCGGCACCCCATCTTCGGCAACATCGTGGACGAGG
TGGCCTACCACGAGAAGTACCCCACCATCTACCACCTGAGAAAGAAACTGGTGG
ACAGCACCGACAAGGCCGACCTGCGGCTGATCTATCTGGCCCTGGCCCACATGA
TCAAGTTCCGGGGCCACTTCCTGATCGAGGGCGACCTGAACCCCGACAACAGCG
ACGTGGACAAGCTGTTCATCCAGCTGGTGCAGACCTACAACCAGCTGTTCGAGG
AAAACCCCATCAACGCCAGCGGCGTGGACGCCAAGGCCATCCTGTCTGCCAGAC
TGAGCAAGAGCAGACGGCTGGAAAATCTGATCGCCCAGCTGCCCGGCGAGAAGA
AGAATGGCCTGTTCGGAAACCTGATTGCCCTGAGCCTGGGCCTGACCCCCAACTT
CAAGAGCAACTTCGACCTGGCCGAGGATGCCAAACTGCAGCTGAGCAAGGACAC
CTACGACGACGACCTGGACAACCTGCTGGCCCAGATCGGCGACCAGTACGCCGA
CCTGTTTCTGGCCGCCAAGAACCTGTCCGACGCCATCCTGCTGAGCGACATCCTG
AGAGTGAACACCGAGATCACCAAGGCCCCCCTGAGCGCCTCTATGATCAAGAGA
TACGACGAGCACCACCAGGACCTGACCCTGCTGAAAGCTCTCGTGCGGCAGCAG
CTGCCTGAGAAGTACAAAGAGATTTTCTTCGACCAGAGCAAGAACGGCTACGCC
GGCTACATTGACGGCGGAGCCAGCCAGGAAGAGTTCTACAAGTTCATCAAGCCC
ATCCTGGAAAAGATGGACGGCACCGAGGAACTGCTCGTGAAGCTGAACAGAGAG
GACCTGCTGCGGAAGCAGCGGACCTTCGACAACGGCAGCATCCCCCACCAGATC
CACCTGGGAGAGCTGCACGCCATTCTGCGGCGGCAGGAAGATTTTTACCCATTCC
TGAAGGACAACCGGGAAAAGATCGAGAAGATCCTGACCTTCCGCATCCCCTACT
ACGTGGGCCCTCTGGCCAGGGGAAACAGCAGATTCGCCTGGATGACCAGAAAGA
GCGAGGAAACCATCACCCCCTGGAACTTCGAGGAAGTGGTGGACAAGGGCGCTT
CCGCCCAGAGCTTCATCGAGCGGATGACCAACTTCGATAAGAACCTGCCCAACG
AGAAGGTGCTGCCCAAGCACAGCCTGCTGTACGAGTACTTCACCGTGTATAACG
AGCTGACCAAAGTGAAATACGTGACCGAGGGAATGAGAAAGCCCGCCTTCCTGA
GCGGCGAGCAGAAAAAGGCCATCGTGGACCTGCTGTTCAAGACCAACCGGAAAG
TGACCGTGAAGCAGCTGAAAGAGGACTACTTCAAGAAAATCGAGTGCTTCGACT
CCGTGGAAATCTCCGGCGTGGAAGATCGGTTCAACGCCTCCCTGGGCACATACC
ACGATCTGCTGAAAATTATCAAGGACAAGGACTTCCTGGACAATGAGGAAAACG
AGGACATTCTGGAAGATATCGTGCTGACCCTGACACTGTTTGAGGACAGAGAGA
TGATCGAGGAACGGCTGAAAACCTATGCCCACCTGTTCGACGACAAAGTGATGA
AGCAGCTGAAGCGGCGGAGATACACCGGCTGGGGCAGGCTGAGCCGGAAGCTG
ATCAACGGCATCCGGGACAAGCAGTCCGGCAAGACAATCCTGGATTTCCTGAAG
TCCGACGGCTTCGCCAACAGAAACTTCATGCAGCTGATCCACGACGACAGCCTG
ACCTTTAAAGAGGACATCCAGAAAGCCCAGGTGTCCGGCCAGGGCGATAGCCTG
CACGAGCACATTGCCAATCTGGCCGGCAGCCCCGCCATTAAGAAGGGCATCCTG -continued

CAGACAGTGAAGGTGGTGGACGAGCTCGTGAAAGTGATGGGCCGGCACAAGCCC

GAGAACATCGTGATCGAAATGGCCAGAGAGAACCAGACCACCCAGAAGGGACA

GAAGAACAGCCGCGAGAGAATGAAGCGGATCGAAGAGGGCATCAAAGAGCTGG

GCAGCCAGATCCTGAAAGAACACCCCGTGGAAAACACCCAGCTGCAGAACGAG

AAGCTGTACCTGTACTACCTGCAGAATGGGCGGGATATGTACGTGGACCAGGAA

CTGGACATCAACCGGCTGTCCGACTACGATGTGGACCATATCGTGCCTCAGAGCT

TTCTGAAGGACGACTCCATCGACAACAAGGTGCTGACCAGAAGCGACAAGAACC

GGGGCAAGAGCGACAACGTGCCCTCCGAAGAGGTCGTGAAGAAGATGAAGAAC

TACTGGCGGCAGCTGCTGAACGCCAAGCTGATTACCCAGAGAAAGTTCGACAAT

CTGACCAAGGCCGAGAGAGGCGGCCTGAGCGAACTGGATAAGGCCGGCTTCATC

AAGAGACAGCTGGTGGAAACCCGGCAGATCACAAAGCACGTGGCACAGATCCTG

GACTCCCGGATGAACACTAAGTACGACGAGAATGACAAGCTGATCCGGGAAGTG

AAAGTGATCACCCTGAAGTCCAAGCTGGTGTCCGATTTCCGGAAGGATTTCCAGT

TTTACAAAGTGCGCGAGATCAACAACTACCACCACGCCCACGACGCCTACCTGA

ACGCCGTCGTGGGAACCGCCCTGATCAAAAAGTACCCTAAGCTGGAAAGCGAGT

TCGTGTACGGCGACTACAAGGTGTACGACGTGCGGAAGATGATCGCCAAGAGCG

AGCAGGAAATCGGCAAGGCTACCGCCAAGTACTTCTTCTACAGCAACATCATGA

ACTTTTTCAAGACCGAGATTACCCTGGCCAACGGCGAGATCCGGAAGCGGCCTCT

GATCGAGACAAACGGCGAAACCGGGGAGATCGTGTGGGATAAGGGCCGGGATTT

TGCCACCGTGCGGAAAGTGCTGAGCATGCCCCAAGTGAATATCGTGAAAAAGAC

CGAGGTGCAGACAGGCGGCTTCAGCAAAGAGTCTATCCTGCCCAAGAGGAACAG

CGATAAGCTGATCGCCAGAAAGAAGGACTGGGACCCTAAGAAGTACGGCGGCTT

CGACAGCCCCACCGTGGCCTATTCTGTGCTGGTGGTGGCCAAAGTGGAAAAGGG

CAAGTCCAAGAAACTGAAGAGTGTGAAAGAGCTGCTGGGGATCACCATCATGGA

AAGAAGCAGCTTCGAGAAGAATCCCATCGACTTTCTGGAAGCCAAGGGCTACAA

AGAAGTGAAAAAGGACCTGATCATCAAGCTGCCTAAGTACTCCCTGTTCGAGCT

GGAAAACGGCCGGAAGAGAATGCTGGCCTCTGCCGGCGAACTGCAGAAGGGAA

ACGAACTGGCCCTGCCCTCCAAATATGTGAACTTCCTGTACCTGGCCAGCCACTA

TGAGAAGCTGAAGGGCTCCCCCGAGGATAATGAGCAGAAACAGCTGTTTGTGGA

ACAGCACAAGCACTACCTGGACGAGATCATCGAGCAGATCAGCGAGTTCTCCAA

GAGAGTGATCCTGGCCGACGCTAATCTGGACAAAGTGCTGTCCGCCTACAACAA

GCACCGGGATAAGCCCATCAGAGAGCAGGCCGAGAATATCATCCACCTGTTTAC

CCTGACCAATCTGGGAGCCCCTGCCGCCTTCAAGTACTTTGACACCACCATCGAC

CGGAAGAGGTACACCAGCACCAAAGAGGTGCTGGACGCCACCCTGATCCACCAG

AGCATCACCGGCCTGTACGAGACACGGATCGACCTGTCTCAGCTGGGAGGCGAC

AAAAGGCCGGCGGCCACGAAAAAGGCCGGCCAGGCAAAAAAGAAAAAG (SEQ ID NO: 112)

ATGCCCTTGCCACCTGGTTGGGAGCAGAGAGTGGACCAGCACGGGCGAGTTTAC

TATGTAGATCATGTTGAGAAAAGAACAACATGGGATAGACCAGAACCTCTACCT

CCTGGCTGGGAACGGCGGGTTGACAACATGGGACGTATTTATTATGTTGACCATT

TCACAAGAACAACAACGTGGCAGAGGCCAACACTGGAATCCGTCCGGAACTATG

-continued

AACAATGGCAGCTACAGCGTAGTCAGCTTCAAGGAGCAATGCAGCAGTTTAACC

AGAGATTCATTTATGGGAATCAAGATTTATTTGCTACATCACAAAGTAAAGAATT

TGATCCTCTTGGTCCATTGCCACCTGGATGGGAGAAGAGAACAGACAGCAATGG

CAGAGTATATTTCGTCAACCACAACACACGAATTACACAATGGGAAGACCCCAG

AAGTCAAGGTCAATTAAATGAAAAGCCCTTACCTGAAGGTTGGGAAATGAGATT

CACAGTGGATGGAATTCCATATTTTGTGGACCACAATAGAAGAACTACCACCTAT

ATAGATCCCCGCACAGGCGGAGGAACCGGTGCCACCATGGACTATAAGGACCAC

GACGGAGACTACAAGGATCATGATATTGATTACAAAGACGATGACGATAAGATG

GCCCCAAAGAAGAAGCGGAAGGTCGGTATCCACGGAGTCCCAGCAGCCGACAA

GAAGTACAGCATCGGCCTGGACATCGGCACCAACTCTGTGGGCTGGGCCGTGAT

CACCGACGAGTACAAGGTGCCCAGCAAGAAATTCAAGGTGCTGGGCAACACCGA

CCGGCACAGCATCAAGAAGAACCTGATCGGAGCCCTGCTGTTCGACAGCGGCGA

AACAGCCGAGGCCACCCGGCTGAAGAGAACCGCCAGAAGAAGATACACCAGAC

GGAAGAACCGGATCTGCTATCTGCAAGAGATCTTCAGCAACGAGATGGCCAAGG

TGGACGACAGCTTCTTCCACAGACTGGAAGAGTCCTTCCTGGTGGAAGAGGATA

AGAAGCACGAGCGGCACCCCATCTTCGGCAACATCGTGGACGAGGTGGCCTACC

ACGAGAAGTACCCCACCATCTACCACCTGAGAAAGAAACTGGTGGACAGCACCG

ACAAGGCCGACCTGCGGCTGATCTATCTGGCCCTGGCCCACATGATCAAGTTCCG

GGGCCACTTCCTGATCGAGGGCGACCTGAACCCCGACAACAGCGACGTGGACAA

GCTGTTCATCCAGCTGGTGCAGACCTACAACCAGCTGTTCGAGGAAAACCCCATC

AACGCCAGCGGCGTGGACGCCAAGGCCATCCTGTCTGCCAGACTGAGCAAGAGC

AGACGGCTGGAAAATCTGATCGCCCAGCTGCCCGGCGAGAAGAAGAATGGCCTG

TTCGGAAACCTGATTGCCCTGAGCCTGGGCCTGACCCCCAACTTCAAGAGCAACT

TCGACCTGGCCGAGGATGCCAAACTGCAGCTGAGCAAGGACACCTACGACGACG

ACCTGGACAACCTGCTGGCCCAGATCGGCGACCAGTACGCCGACCTGTTTCTGGC

CGCCAAGAACCTGTCCGACGCCATCCTGCTGAGCGACATCCTGAGAGTGAACAC

CGAGATCACCAAGGCCCCCCTGAGCGCCTCTATGATCAAGAGATACGACGAGCA

CCACCAGGACCTGACCCTGCTGAAAGCTCTCGTGCGGCAGCAGCTGCCTGAGAA

GTACAAAGAGATTTTCTTCGACCAGAGCAAGAACGGCTACGCCGGCTACATTGA

CGGCGGAGCCAGCCAGGAAGAGTTCTACAAGTTCATCAAGCCCATCCTGGAAAA

GATGGACGGCACCGAGGAACTGCTCGTGAAGCTGAACAGAGAGGACCTGCTGCG

GAAGCAGCGGACCTTCGACAACGGCAGCATCCCCCACCAGATCCACCTGGGAGA

GCTGCACGCCATTCTGCGGCGGCAGGAAGATTTTTACCCATTCCTGAAGGACAAC

CGGGAAAAGATCGAGAAGATCCTGACCTTCCGCATCCCCTACTACGTGGGCCCTC

TGGCCAGGGGAAACAGCAGATTCGCCTGGATGACCAGAAAGAGCGAGGAAACC

ATCACCCCCTGGAACTTCGAGGAAGTGGTGGACAAGGGCGCTTCCGCCCAGAGC

TTCATCGAGCGGATGACCAACTTCGATAAGAACCTGCCCAACGAGAAGGTGCTG

CCCAAGCACAGCCTGCTGTACGAGTACTTCACCGTGTATAACGAGCTGACCAAA

GTGAAATACGTGACCGAGGGAATGAGAAAGCCCGCCTTCCTGAGCGGCGAGCAG

AAAAAGGCCATCGTGGACCTGCTGTTCAAGACCAACCGGAAAGTGACCGTGAAG

-continued

CAGCTGAAAGAGGACTACTTCAAGAAAATCGAGTGCTTCGACTCCGTGGAAATC

TCCGGCGTGGAAGATCGGTTCAACGCCTCCCTGGGCACATACCACGATCTGCTGA

AAATTATCAAGGACAAGGACTTCCTGGACAATGAGGAAAACGAGGACATTCTGG

AAGATATCGTGCTGACCCTGACACTGTTTGAGGACAGAGAGATGATCGAGGAAC

GGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCC

GGGACAAGCAGTCCGGCAAGACAATCCTGGATTTCCTGAAGTCCGACGGCTTCG

CCAACAGAAACTTCATGCAGCTGATCCACGACGACAGCCTGACCTTTAAAGAGG

ACATCCAGAAAGCCCAGGTGTCCGGCCAGGGCGATAGCCTGCACGAGCACATTG

CCAATCTGGCCGGCAGCCCCGCCATTAAGAAGGGCATCCTGCAGACAGTGAAGG

TGGTGGACGAGCTCGTGAAAGTGATGGGCCGGCACAAGCCCGAGAACATCGTGA

TCGAAATGGCCAGAGAGAACCAGACCACCCAGAAGGGACAGAAGAACAGCCGC

GAGAGAATGAAGCGGATCGAAGAGGGCATCAAAGAGCTGGGCAGCCAGATCCT

GAAAGAACACCCCGTGGAAAACACCCAGCTGCAGAACGAGAAGCTGTACCTGTA

CTACCTGCAGAATGGGCGGGATATGTACGTGGACCAGGAACTGGACATCAACCG

GCTGTCCGACTACGATGTGGACCATATCGTGCCTCAGAGCTTTCTGAAGGACGAC

TCCATCGACAACAAGGTGCTGACCAGAAGCGACAAGAACCGGGGCAAGAGCGA

CAACGTGCCCTCCGAAGAGGTCGTGAAGAAGATGAAGAACTACTGGCGGCAGCT

GCTGAACGCCAAGCTGATTACCCAGAGAAAGTTCGACAATCTGACCAAGGCCGA

GAGAGGCGGCCTGAGCGAACTGGATAAGGCCGGCTTCATCAAGAGACAGCTGGT

GGAAACCCGGCAGATCACAAAGCACGTGGCACAGATCCTGGACTCCCGGATGAA

CACTAAGTACGACGAGAATGACAAGCTGATCCGGGAAGTGAAAGTGATCACCCT

GAAGTCCAAGCTGGTGTCCGATTTCCGGAAGGATTTCCAGTTTTACAAAGTGCGC

GAGATCAACAACTACCACCACGCCCACGACGCCTACCTGAACGCCGTCGTGGGA

ACCGCCCTGATCAAAAAGTACCCTAAGCTGGAAAGCGAGTTCGTGTACGGCGAC

TACAAGGTGTACGACGTGCGGAAGATGATCGCCAAGAGCGAGCAGGAAATCGGC

AAGGCTACCGCCAAGTACTTCTTCTACAGCAACATCATGAACTTTTTCAAGACCG

AGATTACCCTGGCCAACGGCGAGATCCGGAAGCGGCCTCTGATCGAGACAAACG

GCGAAACCGGGGAGATCGTGTGGGATAAGGGCCGGGATTTTGCCACCGTGCGGA

AAGTGCTGAGCATGCCCCAAGTGAATATCGTGAAAAAGACCGAGGTGCAGACAG

GCGGCTTCAGCAAAGAGTCTATCCTGCCCAAGAGGAACAGCGATAAGCTGATCG

CCAGAAAGAAGGACTGGGACCCTAAGAAGTACGGCGGCTTCGACAGCCCCACCG

TGGCCTATTCTGTGCTGGTGGTGGCCAAAGTGGAAAAGGGCAAGTCCAAGAAAC

TGAAGAGTGTGAAAGAGCTGCTGGGGATCACCATCATGGAAAGAAGCAGCTTCG

AGAAGAATCCCATCGACTTTCTGGAAGCCAAGGGCTACAAAGAAGTGAAAAAGG

ACCTGATCATCAAGCTGCCTAAGTACTCCCTGTTCGAGCTGGAAAACGGCCGGAA

GAGAATGCTGGCCTCTGCCGGCGAACTGCAGAAGGGAAACGAACTGGCCCTGCC

CTCCAAATATGTGAACTTCCTGTACCTGGCCAGCCACTATGAGAAGCTGAAGGGC

TCCCCCGAGGATAATGAGCAGAAACAGCTGTTTGTGGAACAGCACAAGCACTAC

CTGGACGAGATCATCGAGCAGATCAGCGAGTTCTCCAAGAGAGTGATCCTGGCC

GACGCTAATCTGGACAAAGTGCTGTCCGCCTACAACAAGCACCGGGATAAGCCC

-continued

ATCAGAGAGCAGGCCGAGAATATCATCCACCTGTTTACCCTGACCAATCTGGGA

GCCCCTGCCGCCTTCAAGTACTTTGACACCACCATCGACCGGAAGAGGTACACCA

GCACCAAAGAGGTGCTGGACGCCACCCTGATCCACCAGAGCATCACCGGCCTGT

ACGAGACACGGATCGACCTGTCTCAGCTGGGAGGCGACAAAAGGCCGGCGGCCA

CGAAAAAGGCCGGCCAGGCAAAAAAGAAAAAG

Nucleic acids encoding any of the proteins described herein may be in any number of nucleic acid "vectors" known in the art. As used herein, a "vector" may include any nucleic acid or nucleic acid-bearing particle, cell, or organism capable of being used to transfer a nucleic acid into a host cell. The term "vector" includes both viral and nonviral products and means for introducing the nucleic acid into a cell. A "vector" can be used in vitro, ex vivo, or in vivo. Non-viral vectors include plasmids, cosmids, artificial chromosomes (e.g., bacterial artificial chromosomes or yeast artificial chromosomes) and can comprise liposomes, electrically charged lipids (cytofectins), DNA-protein complexes, and biopolymers, for example. Viral vectors include retroviruses, lentiviruses, adeno-associated virus, pox viruses, baculovirus, reoviruses, vaccinia viruses, herpes simplex viruses, Epstein-Barr viruses, and adenovirus vectors, for example. Vectors can also comprise the entire genome sequence or recombinant genome sequence of a virus. A vector can also comprise a portion of the genome that comprises the functional sequences for production of a virus capable of infecting, entering, or being introduced to a cell to deliver nucleic acid therein.

Expression of any of the fusion proteins, described herein, may be controlled by any regulatory sequence (e.g. a promoter sequence) known in the art. Regulatory sequences, as described herein, are nucleic acid sequences that regulate the expression of a nucleic acid sequence. A regulatory or control sequence may include sequences that are responsible for expressing a particular nucleic acid (i.e. a Cas9 cargo protein) or may include other sequences, such as heterologous, synthetic, or partially synthetic sequences. The sequences can be of eukaryotic, prokaryotic or viral origin that stimulate or repress transcription of a gene in a specific or non-specific manner and in an inducible or non-inducible manner. Regulatory or control regions may include origins of replication, RNA splice sites, introns, chimeric or hybrid introns, promoters, enhancers, transcriptional termination sequences, poly A sites, locus control regions, signal sequences that direct the polypeptide into the secretory pathways of the target cell, and introns. A heterologous regulatory region is not naturally associated with the expressed nucleic acid it is linked to. Included among the heterologous regulatory regions are regulatory regions from a different species, regulatory regions from a different gene, hybrid regulatory sequences, and regulatory sequences that do not occur in nature, but which are designed by one of ordinary skill in the art.

The term operably linked refers to an arrangement of sequences or regions wherein the components are configured so as to perform their usual or intended function. Thus, a regulatory or control sequence operably linked to a coding sequence is capable of affecting the expression of the coding sequence. The regulatory or control sequences need not be contiguous with the coding sequence, so long as they function to direct the proper expression or polypeptide production. Thus, for example, intervening untranslated but transcribed sequences can be present between a promoter sequence and the coding sequence and the promoter sequence can still be considered operably linked to the coding sequence. A promoter sequence, as described herein, is a DNA regulatory region a short distance from the 5' end of a gene that acts as the binding site for RNA polymerase. The promoter sequence may bind RNA polymerase in a cell and/or initiate transcription of a downstream (3' direction) coding sequence. The promoter sequence may be a promoter capable of initiating transcription in prokaryotes or eukaryotes. Some non-limiting examples of eukaryotic promoters include the cytomegalovirus (CMV) promoter, the chicken 3-actin (CBA) promoter, and a hybrid form of the CBA promoter (CBh).

In certain embodiments, the Cas9 cargo protein is expressed from the pX330 plasmid (Addgene). An exemplary nucleic acid sequence of the pX330 plasmid with the 5' AgeI cloning site underlined (single underline) and the 3' EcoRI cloning site underlined (double underlined) is shown as (SEQ ID NO: 34). Any of the nucleic acids encoding the WW domains or WW domain variants, described herein, may be cloned, in frame, with the sequence encoding Cas9 from SEQ ID NO: 34. For example, the two ITCH WW domains or the four ITCH WW domains encoded in the nucleic acid sequences (SEQ ID NO: 32), or (SEQ ID NO: 33) may be cloned into the 5' AgeI cloning site or the 3' EcoRI cloning site. It should be appreciated that a nucleic acid encoding any of the WW domains or WW domain variants, described herein, may be cloned into the Cas9 sequence of (SEQ ID NO: 34) and the examples provided are not meant to be limiting.

(SEQ ID NO: 34)

1 gagggcctat ttcccatgat tccttcatat ttgcatatac gatacaaggc tgttagagag 61 ataattggaa ttaatttgac tgtaaacaca aagatattag tacaaaatac gtgacgtaga 121 aagtaataat ttcttgggta gtttgcagtt ttaaaattat gttttaaaat ggactatcat 181 atgcttaccg taacttgaaa gtatttcgat ttcttggctt tatatatctt GTGGAAAGGA 241 CGAAACACCg gGTCTTCgaG AAGACctgtt ttagagctaG AAAtagcaag ttaaaataag 301 gctagtccgt tatcaacttg aaaaagtggc accgagtcgg tgcTTTTTTg ttttagagct -continued

```
 361 agaaatagca agttaaaata aggctagtcc gtTTTTagcg cgtgcgccaa ttctgcagac
 421 aaatggctct agaggtaccc gttacataac ttacggtaaa tggcccgcct ggctgaccgc
 481 ccaacgaccc ccgcccattg acgtcaatag taacgccaat agggactttc cattgacgtc
 541 aatgggtgga gtatttacgg taaactgccc acttggcagt acatcaagtg tatcatatgc
 601 caagtacgcc ccctattgac gtcaatgacg gtaaatggcc cgcctggcat tGtgcccagt
 661 acatgacctt atgggacttt cctacttggc agtacatcta cgtattagtc atcgctatta
 721 ccatggtcga ggtgagcccc acgttctgct tcactctccc catctccccc ccctccccac
 781 ccccaatttt gtatttattt atttttttaat tattttgtgc agcgatgggg gcgggggggg
 841 ggggggggcg cgcgccaggc ggggcggggc ggggcgaggg gcggggcggg gcgaggcgga
 901 gaggtgcggc ggcagccaat cagagcggcg cgctccgaaa gtttcctttt atggcgaggc
 961 ggcggcggcg gcggccctat aaaaagcgaa gcgcgcggcg ggcgggagtc gctgcgacgc
1021 tgccttcgcc ccgtgccccg ctccgccgcc gcctcgcgcc gcccgccccg gctctgactg
1081 accgcgttac tcccacaggt gagcgggcgg gacggccctt ctcctccggg ctgtaattag
1141 ctgagcaaga ggtaagggtt taagggatgg ttggttggtg gggtattaat gtttaattac
1201 ctggagcacc tgcctgaaat cacttttttt caggttGGac cggtgccacc ATGGACTATA
1261 AGGACCACGA CGGAGACTAC AAGGATCATG ATATTGATTA CAAAGACGAT GACGATAAGA
1321 TGGCCCCAAA GAAGAAGCGG AAGGTCGGTA TCCACGGAGT CCCAGCAGCC GACAAGAAGT
1381 ACAGCATCGG CCTGGACATC GGCACCAACT CTGTGGGCTG GGCCGTGATC ACCGACGAGT
1441 ACAAGGTGCC CAGCAAGAAA TTCAAGGTGC TGGGCAACAC CGACCGGCAC AGGATCAAGA
1501 AGAACCTGAT CGGAGCCCTG CTGTTCGACA GCGGCGAAAC AGCCGAGGCC ACCCGGCTGA
1561 AGAGAACCGC CAGAAGAAGA TACACCAGAC GGAAGAACCG GATCTGCTAT CTGCAAGAGA
1621 TCTTCAGCAA CGAGATGGCC AAGGTGGACG ACAGCTTCTT CCACAGACTG GAAGAGTCCT
1681 TCCTGGTGGA AGAGGATAAG AAGCACGAGC GGCACCCCAT CTTCGGCAAC ATCGTGGACG
1741 AGGTGGCCTA CCACGAGAAG TACCCCACCA TCTACCACCT GAGAAAGAAA CTGGTGGACA
1801 GCACCGACAA GGCCGACCTG CGGCTGATCT ATCTGGCCCT GGCCCACATG ATCAAGTTCC
1861 GGGGCCACTT CCTGATCGAG GGCGACCTGA ACCCCGACAA CAGCGACGTG GACAAGCTGT
1921 TCATCCAGCT GGTGCAGACC TACAACCAGC TGTTCGAGGA AAACCCCATC AACGCCAGCG
1981 GCGTGGACGC CAAGGCCATC CTGTCTGCCA GACTGAGCAA GAGCAGACGG CTGGAAAATC
2041 TGATCGCCCA GCTGCCCGGC GAGAAGAAGA ATGGCCTGTT CGGAAACCTG ATTGCCCTGA
2101 GCCTGGGCCT GACCCCCAAC TTCAAGAGCA ACTTCGACCT GGCCGAGGAT GCCAAACTGC
2161 AGGTGAGCAA GGACACCTAC GAGGAGGAGC TGGACAACCT GCTGGCCCAG ATCGGCGACC
2221 AGTACGCCGA CCTGTTTCTG GCCGCCAAGA ACCTGTCCGA CGCCATCCTG CTGAGCGACA
2281 TCCTGAGAGT GAACACCGAG ATCACCAAGG CCCCCCTGAG CGCCTCTATG ATCAAGAGAT
2341 ACGACGAGCA CCACCAGGAC CTGACCCTGC TGAAAGCTCT CGTGCGGCAG CAGCTGCCTG
2401 AGAAGTACAA AGAGATTTTC TTCGACCAGA GCAAGAACGG CTACGCCGGC TACATTGACG
2461 GCGGAGCCAG CCAGGAAGAG TTCTACAAGT TCATCAAGCC CATCCTGGAA AAGATGGACG
2521 GCACCGAGGA ACTGCTCGTG AAGCTGAACA GAGAGGACCT GCTGCGGAAG CAGCGGACCT
2581 TCGACAACGG CAGCATCCCC CACCAGATCC ACCTGGGAGA GCTGCACGCC ATTCTGCGGC
2641 GGCAGGAAGA TTTTTACCCA TTCCTGAAGG ACAACCGGGA AAAGATCGAG AAGATCCTGA
2701 CCTTCCGCAT CCCCTACTAC GTGGGCCCTC TGGCCAGGGG AAACAGCAGA TTCGCCTGGA
```

-continued

2761 TGACCAGAAA GAGCGAGGAA ACCATCACCC CCTGGAACTT CGAGGAAGTG GTGGACAAGG

2821 GCGCTTCCGC CCAGAGCTTC ATCGAGCGGA TGACCAACTT CGATAAGAAC CTGGCCAACG

2881 AGAAGGTGCT GCCCAAGGAC AGCCTGCTGT ACGAGTACTT CACCGTGTAT AACGAGCTGA

2941 CCAAAGTGAA ATAGGTGACC GAGGGAATGA GAAAGCCCGC CTTCCTGAGC GGCGAGCAGA

3001 AAAAGGCCAT CGTGGACCTG CTGTTCAAGA CCAACCGGAA AGTGACCGTG AAGCAGCTGA

3061 AAGAGGACTA CTTCAAGAAA ATCGAGTGCT TCGACTCCGT GGAAATCTCC GGCGTGGAAG

3121 ATCGGTTCAA CGCCTCCCTG GGCACATACC ACGATCTGCT GAAAATTATC AAGGACAAGG

3181 ACTTCCTGGA CAATGAGGAA AAGGAGGACA TTCTGGAAGA TATCGTGCTG ACCCTGACAC

3241 TGTTTGAGGA CAGAGAGATG ATCGAGGAAC GGCTGAAAAC CTATGCCCAC CTGTTCGACG

3301 ACAAAGTGAT GAAGCAGCTG AAGCGGCGGA GATACACCGG CTGGGGCAGG CTGAGCCGGA

3361 AGGTGATCAA CGGCATCCGG GACAAGCAGT CCGGCAAGAC AATCCTGGAT TTCCTGAAGT

3421 CCGACGGCTT CGCCAACAGA AACTTCATGC AGCTGATCCA CGACGACAGC CTGACCTTTA

3481 AAGAGGACAT CCAGAAAGCC CAGGTGTCCG GCCAGGGCGA TAGCCTGCAC GAGCACATTG

3541 CCAATCTGGC CGGCAGCCCC GCCATTAAGA AGGGCATCCT GCAGACAGTG AAGGTGGTGG

3601 ACGAGCTCGT GAAAGTGATG GGCCGGCACA AGCCCGAGAA CATCGTGATC GAAATGGCCA

3661 GAGAGAACCA GACCACCCAG AAGGGACAGA AGAACAGCCG CGAGAGAATG AAGCGGATCG

3721 AAGAGGGCAT CAAAGAGGTG GGCAGCCAGA TCCTGAAAGA ACACCCCGTG GAAAACACCC

3781 AGCTGCAGAA CGAGAAGCTG TACCTGTACT AGCTGCAGAA TGGGCGGGAT ATGTACGTGG

3841 ACCAGGAACT GGACATCAAC CGGCTGTCCG ACTACGATGT GGACCATATC GTGCCTCAGA

3901 GCTTTCTGAA GGACGACTCC ATCGACAACA AGGTGCTGAC CAGAAGGGAC AAGAACCGGG

3961 GCAAGAGCGA CAACGTGCCC TCCGAAGAGG TCGTGAAGAA GATGAAGAAC TACTGGCGGC

4021 AGCTGCTGAA CGCCAAGCTG ATTACCCAGA GAAAGTTCGA CAATCTGACC AAGGCCGAGA

4081 GAGGCGGCCT GAGCGAACTG GATAAGGCCG GCTTCATCAA GAGACAGGTG GTGGAAACCC

4141 GGCAGATCAC AAAGCACGTG GCACAGATCC TGGACTCCCG GATGAACACT AAGTACGACG

4201 AGAATGACAA GCTGATCCGG GAAGTGAAAG TGATCACCCT GAAGTCCAAG CTGGTGTCCG

4261 ATTTCCGGAA GGATTTCCAG TTTTACAAAG TGCGCGAGAT CAACAACTAC CACCACGCCC

4321 ACGACGCCTA CCTGAACGCC GTCGTGGGAA CCGCCCTGAT CAAAAAGTAC CCTAAGCTGG

4381 AAAGCGAGTT CGTGTACGGC GACTACAAGG TGTACGACGT GCGGAAGATG ATCGCCAAGA

4441 GCGAGCAGGA AATCGGCAAG GCTACCGCCA AGTACTTCTT CTACAGCAAC ATCATGAACT

4501 TTTTCAAGAC CGAGATTACC CTGGCCAACG GCGAGATCCG GAAGCGGCCT CTGATCGAGA

4561 CAAACGGCGA AACCGGGGAG ATCGTGTGGG ATAAGGGCCG GGATTTTGCC ACCGTGCGGA

4621 AAGTGCTGAG CATGCCCCAA GTGAATATCG TGAAAAAGAC CGAGGTGCAG ACAGGCGGCT

4681 TCAGCAAAGA GTCTATCCTG CCCAAGAGGA ACAGGGATAA GCTGATCGCC AGAAAGAAGG

4741 ACTGGGACCC TAAGAAGTAC GGCGGCTTCG ACAGCCCCAC CGTGGCCTAT TCTGTGCTGG

4801 TGGTGGCCAA AGTGGAAAAG GGCAAGTCCA AGAAACTGAA GAGTGTGAAA GAGCTGCTGG

4861 GGATCACCAT CATGGAAAGA AGCAGCTTCG AGAAGAATCC CATCGACTTT CTGGAAGCCA

4921 AGGGCTACAA AGAAGTGAAA AAGGACCTGA TCATCAAGCT GCCTAAGTAC TCCCTGTTCG

4981 AGCTGGAAAA CGGCCGGAAG AGAATGCTGG CCTCTGCCGG CGAACTGCAG AAGGGAAACG

5041 AACTGGCCCT GCCCTCCAAA TATGTGAACT TCCTGTACCT GGCCAGCCAC TATGAGAAGC

5101 TGAAGGGCTC CCCCGAGGAT AATGAGCAGA AACAGCTGTT TGTGGAACAG CACAAGCACT

5161 ACCTGGACGA GATCATCGAG CAGATCAGCG AGTTCTCCAA GAGAGTGATC CTGGCCGACG

-continued

5221 CTAATCTGGA CAAAGTGCTG TCCGCCTACA ACAAGCACCG GGATAAGCCC ATCAGAGAGC

5281 AGGCCGAGAA TATCATCCAC CTGTTTACCC TGACCAATCT GGGAGCCCCT GCCGCCTTCA

5341 AGTACTTTGA CACCACCATC GACCGGAAGA GGTACACCAG CACCAAAGAG GTGCTGGACG

5401 CCACCCTGAT CCACCAGAGC ATCACCGGCC TGTACGAGAC ACGGATCGAC CTGTCTCAGC

5461 TGGGAGGCGA *CAAAAGGCCG GCGGCCACGA AAAAGGCCGG CCAGGCAAAA AAGAAAAAG*t 5521 aagaattcCT AGAGCTCGCT GATCAGCCTC GACTGTGCCT TCTAGTTGCC AGCCATCTGT

5581 TGTTTGCCCC TCCCCCGTGC CTTCCTTGAC CCTGGAAGGT GCCACTCCCA CTGTCCTTTC

5641 CTAATAAAAT GAGGAAATTG CATCGCATTG TCTGAGTAGG TGTCATTCTA TTCTGGGGGG

5701 TGGGGTGGGG CAGGACAGGA AGGGGGAGGA TTGGGAAGAg AATAGCAGGC ATGCTGGGGA 5761 gcggccgcag gaacccctag tgatggagtt ggccactccc tctctgcgcg ctcgctcgct 5821 cactgaggcc gggcgaccaa aggtcgcccg acgcccgggc tttgcccggg cggcctcagt 5881 gagcgagcga gcgcgcagct gcctgcaggg gcgcctgatg cggtattttc tccttacgca 5941 tctgtgcggt atttcacacc gcatacgtca aagcaaccat agtacgcgcc ctgtagcggc 6001 gcattaagcg cggcgggtgt ggtggttacg cgcagcgtga ccgctacact tgccagcgcc 6061 ctagcgcccg ctcctttcgc tttcttccct tcctttctcg ccacgttcgc cggctttccc 6121 cgtcaagctc taaatcgggg gctcccttta gggttccgat ttagtgcttt acggcacctc 6181 gaccccaaaa aacttgattt gggtgatggt tcacgtagtg ggccatcgcc ctgatagacg 6241 gtttttcgcc ctttgacgtt ggagtccacg ttctttaata gtggactctt gttccaaact 6301 ggaacaacac tcaaccctat ctcgggctat tcttttgatt tataagggat tttgccgatt 6361 tcggcctatt ggttaaaaaa tgagctgatt taacaaaaat ttaacgcgaa ttttaacaaa 6421 atattaacgt ttacaatttt atggtgcact ctcagtacaa tctgctctga tgccgcatag 6481 ttaagccagc cccgacaccc gccaacaccc gctgacgcgc cctgacgggc ttgtctgctc 6541 ccggcatccg cttacagaca agctgtgacc gtctccggga gctgcatgtg tcagaggttt 6601 tcaccgtcat caccgaaacg cgcgagacga aagggcctcg tgatacgcct atttttatag 6661 gttaatgtca tgataataat ggtttcttag acgtcaggtg gcacttttcg gggaaatgtg 6721 cgcggaaccc ctatttgttt atttttctaa atacattcaa atatgtatcc gctcatgaga 6781 caataaccct gataaatgct tcaataatat tgaaaaagga agagtatgag tattcaacat 6841 ttccgtgtcg cccttattcc cttttttgcg gcattttgcc ttcctgtttt tgctcaccca 6901 gaaacgctgg tgaaagtaaa agatgctgaa gatcagttgg gtgcacgagt gggttacatc 6961 gaactggatc tcaacagcgg taagatcctt gagagttttc gccccgaaga acgttttcca 7021 atgatgagca cttttaaagt tctgctatgt ggcgcggtat tatcccgtat tgacgccggg 7081 caagagcaac tcggtcgccg catacactat tctcagaatg acttggttga gtactcacca 7141 gtcacagaaa agcatcttac ggatggcatg acagtaagag aattatgcag tgctgccata 7201 accatgagtg ataacactgc ggccaactta cttctgacaa cgatcggagg accgaaggag 7261 ctaaccgctt ttttgcacaa catgggggat catgtaactc gccttgatcg ttgggaaccg 7321 gagctgaatg aagccatacc aaacgacgag cgtgacacca cgatgcctgt agcaatggca 7381 acaacgttgc gcaaactatt aactggcgaa ctacttactc tagcttcccg gcaacaatta 7441 atagactgga tggaggcgga taaagttgca ggaccacttc tgcgctcggc ccttccggct 7501 ggctggttta ttgctgataa atctggagcc ggtgagcgtg gaagccgcgg tatcattgca 7561 gcactggggc cagatggtaa gccctcccgt atcgtagtta tctacacgac ggggagtcag -continued

```
7621 gcaactatgg atgaacgaaa tagacagatc gctgagatag gtgcctcact gattaagcat

7681 tggtaactgt cagaccaagt ttactcatat atactttaga ttgatttaaa acttcatttt

7741 taatttaaaa ggatctaggt gaagatcctt tttgataatc tcatgaccaa aatcccttaa

7801 cgtgagtttt cgttccactg agcgtcagac cccgtagaaa agatcaaagg atcttcttga

7861 gatccttttt ttctgcgcgt aatctgctgc ttgcaaacaa aaaaaccacc gctaccagcg

7921 gtggtttgtt tgccggatca agagctacca actctttttc cgaaggtaac tggcttcagc

7981 agagcgcaga taccaaatac tgtccttcta gtgtagccgt agttaggcca ccacttcaag

8041 aactctgtag caccgcctac atacctcgct ctgctaatcc tgttaccagt ggctgctgcc

8101 agtggcgata agtcgtgtct taccgggttg gactcaagac gatagttacc ggataaggcg

8161 cagcggtcgg gctgaacggg gggttcgtgc acacagccca gcttggagcg aacgacctac

8221 accgaactga gatacctaca gcgtgagcta tgagaaagcg ccacgcttcc cgaagggaga

8281 aaggcggaca ggtatccggt aagcggcagg gtcggaacag gagagcgcac gagggagctt

8341 ccagggggaa acgcctggta tctttatagt cctgtcgggt ttcgccacct ctgacttgag

8401 cgtcgatttt tgtgatgctc gtcagggggg cggagcctat ggaaaaacgc cagcaacgcg

8461 gcctttttac ggttcctggc cttttgctgg ccttttgctc acatgt
```

Cells Producing Microvesicles Containing Cargo Proteins

A microvesicle-producing cell of the present invention may be a cell containing any of the expression constructs or any of the cargo proteins described herein. For example, an inventive microvesicle-producing cell may contain one or more recombinant expression constructs encoding (1) a minimal ARRDC1 protein, or PSAP (SEQ ID NO: 122) or PTAP (SEQ ID NO: 23) motif-containing variant thereof, and (2) a cargo protein fused to at least one WW domain, or variant thereof, under the control of a heterologous promoter. In certain embodiments, the expression construct in the microvesicle producing cell encodes a cargo protein with one or more WW domains or variants thereof. In some embodiments, the expression construct encodes a Cas9 cargo protein or variant thereof fused to one or more WW domains or variants thereof. In some embodiments, the expression construct encodes a Cas9 cargo protein or variant thereof fused to at least one WW domain and at least one NLS. In some embodiments, the expression construct further encodes a guide RNA (gRNA). In some embodiments, the expression construct further encodes a TSG101 protein, or a TSG101 protein variant. It should be appreciated that the ARMMs produced by such a microvesicle producing cell typically comprise the WW domain containing cargo proteins encoded by the expression constructs described herein.

Another inventive microvesicle-producing cell may contain a recombinant expression construct encoding (1) a minimal ARRDC1 protein, or a PSAP (SEQ ID NO: 122) or PTAP (SEQ ID NO: 23) motif-containing variant thereof, linked to (2) a Cas9 cargo protein, or variant thereof, under the control of a heterologous promoter. Some aspects of this invention provide a microvesicle-producing cell that comprises a recombinant expression construct encoding (1) a TSG101 protein, or a UEV domain-containing variant thereof, linked to (2) a Cas9 cargo protein or variant thereof, under the control of a heterologous promoter.

Any of the expression constructs, described herein, may be stably inserted into the genome of the cell. In some embodiments, the expression construct is maintained in the cell, but not inserted into the genome of the cell. In some embodiments, the expression construct is in a vector, for example, a plasmid vector, a cosmid vector, a viral vector, or an artificial chromosome. In some embodiments, the expression construct further comprises additional sequences or elements that facilitate the maintenance and/or the replication of the expression construct in the microvesicle-producing cell, or that improve the expression of the fusion protein in the cell. Such additional sequences or elements may include, for example, an origin of replication, an antibiotic resistance cassette, a polyA sequence, and/or a transcriptional isolator. Some expression constructs suitable for the generation of microvesicle producing cells according to aspects of this invention are described elsewhere herein. Methods and reagents for the generation of additional expression constructs suitable for the generation of microvesicle producing cells according to aspects of this invention will be apparent to those of skill in the art based on the present disclosure. In some embodiments, the microvesicle producing cell is a mammalian cell, for example, a mouse cell, a rat cell, a hamster cell, a rodent cell, or a nonhuman primate cell. In some embodiments, the microvesicle producing cell is a human cell.

One skilled in the art may employ conventional techniques, such as molecular or cell biology, virology, microbiology, and recombinant DNA techniques. Exemplary techniques are explained fully in the literature. For example, one may rely on the following general texts to make and use the invention: Sambrook et al., Molecular Cloning: A Laboratory Manual, Second Edition (1989) Cold Spring Harbor Laboratory Press, Cold Spring Harbor, New York, and Sambrook et al. Third Edition (2001); DNA Cloning: A Practical Approach, Volumes I and II (D. N. Glover ed. 1985); Oligonucleotide Synthesis (M. J. Gaited. 1984); Nucleic Acid Hybridization (B. D. Hames & S. J. Higgins eds. (1985)); Transcription and Translation Hames & Higgins, eds. (1984); Animal Cell Culture (RI. Freshney, ed. (1986)); Immobilized Cells And Enzymes (IRL Press, (1986)); Gennaro et al. (eds.) Remington's Pharmaceutical Sciences, 18th edition; B. Perbal, A Practical Guide To Molecular Cloning (1984); F. M. Ausubel et al. (eds.), Current Protocols in Molecular Biology, John Wiley & Sons, Inc. (updates through 2001), Coligan et al. (eds.), Current Protocols in Immunology, John Wiley & Sons, Inc. (updates through 2001); W. Paul et al. (eds.) Fundamental Immunology, Raven Press; E. J. Murray et al. (ed.) Methods in Molecular Biology: Gene Transfer and Expression Protocols, The Humana Press Inc. (1991)(especially vol. 7); and J. E. Celis et al., Cell Biology: A Laboratory Handbook, Academic Press (1994).

Delivery of ARMMs Containing Cargo Proteins

The inventive microvesicles (e.g., ARMMs) containing a cargo protein, described herein, may further have a targeting moiety. The targeting moiety may be used to target the delivery of ARMMs to specific cell types, resulting in the release of the contents of the ARMM into the cytoplasm of the specific targeted cell type. A targeting moiety may selectively bind an antigen of the target cell. For example, the targeting moiety may be a membrane-bound immunoglobulin, an integrin, a receptor, a receptor ligand, an aptamer, a small molecule, or a variant thereof. Any number of cell surface proteins may also be included in an ARMM to facilitate the binding of an ARMM to a target cell and/or to facilitate the uptake of an ARMM into a target cell. Integrins, receptor tyrosine kinases, G-protein coupled receptors, and membrane-bound immunoglobulins suitable for use with embodiments of this invention will be apparent to those of skill in the art and the invention is not limited in this respect. For example, in some embodiments, the integrin is an α1β1, α2β1, α4β1, α5β1, α6β1, αLβ2, αMβ2, αIIbβ3, αVβ3, αVβ5, αVβ6, or a α6β4 integrin. In some embodiments, the receptor tyrosine kinase is a an EGF receptor (ErbB family), insulin receptor, PDGF receptor, FGF receptor, VEGF receptor, HGF receptor, Trk receptor, Eph receptor, AXL receptor, LTK receptor, TIE receptor, ROR receptor, DDR receptor, RET receptor, KLG receptor, RYK receptor, or MuSK receptor. In some embodiments, the G-protein coupled receptor is a rhodopsin-like receptor, the secretin receptor, metabotropic glutamate/pheromone receptor, cyclic AMP receptor, frizzled/smoothened receptor, CXCR4 receptor, CCR5 receptor, or beta-adrenergic receptor.

Any number of membrane-bound immunoglobulins, known in the art, may be used as targeting moieties to target the delivery of ARMMs containing a cargo protein to any number of target cell types. In certain embodiments, the membrane-bound immunoglobulin targeting moiety binds a tumor associated or tumor specific antigen. Some non-limiting examples of tumor antigens include, CA19-9, c-met, PD-1, CTLA-4, ALK, AFP, EGFR, Estrogen receptor (ER), Progesterone receptor (PR), HER2/neu, KIT, B-RAF, S100, MAGE, Thyroglobulin, MUC-1, and PSMA (Bigbee W., et al. "Tumor markers and immunodiagnosis.", *Cancer Medicine.* 6th ed. Hamilton, Ontario, Canada: BC Decker Inc., 2003.; Andriole G, et al. "Mortality results from a randomized prostate-cancer screening trial.", *New England Journal of Medicine,* 360(13):1310-1319, 2009.; Schröder F H, et al. "Screening and prostate-cancer mortality in a randomized European study." New England Journal of Medicine, 360(13):1320-1328, 2009.; Buys S S, et al. "Effect of screening on ovarian cancer mortality: the Prostate, Lung, Colorectal and Ovarian (PLCO) Cancer Screening Randomized Controlled Trial.", *JAMA,* 305(22):2295-2303, 2011; Cramer D W et al. "Ovarian cancer biomarker performance in prostate, lung, colorectal, and ovarian cancer screening trial specimens." *Cancer Prevention Research,* 4(3):365-374, 2011.; Roy D M, et al. "Candidate prognostic markers in breast cancer: focus on extracellular proteases and their inhibitors.", *Breast Cancer.* July 3; 6:81-91, 2014.; Tykodi S S. et al. "PD-1 as an emerging therapeutic target in renal cell carcinoma: current evidence." *Onco Targets Ther.* July 25; 7:1349-59, 2014.; and Weinberg R A. The Biology of Cancer, Garland Science, Taylor & Francis Group LLC, New York, NY, 2007.; the entire contents of each are incorporated herein by reference).

In certain embodiments, the membrane-bound immunoglobulin targeting moiety binds to an antigen of a specific cell type. The cell type may be a stem cell, such as a pluripotent stem cell. Some non-limiting examples of antigens specific to pluripotent stem cells include Oct4 and Nanog, which were the first proteins identified as essential for both early embryo development and pluripotency maintenance in embryonic stem cells (Nichols J, et al. "Formation of pluripotent stem cells in the mammalian embryo depends on the POU transcription factor Oct4.*", Cell.* 95:379-91, 1998; the contents of which are hereby incorporated by reference). In addition to Oct4, Sox2 and Nanog, many other pluripotent stem cell markers have been identified, including Sall4, Dax1, Essrb, Tbx3, Tcl1, Rif1, Nac1 and Zfp281 (Loh Y, et al. "The Oct4 and Nanog transcription network regulates pluripotency in mouse embryonic stem cells.", *Nat Genet.* 38:431-40, 2006). The membrane-bound immunoglobulin targeting moiety may also bind to an antigen of a differentiated cell type. For example, the targeting moiety may bind to an antigen specific for a lung epithelial cell to direct the delivery of ARMM cargo proteins to lung epithelial cells. As a non-limiting example, a membrane-bound immunoglobulin targeting moiety may bind to the alveolar epithelial type 1 cell specific protein $RTI_{40}$ or $HTI_{56}$ to deliver cargo proteins to alveolar epithelial type 1 cells (McElroy M C et al. "The use of alveolar epithelial type I cell-selective markers to investigate lung injury and repair.", *European Respiratory Journal* 24:4, 664-673, 2004; the entire contents of which are hereby incorporated by reference). As another example, the targeting moiety may bind a mucin, such as muc5ac, or muc5b. It should be appreciated that the examples of antigens provided in this application are not limiting and the targeting moiety may be any moiety capable of binding any cellular antigen known in the art.

Some aspects of this invention relate to the recognition that ARMMs are taken up by target cells, and ARMM uptake results in the release of the contents of the ARMM into the cytoplasm of the target cells. In some embodiments, the fusion protein is an agent that affects a desired change in the target cell, for example, a change in cell survival, proliferation rate, a change in differentiation stage, a change in a cell identity, a change in chromatin state, a change in the transcription rate of one or more genes, a change in the transcriptional profile, or a post-transcriptional change in gene compression of the target cell. It will be understood by those of skill in the art, that the agent to be delivered will be chosen according to the desired effect in the target cell.

The genome of the target cell may be edited by a nuclease delivered to the cell via a strategy or method disclosed herein, e.g., by a RNA-programmable nuclease (e.g., Cas9), a TALEN, or a zinc-finger nuclease, or a plurality or combination of such nucleases. Some non-limiting aspects of this invention relate to the recognition that ARMMs can be used to deliver a cargo protein fused to at least one WW domain, or variant thereof, or a Cas9 fusion protein in ARMMs to the target cell or a population of target cells, for example, by contacting the target cell with ARMMs comprising the fusion protein to be delivered. Accordingly, some aspects of this invention provide ARMMs that comprise a fusion protein, for example, a Cas9 protein, or variant thereof, fused to a WW domain, a minimal ARRDC1protein, or variant thereof, or a TSG101 protein or variant thereof.

Using any of the nucleases, described herein, or any of the nucleases known in the art, a single- or double-strand break may be introduced at a specific site within the genome of a target cell by the nuclease, resulting in a disruption of the targeted genomic sequence. In some embodiments, the targeted genomic sequence is a nucleic acid sequence within the coding region of a gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele. In some embodiments, the insertion is detected by a suitable assay, e.g., a DNA sequencing assay, a southern blot assay, or an assay for a reporter gene encoded by the co-delivered nucleic acid, e.g., a fluorescent protein or resistance to an antibiotic. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial disruption of the function of a gene.

In some embodiments, cells from a subject are obtained and a nuclease is delivered to the cells by a system or method provided herein ex vivo. In some embodiments, the treated cells are selected for those cells in which a desired nuclease-mediated genomic editing event has been effected. In some embodiments, treated cells carrying a desired genomic mutation or alteration are returned to the subject they were obtained from.

Methods for engineering, generation, and isolation of nucleases targeting specific sequences, e.g., Cas9, TALE, or zinc finger nucleases, and editing cellular genomes at specific target sequences, are well known in the art (see, e.g., Mani et al., Biochemical and Biophysical Research Communications 335:447-457, 2005; Perez et al., Nature Biotechnology 26:808-16, 2008; Kim et al., Genome Research, 19:1279-88, 2009; Urnov et al., Nature 435:646-51, 2005; Carroll et al., Gene Therapy 15:1463-68, 2005; Lombardo et al., Nature Biotechnology 25:1298-306, 2007; Kandavelou et al., Biochemical and Biophysical Research Communications 388:56-61, 2009; and Hockemeyer et al., Nature Biotechnology 27(9):851-59, 2009, as well as the reference recited in the respective section for each nuclease). The skilled artisan will be able to ascertain suitable methods for use in the context of the present disclosure based on the guidance provided herein.

As another example, to augment the differentiation stage of a target cell, for example, to reprogram a differentiated target cell into an embryonic stem cell-like stage, the cell is contacted, in some embodiments, with ARMMs with reprogramming factors, for example, Oct4, Sox2, c-Myc, and/or KLF4 that are fused to at least one WW domain, or variant thereof. Similarly, to affect the change in the chromatin state of a target cell, the cell is contacted, in some embodiments, with ARMMs containing a chromatin modulator, for example, a DNA methyltransferase, or a histone deacetylase fused to at least one WW domain, or variant thereof. For another example, if survival of the target cell is to be diminished, the target cell, in some embodiments, is contacted with ARMMs comprising a cytotoxic agent, for example, a cytotoxic protein fused to at least one WW domain or variant thereof. Additional agents suitable for inclusion into ARMMs and for a ARMM-mediated delivery to a target cell or target cell population will be apparent to those skilled in the art, and the invention is not limited in this respect.

In some embodiments, the ARMMs comprising a cargo fused to a WW domain, or variant thereof are provided that further include a detectable label. Such ARMMs allow for the labeling of a target cell without genetic manipulation. Detectable labels suitable for direct delivery to target cells are known in the art, and include, but are not limited to, fluorescent proteins, fluorescent dyes, membrane-bound dyes, and enzymes, for example, membrane-bound or cytosolic enzymes, catalyzing the reaction resulting in a detectable reaction product. Detectable labels suitable according to some aspects of this invention further include membrane-bound antigens, for example, membrane-bound ligands that can be detected with commonly available antibodies or antigen binding agents.

In some embodiments, ARMMs are provided that comprise a WW domain containing protein or a fusion protein comprising a WW domain or variant thereof to be delivered to a target cell. In some embodiments, the fusion protein is or comprises a transcription factor, a transcriptional repressor, a fluorescent protein, a kinase, a phosphatase, a protease, a ligase, a chromatin modulator, or a recombinase. In some embodiments, the protein is a therapeutic protein. In some embodiments the protein is a protein that affects a change in the state or identity of a target cell. For example, in some embodiments, the protein is a reprogramming factor. Suitable transcription factors, transcriptional repressors, fluorescent proteins, kinases, phosphatases, proteases, ligases, chromatin modulators, recombinases, and reprogramming factors may be fused to one or more WW domains to facilitate their incorporation into ARMMs and their function may be tested by any methods that are known to those skilled in the art, and the invention is not limited in this respect.

Methods for isolating the ARMMs described herein are also provided. One exemplary method includes collecting the culture medium, or supernatant, of a cell culture comprising microvesicle-producing cells. In some embodiments, the cell culture comprises cells obtained from a subject, for example, cells suspected to exhibit a pathological phenotype, for example, a hyperproliferative phenotype. In some embodiments, the cell culture comprises genetically engineered cells producing ARMMs, for example, cells expressing a recombinant ARMM protein, for example, a recombinant ARRDC1 or TSG101 protein, such as a minimal ARRDC1 or TSG101 protein fused to a Cas9 protein or variant thereof. In some embodiments, the supernatant is pre-cleared of cellular debris by centrifugation, for example, by two consecutive centrifugations of increasing G value (e.g., 500G and 2000G). In some embodiments, the method comprises passing the supernatant through a 0.2 μm filter, eliminating all large pieces of cell debris and whole cells. In some embodiments, the supernatant is subjected to ultracentrifugation, for example, at 120,000G for 2 hours, depending on the volume of centrifugate. The pellet obtained comprises microvesicles. In some embodiments, exosomes are depleted from the microvesicle pellet by staining and/or sorting (e.g., by FACS or MACS) using an exosome marker as described herein. Isolated or enriched ARMMs can be suspended in culture media or a suitable buffer, as described herein.

Methods of Microvesicle-Mediated Delivery of Cargos

Some aspects of this invention provide a method of delivering an agent, for example, a cargo fused to a WW domain (e.g., a Cas9 protein fused to a WW domain) to a target cell. The target cell can be contacted with an ARMM comprising a minimal ARRDC1 in different ways. For example, a target cell may be contacted directly with an ARMM as described herein, or with an isolated ARMM from a microvesicle producing cell. The contacting can be done in vitro by administering the ARMM to the target cell in a culture dish, or in vivo by administering the ARMM to a subject. Alternatively, the target cell can be contacted with a microvesicle producing cell as described herein, for example, in vitro by co-culturing the target cell and the microvesicle producing cell, or in vivo by administering a microvesicle producing cell to a subject harboring the target cell. Accordingly, the method may include contacting the target cell with a microvesicle, for example, an ARMM containing any of the cargo proteins to be delivered, as described herein. The target cell may be contacted with a microvesicle-producing cell, as described herein, or with an isolated microvesicle that has a lipid bilayer, a minimal ARRDC1 protein or variant thereof, and a cargo protein.

It should be appreciated that the target cell may be of any origin. For example, the target cell may be a human cell. The target cell may be a mammalian cell. Some non-limiting examples of a mammalian cell include a mouse cell, a rat cell, hamster cell, a rodent cell, and a nonhuman primate cell. It should also be appreciated that the target cell may be of any cell type. For example, the target cell may be a stem cell, which may include embryonic stem cells, induced pluripotent stem cells (iPS cells), fetal stem cells, cord blood stem cells, or adult stem cells (i.e., tissue specific stem cells). In other cases, the target cell may be any differentiated cell type found in a subject. In some embodiments, the target cell is a cell in vitro, and the method includes administering the microvesicle to the cell in vitro, or co-culturing the target cell with the microvesicle-producing cell in vitro. In some embodiments, the target cell is a cell in a subject, and the method comprises administering the microvesicle or the microvesicle-producing cell to the subject. In some embodiments, the subject is a mammalian subject, for example, a rodent, a mouse, a rat, a hamster, or a non-human primate. In some embodiments, the subject is a human subject.

In some embodiments, the target cell is a pathological cell. In some embodiments, the target cell is a cancer cell. In some embodiments, the microvesicle is associated with a binding agent that selectively binds an antigen on the surface of the target cell. In some embodiments, the antigen of the target cell is a cell surface antigen. In some embodiments, the binding agent is a membrane-bound immunoglobulin, an integrin, a receptor, or a receptor ligand. Suitable surface antigens of target cells, for example of specific target cell types, e.g. cancer cells, are known to those of skill in the art, as are suitable binding agents that specifically bind such antigens. Methods for producing membrane-bound binding agents, for example, membrane-bound immunoglobulin, for example, membrane-bound antibodies or antibody fragments that specifically bind a surface antigen expressed on the surface of cancer cells, are also known to those of skill in the art. The choice of the binding agent will depend, of course, on the identity or the type of target cell. Cell surface antigens specifically expressed on various types of cells that can be targeted by ARMMs comprising membrane-bound binding agents will be apparent to those of skill in the art. It will be appreciated that the present invention is not limited in this respect.

Co-Culture Systems

Some aspects of this invention provide in vitro cell culture systems having at least two types of cells: microvesicle producing cells, and target cells that take up the microvesicles produced. Accordingly, in the co-culture systems provided herein, there is a shuffling of the contents of the microvesicles (e.g., ARMMs comprising minimal ARRDC1) to the target cells. Such co-culture systems allow for the expression of a gene product or multiple gene products generated by the microvesicle producing cells in the target cells without genetic manipulation of the target cells.

In some embodiments, a co-culture system is provided that comprises (a) a microvesicle-producing cell population having a recombinant expression construct encoding (i) a minimal ARRDC1 protein, or variant thereof, fused to a cargo (e.g., an endonuclease such as a Cas9 protein or variant thereof) under the control of a heterologous promoter, and/or (ii) a TSG101 protein or variant thereof fused to a Cas9 protein variant thereof under the control of a heterologous promoter, and/or (iii) a cargo protein fused to a WW domain; and (b) a target cell population. In some embodiments, the minimal ARRDC1 variant comprises a PSAP (SEQ ID NO: 122) or PTAP (SEQ ID NO: 123) motif, and/or the TSG101 variant comprises a UEV domain. In some embodiments, the expression construct further encodes a guide RNA (gRNA) which may comprise a nucleotide sequence that complements a target site to mediate binding of a nuclease (e.g., a Cas9 nuclease) to a target site thereby providing the sequence specificity of the nuclease:RNA complex. In some embodiments, the host cell comprises a plurality of expression constructs encoding a plurality of minimal ARRDC1:Cas9 fusion proteins and/or TSG101:Cas9 fusion proteins and/or cargo proteins fused to a WW domain.

One exemplary application of a co-culture system as provided herein is the programming or reprogramming of a target cell without genetic manipulation. For example, in some embodiments, the target cell is a differentiated cell, for example, a fibroblast cell. In some embodiments, the microvesicle producing cells are feeder cells or non-proliferating cells. In some embodiments, the microvesicle producing cells produce ARMMs comprising a reprogramming factor fused to one or more WW domains, or a plurality of reprogramming factors that are fused to one or more WW domains. In some embodiments, co-culture of the differentiated target cells with the microvesicle producing cells results in the reprogramming of the differentiated target cells to an embryonic state. In some embodiments, co-culture of the differentiated target cells with the microvesicle producing cells results in the programming, or trans-differentiation, of the target cells to a differentiated cell states that is different from the original cell state of the target cells.

Another exemplary application of a co-culture system, as provided herein, is the directed differentiation of embryonic stem cells. In some embodiments, the target cells are undifferentiated embryonic stem cells, and the microvesicle producing cells express one or more differentiation factors fused to one or more WW domains, for example, signaling molecules or transcription factors that trigger or facilitate the differentiation of the embryonic stem cells into differentiated cells of a desired lineage, for example neuronal cells, or mesenchymal cells.

Yet another exemplary application of a co-culture system, as provided herein, is the maintenance of stem cells, for example, of embryonic stem cells or of adult stem cells in an undifferentiated state. In some such embodiments, the microvesicle producing cells express signaling molecules and/or transcription factors fused to one or more WW domains that promote stem cell maintenance and/or inhibit stem cell differentiation. The microvesicle producing cells may create a microenvironment for the stem cells that mimics a naturally occurring stem cell niche.

The microvesicle-producing cell of a culture system may be a cell of any type or origin that is capable of producing any of the ARMMs described herein. For example, the microvesicle-producing cell may be a mammalian cell, examples of which include but are not limited to, a cell from a rodent, a mouse, a rat, a hamster, or a non-human primate. The microvesicle-producing cell may also be from a human. One non-limiting example of a microvesicle-producing cell capable of producing an ARMM is a human embryonic kidney 293T cell. The microvesicle-producing cell may be a proliferating or a non-proliferating cell. In some embodiments, the microvesicle-producing cell is a feeder cell which supports the growth of other cells in the culture. Feeder cells may provide attachment substrates, nutrients, or other factors that are needed for the growth of cells in culture.

The target cell of the culture system can be a cell of any type or origin, which may be contacted with an ARMM from any of the microvesicle-producing cells, described herein. For example, the target cell may be a mammalian cell, examples of which include but are not limited to, a cell from a rodent, a mouse, a rat, a hamster, or a non-human primate. The target cell may also be from a human. The target cell may be from an established cell line (e.g., a 293T cell), or a primary cell cultured ex vivo (e.g., cells obtained from a subject and grown in culture). Target cells may be hematologic cells (e.g., hematopoietic stem cells, leukocytes, thrombocytes or erythrocytes), or cells from solid tissues, such as liver cells, kidney cells, lung cells, heart cells bone cells, skin cells, brain cells, or any other cell found in a subject. Cells obtained from a subject can be contacted with an ARMM from a microvesicle-producing cell and subsequently re-introduced into the same or another subject. In some embodiments, the target cell is a stem cell. The stem cell may be a totipotent stem cell that can differentiate into embryonic and extraembryonic cell types. The stem cell may also be a pluripotent stem cell, a multipotent stem cell, an oligopotent stem cell or a unipotent stem cell. In other embodiments, the target cell is a differentiated cell.

Method of Gene Editing

Some aspects of the invention provide methods for gene editing by contacting a target cell with ARMMs that contain any of the RNA-programmable fusion proteins (i.e., Cas9 fusion proteins) described herein. Other aspects of the invention provide methods for gene editing by contacting a target cell with a microvesicle-producing cell comprising a recombinant expression construct encoding any of the RNA-programmable fusion proteins described herein. The RNA-guided or RNA-programmable fusion protein may be delivered to a target cell by any of the systems or methods provided herein. For example, the RNA-programmable fusion protein may contain a Cas9 nuclease, or variants thereof, one or more WW domains, or variants thereof, or optionally one or more NLSs which may be delivered to a target cell by the systems or methods provided herein.

In some embodiments, the RNA-programmable nuclease includes any of the Cas9 fusion proteins described herein. Because RNA-programmable nucleases (i.e., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. Science 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. Nature biotechnology 31, 227-229 (2013); Jinek, M. et al. RNA-programmed genome editing in human cells. eLife 2, e00471 (2013); Dicarlo, J. E. et al. Genome engineering in Saccharomyces cerevisiae using CRISPR-Cas systems. Nucleic acids research (2013); Jiang, W. et al. RNA-guided editing of bacterial genomes using CRISPR-Cas systems. Nature biotechnology 31, 233-239 (2013); the entire contents of each of which are incorporated herein by reference).

Some aspects of this disclosure provide fusion proteins that have an RNA-guided or RNA-programmable fusion protein (i.e., a Cas9 protein, or Cas9 variant) that can bind to a gRNA, which, in turn, binds a target nucleic acid sequence; and a DNA-editing domain. Some non-limiting examples of DNA-editing domains include, but are not limited to, nucleases, nickases, recombinases or deaminases. As one example, a deaminase domain that can deaminate a nucleobase, such as, for example, cytidine is fused to an RNA-guided or RNA-programmable fusion protein. In some embodiments, the deaminase is fused to any of the Cas9 fusion proteins, described herein. The deamination of a nucleobase by a deaminase can lead to a point mutation at the respective residue, which is referred to herein as nucleic acid editing. Cargo proteins having a Cas9 protein or Cas9 variant, a DNA editing domain, and a protein capable of facilitating the incorporation of the cargo protein into an ARMM (e.g., a WW domain, a minimal ARRDC1 protein, or a TSG101 protein) can thus be used for the targeted editing of nucleic acid sequences. It should be appreciated that any number of DNA editing domains (e.g., nucleases, nickases, recombinases and deaminases) known in the art may be fused to an (i) RNA-guided or RNA-programmable fusion protein (e.g., Cas9 or a Cas9 variant), and (ii) one or more WW domains or WW domain variants, or (iii) a minimal ARRDC1 protein, or variant thereof, or (iv) a TSG101 protein, or variant thereof. Such fusion proteins are useful for targeted editing of DNA in vitro, e.g., for the generation of mutant cells or animals; for the introduction of targeted mutations, e.g., for the correction of genetic defects in cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a subject. It should also be appreciated that any of the cargo proteins, described herein, are useful for targeted editing of DNA in vivo, e.g., for the generation of mutant cells in a subject. Delivery of ARMMs containing any of the fusion proteins, described herein, may be administered to a subject by any of the methods or systems, described herein.

The methods of gene editing, described herein, may result in the correction of a genetic defect, e.g., in the correction of a point mutation that leads to a loss of function in a gene product. In some embodiments, the genetic defect is associated with a disease or disorder, e.g., a lysosomal storage disorder or a metabolic disease, such as, for example, type I diabetes. In some embodiments, the methods provided herein are used to introduce a deactivating point mutation into a gene or allele that encodes a gene product that is associated with a disease or disorder. For example, in some embodiments, methods are provided herein that employ an RNA-guided or RNA-programmable fusion protein (i.e., a Cas9 protein, or Cas9 variant) fused to a DNA editing cargo protein and at least one WW domain, or variant thereof, or a minimal ARRDC1 protein, or variant thereof, or a TSG101 protein, or variant thereof, to introduce a deactivating point mutation into an oncogene. A deactivating mutation may, in some embodiments, generate a premature stop codon in a coding sequence, which results in the expression of a truncated gene product, e.g., a truncated protein lacking a function of the full-length protein.

The purpose of the methods provide herein may be used to restore the function of a dysfunctional gene via genome editing. The cargo proteins provided herein can be validated for gene editing-based human therapeutics in vitro, e.g., by correcting a disease-associated mutation in human cell culture. It will be understood by the skilled artisan that the cargo proteins provided herein, e.g., the fusion proteins comprising a Cas9 protein or Cas9 variant, a nucleic acid editing domain, and at least one WW domain or a minimal ARRDC1 protein or a TSG101 protein, can be used to correct any single point T>C or A>G mutation. For example, deamination of the mutant C back to U corrects the mutation, and in the latter case, deamination of the C that is base-paired with the mutant G, followed by a round of replication, corrects the mutation.

An exemplary disease-relevant mutation that can be corrected by the instantly provided cargo proteins in vitro or in vivo is the H1047R (A3140G) polymorphism in the PIK3CA protein. The phosphoinositide-3-kinase, catalytic alpha subunit (PIK3CA) protein acts to phosphorylate the 3-OH group of the inositol ring of phosphatidylinositol. The PIK3CA gene has been found to be mutated in many different carcinomas, and thus it is considered to be a very potent oncogene (Lee J W et al. "PIK3CA gene is frequently mutated in breast carcinomas and hepatocellular carcinomas.", *Oncogene*. 2005; 24(8):1477-80; the entire contents of which are hereby incorporated by reference). In fact, the A3140G mutation is present in several NCI-60 cancer cell lines such as the HCT116, SKOV3, and T47D cell lines, which are readily available from the American Type Culture Collection (ATCC) (Ikediobi O N et al. "Mutation analysis of 24 known cancer genes in the NCI-60 cell line set.", *Mol Cancer Ther.* 2006; 5(11):2606-12).

In some embodiments, a cell carrying a mutation to be corrected, e.g., a cell carrying a point mutation resulting in a H1047R or A3140G substitution in the PIK3CA protein are contacted with an ARMM containing (i) a Cas9 protein or Cas9 variant fused to (ii) at least one WW domain or variant thereof, or a minimal ARRDC1 protein or variant thereof, or a TSG101 protein or variant thereof, (iii) a deaminase fusion protein and an appropriately designed gRNA targeting the fusion protein to the respective mutation site in the encoding PIK3CA gene. Control experiments can be performed where the gRNAs are designed to target the fusion proteins to non-C residues that are within the PIK3CA gene. Genomic DNA of the treated cells can be extracted and the relevant sequence of the PIK3CA genes PCR amplified and sequenced to assess the activities of the fusion proteins in human cell culture.

It will be understood that the example of correcting point mutations in PIK3CA is provided for illustration purposes, and is not meant to limit the instant disclosure. The skilled artisan will understand that the instantly disclosed DNA-editing cargo proteins, described herein, can be used to correct other point mutations and mutations associated with other cancers and with diseases other than cancer.

The successful correction of mutations in disease-associated genes and alleles using any of the ARMMs or fusion proteins, described herein, opens up new strategies for gene correction with applications in disease therapeutics and gene study. Site-specific nucleotide modification proteins like the disclosed Cas9 variants fused to DNA-editing domains and at least one WW protein or a minimal ARRDC1 protein or a TSG101 protein also have applications in "reverse" gene therapy, where certain gene functions are purposely suppressed or abolished. In these cases, site-specifically mutating Trp (TGG), Gln (CAA and CAG), or Arg (CGA) residues to premature stop codons (TAA, TAG, TGA) can be used to abolish protein function in vitro, ex vivo, or in vivo.

The instant disclosure provides methods for the treatment of a subject diagnosed with a disease associated or caused by a mutation that can be corrected by any of the DNA editing cargo proteins provided herein. For example, in some embodiments, a method is provided that comprises administering to a subject having such a disease, (e.g., a cancer associated with a PIK3CA point mutation) as described above, an effective amount of ARMMs containing any of the cargo proteins, described herein, that corrects the point mutation or introduces a deactivating mutation into the disease-associated gene. It should be appreciated that the inventive ARMMs may be used to target the delivery of any of the cargo proteins, described herein, to any target cell, described herein. In some embodiments, the disease is a neoplastic disease. In some embodiments, the disease is a metabolic disease. In some embodiments, the disease is a lysosomal storage disease. Other diseases that can be treated by correcting a mutation or introducing a deactivating mutation into a disease-associated gene will be known to those of skill in the art, and the disclosure is not limited in this respect.

In some embodiments, the genome of the target cell is edited by a nuclease delivered to the target cell via a system or method disclosed herein, e.g., by delivering any of the Cas9 fusion proteins using any of the ARMMs or ARMM producing cells described herein. In some embodiments, a single- or double-strand break is introduced at a specific site within the genome of a target cell by a Cas9 protein, resulting in a disruption of the targeted genomic sequence. In some embodiments, the targeted genomic sequence is a nucleic acid sequence within the coding region of a gene. In some embodiments, the targeted genomic sequence is a nucleic acid sequence outside the coding region of a gene, for example, the targeted genomic sequence may be within the promoter region of a gene. In some embodiments, the strand break introduced by the nuclease leads to a mutation within the target gene that impairs the expression of the encoded gene product.

A nucleic acid (e.g., a gRNA) may be associated with an RNA-guided protein (e.g., a Cas9 protein, or Cas9 variant) fused to a DNA editing domain and at least one WW domain, or variant thereof, or a minimal ARRDC1 protein, or variant thereof, or a TSG101 protein, or variant thereof. Typically, a gRNA contains a nucleotide sequence that complements a target site, which mediates binding of the protein:RNA complex to a target site and providing the sequence specificity of the protein:RNA complex. Accordingly, a nucleic acid (e.g., a gRNA) may be co-expressed with any of the cargo proteins, described herein, in order to confer target sequence specificity to any of the RNA-guided fusion proteins, described herein. As one non-limiting example, a Cas9 variant fused to a WW domain may be co-expressed in a cell with a gRNA such that the gRNA associates with the Cas9 fusion protein and the Cas9 fusion protein, in complex with the gRNA, is loaded into an ARMM. In some embodiments, the nucleic acid has a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele.

In certain embodiments, a catalytically inactive Cas9 fusion protein is used to activate or repress gene expression by fusing the inactive enzyme (that retains its gRNA-binding ability) to known regulatory domains. Cas9 variants that can be used to control gene expression have been described in detail, for example, in U.S. patent application number, U.S. Ser. No. 14/216,655, filed Mar. 17, 2014 (published as US 2014-0273226 A1) by Wu F. et al., entitled Crispr/cas systems for genomic modification and gene modulation, and in PCT application number PCT/US2013/074736, filed on Dec. 12, 2013 (published as WO 2014/093655 A2) by Zhang F. et al., entitled Engineering and optimization of systems, methods and compositions for sequence manipulation with functional domains; the entire contents of each are incorporated herein by reference. For example, a catalytically inactive Cas9 fusion protein may be fused to a transcriptional activator (e.g. VP64). In certain embodiments, any of the Cas9 fusion proteins described herein may be when fused to a transcriptional activator to up-regulating gene transcription of targeted genes to enhance expression. In some embodiments, a catalytically inactive Cas9 fusion protein may be fused to a transcriptional repressor (e.g. KRAB). In certain embodiments, any of the Cas9 fusion proteins described herein may be fused to a transcriptional repressor to down-regulate gene transcription of targeted genes to reduce expression. In some embodiments, the delivery of a nuclease to a target cell results in a clinically or therapeutically beneficial disruption or enhancement of the function of a gene. It should be appreciated that the methods described herein are not meant to be limiting and may include any method of using Cas9 that is well known in the art.

The function and advantage of these and other embodiments of the present invention will be more fully understood from the Examples below. The following Examples are intended to illustrate the benefits of the present invention and to describe particular embodiments, but are not intended to exemplify the full scope of the invention. Accordingly, it will be understood that the Examples are not meant to limit the scope of the invention.

EXAMPLES

Figure 2B:
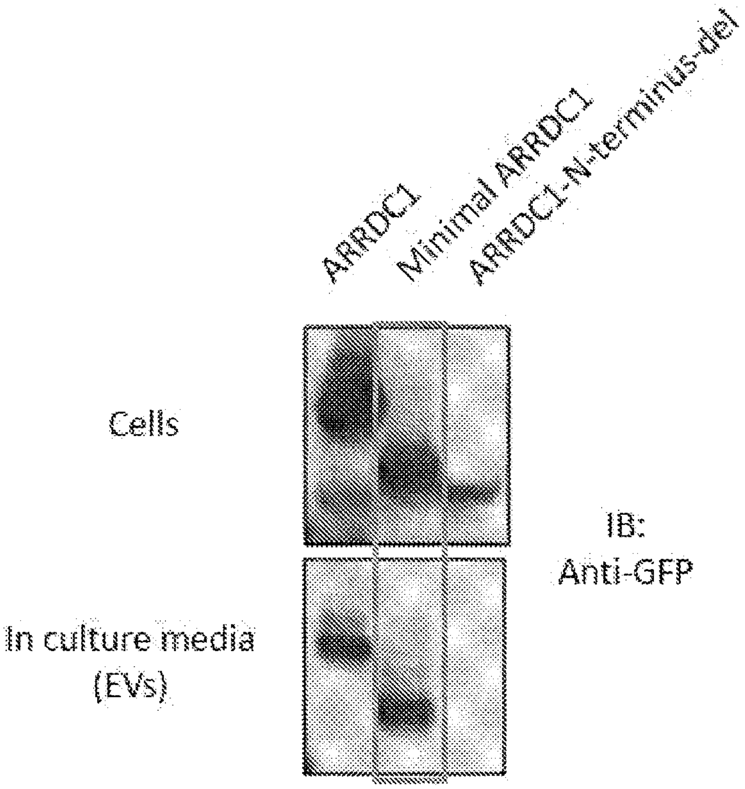
Figure 2C:
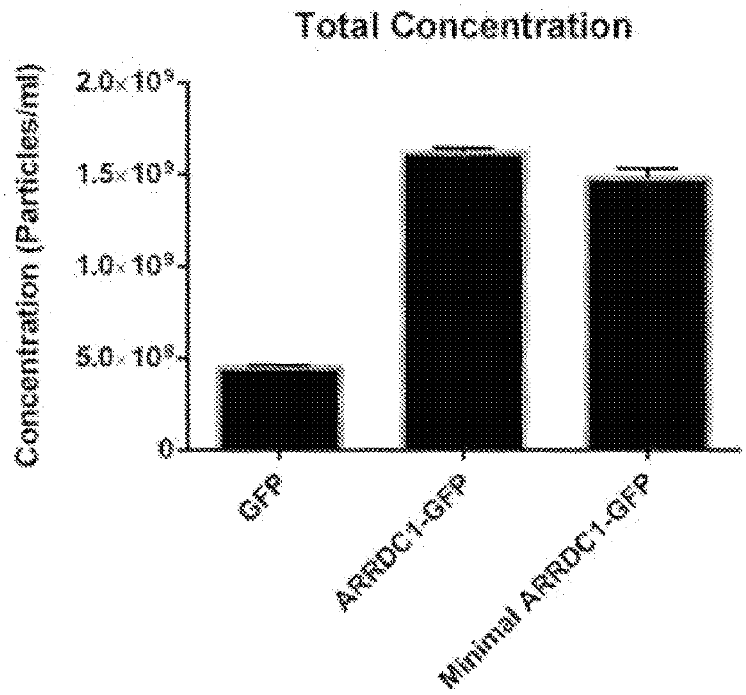

Example 1: Minimal ARRDC1 Drives ARMMs Formation and Budding as Efficiently as Full-Length ARRDC1 Protein An ARRDC1 construct was made that contains the arrestin domain, PSAP (SEQ ID NO: 122) motif and the two PPXY motifs. This "minimal" ARRDC1 is about 330 amino acid long (100 amino acids shorter than the full-length ARRDC1 (FIG. 1 and FIG. 5). When expressed in HEK293T cells, the minimal ARRDC1 buds into EVs as efficiently as the full-length ARRDC1 (FIG. 2B). As a negative control, another ARRDC1 construct that is of a similar size but lacks part of the N-terminal arrestin domain did not bud. Importantly, the number of extracellular vesicles made by minimal ARRDC1 expression is comparable with that of the full-length ARRDC1 (FIG. 2C). These data indicate that the minimal ARRDC1 is able to drive ARMMs formation and budding as efficiently as the full-length ARRDC1 protein.

Example 2: Minimal ARRDC1 in Packaging Cargos into ARMMs

Figure 3A:
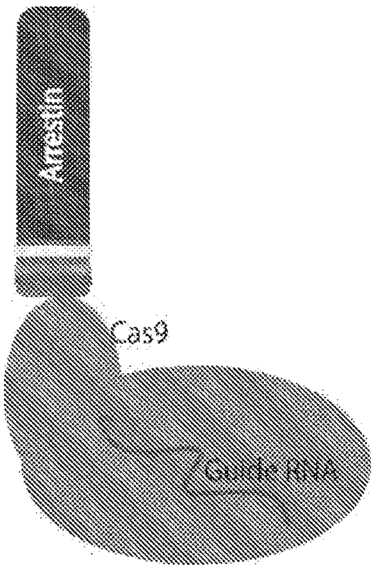
FIGS. 3A-3C—FIG. 3A is a schematic showing fusion of a minimal ARRDC1 to Cas9.
Figure 3B:
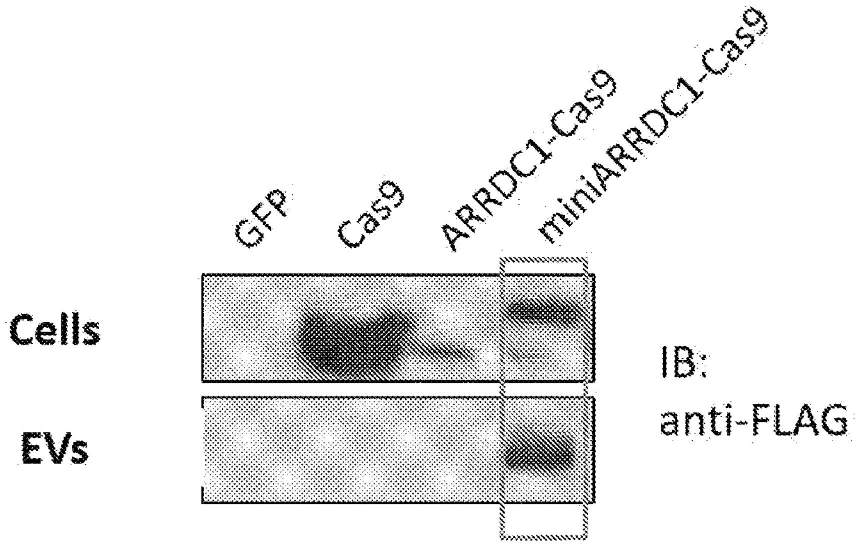
Figure 3C:
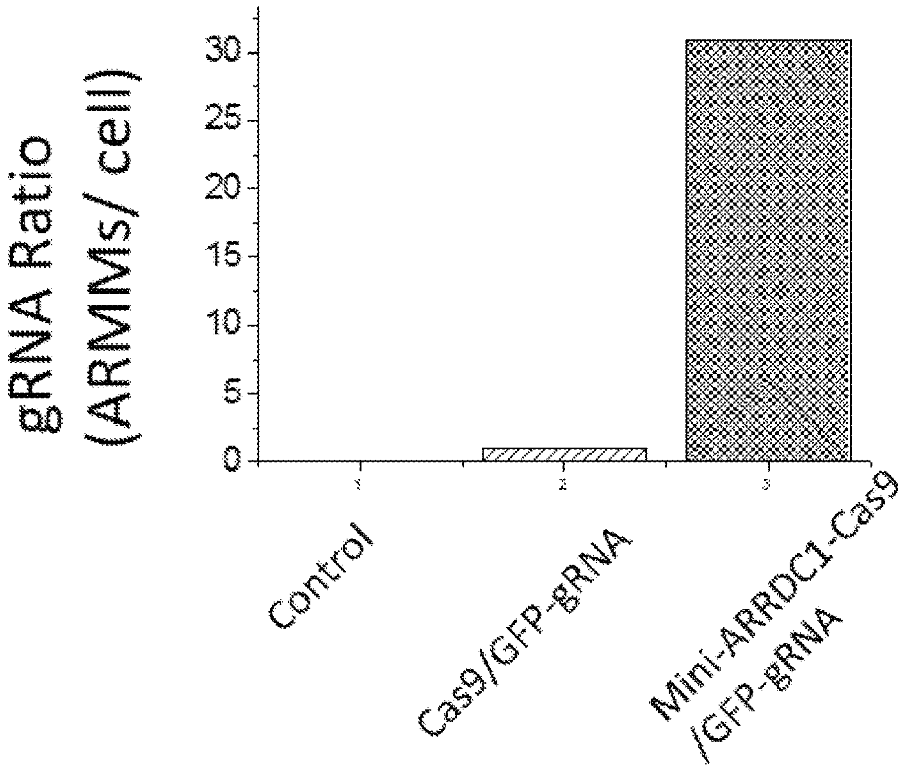
Figure 4:
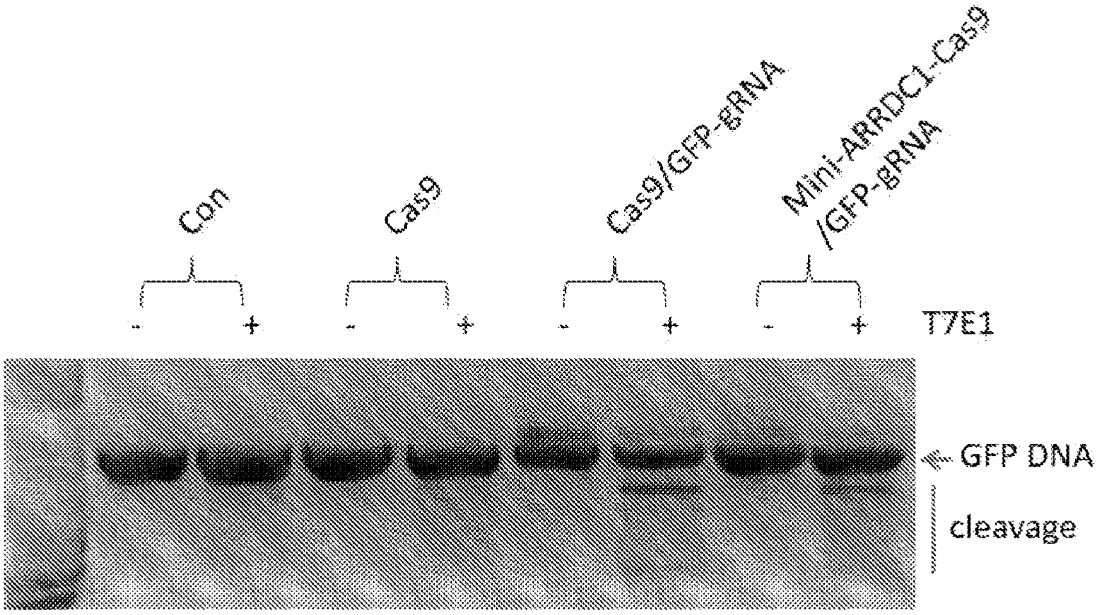
FIG. 4 shows gene editing activity of miniARRDC1-Cas9. Cas9, ARRDC1-Cas9, and miniARRDC1-Cas9 along with a guide RNA (gRNA) targeting a single copy GFP gene transfected into U2OS cells. 48 hours post transfection, genomic DNAs were isolated and the GFP fragment containing the gRNA targeting site was amplified and analyzed by the T7E1 cleavage assay to detect indels (insertion or deletions).

The ability of minimal ARRDC1 in packaging cargos into ARMMs was tested. A fusion construct of minimal ARRDC1 to the Cas9 protein (FIG. 3A) was made. When expressed in HEK293T cells, the miniARRDC1-Cas9 protein is able to bud into the extracellular vesicles (EVs), whereas the Cas9 fusion to full length ARRDC1 did not bud out (FIG. 3B). Moreover, the guide RNA (gRNA) associated with Cas9 was much more enriched in ARMMs produced from miniARRDC1-Cas9 fusion protein than the control Cas9. Importantly, the miniARRDC1-Cas9 fusion protein maintains efficient gene editing activity as evidenced by an assay targeting the GFP DNA locus (FIG. 4). These results indicate that the minimal ARRDC1 is able to package Cas9 and associated gRNA into ARMMs via direction.

REFERENCES

1. Hurley J H, Boura E, Carlson L A, & Rozycki B (2010) Membrane budding. Cell 143:875-887.
2. Thery C, Ostrowski M, & Segura E (2009) Membrane vesicles as conveyors of immune responses. Nat Rev Immunol 9:581-593.
3. Henne W M, Buchkovich N J, & Emr S D (2011) The ESCRT pathway. Dev Cell 21:77-91.
4. Katzmann D J, Odorizzi G, & Emr S D (2002) Receptor downregulation and multivesicular-body sorting. Nat Rev Mol Cell Biol 3:893-905.
5. Babst M, Odorizzi G, Estepa E J, & Emr S D (2000) Mammalian tumor susceptibility gene 101 (TSG101) and the yeast homologue, Vps23p, both function in late endosomal trafficking. Traffic 1:248-258.
6. Lu Q, Hope L W, Brasch M, Reinhard C, & Cohen S N (2003) TSG101 interaction with HRS mediates endosomal trafficking and receptor down-regulation. Proc Natl Acad Sci USA 100:7626-7631.
7. Pornillos O, Alam S L, Davis D R, & Sundquist W I (2002) Structure of the Tsg101 UEV domain in complex with the PTAP motif of the HIV-1 p6 protein. Nat Struct Biol 9:812-817.
8. Pornillos O, Alam S L, Rich R L, Myszka D G, Davis D R, & Sundquist W I (2002) Structure and functional interactions of the Tsg101 UEV domain. EMBO J 21:2397-2406.
9. Sundquist W I, Schubert H L, Kelly B N, Hill G C, Holton J M, & Hill C P (2004) Ubiquitin recognition by the human TSG101 protein. Mol Cell 13:783-789.
10. Bache K G, Brech A, Mehlum A, & Stenmark H (2003) Hrs regulates multivesicular body formation via ESCRT recruitment to endosomes. J Cell Biol 162:435-442.
11. Pornillos O, Higginson D S, Stray K M, Fisher R D, Garrus J E, Payne M, He G P, Wang H E, Morham S G, & Sundquist W I (2003) HIV Gag mimics the Tsg101-recruiting activity of the human Hrs protein. J Cell Biol 162:425-434.

12. von Schwedler U K, Stuchell M, Muller B, Ward D M, Chung H Y, Morita E, Wang H E, Davis T, He G P, Cimbora D M, et al. (2003) The protein network of HIV budding. Cell 114:701-713.
13. Hurley J H & Stenmark H (2011) Molecular mechanisms of ubiquitin-dependent membrane traffic. Annu Rev Biophys 40:119-142.
14. Schorey J S & Bhatnagar S (2008) Exosome function: from tumor immunology to pathogen biology. Traffic 9:871-881.
15. Thery C, Zitvogel L, & Amigorena S (2002) Exosomes: composition, biogenesis and function. Nat Rev Immunol 2:569-579.
16. Bieniasz P D (2009) The cell biology of HIV-1 virion genesis. Cell Host Microbe 5:550-558.
17. Demirov D G & Freed E O (2004) Retrovirus budding. Virus Res 106:87-102.
18. Morita E & Sundquist W I (2004) Retrovirus budding. Annu Rev Cell Dev Biol 20:395-425.
19. Garrus J E, von Schwedler U K, Pornillos O W, Morham S G, Zavitz K H, Wang H E, Wettstein D A, Stray K M, Cote M, Rich R L, et al. (2001) Tsg101 and the vacuolar protein sorting pathway are essential for HIV-1 budding. Cell 107:55-65.
20. VerPlank L, Bouamr F, LaGrassa T J, Agresta B, Kikonyogo A, Leis J, & Carter C A (2001) Tsgl01, a homologue of ubiquitin-conjugating (E2) enzymes, binds the L domain in HIV type 1 Pr55(Gag). Proc Natl Acad Sci USA 98:7724-7729.
21. Martin-Serrano J, Zang T, & Bieniasz P D (2001) HIV-1 and Ebola virus encode small peptide motifs that recruit Tsg101 to sites of particle assembly to facilitate egress. Nat Med 7:1313-1319.
22. Martin-Serrano J, Zang T, & Bieniasz P D (2003) Role of ESCRT-I in retroviral budding. J Virol 77:4794-4804.
23. Demirov D G, Ono A, Orenstein J M, & Freed E O (2002) Overexpression of the N-terminal domain of TSG101 inhibits HIV-1 budding by blocking late domain function.
Proc Natl Acad Sci USA 99:955-960.
24. Gottlinger H G, Dorfman T, Sodroski J G, & Haseltine W A (1991) Effect of mutations affecting the p6 gag protein on human immunodeficiency virus particle release. Proc Natl Acad Sci USA 88:3195-3199.
25. Huang M, Orenstein J M, Martin M A, & Freed E O (1995) p6Gag is required for particle production from full-length human immunodeficiency virus type 1 molecular clones expressing protease. J Virol 69:6810-6818.
26. Freed E O & Mouland A J (2006) The cell biology of HIV-1 and other retroviruses. Retrovirology 3:77.
27. Martin-Serrano J & Neil S J Host factors involved in retroviral budding and release. Nat Rev Microbiol 9:519-531.
28. Rauch S & Martin-Serrano J (2011) Multiple interactions between the ESCRT machinery and arrestin-related proteins: implications for PPXY-dependent budding. J Virol 85:3546-3556.
29. Ono A & Freed E O (2004) Cell-type-dependent targeting of human immunodeficiency virus type 1 assembly to the plasma membrane and the multivesicular body. J Virol 78:1552-1563.
30. Pisitkun T, Shen R F, & Knepper M A (2004) Identification and proteomic profiling of exosomes in human urine. Proc Natl Acad Sci USA 101:13368-13373.
31. Welton J L, Khanna S, Giles P J, Brennan P, Brewis I A, Staffurth J, Mason M D, & Clayton A (2010) Proteomics analysis of bladder cancer exosomes. Mol Cell Proteomics 9:1324-1338.
32. Mathivanan S, Lim J W, Tauro B J, Ji H, Moritz R L, & Simpson R J (2009) Proteomics analysis of A33 immunoaffinity-purified exosomes released from the human colon tumor cell line LIM1215 reveals a tissue-specific protein signature. Mol Cell Proteomics 9:197-208.
33. Razi M & Futter C E (2006) Distinct roles for Tsg101 and Hrs in multivesicular body formation and inward vesiculation. Mol Biol Cell 17:3469-3483.
34. Hammarstedt M & Garoff H (2004) Passive and active inclusion of host proteins in human immunodeficiency virus type 1 gag particles during budding at the plasma membrane. J Virol 78:5686-5697.
35. Babst M (2005) A protein's final ESCRT. Traffic 6:2-9.
36. Scott A, Chung H Y, Gonciarz-Swiatek M, Hill G C, Whitby F G, Gaspar J, Holton J M, Viswanathan R, Ghaffarian S, Hill C P, et al. (2005) Structural and mechanistic studies of VPS4 proteins. EMBO J 24:3658-3669.
37. Alvarez C E (2008) On the origins of arrestin and rhodopsin. BMC Evol Biol 8:222.
38. Lefkowitz R J & Shenoy S K (2005) Transduction of receptor signals by beta-arrestins.
Science 308:512-517.
39. Draheim K M, Chen H B, Tao Q, Moore N, Roche M, & Lyle S (2010) ARRDC3 suppresses breast cancer progression by negatively regulating integrin beta4. Oncogene 29:5032-5047.
40. Nabhan J F, Pan H, & Lu Q (2010) Arrestin domain-containing protein 3 recruits the NEDD4 E3 ligase to mediate ubiquitination of the beta2-adrenergic receptor. EMBO Rep 11:605-611.
41. Chantry A (2011) WWP2 ubiquitin ligase and its isoforms: new biological insight and promising disease targets. Cell Cycle 10:2437-2439.
42. Rotin D & Kumar S (2009) Physiological functions of the HECT family of ubiquitin ligases. Nat Rev Mol Cell Biol 10:398-409.
43. Denzer K, Kleijmeer M J, Heijnen H F, Stoorvogel W, & Geuze H J (2000) Exosome: from internal vesicle of the multivesicular body to intercellular signaling device. J Cell Sci 113 Pt 19:3365-3374.
44. Komada M & Soriano P (1999) Hrs, a FYVE finger protein localized to early endosomes, is implicated in vesicular traffic and required for ventral folding morphogenesis. Genes Dev 13:1475-1485.
45. Ono A, Demirov D, & Freed E O (2000) Relationship between human immunodeficiency virus type 1 Gag multimerization and membrane binding. J Virol 74:5142-5150.
46. Fujii K, Hurley J H, & Freed E O (2007) Beyond Tsgl01: the role of Alix in 'ESCRTing' HIV-1. Nat Rev Microbiol 5:912-916.
47. Wehman A M, Poggioli C, Schweinsberg P, Grant B D, & Nance J (2011) The P4-ATPase TAT-5 Inhibits the Budding of Extracellular Vesicles in C. elegans Embryos. Curr Biol 21:1951-1959.
48. Skog J, Wurdinger T, van Rijn S, Meijer D H, Gainche L, Sena-Esteves M, Curry W T, Jr., Carter B S, Krichevsky A M, & Breakefield X O (2008) Glioblastoma microvesicles transport RNA and proteins that promote tumour growth and provide diagnostic biomarkers. Nat Cell Biol 10:1470-1476.

49. Valadi H, Ekstrom K, Bossios A, Sjostrand M, Lee J J, & Lotvall J O (2007) Exosome-mediated transfer of mRNAs and microRNAs is a novel mechanism of genetic exchange between cells. Nat Cell Biol 9:654-659.

All publications, patents and sequence database entries mentioned herein, including those items listed above, are hereby incorporated by reference in their entirety as if each individual publication or patent was specifically and individually indicated to be incorporated by reference. In case of conflict, the present application, including any definitions herein, will control.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus, for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value within the range may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A minimal arrestin domain-containing protein 1 (ARRDC1) comprising:
- an arrestin domain,
- at least one PSAP (SEQ ID NO: 122) or PTAP (SEQ ID NO: 123) motif, and
- at least one PPXY motif, wherein the minimal ARRDC1 comprises an amino acid sequence that is at least 85% identical to the amino acid sequence set for in SEQ ID NO: 1 and is capable of driving formation of ARRDC1-mediated microvesicles (ARMMs).

2. The minimal ARRDC1 of claim 1, wherein the ARRDC1 comprises at least two PPXY motifs.

3. The minimal ARRDC1 of claim 2, wherein at least one PPXY motif is PPEY (SEQ ID NO: 124), and wherein at least one PPXY motif is PPSY (SEQ ID NO: 125).

4. The minimal ARRDC1 of claim 1, wherein the minimal ARRDC1 is less than 400 amino acids in length.

5. The minimal ARRDC1 of claim 1, wherein the minimal ARRDC1 is less than 350 amino acids in length.

6. The minimal ARRDC1 of claim 1, wherein the at least one PPXY motif is either PPEY (SEQ ID NO: 124) or PPSY (SEQ ID NO: 125).

7. A minimal ARRDC1 fusion protein comprising the minimal ARRDC1 protein of claim 1
and
a Cas9 protein or a variant thereof.

8. A nucleic acid comprising a nucleotide sequence encoding the minimal arrestin domain-containing protein 1 (ARRDC1) of claim 1.

9. An arrestin domain-containing protein 1 (ARRDC1)-mediated microvesicle (ARMM) comprising:
a lipid bilayer and a minimal ARRDC1 protein, wherein the minimal ARRDC1 protein comprises the minimal ARRDC1 protein of claim 1.

10. The microvesicle of claim 9, wherein the microvesicle further comprises an agent.

11. The microvesicle of claim 10, wherein the agent is covalently bound to the minimal ARRDC1 protein, or the TSG 101 protein or fragment thereof.

12. The microvesicle of claim 10, wherein the agent is conjugated to the minimal ARRDC1 protein or the TSG101 protein or fragment thereof via a linker.

13. The microvesicle of claim 12 wherein the linker is a cleavable linker.

14. The microvesicle of claim 10, wherein the agent is fused to at least one WW domain or variant thereof.

15. The microvesicle of claim 10, wherein the agent is selected from the group consisting of a nucleic acid, a protein, and a small molecule.

16. The microvesicle of claim 15, wherein the nucleic acid comprises an RNA.

17. The microvesicle of claim 15, wherein the nucleic acid comprises a DNA.

18. The microvesicle of claim 10, wherein the agent comprises a detectable label.

19. The microvesicle of claim 10, wherein the agent comprises a therapeutic agent.

20. The microvesicle of claim 10, wherein the agent comprises a cytotoxic agent.

21. The microvesicle of claim 10, wherein the agent comprises a protein.

22. The microvesicle of claim 9, wherein the microvesicle further comprises a TSG101 protein or fragment thereof.

23. The microvesicle of claim 9, wherein the microvesicle further comprises an integrin, a receptor tyrosine kinase, a G-protein coupled receptor, or a membrane-bound immunoglobulin.

24. The microvesicle of claim 9, wherein the microvesicle diameter is from about 30 nm to about 500 nm.

25. An arrestin domain-containing protein 1 (ARRDC1)-mediated microvesicle (ARMM) comprising:

a lipid bilayer;

a minimal ARRDC1 protein, wherein the minimal ARRDC1 protein comprises the minimal ARRDC1 protein of claim 1; and a Cas9 cargo protein or a variant thereof, wherein the Cas9 cargo protein or the variant thereof is linked to the minimal ARRDC1 protein.

26. The microvesicle of claim 25, wherein the minimal ARRDC1 protein is covalently linked to the Cas9 cargo protein.

27. An arrestin domain-containing protein 1 (ARRDC1)-mediated microvesicle (ARMM), comprising:

a lipid bilayer;

a minimal ARRDC1 protein, wherein the minimal ARRDC1 protein comprises the minimal ARRDC1 protein of claim 1;

a TSG101 protein or variant thereof; and a Cas9 protein or a variant thereof, wherein the Cas9 protein or the variant thereof is linked to the TSG101 protein or variant thereof.

28. A microvesicle-producing cell comprising:

a recombinant expression construct encoding a minimal ARRDC1 protein of claim 1 under the control of a heterologous promoter, and a recombinant expression construct encoding a cargo protein under the control of a heterologous promoter.

29. The microvesicle-producing cell of claim 28, wherein the cargo protein is fused to at least one WW domain or variant thereof.

30. A microvesicle-producing cell comprising:

a recombinant expression construct encoding the minimal ARRDC1 protein of claim 1 under the control of a heterologous promoter; and wherein the minimal ARRDC1 protein is linked to a Cas9 cargo protein or a variant thereof.

31. A method of delivering a cargo to a target cell, the method comprising contacting the target cell with the microvesicle of claim 9.

32. A method of gene editing comprising contacting a target cell with the microvesicle of claim 25.

33. A method of gene editing comprising contacting a target cell with the microvesicle-producing cell of claim 30.

* * * * *

SEQUENCE LISTING

```
<160> NUMBER OF SEQ ID NOS: 124

<210> SEQ ID NO 1
<211> LENGTH: 330
<212> TYPE: PRT
<213> ORGANISM: Artificial Sequence
<220> FEATURE:
<223> OTHER INFORMATION: Synthetic Polypeptide

<400> SEQUENCE: 1

Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
```

-continued

```
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile His Asp Val Arg Thr Ile Ala Glu
    210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270

Ala Thr Val Thr Leu Pro Val Phe Ile Gly Asn Ile Ala Val Asn His
        275                 280                 285

Ala Pro Val Ser Pro Arg Pro Gly Leu Gly Leu Pro Pro Gly Ala Pro
    290                 295                 300

Pro Leu Val Val Pro Ser Ala Pro Pro Gln Glu Glu Ala Glu Pro Pro
305                 310                 315                 320

Glu Tyr Pro Tyr Glu Ala Pro Pro Ser Tyr
                325                 330


<210> SEQ ID NO 2
<211> LENGTH: 1367
<212> TYPE: PRT
<213> ORGANISM: Streptococcus pyogenes

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80
```

-continued

```
Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
```

```
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Ala Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Gly Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly His Ser Leu
705                 710                 715                 720

His Glu Gln Ile Ala Asn Leu Ala Gly Ser Pro Ala Ile Lys Lys Gly
                725                 730                 735

Ile Leu Gln Thr Val Lys Ile Val Asp Glu Leu Val Lys Val Met Gly
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Ile Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925
```

-continued

```
His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990

Gly Thr Ala Leu Ile Lys Lys Tyr  Pro Lys Leu Glu Ser  Glu Phe Val
        995                 1000                1005

Tyr Gly  Asp Tyr Lys Val Tyr  Asp Val Arg Lys Met  Ile Ala Lys
    1010                 1015                1020

Ser Glu  Gln Glu Ile Gly Lys  Ala Thr Ala Lys Tyr  Phe Phe Tyr
    1025                 1030                1035

Ser Asn  Ile Met Asn Phe Phe  Lys Thr Glu Ile Thr  Leu Ala Asn
    1040                 1045                1050

Gly Glu  Ile Arg Lys Arg Pro  Leu Ile Glu Thr Asn  Gly Glu Thr
    1055                 1060                1065

Gly Glu  Ile Val Trp Asp Lys  Gly Arg Asp Phe Ala  Thr Val Arg
    1070                 1075                1080

Lys Val  Leu Ser Met Pro Gln  Val Asn Ile Val Lys  Lys Thr Glu
    1085                 1090                1095

Val Gln  Thr Gly Gly Phe Ser  Lys Glu Ser Ile Leu  Pro Lys Arg
    1100                 1105                1110

Asn Ser  Asp Lys Leu Ile Ala  Arg Lys Lys Asp Trp  Asp Pro Lys
    1115                 1120                1125

Lys Tyr  Gly Gly Phe Asp Ser  Pro Thr Val Ala Tyr  Ser Val Leu
    1130                 1135                1140

Val Val  Ala Lys Val Glu Lys  Gly Lys Ser Lys Lys  Leu Lys Ser
    1145                 1150                1155

Val Lys  Glu Leu Leu Gly Ile  Thr Ile Met Glu Arg  Ser Ser Phe
    1160                 1165                1170

Glu Lys  Asn Pro Ile Asp Phe  Leu Glu Ala Lys Gly  Tyr Lys Glu
    1175                 1180                1185

Val Lys  Lys Asp Leu Ile Ile  Lys Leu Pro Lys Tyr  Ser Leu Phe
    1190                 1195                1200

Glu Leu  Glu Asn Gly Arg Lys  Arg Met Leu Ala Ser  Ala Gly Glu
    1205                 1210                1215

Leu Gln  Lys Gly Asn Glu Leu  Ala Leu Pro Ser Lys  Tyr Val Asn
    1220                 1225                1230

Phe Leu  Tyr Leu Ala Ser His  Tyr Glu Lys Leu Lys  Gly Ser Pro
    1235                 1240                1245

Glu Asp  Asn Glu Gln Lys Gln  Leu Phe Val Glu Gln  His Lys His
    1250                 1255                1260

Tyr Leu  Asp Glu Ile Ile Glu  Gln Ile Ser Glu Phe  Ser Lys Arg
    1265                 1270                1275

Val Ile  Leu Ala Asp Ala Asn  Leu Asp Lys Val Leu  Ser Ala Tyr
    1280                 1285                1290

Asn Lys  His Arg Asp Lys Pro  Ile Arg Glu Gln Ala  Glu Asn Ile
    1295                 1300                1305

Ile His  Leu Phe Thr Leu Thr  Asn Leu Gly Ala Pro  Ala Ala Phe
    1310                 1315                1320
```

```
Lys Tyr  Phe Asp Thr Thr Ile  Asp Arg Lys Arg Tyr  Thr Ser Thr
    1325                 1330                 1335

Lys Glu  Val Leu Asp Ala Thr  Leu Ile His Gln Ser  Ile Thr Gly
    1340                 1345                 1350

Leu Tyr  Glu Thr Arg Ile Asp  Leu Ser Gln Leu Gly  Gly Asp
    1355                 1360                 1365


<210> SEQ ID NO 3
<211> LENGTH: 4212
<212> TYPE: DNA
<213> ORGANISM: Homo Sapiens

<400> SEQUENCE: 3

atggataaaa agtattctat tggtttagac atcggcacta attccgttgg atgggctgtc     60

ataaccgatg aatacaaagt accttcaaag aaatttaagg tgttggggaa cacagaccgt    120

cattcgatta aaaagaatct tatcggtgcc ctcctattcg atagtggcga aacggcagag    180

gcgactcgcc tgaaacgaac cgctcggaga aggtatacac gtcgcaagaa ccgaatatgt    240

tacttacaag aaatttttag caatgagatg gccaaagttg acgattcttt ctttcaccgt    300

ttggaagagt ccttccttgt cgaagaggac aagaaacatg aacggcaccc catctttgga    360

aacatagtag atgaggtggc atatcatgaa aagtacccaa cgatttatca cctcagaaaa    420

aagctagttg actcaactga taaagcggac ctgaggttaa tctacttggc tcttgcccat    480

atgataaagt tccgtgggca ctttctcatt gagggtgatc taaatccgga caactcggat    540

gtcgacaaac tgttcatcca gttagtacaa acctataatc agttgtttga agagaaccct    600

ataaatgcaa gtggcgtgga tgcgaaggct attcttagcg cccgcctctc taaatcccga    660

cggctagaaa acctgatcgc acaattaccc ggagagaaga aaaatgggtt gttcggtaac    720

cttatagcgc tctcactagg cctgacacca aattttaagt cgaacttcga cttagctgaa    780

gatgccaaat tgcagcttag taaggacacg tacgatgacg atctcgacaa tctactggca    840

caaattggag atcagtatgc ggacttattt ttggctgcca aaaaccttag cgatgcaatc    900

ctcctatctg acatactgag agttaatact gagattacca aggcgccgtt atccgcttca    960

atgatcaaaa ggtacgatga acatcaccaa gacttgacac ttctcaaggc cctagtccgt   1020

cagcaactgc ctgagaaata taaggaaata ttctttgatc agtcgaaaaa cgggtacgca   1080

ggttatattg acggcggagc gagtcaagag gaattctaca agtttatcaa acccatatta   1140

gagaagatgg atgggacgga agagttgctt gtaaaactca atcgcgaaga tctactgcga   1200

aagcagcgga ctttcgacaa cggtagcatt ccacatcaaa tccacttagg cgaattgcat   1260

gctatactta gaaggcagga ggatttttat ccgttcctca aagacaatcg tgaaaagatt   1320

gagaaaatcc taacctttcg cataccttac tatgtgggac ccctggcccg agggaactct   1380

cggttcgcat ggatgacaag aaagtccgaa gaaacgatta ctccatggaa ttttgaggaa   1440

gttgtcgata aaggtgcgtc agctcaatcg ttcatcgaga ggatgaccaa ctttgacaag   1500

aatttaccga acgaaaaagt attgcctaag cacagtttac tttacgagta tttcacagtg   1560

tacaatgaac tcacgaaagt taagtatgtc actgagggca tgcgtaaacc cgcctttcta   1620

agcggagaac agaagaaagc aatagtagat ctgttattca agaccaaccg caaagtgaca   1680

gttaagcaat tgaaagagga ctactttaag aaaattgaat gcttcgattc tgtcgagatc   1740

tccggggtag aagatcgatt taatgcgtca cttggtacgt atcatgacct cctaaagata   1800

attaaagata aggacttcct ggataacgaa gagaatgaag atatcttaga agatatagtg   1860
```

```
ttgactctta ccctctttga agatcgggaa atgattgagg aaagactaaa aacatacgct   1920
cacctgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100
tctttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatcac   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agaggggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca aagtaatcac tttaaagtca   2880
aaattggtgt cggacttcag aaaggatttt caattctata aagttaggga gataaataac   2940
taccaccatg cgcacgacgc ttatcttaat gccgtcgtag ggaccgcact cattaagaaa   3000
tacccgaagc tagaaagtga gtttgtgtat ggtgattaca aagtttatga cgtccgtaag   3060
atgatcgcga aaagcgaaca ggagataggc aaggctacag ccaaatactt cttttattct   3120
aacattatga atttctttaa gacggaaatc actctggcaa acggagagat acgcaaacga   3180
cctttaattg aaaccaatgg ggagacaggt gaaatcgtat gggataaggg ccgggacttc   3240
gcgacggtga gaaaagtttt gtccatgccc caagtcaaca tagtaaagaa aactgaggtg   3300
cagaccggag ggttttcaaa ggaatcgatt cttccaaaaa ggaatagtga taagctcatc   3360
gctcgtaaaa aggactggga cccgaaaaag tacggtggct tcgatagccc tacagttgcc   3420
tattctgtcc tagtagtggc aaaagttgag aagggaaaat ccaagaaact gaagtcagtc   3480
aaagaattat tggggataac gattatggag cgctcgtctt ttgaaaagaa ccccatcgac   3540
ttccttgagg cgaaaggtta caaggaagta aaaaaggatc tcataattaa actaccaaag   3600
tatagtctgt ttgagttaga aaatggccga aaacggatgt tggctagcgc cggagagctt   3660
caaaagggga acgaactcgc actaccgtct aaatacgtga atttcctgta tttagcgtcc   3720
cattacgaga agttgaaagg ttcacctgaa gataacgaac agaagcaact tttgttgag    3780
cagcacaaac attatctcga cgaaatcata gagcaaattt cggaattcag taagagagtc   3840
atcctagctg atgccaatct ggacaaagta ttaagcgcat acaacaagca cagggataaa   3900
cccatacgtg agcaggcgga aaatattatc catttgttta ctcttaccaa cctcggcgct   3960
ccagccgcat tcaagtattt tgacacaacg atagatcgca aacgatacac ttctaccaag   4020
gaggtgctag acgcgacact gattcaccaa tccatcacgg gattatatga aactcggata   4080
gatttgtcac agcttggggg tgacggatcc cccaagaaga agaggaaagt ctcgagcgac   4140
tacaaagacc atgacggtga ttataaagat catgacatcg attacaagga tgacgatgac   4200
aaggctgcag ga                                                       4212
```

<210> SEQ ID NO 4
<211> LENGTH: 1368
<212> TYPE: PRT
<213> ORGANISM: Homo Sapiens

<400> SEQUENCE: 4

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
```

-continued

```
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800
```

-continued

```
Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200
```

-continued

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 5
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 5

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

```
Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
```

-continued

```
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035
```

Tyr Ser Asn Ile Met Asn Phe Phe Lys Thr Glu Ile Thr Leu Ala
1040 1045 1050

Asn Gly Glu Ile Arg Lys Arg Pro Leu Ile Glu Thr Asn Gly Glu
1055 1060 1065

Thr Gly Glu Ile Val Trp Asp Lys Gly Arg Asp Phe Ala Thr Val
1070 1075 1080

Arg Lys Val Leu Ser Met Pro Gln Val Asn Ile Val Lys Lys Thr
1085 1090 1095

Glu Val Gln Thr Gly Gly Phe Ser Lys Glu Ser Ile Leu Pro Lys
1100 1105 1110

Arg Asn Ser Asp Lys Leu Ile Ala Arg Lys Lys Asp Trp Asp Pro
1115 1120 1125

Lys Lys Tyr Gly Gly Phe Asp Ser Pro Thr Val Ala Tyr Ser Val
1130 1135 1140

Leu Val Val Ala Lys Val Glu Lys Gly Lys Ser Lys Lys Leu Lys
1145 1150 1155

Ser Val Lys Glu Leu Leu Gly Ile Thr Ile Met Glu Arg Ser Ser
1160 1165 1170

Phe Glu Lys Asn Pro Ile Asp Phe Leu Glu Ala Lys Gly Tyr Lys
1175 1180 1185

Glu Val Lys Lys Asp Leu Ile Ile Lys Leu Pro Lys Tyr Ser Leu
1190 1195 1200

Phe Glu Leu Glu Asn Gly Arg Lys Arg Met Leu Ala Ser Ala Gly
1205 1210 1215

Glu Leu Gln Lys Gly Asn Glu Leu Ala Leu Pro Ser Lys Tyr Val
1220 1225 1230

Asn Phe Leu Tyr Leu Ala Ser His Tyr Glu Lys Leu Lys Gly Ser
1235 1240 1245

Pro Glu Asp Asn Glu Gln Lys Gln Leu Phe Val Glu Gln His Lys
1250 1255 1260

His Tyr Leu Asp Glu Ile Ile Glu Gln Ile Ser Glu Phe Ser Lys
1265 1270 1275

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 6
<211> LENGTH: 922
<212> TYPE: PRT
<213> ORGANISM: Homo Sapiens

<400> SEQUENCE: 6

Met Ala Thr Ala Ser Pro Arg Ser Asp Thr Ser Asn Asn His Ser Gly
1 5 10 15

Arg Leu Gln Leu Gln Val Thr Val Ser Ser Ala Lys Leu Lys Arg Lys

-continued

```
            20                  25                  30

Lys Asn Trp Phe Gly Thr Ala Ile Tyr Thr Glu Val Val Val Asp Gly
        35                  40                  45

Glu Ile Thr Lys Thr Ala Lys Ser Ser Ser Ser Ser Asn Pro Lys Trp
    50                  55                  60

Asp Glu Gln Leu Thr Val Asn Val Thr Pro Gln Thr Thr Leu Glu Phe
65                  70                  75                  80

Gln Val Trp Ser His Arg Thr Leu Lys Ala Asp Ala Leu Leu Gly Lys
                85                  90                  95

Ala Thr Ile Asp Leu Lys Gln Ala Leu Leu Ile His Asn Arg Lys Leu
            100                 105                 110

Glu Arg Val Lys Glu Gln Leu Lys Leu Ser Leu Glu Asn Lys Asn Gly
        115                 120                 125

Ile Ala Gln Thr Gly Glu Leu Thr Val Val Leu Asp Gly Leu Val Ile
    130                 135                 140

Glu Gln Glu Asn Ile Thr Asn Cys Ser Ser Ser Pro Thr Ile Glu Ile
145                 150                 155                 160

Gln Glu Asn Gly Asp Ala Leu His Glu Asn Gly Glu Pro Ser Ala Arg
                165                 170                 175

Thr Thr Ala Arg Leu Ala Val Glu Gly Thr Asn Gly Ile Asp Asn His
            180                 185                 190

Val Pro Thr Ser Thr Leu Val Gln Asn Ser Cys Cys Ser Tyr Val Val
        195                 200                 205

Asn Gly Asp Asn Thr Pro Ser Ser Pro Ser Gln Val Ala Ala Arg Pro
    210                 215                 220

Lys Asn Thr Pro Ala Pro Lys Pro Leu Ala Ser Glu Pro Ala Asp Asp
225                 230                 235                 240

Thr Val Asn Gly Glu Ser Ser Ser Phe Ala Pro Thr Asp Asn Ala Ser
                245                 250                 255

Val Thr Gly Thr Pro Val Val Ser Glu Glu Asn Ala Leu Ser Pro Asn
            260                 265                 270

Cys Thr Ser Thr Thr Val Glu Asp Pro Pro Val Gln Glu Ile Leu Thr
        275                 280                 285

Ser Ser Glu Asn Asn Glu Cys Ile Pro Ser Thr Ser Ala Glu Leu Glu
    290                 295                 300

Ser Glu Ala Arg Ser Ile Leu Glu Pro Asp Thr Ser Asn Ser Arg Ser
305                 310                 315                 320

Ser Ser Ala Phe Glu Ala Ala Lys Ser Arg Gln Pro Asp Gly Cys Met
                325                 330                 335

Asp Pro Val Arg Gln Gln Ser Gly Asn Ala Asn Thr Glu Thr Leu Pro
            340                 345                 350

Ser Gly Trp Glu Gln Arg Lys Asp Pro His Gly Arg Thr Tyr Tyr Val
        355                 360                 365

Asp His Asn Thr Arg Thr Thr Thr Trp Glu Arg Pro Gln Pro Leu Pro
    370                 375                 380

Pro Gly Trp Glu Arg Arg Val Asp Asp Arg Arg Arg Val Tyr Tyr Val
385                 390                 395                 400

Asp His Asn Thr Arg Thr Thr Thr Trp Gln Arg Pro Thr Met Glu Ser
                405                 410                 415

Val Arg Asn Phe Glu Gln Trp Gln Ser Gln Arg Asn Gln Leu Gln Gly
            420                 425                 430

Ala Met Gln Gln Phe Asn Gln Arg Tyr Leu Tyr Ser Ala Ser Met Leu
        435                 440                 445
```

-continued

```
Ala Ala Glu Asn Asp Pro Tyr Gly Pro Leu Pro Pro Gly Trp Glu Lys
    450                 455                 460

Arg Val Asp Ser Thr Asp Arg Val Tyr Phe Val Asn His Asn Thr Lys
465                 470                 475                 480

Thr Thr Gln Trp Glu Asp Pro Arg Thr Gln Gly Leu Gln Asn Glu Glu
                485                 490                 495

Pro Leu Pro Glu Gly Trp Glu Ile Arg Tyr Thr Arg Glu Gly Val Arg
            500                 505                 510

Tyr Phe Val Asp His Asn Thr Arg Thr Thr Thr Phe Lys Asp Pro Arg
        515                 520                 525

Asn Gly Lys Ser Ser Val Thr Lys Gly Gly Pro Gln Ile Ala Tyr Glu
    530                 535                 540

Arg Gly Phe Arg Trp Lys Leu Ala His Phe Arg Tyr Leu Cys Gln Ser
545                 550                 555                 560

Asn Ala Leu Pro Ser His Val Lys Ile Asn Val Ser Arg Gln Thr Leu
                565                 570                 575

Phe Glu Asp Ser Phe Gln Gln Ile Met Ala Leu Lys Pro Tyr Asp Leu
            580                 585                 590

Arg Arg Arg Leu Tyr Val Ile Phe Arg Gly Glu Glu Gly Leu Asp Tyr
        595                 600                 605

Gly Gly Leu Ala Arg Glu Trp Phe Phe Leu Leu Ser His Glu Val Leu
    610                 615                 620

Asn Pro Met Tyr Cys Leu Phe Glu Tyr Ala Gly Lys Asn Asn Tyr Cys
625                 630                 635                 640

Leu Gln Ile Asn Pro Ala Ser Thr Ile Asn Pro Asp His Leu Ser Tyr
                645                 650                 655

Phe Cys Phe Ile Gly Arg Phe Ile Ala Met Ala Leu Phe His Gly Lys
            660                 665                 670

Phe Ile Asp Thr Gly Phe Ser Leu Pro Phe Tyr Lys Arg Met Leu Ser
        675                 680                 685

Lys Lys Leu Thr Ile Lys Asp Leu Glu Ser Ile Asp Thr Glu Phe Tyr
    690                 695                 700

Asn Ser Leu Ile Trp Ile Arg Asp Asn Asn Ile Glu Glu Cys Gly Leu
705                 710                 715                 720

Glu Met Tyr Phe Ser Val Asp Met Glu Ile Leu Gly Lys Val Thr Ser
                725                 730                 735

His Asp Leu Lys Leu Gly Gly Ser Asn Ile Leu Val Thr Glu Glu Asn
            740                 745                 750

Lys Asp Glu Tyr Ile Gly Leu Met Thr Glu Trp Arg Phe Ser Arg Gly
        755                 760                 765

Val Gln Glu Gln Thr Lys Ala Phe Leu Asp Gly Phe Asn Glu Val Val
    770                 775                 780

Pro Leu Gln Trp Leu Gln Tyr Phe Asp Glu Lys Glu Leu Glu Val Met
785                 790                 795                 800

Leu Cys Gly Met Gln Glu Val Asp Leu Ala Asp Trp Gln Arg Asn Thr
                805                 810                 815

Val Tyr Arg His Tyr Thr Arg Asn Ser Lys Gln Ile Ile Trp Phe Trp
            820                 825                 830

Gln Phe Val Lys Glu Thr Asp Asn Glu Val Arg Met Arg Leu Leu Gln
        835                 840                 845

Phe Val Thr Gly Thr Cys Arg Leu Pro Leu Gly Gly Phe Ala Glu Leu
    850                 855                 860
```

```
Met Gly Ser Asn Gly Pro Gln Lys Phe Cys Ile Glu Lys Val Gly Lys
865                 870                 875                 880

Asp Thr Trp Leu Pro Arg Ser His Thr Cys Phe Asn Arg Leu Asp Leu
                885                 890                 895

Pro Pro Tyr Lys Ser Tyr Glu Gln Leu Lys Glu Lys Leu Leu Phe Ala
            900                 905                 910

Ile Glu Glu Thr Glu Gly Phe Gly Gln Glu
        915                 920


<210> SEQ ID NO 7
<211> LENGTH: 870
<212> TYPE: PRT
<213> ORGANISM: Homo Sapiens

<400> SEQUENCE: 7

Met Ala Ser Ala Ser Ser Ser Arg Ala Gly Val Ala Leu Pro Phe Glu
1               5                   10                  15

Lys Ser Gln Leu Thr Leu Lys Val Val Ser Ala Lys Pro Lys Val His
            20                  25                  30

Asn Arg Gln Pro Arg Ile Asn Ser Tyr Val Glu Val Ala Val Asp Gly
        35                  40                  45

Leu Pro Ser Glu Thr Lys Lys Thr Gly Lys Arg Ile Gly Ser Ser Glu
    50                  55                  60

Leu Leu Trp Asn Glu Ile Ile Ile Leu Asn Val Thr Ala Gln Ser His
65                  70                  75                  80

Leu Asp Leu Lys Val Trp Ser Cys His Thr Leu Arg Asn Glu Leu Leu
                85                  90                  95

Gly Thr Ala Ser Val Asn Leu Ser Asn Val Leu Lys Asn Asn Gly Gly
            100                 105                 110

Lys Met Glu Asn Met Gln Leu Thr Leu Asn Leu Gln Thr Glu Asn Lys
        115                 120                 125

Gly Ser Val Val Ser Gly Gly Glu Leu Thr Ile Phe Leu Asp Gly Pro
    130                 135                 140

Thr Val Asp Leu Gly Asn Val Pro Asn Gly Ser Ala Leu Thr Asp Gly
145                 150                 155                 160

Ser Gln Leu Pro Ser Arg Asp Ser Ser Gly Thr Ala Val Ala Pro Glu
                165                 170                 175

Asn Arg His Gln Pro Pro Ser Thr Asn Cys Phe Gly Gly Arg Ser Arg
            180                 185                 190

Thr His Arg His Ser Gly Ala Ser Ala Arg Thr Thr Pro Ala Thr Gly
        195                 200                 205

Glu Gln Ser Pro Gly Ala Arg Ser Arg His Arg Gln Pro Val Lys Asn
    210                 215                 220

Ser Gly His Ser Gly Leu Ala Asn Gly Thr Val Asn Asp Glu Pro Thr
225                 230                 235                 240

Thr Ala Thr Asp Pro Glu Glu Pro Ser Val Val Gly Val Thr Ser Pro
                245                 250                 255

Pro Ala Ala Pro Leu Ser Val Thr Pro Asn Pro Asn Thr Thr Ser Leu
            260                 265                 270

Pro Ala Pro Ala Thr Pro Ala Glu Gly Glu Glu Pro Ser Thr Ser Gly
        275                 280                 285

Thr Gln Gln Leu Pro Ala Ala Ala Gln Ala Pro Asp Ala Leu Pro Ala
    290                 295                 300

Gly Trp Glu Gln Arg Glu Leu Pro Asn Gly Arg Val Tyr Tyr Val Asp
305                 310                 315                 320
```

-continued

His Asn Thr Lys Thr Thr Thr Trp Glu Arg Pro Leu Pro Pro Gly Trp
325 330 335

Glu Lys Arg Thr Asp Pro Arg Gly Arg Phe Tyr Tyr Val Asp His Asn
340 345 350

Thr Arg Thr Thr Thr Trp Gln Arg Pro Thr Ala Glu Tyr Val Arg Asn
355 360 365

Tyr Glu Gln Trp Gln Ser Gln Arg Asn Gln Leu Gln Gly Ala Met Gln
370 375 380

His Phe Ser Gln Arg Phe Leu Tyr Gln Ser Ser Ser Ala Ser Thr Asp
385 390 395 400

His Asp Pro Leu Gly Pro Leu Pro Pro Gly Trp Glu Lys Arg Gln Asp
405 410 415

Asn Gly Arg Val Tyr Tyr Val Asn His Asn Thr Arg Thr Thr Gln Trp
420 425 430

Glu Asp Pro Arg Thr Gln Gly Met Ile Gln Glu Pro Ala Leu Pro Pro
435 440 445

Gly Trp Glu Met Lys Tyr Thr Ser Glu Gly Val Arg Tyr Phe Val Asp
450 455 460

His Asn Thr Arg Thr Thr Thr Phe Lys Asp Pro Arg Pro Gly Phe Glu
465 470 475 480

Ser Gly Thr Lys Gln Gly Ser Pro Gly Ala Tyr Asp Arg Ser Phe Arg
485 490 495

Trp Lys Tyr His Gln Phe Arg Phe Leu Cys His Ser Asn Ala Leu Pro
500 505 510

Ser His Val Lys Ile Ser Val Ser Arg Gln Thr Leu Phe Glu Asp Ser
515 520 525

Phe Gln Gln Ile Met Asn Met Lys Pro Tyr Asp Leu Arg Arg Arg Leu
530 535 540

Tyr Ile Ile Met Arg Gly Glu Glu Gly Leu Asp Tyr Gly Gly Ile Ala
545 550 555 560

Arg Glu Trp Phe Phe Leu Leu Ser His Glu Val Leu Asn Pro Met Tyr
565 570 575

Cys Leu Phe Glu Tyr Ala Gly Lys Asn Asn Tyr Cys Leu Gln Ile Asn
580 585 590

Pro Ala Ser Ser Ile Asn Pro Asp His Leu Thr Tyr Phe Arg Phe Ile
595 600 605

Gly Arg Phe Ile Ala Met Ala Leu Tyr His Gly Lys Phe Ile Asp Thr
610 615 620

Gly Phe Thr Leu Pro Phe Tyr Lys Arg Met Leu Asn Lys Arg Pro Thr
625 630 635 640

Leu Lys Asp Leu Glu Ser Ile Asp Pro Glu Phe Tyr Asn Ser Ile Val
645 650 655

Trp Ile Lys Glu Asn Asn Leu Glu Glu Cys Gly Leu Glu Leu Tyr Phe
660 665 670

Ile Gln Asp Met Glu Ile Leu Gly Lys Val Thr Thr His Glu Leu Lys
675 680 685

Glu Gly Gly Glu Ser Ile Arg Val Thr Glu Glu Asn Lys Glu Glu Tyr
690 695 700

Ile Met Leu Leu Thr Asp Trp Arg Phe Thr Arg Gly Val Glu Glu Gln
705 710 715 720

Thr Lys Ala Phe Leu Asp Gly Phe Asn Glu Val Ala Pro Leu Glu Trp
725 730 735

```
Leu Arg Tyr Phe Asp Glu Lys Glu Leu Glu Leu Met Leu Cys Gly Met
            740                 745                 750

Gln Glu Ile Asp Met Ser Asp Trp Gln Lys Ser Thr Ile Tyr Arg His
        755                 760                 765

Tyr Thr Lys Asn Ser Lys Gln Ile Gln Trp Phe Trp Gln Val Val Lys
    770                 775                 780

Glu Met Asp Asn Glu Lys Arg Ile Arg Leu Leu Gln Phe Val Thr Gly
785                 790                 795                 800

Thr Cys Arg Leu Pro Val Gly Gly Phe Ala Glu Leu Ile Gly Ser Asn
                805                 810                 815

Gly Pro Gln Lys Phe Cys Ile Asp Lys Val Gly Lys Glu Thr Trp Leu
            820                 825                 830

Pro Arg Ser His Thr Cys Phe Asn Arg Leu Asp Leu Pro Pro Tyr Lys
        835                 840                 845

Ser Tyr Glu Gln Leu Arg Glu Lys Leu Leu Tyr Ala Ile Glu Glu Thr
    850                 855                 860

Glu Gly Phe Gly Gln Glu
865                 870


<210> SEQ ID NO 8
<211> LENGTH: 1319
<212> TYPE: PRT
<213> ORGANISM: Homo Sapiens

<400> SEQUENCE: 8

Met Ala Gln Ser Leu Arg Leu His Phe Ala Ala Arg Arg Ser Asn Thr
1               5                   10                  15

Tyr Pro Leu Ser Glu Thr Ser Gly Asp Asp Leu Asp Ser His Val His
            20                  25                  30

Met Cys Phe Lys Arg Pro Thr Arg Ile Ser Thr Ser Asn Val Val Gln
        35                  40                  45

Met Lys Leu Thr Pro Arg Gln Thr Ala Leu Ala Pro Leu Ile Lys Glu
    50                  55                  60

Asn Val Gln Ser Gln Glu Arg Ser Ser Val Pro Ser Ser Glu Asn Val
65                  70                  75                  80

Asn Lys Lys Ser Ser Cys Leu Gln Ile Ser Leu Gln Pro Thr Arg Tyr
                85                  90                  95

Ser Gly Tyr Leu Gln Ser Ser Asn Val Leu Ala Asp Ser Asp Asp Ala
            100                 105                 110

Ser Phe Thr Cys Ile Leu Lys Asp Gly Ile Tyr Ser Ser Ala Val Val
        115                 120                 125

Asp Asn Glu Leu Asn Ala Val Asn Asp Gly His Leu Val Ser Ser Pro
    130                 135                 140

Ala Ile Cys Ser Gly Ser Leu Ser Asn Phe Ser Thr Ser Asp Asn Gly
145                 150                 155                 160

Ser Tyr Ser Ser Asn Gly Ser Asp Phe Gly Ser Cys Ala Ser Ile Thr
                165                 170                 175

Ser Gly Gly Ser Tyr Thr Asn Ser Val Ile Ser Asp Ser Ser Ser Tyr
            180                 185                 190

Thr Phe Pro Pro Ser Asp Asp Thr Phe Leu Gly Gly Asn Leu Pro Ser
        195                 200                 205

Asp Ser Thr Ser Asn Arg Ser Val Pro Asn Arg Asn Thr Thr Pro Cys
    210                 215                 220

Glu Ile Phe Ser Arg Ser Thr Ser Thr Asp Pro Phe Val Gln Asp Asp
225                 230                 235                 240
```

-continued

```
Leu Glu His Gly Leu Glu Ile Met Lys Leu Pro Val Ser Arg Asn Thr
                245                 250                 255

Lys Ile Pro Leu Lys Arg Tyr Ser Ser Leu Val Ile Phe Pro Arg Ser
            260                 265                 270

Pro Ser Thr Thr Arg Pro Thr Ser Pro Thr Ser Leu Cys Thr Leu Leu
        275                 280                 285

Ser Lys Gly Ser Tyr Gln Thr Ser His Gln Phe Ile Ile Ser Pro Ser
    290                 295                 300

Glu Ile Ala His Asn Glu Asp Gly Thr Ser Ala Lys Gly Phe Leu Ser
305                 310                 315                 320

Thr Ala Val Asn Gly Leu Arg Leu Ser Lys Thr Ile Cys Thr Pro Gly
                325                 330                 335

Glu Val Arg Asp Ile Arg Pro Leu His Arg Lys Gly Ser Leu Gln Lys
            340                 345                 350

Lys Ile Val Leu Ser Asn Asn Thr Pro Arg Gln Thr Val Cys Glu Lys
        355                 360                 365

Ser Ser Glu Gly Tyr Ser Cys Val Ser Val His Phe Thr Gln Arg Lys
    370                 375                 380

Ala Ala Thr Leu Asp Cys Glu Thr Thr Asn Gly Asp Cys Lys Pro Glu
385                 390                 395                 400

Met Ser Glu Ile Lys Leu Asn Ser Asp Ser Glu Tyr Ile Lys Leu Met
                405                 410                 415

His Arg Thr Ser Ala Cys Leu Pro Ser Ser Gln Asn Val Asp Cys Gln
            420                 425                 430

Ile Asn Ile Asn Gly Glu Leu Glu Arg Pro His Ser Gln Met Asn Lys
        435                 440                 445

Asn His Gly Ile Leu Arg Arg Ser Ile Ser Leu Gly Gly Ala Tyr Pro
    450                 455                 460

Asn Ile Ser Cys Leu Ser Ser Leu Lys His Asn Cys Ser Lys Gly Gly
465                 470                 475                 480

Pro Ser Gln Leu Leu Ile Lys Phe Ala Ser Gly Asn Glu Gly Lys Val
                485                 490                 495

Asp Asn Leu Ser Arg Asp Ser Asn Arg Asp Cys Thr Asn Glu Leu Ser
            500                 505                 510

Asn Ser Cys Lys Thr Arg Asp Asp Phe Leu Gly Gln Val Asp Val Pro
        515                 520                 525

Leu Tyr Pro Leu Pro Thr Glu Asn Pro Arg Leu Glu Arg Pro Tyr Thr
    530                 535                 540

Phe Lys Asp Phe Val Leu His Pro Arg Ser His Lys Ser Arg Val Lys
545                 550                 555                 560

Gly Tyr Leu Arg Leu Lys Met Thr Tyr Leu Pro Lys Thr Ser Gly Ser
                565                 570                 575

Glu Asp Asp Asn Ala Glu Gln Ala Glu Glu Leu Glu Pro Gly Trp Val
            580                 585                 590

Val Leu Asp Gln Pro Asp Ala Ala Cys His Leu Gln Gln Gln Gln Glu
        595                 600                 605

Pro Ser Pro Leu Pro Pro Gly Trp Glu Glu Arg Gln Asp Ile Leu Gly
    610                 615                 620

Arg Thr Tyr Tyr Val Asn His Glu Ser Arg Arg Thr Gln Trp Lys Arg
625                 630                 635                 640

Pro Thr Pro Gln Asp Asn Leu Thr Asp Ala Glu Asn Gly Asn Ile Gln
                645                 650                 655
```

-continued

```
Leu Gln Ala Gln Arg Ala Phe Thr Thr Arg Arg Gln Ile Ser Glu Glu
            660                 665                 670

Thr Glu Ser Val Asp Asn Arg Glu Ser Ser Glu Asn Trp Glu Ile Ile
        675                 680                 685

Arg Glu Asp Glu Ala Thr Met Tyr Ser Asn Gln Ala Phe Pro Ser Pro
    690                 695                 700

Pro Pro Ser Ser Asn Leu Asp Val Pro Thr His Leu Ala Glu Glu Leu
705                 710                 715                 720

Asn Ala Arg Leu Thr Ile Phe Gly Asn Ser Ala Val Ser Gln Pro Ala
                725                 730                 735

Ser Ser Ser Asn His Ser Ser Arg Arg Gly Ser Leu Gln Ala Tyr Thr
            740                 745                 750

Phe Glu Glu Gln Pro Thr Leu Pro Val Leu Leu Pro Thr Ser Ser Gly
        755                 760                 765

Leu Pro Pro Gly Trp Glu Glu Lys Gln Asp Glu Arg Gly Arg Ser Tyr
    770                 775                 780

Tyr Val Asp His Asn Ser Arg Thr Thr Thr Trp Thr Lys Pro Thr Val
785                 790                 795                 800

Gln Ala Thr Val Glu Thr Ser Gln Leu Thr Ser Ser Gln Ser Ser Ala
                805                 810                 815

Gly Pro Gln Ser Gln Ala Ser Thr Ser Asp Ser Gly Gln Gln Val Thr
            820                 825                 830

Gln Pro Ser Glu Ile Glu Gln Gly Phe Leu Pro Lys Gly Trp Glu Val
        835                 840                 845

Arg His Ala Pro Asn Gly Arg Pro Phe Phe Ile Asp His Asn Thr Lys
    850                 855                 860

Thr Thr Thr Trp Glu Asp Pro Arg Leu Lys Ile Pro Ala His Leu Arg
865                 870                 875                 880

Gly Lys Thr Ser Leu Asp Thr Ser Asn Asp Leu Gly Pro Leu Pro Pro
                885                 890                 895

Gly Trp Glu Glu Arg Thr His Thr Asp Gly Arg Ile Phe Tyr Ile Asn
            900                 905                 910

His Asn Ile Lys Arg Thr Gln Trp Glu Asp Pro Arg Leu Glu Asn Val
        915                 920                 925

Ala Ile Thr Gly Pro Ala Val Pro Tyr Ser Arg Asp Tyr Lys Arg Lys
    930                 935                 940

Tyr Glu Phe Phe Arg Arg Lys Leu Lys Lys Gln Asn Asp Ile Pro Asn
945                 950                 955                 960

Lys Phe Glu Met Lys Leu Arg Arg Ala Thr Val Leu Glu Asp Ser Tyr
                965                 970                 975

Arg Arg Ile Met Gly Val Lys Arg Ala Asp Phe Leu Lys Ala Arg Leu
            980                 985                 990

Trp Ile Glu Phe Asp Gly Glu Lys  Gly Leu Asp Tyr Gly  Gly Val Ala
        995                 1000                1005

Arg Glu  Trp Phe Phe Leu Ile  Ser Lys Glu Met Phe  Asn Pro Tyr
    1010                1015                1020

Tyr Gly  Leu Phe Glu Tyr Ser  Ala Thr Asp Asn Tyr  Thr Leu Gln
    1025                1030                1035

Ile Asn  Pro Asn Ser Gly Leu  Cys Asn Glu Asp His  Leu Ser Tyr
    1040                1045                1050

Phe Lys  Phe Ile Gly Arg Val  Ala Gly Met Ala Val  Tyr His Gly
    1055                1060                1065

Lys Leu  Leu Asp Gly Phe Phe  Ile Arg Pro Phe Tyr  Lys Met Met
```

-continued

```
    1070                1075                1080

Leu His  Lys Pro Ile Thr Leu  His Asp Met Glu Ser  Val Asp Ser
    1085                1090                1095

Glu Tyr  Tyr Asn Ser Leu Arg  Trp Ile Leu Glu Asn  Asp Pro Thr
    1100                1105                1110

Glu Leu  Asp Leu Arg Phe Ile  Ile Asp Glu Glu Leu  Phe Gly Gln
    1115                1120                1125

Thr His  Gln His Glu Leu Lys  Asn Gly Gly Ser Glu  Ile Val Val
    1130                1135                1140

Thr Asn  Lys Asn Lys Lys Glu  Tyr Ile Tyr Leu Val  Ile Gln Trp
    1145                1150                1155

Arg Phe  Val Asn Arg Ile Gln  Lys Gln Met Ala Ala  Phe Lys Glu
    1160                1165                1170

Gly Phe  Phe Glu Leu Ile Pro  Gln Asp Leu Ile Lys  Ile Phe Asp
    1175                1180                1185

Glu Asn  Glu Leu Glu Leu Leu  Met Cys Gly Leu Gly  Asp Val Asp
    1190                1195                1200

Val Asn  Asp Trp Arg Glu His  Thr Lys Tyr Lys Asn  Gly Tyr Ser
    1205                1210                1215

Ala Asn  His Gln Val Ile Gln  Trp Phe Trp Lys Ala  Val Leu Met
    1220                1225                1230

Met Asp  Ser Glu Lys Arg Ile  Arg Leu Leu Gln Phe  Val Thr Gly
    1235                1240                1245

Thr Ser  Arg Val Pro Met Asn  Gly Phe Ala Glu Leu  Tyr Gly Ser
    1250                1255                1260

Asn Gly  Pro Gln Ser Phe Thr  Val Glu Gln Trp Gly  Thr Pro Glu
    1265                1270                1275

Lys Leu  Pro Arg Ala His Thr  Cys Phe Asn Arg Leu  Asp Leu Pro
    1280                1285                1290

Pro Tyr  Glu Ser Phe Glu Glu  Leu Trp Asp Lys Leu  Gln Met Ala
    1295                1300                1305

Ile Glu  Asn Thr Gln Gly Phe  Asp Gly Val Asp
    1310                1315


<210> SEQ ID NO 9
<211> LENGTH: 955
<212> TYPE: PRT
<213> ORGANISM: Homo Sapiens

<400> SEQUENCE: 9

Met Ala Thr Gly Leu Gly Glu Pro Val Tyr Gly Leu Ser Glu Asp Glu
1               5                   10                  15

Gly Glu Ser Arg Ile Leu Arg Val Lys Val Val Ser Gly Ile Asp Leu
            20                  25                  30

Ala Lys Lys Asp Ile Phe Gly Ala Ser Asp Pro Tyr Val Lys Leu Ser
        35                  40                  45

Leu Tyr Val Ala Asp Glu Asn Arg Glu Leu Ala Leu Val Gln Thr Lys
    50                  55                  60

Thr Ile Lys Lys Thr Leu Asn Pro Lys Trp Asn Glu Glu Phe Tyr Phe
65                  70                  75                  80

Arg Val Asn Pro Ser Asn His Arg Leu Leu Phe Glu Val Phe Asp Glu
                85                  90                  95

Asn Arg Leu Thr Arg Asp Asp Phe Leu Gly Gln Val Asp Val Pro Leu
            100                 105                 110
```

-continued

```
Ser His Leu Pro Thr Glu Asp Pro Thr Met Glu Arg Pro Tyr Thr Phe
        115                 120                 125

Lys Asp Phe Leu Leu Arg Pro Arg Ser His Lys Ser Arg Val Lys Gly
    130                 135                 140

Phe Leu Arg Leu Lys Met Ala Tyr Met Pro Lys Asn Gly Gly Gln Asp
145                 150                 155                 160

Glu Glu Asn Ser Asp Gln Arg Asp Asp Met Glu His Gly Trp Glu Val
                165                 170                 175

Val Asp Ser Asn Asp Ser Ala Ser Gln His Gln Glu Glu Leu Pro Pro
            180                 185                 190

Pro Pro Leu Pro Pro Gly Trp Glu Glu Lys Val Asp Asn Leu Gly Arg
        195                 200                 205

Thr Tyr Tyr Val Asn His Asn Asn Arg Thr Thr Gln Trp His Arg Pro
    210                 215                 220

Ser Leu Met Asp Val Ser Ser Glu Ser Asp Asn Asn Ile Arg Gln Ile
225                 230                 235                 240

Asn Gln Glu Ala Ala His Arg Arg Phe Arg Ser Arg Arg His Ile Ser
                245                 250                 255

Glu Asp Leu Glu Pro Glu Pro Ser Glu Gly Gly Asp Val Pro Glu Pro
            260                 265                 270

Trp Glu Thr Ile Ser Glu Glu Val Asn Ile Ala Gly Asp Ser Leu Gly
        275                 280                 285

Leu Ala Leu Pro Pro Pro Pro Ala Ser Pro Gly Ser Arg Thr Ser Pro
    290                 295                 300

Gln Glu Leu Ser Glu Glu Leu Ser Arg Arg Leu Gln Ile Thr Pro Asp
305                 310                 315                 320

Ser Asn Gly Glu Gln Phe Ser Ser Leu Ile Gln Arg Glu Pro Ser Ser
                325                 330                 335

Arg Leu Arg Ser Cys Ser Val Thr Asp Ala Val Ala Glu Gln Gly His
            340                 345                 350

Leu Pro Pro Pro Ser Val Ala Tyr Val His Thr Thr Pro Gly Leu Pro
        355                 360                 365

Ser Gly Trp Glu Glu Arg Lys Asp Ala Lys Gly Arg Thr Tyr Tyr Val
    370                 375                 380

Asn His Asn Asn Arg Thr Thr Thr Trp Thr Arg Pro Ile Met Gln Leu
385                 390                 395                 400

Ala Glu Asp Gly Ala Ser Gly Ser Ala Thr Asn Ser Asn Asn His Leu
                405                 410                 415

Ile Glu Pro Gln Ile Arg Arg Pro Arg Ser Leu Ser Ser Pro Thr Val
            420                 425                 430

Thr Leu Ser Ala Pro Leu Glu Gly Ala Lys Asp Ser Pro Val Arg Arg
        435                 440                 445

Ala Val Lys Asp Thr Leu Ser Asn Pro Gln Ser Pro Gln Pro Ser Pro
    450                 455                 460

Tyr Asn Ser Pro Lys Pro Gln His Lys Val Thr Gln Ser Phe Leu Pro
465                 470                 475                 480

Pro Gly Trp Glu Met Arg Ile Ala Pro Asn Gly Arg Pro Phe Phe Ile
                485                 490                 495

Asp His Asn Thr Lys Thr Thr Thr Trp Glu Asp Pro Arg Leu Lys Phe
            500                 505                 510

Pro Val His Met Arg Ser Lys Thr Ser Leu Asn Pro Asn Asp Leu Gly
        515                 520                 525

Pro Leu Pro Pro Gly Trp Glu Glu Arg Ile His Leu Asp Gly Arg Thr
```

-continued

```
    530                 535                 540

Phe Tyr Ile Asp His Asn Ser Lys Ile Thr Gln Trp Glu Asp Pro Arg
545                 550                 555                 560

Leu Gln Asn Pro Ala Ile Thr Gly Pro Ala Val Pro Tyr Ser Arg Glu
                565                 570                 575

Phe Lys Gln Lys Tyr Asp Tyr Phe Arg Lys Lys Leu Lys Lys Pro Ala
            580                 585                 590

Asp Ile Pro Asn Arg Phe Glu Met Lys Leu His Arg Asn Asn Ile Phe
        595                 600                 605

Glu Glu Ser Tyr Arg Arg Ile Met Ser Val Lys Arg Pro Asp Val Leu
    610                 615                 620

Lys Ala Arg Leu Trp Ile Glu Phe Glu Ser Glu Lys Gly Leu Asp Tyr
625                 630                 635                 640

Gly Gly Val Ala Arg Glu Trp Phe Phe Leu Leu Ser Lys Glu Met Phe
                645                 650                 655

Asn Pro Tyr Tyr Gly Leu Phe Glu Tyr Ser Ala Thr Asp Asn Tyr Thr
            660                 665                 670

Leu Gln Ile Asn Pro Asn Ser Gly Leu Cys Asn Glu Asp His Leu Ser
        675                 680                 685

Tyr Phe Thr Phe Ile Gly Arg Val Ala Gly Leu Ala Val Phe His Gly
    690                 695                 700

Lys Leu Leu Asp Gly Phe Phe Ile Arg Pro Phe Tyr Lys Met Met Leu
705                 710                 715                 720

Gly Lys Gln Ile Thr Leu Asn Asp Met Glu Ser Val Asp Ser Glu Tyr
                725                 730                 735

Tyr Asn Ser Leu Lys Trp Ile Leu Glu Asn Asp Pro Thr Glu Leu Asp
            740                 745                 750

Leu Met Phe Cys Ile Asp Glu Glu Asn Phe Gly Gln Thr Tyr Gln Val
        755                 760                 765

Asp Leu Lys Pro Asn Gly Ser Glu Ile Met Val Thr Asn Glu Asn Lys
    770                 775                 780

Arg Glu Tyr Ile Asp Leu Val Ile Gln Trp Arg Phe Val Asn Arg Val
785                 790                 795                 800

Gln Lys Gln Met Asn Ala Phe Leu Glu Gly Phe Thr Glu Leu Leu Pro
                805                 810                 815

Ile Asp Leu Ile Lys Ile Phe Asp Glu Asn Glu Leu Glu Leu Leu Met
            820                 825                 830

Cys Gly Leu Gly Asp Val Asp Val Asn Asp Trp Arg Gln His Ser Ile
        835                 840                 845

Tyr Lys Asn Gly Tyr Cys Pro Asn His Pro Val Ile Gln Trp Phe Trp
    850                 855                 860

Lys Ala Val Leu Leu Met Asp Ala Glu Lys Arg Ile Arg Leu Leu Gln
865                 870                 875                 880

Phe Val Thr Gly Thr Ser Arg Val Pro Met Asn Gly Phe Ala Glu Leu
                885                 890                 895

Tyr Gly Ser Asn Gly Pro Gln Leu Phe Thr Ile Glu Gln Trp Gly Ser
            900                 905                 910

Pro Glu Lys Leu Pro Arg Ala His Thr Cys Phe Asn Arg Leu Asp Leu
        915                 920                 925

Pro Pro Tyr Glu Thr Phe Glu Asp Leu Arg Glu Lys Leu Leu Met Ala
    930                 935                 940

Val Glu Asn Ala Gln Gly Phe Glu Gly Val Asp
945                 950                 955
```

<210> SEQ ID NO 10
<211> LENGTH: 757
<212> TYPE: PRT
<213> ORGANISM: Homo Sapiens

<400> SEQUENCE: 10

```
Met Ser Asn Pro Gly Thr Arg Arg Asn Gly Ser Ser Ile Lys Ile Arg
1               5                   10                  15

Leu Thr Val Leu Cys Ala Lys Asn Leu Ala Lys Lys Asp Phe Phe Arg
            20                  25                  30

Leu Pro Asp Pro Phe Ala Lys Ile Val Val Asp Gly Ser Gly Gln Cys
        35                  40                  45

His Ser Thr Asp Thr Val Lys Asn Thr Leu Asp Pro Lys Trp Asn Gln
    50                  55                  60

His Tyr Asp Leu Tyr Val Gly Lys Thr Asp Ser Ile Thr Ile Ser Val
65                  70                  75                  80

Trp Asn His Lys Lys Ile His Lys Lys Gln Gly Ala Gly Phe Leu Gly
                85                  90                  95

Cys Val Arg Leu Leu Ser Asn Ala Ile Ser Arg Leu Lys Asp Thr Gly
            100                 105                 110

Tyr Gln Arg Leu Asp Leu Cys Lys Leu Asn Pro Ser Asp Thr Asp Ala
        115                 120                 125

Val Arg Gly Gln Ile Val Val Ser Leu Gln Thr Arg Asp Arg Ile Gly
    130                 135                 140

Thr Gly Gly Ser Val Val Asp Cys Arg Gly Leu Leu Glu Asn Glu Gly
145                 150                 155                 160

Thr Val Tyr Glu Asp Ser Gly Pro Gly Arg Pro Leu Ser Cys Phe Met
                165                 170                 175

Glu Glu Pro Ala Pro Tyr Thr Asp Ser Thr Gly Ala Ala Ala Gly Gly
            180                 185                 190

Gly Asn Cys Arg Phe Val Glu Ser Pro Ser Gln Asp Gln Arg Leu Gln
        195                 200                 205

Ala Gln Arg Leu Arg Asn Pro Asp Val Arg Gly Ser Leu Gln Thr Pro
    210                 215                 220

Gln Asn Arg Pro His Gly His Gln Ser Pro Glu Leu Pro Glu Gly Tyr
225                 230                 235                 240

Glu Gln Arg Thr Thr Val Gln Gly Gln Val Tyr Phe Leu His Thr Gln
                245                 250                 255

Thr Gly Val Ser Thr Trp His Asp Pro Arg Ile Pro Ser Pro Ser Gly
            260                 265                 270

Thr Ile Pro Gly Gly Asp Ala Ala Phe Leu Tyr Glu Phe Leu Leu Gln
        275                 280                 285

Gly His Thr Ser Glu Pro Arg Asp Leu Asn Ser Val Asn Cys Asp Glu
    290                 295                 300

Leu Gly Pro Leu Pro Pro Gly Trp Glu Val Arg Ser Thr Val Ser Gly
305                 310                 315                 320

Arg Ile Tyr Phe Val Asp His Asn Asn Arg Thr Thr Gln Phe Thr Asp
                325                 330                 335

Pro Arg Leu His His Ile Met Asn His Gln Cys Gln Leu Lys Glu Pro
            340                 345                 350

Ser Gln Pro Leu Pro Leu Pro Ser Glu Gly Ser Leu Glu Asp Glu Glu
        355                 360                 365

Leu Pro Ala Gln Arg Tyr Glu Arg Asp Leu Val Gln Lys Leu Lys Val
```

```
    370                 375                 380

Leu Arg His Glu Leu Ser Leu Gln Gln Pro Gln Ala Gly His Cys Arg
385                 390                 395                 400

Ile Glu Val Ser Arg Glu Glu Ile Phe Glu Glu Ser Tyr Arg Gln Ile
                405                 410                 415

Met Lys Met Arg Pro Lys Asp Leu Lys Lys Arg Leu Met Val Lys Phe
            420                 425                 430

Arg Gly Glu Glu Gly Leu Asp Tyr Gly Gly Val Ala Arg Glu Trp Leu
        435                 440                 445

Tyr Leu Leu Cys His Glu Met Leu Asn Pro Tyr Tyr Gly Leu Phe Gln
    450                 455                 460

Tyr Ser Thr Asp Asn Ile Tyr Met Leu Gln Ile Asn Pro Asp Ser Ser
465                 470                 475                 480

Ile Asn Pro Asp His Leu Ser Tyr Phe His Phe Val Gly Arg Ile Met
                485                 490                 495

Gly Leu Ala Val Phe His Gly His Tyr Ile Asn Gly Gly Phe Thr Val
            500                 505                 510

Pro Phe Tyr Lys Gln Leu Leu Gly Lys Pro Ile Gln Leu Ser Asp Leu
        515                 520                 525

Glu Ser Val Asp Pro Glu Leu His Lys Ser Leu Val Trp Ile Leu Glu
    530                 535                 540

Asn Asp Ile Thr Pro Val Leu Asp His Thr Phe Cys Val Glu His Asn
545                 550                 555                 560

Ala Phe Gly Arg Ile Leu Gln His Glu Leu Lys Pro Asn Gly Arg Asn
                565                 570                 575

Val Pro Val Thr Glu Glu Asn Lys Lys Glu Tyr Val Arg Leu Tyr Val
            580                 585                 590

Asn Trp Arg Phe Met Arg Gly Ile Glu Ala Gln Phe Leu Ala Leu Gln
        595                 600                 605

Lys Gly Phe Asn Glu Leu Ile Pro Gln His Leu Leu Lys Pro Phe Asp
    610                 615                 620

Gln Lys Glu Leu Glu Leu Ile Ile Gly Gly Leu Asp Lys Ile Asp Leu
625                 630                 635                 640

Asn Asp Trp Lys Ser Asn Thr Arg Leu Lys His Cys Val Ala Asp Ser
                645                 650                 655

Asn Ile Val Arg Trp Phe Trp Gln Ala Val Glu Thr Phe Asp Glu Glu
            660                 665                 670

Arg Arg Ala Arg Leu Leu Gln Phe Val Thr Gly Ser Thr Arg Val Pro
        675                 680                 685

Leu Gln Gly Phe Lys Ala Leu Gln Gly Ser Thr Gly Ala Ala Gly Pro
    690                 695                 700

Arg Leu Phe Thr Ile His Leu Ile Asp Ala Asn Thr Asp Asn Leu Pro
705                 710                 715                 720

Lys Ala His Thr Cys Phe Asn Arg Ile Asp Ile Pro Pro Tyr Glu Ser
                725                 730                 735

Tyr Glu Lys Leu Tyr Glu Lys Leu Leu Thr Ala Val Glu Glu Thr Cys
            740                 745                 750

Gly Phe Ala Val Glu
        755
```

<210> SEQ ID NO 11
<211> LENGTH: 748
<212> TYPE: PRT
<213> ORGANISM: Homo Sapiens

<400> SEQUENCE: 11

Met Ser Asn Pro Gly Gly Arg Arg Asn Gly Pro Val Lys Leu Arg Leu
1 5 10 15

Thr Val Leu Cys Ala Lys Asn Leu Val Lys Lys Asp Phe Phe Arg Leu
20 25 30

Pro Asp Pro Phe Ala Lys Val Val Val Asp Gly Ser Gly Gln Cys His
35 40 45

Ser Thr Asp Thr Val Lys Asn Thr Leu Asp Pro Lys Trp Asn Gln His
50 55 60

Tyr Asp Leu Tyr Ile Gly Lys Ser Asp Ser Val Thr Ile Ser Val Trp
65 70 75 80

Asn His Lys Lys Ile His Lys Lys Gln Gly Ala Gly Phe Leu Gly Cys
85 90 95

Val Arg Leu Leu Ser Asn Ala Ile Asn Arg Leu Lys Asp Thr Gly Tyr
100 105 110

Gln Arg Leu Asp Leu Cys Lys Leu Gly Pro Asn Asp Asn Asp Thr Val
115 120 125

Arg Gly Gln Ile Val Val Ser Leu Gln Ser Arg Asp Arg Ile Gly Thr
130 135 140

Gly Gly Gln Val Val Asp Cys Ser Arg Leu Phe Asp Asn Asp Leu Pro
145 150 155 160

Asp Gly Trp Glu Glu Arg Arg Thr Ala Ser Gly Arg Ile Gln Tyr Leu
165 170 175

Asn His Ile Thr Arg Thr Thr Gln Trp Glu Arg Pro Thr Arg Pro Ala
180 185 190

Ser Glu Tyr Ser Ser Pro Gly Arg Pro Leu Ser Cys Phe Val Asp Glu
195 200 205

Asn Thr Pro Ile Ser Gly Thr Asn Gly Ala Thr Cys Gly Gln Ser Ser
210 215 220

Asp Pro Arg Leu Ala Glu Arg Arg Val Arg Ser Gln Arg His Arg Asn
225 230 235 240

Tyr Met Ser Arg Thr His Leu His Thr Pro Pro Asp Leu Pro Glu Gly
245 250 255

Tyr Glu Gln Arg Thr Thr Gln Gln Gly Gln Val Tyr Phe Leu His Thr
260 265 270

Gln Thr Gly Val Ser Thr Trp His Asp Pro Arg Val Pro Arg Asp Leu
275 280 285

Ser Asn Ile Asn Cys Glu Glu Leu Gly Pro Leu Pro Pro Gly Trp Glu
290 295 300

Ile Arg Asn Thr Ala Thr Gly Arg Val Tyr Phe Val Asp His Asn Asn
305 310 315 320

Arg Thr Thr Gln Phe Thr Asp Pro Arg Leu Ser Ala Asn Leu His Leu
325 330 335

Val Leu Asn Arg Gln Asn Gln Leu Lys Asp Gln Gln Gln Gln Gln Val
340 345 350

Val Ser Leu Cys Pro Asp Asp Thr Glu Cys Leu Thr Val Pro Arg Tyr
355 360 365

Lys Arg Asp Leu Val Gln Lys Leu Lys Ile Leu Arg Gln Glu Leu Ser
370 375 380

Gln Gln Gln Pro Gln Ala Gly His Cys Arg Ile Glu Val Ser Arg Glu
385 390 395 400

Glu Ile Phe Glu Glu Ser Tyr Arg Gln Val Met Lys Met Arg Pro Lys

```
                405                 410                 415

Asp Leu Trp Lys Arg Leu Met Ile Lys Phe Arg Gly Glu Glu Gly Leu
            420                 425                 430

Asp Tyr Gly Gly Val Ala Arg Glu Trp Leu Tyr Leu Leu Ser His Glu
        435                 440                 445

Met Leu Asn Pro Tyr Tyr Gly Leu Phe Gln Tyr Ser Arg Asp Asp Ile
    450                 455                 460

Tyr Thr Leu Gln Ile Asn Pro Asp Ser Ala Val Asn Pro Glu His Leu
465                 470                 475                 480

Ser Tyr Phe His Phe Val Gly Arg Ile Met Gly Met Ala Val Phe His
                485                 490                 495

Gly His Tyr Ile Asp Gly Gly Phe Thr Leu Pro Phe Tyr Lys Gln Leu
            500                 505                 510

Leu Gly Lys Ser Ile Thr Leu Asp Asp Met Glu Leu Val Asp Pro Asp
        515                 520                 525

Leu His Asn Ser Leu Val Trp Ile Leu Glu Asn Asp Ile Thr Gly Val
    530                 535                 540

Leu Asp His Thr Phe Cys Val Glu His Asn Ala Tyr Gly Glu Ile Ile
545                 550                 555                 560

Gln His Glu Leu Lys Pro Asn Gly Lys Ser Ile Pro Val Asn Glu Glu
                565                 570                 575

Asn Lys Lys Glu Tyr Val Arg Leu Tyr Val Asn Trp Arg Phe Leu Arg
            580                 585                 590

Gly Ile Glu Ala Gln Phe Leu Ala Leu Gln Lys Gly Phe Asn Glu Val
        595                 600                 605

Ile Pro Gln His Leu Leu Lys Thr Phe Asp Glu Lys Glu Leu Glu Leu
    610                 615                 620

Ile Ile Cys Gly Leu Gly Lys Ile Asp Val Asn Asp Trp Lys Val Asn
625                 630                 635                 640

Thr Arg Leu Lys His Cys Thr Pro Asp Ser Asn Ile Val Lys Trp Phe
                645                 650                 655

Trp Lys Ala Val Glu Phe Phe Asp Glu Glu Arg Arg Ala Arg Leu Leu
            660                 665                 670

Gln Phe Val Thr Gly Ser Ser Arg Val Pro Leu Gln Gly Phe Lys Ala
        675                 680                 685

Leu Gln Gly Ala Ala Gly Pro Arg Leu Phe Thr Ile His Gln Ile Asp
    690                 695                 700

Ala Cys Thr Asn Asn Leu Pro Lys Ala His Thr Cys Phe Asn Arg Ile
705                 710                 715                 720

Asp Ile Pro Pro Tyr Glu Ser Tyr Glu Lys Leu Tyr Glu Lys Leu Leu
                725                 730                 735

Thr Ala Ile Glu Glu Thr Cys Gly Phe Ala Val Glu
            740                 745


<210> SEQ ID NO 12
<211> LENGTH: 903
<212> TYPE: PRT
<213> ORGANISM: Homo Sapiens

<400> SEQUENCE: 12

Met Ser Asp Ser Gly Ser Gln Leu Gly Ser Met Gly Ser Leu Thr Met
1               5                   10                  15

Lys Ser Gln Leu Gln Ile Thr Val Ile Ser Ala Lys Leu Lys Glu Asn
            20                  25                  30
```

```
Lys Lys Asn Trp Phe Gly Pro Ser Pro Tyr Val Glu Val Thr Val Asp
        35                  40                  45

Gly Gln Ser Lys Lys Thr Glu Lys Cys Asn Asn Thr Asn Ser Pro Lys
    50                  55                  60

Trp Lys Gln Pro Leu Thr Val Ile Val Thr Pro Val Ser Lys Leu His
65                  70                  75                  80

Phe Arg Val Trp Ser His Gln Thr Leu Lys Ser Asp Val Leu Leu Gly
                85                  90                  95

Thr Ala Ala Leu Asp Ile Tyr Glu Thr Leu Lys Ser Asn Asn Met Lys
            100                 105                 110

Leu Glu Glu Val Val Val Thr Leu Gln Leu Gly Gly Asp Lys Glu Pro
        115                 120                 125

Thr Glu Thr Ile Gly Asp Leu Ser Ile Cys Leu Asp Gly Leu Gln Leu
    130                 135                 140

Glu Ser Glu Val Val Thr Asn Gly Glu Thr Thr Cys Ser Glu Asn Gly
145                 150                 155                 160

Val Ser Leu Cys Leu Pro Arg Leu Glu Cys Asn Ser Ala Ile Ser Ala
                165                 170                 175

His Cys Asn Leu Cys Leu Pro Gly Leu Ser Asp Ser Pro Ile Ser Ala
            180                 185                 190

Ser Arg Val Ala Gly Phe Thr Gly Ala Ser Gln Asn Asp Asp Gly Ser
        195                 200                 205

Arg Ser Lys Asp Glu Thr Arg Val Ser Thr Asn Gly Ser Asp Asp Pro
    210                 215                 220

Glu Asp Ala Gly Ala Gly Glu Asn Arg Arg Val Ser Gly Asn Asn Ser
225                 230                 235                 240

Pro Ser Leu Ser Asn Gly Gly Phe Lys Pro Ser Arg Pro Pro Arg Pro
                245                 250                 255

Ser Arg Pro Pro Pro Pro Thr Pro Arg Arg Pro Ala Ser Val Asn Gly
            260                 265                 270

Ser Pro Ser Ala Thr Ser Glu Ser Asp Gly Ser Ser Thr Gly Ser Leu
        275                 280                 285

Pro Pro Thr Asn Thr Asn Thr Asn Thr Ser Glu Gly Ala Thr Ser Gly
    290                 295                 300

Leu Ile Ile Pro Leu Thr Ile Ser Gly Gly Ser Gly Pro Arg Pro Leu
305                 310                 315                 320

Asn Pro Val Thr Gln Ala Pro Leu Pro Pro Gly Trp Glu Gln Arg Val
                325                 330                 335

Asp Gln His Gly Arg Val Tyr Tyr Val Asp His Val Glu Lys Arg Thr
            340                 345                 350

Thr Trp Asp Arg Pro Glu Pro Leu Pro Pro Gly Trp Glu Arg Arg Val
        355                 360                 365

Asp Asn Met Gly Arg Ile Tyr Tyr Val Asp His Phe Thr Arg Thr Thr
    370                 375                 380

Thr Trp Gln Arg Pro Thr Leu Glu Ser Val Arg Asn Tyr Glu Gln Trp
385                 390                 395                 400

Gln Leu Gln Arg Ser Gln Leu Gln Gly Ala Met Gln Gln Phe Asn Gln
                405                 410                 415

Arg Phe Ile Tyr Gly Asn Gln Asp Leu Phe Ala Thr Ser Gln Ser Lys
            420                 425                 430

Glu Phe Asp Pro Leu Gly Pro Leu Pro Pro Gly Trp Glu Lys Arg Thr
        435                 440                 445

Asp Ser Asn Gly Arg Val Tyr Phe Val Asn His Asn Thr Arg Ile Thr
```

-continued

```
    450                 455                 460

Gln Trp Glu Asp Pro Arg Ser Gln Gly Gln Leu Asn Glu Lys Pro Leu
465                 470                 475                 480

Pro Glu Gly Trp Glu Met Arg Phe Thr Val Asp Gly Ile Pro Tyr Phe
                485                 490                 495

Val Asp His Asn Arg Arg Thr Thr Thr Tyr Ile Asp Pro Arg Thr Gly
            500                 505                 510

Lys Ser Ala Leu Asp Asn Gly Pro Gln Ile Ala Tyr Val Arg Asp Phe
        515                 520                 525

Lys Ala Lys Val Gln Tyr Phe Arg Phe Trp Cys Gln Gln Leu Ala Met
    530                 535                 540

Pro Gln His Ile Lys Ile Thr Val Thr Arg Lys Thr Leu Phe Glu Asp
545                 550                 555                 560

Ser Phe Gln Gln Ile Met Ser Phe Ser Pro Gln Asp Leu Arg Arg Arg
                565                 570                 575

Leu Trp Val Ile Phe Pro Gly Glu Glu Gly Leu Asp Tyr Gly Gly Val
            580                 585                 590

Ala Arg Glu Trp Phe Phe Leu Leu Ser His Glu Val Leu Asn Pro Met
        595                 600                 605

Tyr Cys Leu Phe Glu Tyr Ala Gly Lys Asp Asn Tyr Cys Leu Gln Ile
    610                 615                 620

Asn Pro Ala Ser Tyr Ile Asn Pro Asp His Leu Lys Tyr Phe Arg Phe
625                 630                 635                 640

Ile Gly Arg Phe Ile Ala Met Ala Leu Phe His Gly Lys Phe Ile Asp
                645                 650                 655

Thr Gly Phe Ser Leu Pro Phe Tyr Lys Arg Ile Leu Asn Lys Pro Val
            660                 665                 670

Gly Leu Lys Asp Leu Glu Ser Ile Asp Pro Glu Phe Tyr Asn Ser Leu
        675                 680                 685

Ile Trp Val Lys Glu Asn Asn Ile Glu Glu Cys Asp Leu Glu Met Tyr
    690                 695                 700

Phe Ser Val Asp Lys Glu Ile Leu Gly Glu Ile Lys Ser His Asp Leu
705                 710                 715                 720

Lys Pro Asn Gly Gly Asn Ile Leu Val Thr Glu Glu Asn Lys Glu Glu
                725                 730                 735

Tyr Ile Arg Met Val Ala Glu Trp Arg Leu Ser Arg Gly Val Glu Glu
            740                 745                 750

Gln Thr Gln Ala Phe Phe Glu Gly Phe Asn Glu Ile Leu Pro Gln Gln
        755                 760                 765

Tyr Leu Gln Tyr Phe Asp Ala Lys Glu Leu Glu Val Leu Leu Cys Gly
    770                 775                 780

Met Gln Glu Ile Asp Leu Asn Asp Trp Gln Arg His Ala Ile Tyr Arg
785                 790                 795                 800

His Tyr Ala Arg Thr Ser Lys Gln Ile Met Trp Phe Trp Gln Phe Val
                805                 810                 815

Lys Glu Ile Asp Asn Glu Lys Arg Met Arg Leu Leu Gln Phe Val Thr
            820                 825                 830

Gly Thr Cys Arg Leu Pro Val Gly Gly Phe Ala Asp Leu Met Gly Ser
        835                 840                 845

Asn Gly Pro Gln Lys Phe Cys Ile Glu Lys Val Gly Lys Glu Asn Trp
    850                 855                 860

Leu Pro Arg Ser His Thr Cys Phe Asn Arg Leu Asp Leu Pro Pro Tyr
865                 870                 875                 880
```

```
Lys Ser Tyr Glu Gln Leu Lys Glu Lys Leu Leu Phe Ala Ile Glu Glu
                885                 890                 895

Thr Glu Gly Phe Gly Gln Glu
            900


<210> SEQ ID NO 13
<211> LENGTH: 1606
<212> TYPE: PRT
<213> ORGANISM: Homo Sapiens

<400> SEQUENCE: 13

Met Leu Leu His Leu Cys Ser Val Lys Asn Leu Tyr Gln Asn Arg Phe
1               5                   10                  15

Leu Gly Leu Ala Ala Met Ala Ser Pro Ser Arg Asn Ser Gln Ser Arg
            20                  25                  30

Arg Arg Cys Lys Glu Pro Leu Arg Tyr Ser Tyr Asn Pro Asp Gln Phe
        35                  40                  45

His Asn Met Asp Leu Arg Gly Gly Pro His Asp Gly Val Thr Ile Pro
    50                  55                  60

Arg Ser Thr Ser Asp Thr Asp Leu Val Thr Ser Asp Ser Arg Ser Thr
65                  70                  75                  80

Leu Met Val Ser Ser Ser Tyr Tyr Ser Ile Gly His Ser Gln Asp Leu
                85                  90                  95

Val Ile His Trp Asp Ile Lys Glu Glu Val Asp Ala Gly Asp Trp Ile
            100                 105                 110

Gly Met Tyr Leu Ile Asp Glu Val Leu Ser Glu Asn Phe Leu Asp Tyr
        115                 120                 125

Lys Asn Arg Gly Val Asn Gly Ser His Arg Gly Gln Ile Ile Trp Lys
    130                 135                 140

Ile Asp Ala Ser Ser Tyr Phe Val Glu Pro Glu Thr Lys Ile Cys Phe
145                 150                 155                 160

Lys Tyr Tyr His Gly Val Ser Gly Ala Leu Arg Ala Thr Thr Pro Ser
                165                 170                 175

Val Thr Val Lys Asn Ser Ala Ala Pro Ile Phe Lys Ser Ile Gly Ala
            180                 185                 190

Asp Glu Thr Val Gln Gly Gln Gly Ser Arg Arg Leu Ile Ser Phe Ser
        195                 200                 205

Leu Ser Asp Phe Gln Ala Met Gly Leu Lys Lys Gly Met Phe Phe Asn
    210                 215                 220

Pro Asp Pro Tyr Leu Lys Ile Ser Ile Gln Pro Gly Lys His Ser Ile
225                 230                 235                 240

Phe Pro Ala Leu Pro His His Gly Gln Glu Arg Arg Ser Lys Ile Ile
                245                 250                 255

Gly Asn Thr Val Asn Pro Ile Trp Gln Ala Glu Gln Phe Ser Phe Val
            260                 265                 270

Ser Leu Pro Thr Asp Val Leu Glu Ile Glu Val Lys Asp Lys Phe Ala
        275                 280                 285

Lys Ser Arg Pro Ile Ile Lys Arg Phe Leu Gly Lys Leu Ser Met Pro
    290                 295                 300

Val Gln Arg Leu Leu Glu Arg His Ala Ile Gly Asp Arg Val Val Ser
305                 310                 315                 320

Tyr Thr Leu Gly Arg Arg Leu Pro Thr Asp His Val Ser Gly Gln Leu
                325                 330                 335

Gln Phe Arg Phe Glu Ile Thr Ser Ser Ile His Pro Asp Asp Glu Glu
```

-continued

```
            340                 345                 350

Ile Ser Leu Ser Thr Glu Pro Glu Ser Ala Gln Ile Gln Asp Ser Pro
        355                 360                 365

Met Asn Asn Leu Met Glu Ser Gly Ser Gly Glu Pro Arg Ser Glu Ala
    370                 375                 380

Pro Glu Ser Ser Glu Ser Trp Lys Pro Glu Gln Leu Gly Glu Gly Ser
385                 390                 395                 400

Val Pro Asp Gly Pro Gly Asn Gln Ser Ile Glu Leu Ser Arg Pro Ala
                405                 410                 415

Glu Glu Ala Ala Val Ile Thr Glu Ala Gly Asp Gln Gly Met Val Ser
            420                 425                 430

Val Gly Pro Glu Gly Ala Gly Glu Leu Leu Ala Gln Val Gln Lys Asp
        435                 440                 445

Ile Gln Pro Ala Pro Ser Ala Glu Glu Leu Ala Glu Gln Leu Asp Leu
    450                 455                 460

Gly Glu Glu Ala Ser Ala Leu Leu Leu Glu Asp Gly Glu Ala Pro Ala
465                 470                 475                 480

Ser Thr Lys Glu Glu Pro Leu Glu Glu Glu Ala Thr Thr Gln Ser Arg
                485                 490                 495

Ala Gly Arg Glu Glu Glu Glu Lys Glu Gln Glu Glu Glu Gly Asp Val
            500                 505                 510

Ser Thr Leu Glu Gln Gly Glu Gly Arg Leu Gln Leu Arg Ala Ser Val
        515                 520                 525

Lys Arg Lys Ser Arg Pro Cys Ser Leu Pro Val Ser Glu Leu Glu Thr
    530                 535                 540

Val Ile Ala Ser Ala Cys Gly Asp Pro Glu Thr Pro Arg Thr His Tyr
545                 550                 555                 560

Ile Arg Ile His Thr Leu Leu His Ser Met Pro Ser Ala Gln Gly Gly
                565                 570                 575

Ser Ala Ala Glu Glu Glu Asp Gly Ala Glu Glu Glu Ser Thr Leu Lys
            580                 585                 590

Asp Ser Ser Glu Lys Asp Gly Leu Ser Glu Val Asp Thr Val Ala Ala
        595                 600                 605

Asp Pro Ser Ala Leu Glu Glu Asp Arg Glu Glu Pro Glu Gly Ala Thr
    610                 615                 620

Pro Gly Thr Ala His Pro Gly His Ser Gly Gly His Phe Pro Ser Leu
625                 630                 635                 640

Ala Asn Gly Ala Ala Gln Asp Gly Asp Thr His Pro Ser Thr Gly Ser
                645                 650                 655

Glu Ser Asp Ser Ser Pro Arg Gln Gly Gly Asp His Ser Cys Glu Gly
            660                 665                 670

Cys Asp Ala Ser Cys Cys Ser Pro Ser Cys Tyr Ser Ser Ser Cys Tyr
        675                 680                 685

Ser Thr Ser Cys Tyr Ser Ser Ser Cys Tyr Ser Ala Ser Cys Tyr Ser
    690                 695                 700

Pro Ser Cys Tyr Asn Gly Asn Arg Phe Ala Ser His Thr Arg Phe Ser
705                 710                 715                 720

Ser Val Asp Ser Ala Lys Ile Ser Glu Ser Thr Val Phe Ser Ser Gln
                725                 730                 735

Asp Asp Glu Glu Glu Asn Ser Ala Phe Glu Ser Val Pro Asp Ser
            740                 745                 750

Met Gln Ser Pro Glu Leu Asp Pro Glu Ser Thr Asn Gly Ala Gly Pro
        755                 760                 765
```

```
Trp Gln Asp Glu Leu Ala Ala Pro Ser Gly His Val Glu Arg Ser Pro
    770                 775                 780

Glu Gly Leu Glu Ser Pro Val Ala Gly Pro Ser Asn Arg Arg Glu Gly
785                 790                 795                 800

Glu Cys Pro Ile Leu His Asn Ser Gln Pro Val Ser Gln Leu Pro Ser
                805                 810                 815

Leu Arg Pro Glu His His His Tyr Pro Thr Ile Asp Glu Pro Leu Pro
            820                 825                 830

Pro Asn Trp Glu Ala Arg Ile Asp Ser His Gly Arg Val Phe Tyr Val
        835                 840                 845

Asp His Val Asn Arg Thr Thr Thr Trp Gln Arg Pro Thr Ala Ala Ala
    850                 855                 860

Thr Pro Asp Gly Met Arg Arg Ser Gly Ser Ile Gln Gln Met Glu Gln
865                 870                 875                 880

Leu Asn Arg Arg Tyr Gln Asn Ile Gln Arg Thr Ile Ala Thr Glu Arg
                885                 890                 895

Ser Glu Glu Asp Ser Gly Ser Gln Ser Cys Glu Gln Ala Pro Ala Gly
            900                 905                 910

Gly Gly Gly Gly Gly Gly Ser Asp Ser Glu Ala Glu Ser Ser Gln Ser
        915                 920                 925

Ser Leu Asp Leu Arg Arg Glu Gly Ser Leu Ser Pro Val Asn Ser Gln
    930                 935                 940

Lys Ile Thr Leu Leu Leu Gln Ser Pro Ala Val Lys Phe Ile Thr Asn
945                 950                 955                 960

Pro Glu Phe Phe Thr Val Leu His Ala Asn Tyr Ser Ala Tyr Arg Val
                965                 970                 975

Phe Thr Ser Ser Thr Cys Leu Lys His Met Ile Leu Lys Val Arg Arg
            980                 985                 990

Asp Ala Arg Asn Phe Glu Arg Tyr  Gln His Asn Arg Asp  Leu Val Asn
        995                 1000                 1005

Phe Ile  Asn Met Phe Ala Asp  Thr Arg Leu Glu Leu  Pro Arg Gly
    1010                 1015                 1020

Trp Glu  Ile Lys Thr Asp Gln  Gln Gly Lys Ser Phe  Phe Val Asp
    1025                 1030                 1035

His Asn  Ser Arg Ala Thr Thr  Phe Ile Asp Pro Arg  Ile Pro Leu
    1040                 1045                 1050

Gln Asn  Gly Arg Leu Pro Asn  His Leu Thr His Arg  Gln His Leu
    1055                 1060                 1065

Gln Arg  Leu Arg Ser Tyr Ser  Ala Gly Glu Ala Ser  Glu Val Ser
    1070                 1075                 1080

Arg Asn  Arg Gly Ala Ser Leu  Leu Ala Arg Pro Gly  His Ser Leu
    1085                 1090                 1095

Val Ala  Ala Ile Arg Ser Gln  His Gln His Glu Ser  Leu Pro Leu
    1100                 1105                 1110

Ala Tyr  Asn Asp Lys Ile Val  Ala Phe Leu Arg Gln  Pro Asn Ile
    1115                 1120                 1125

Phe Glu  Met Leu Gln Glu Arg  Gln Pro Ser Leu Ala  Arg Asn His
    1130                 1135                 1140

Thr Leu  Arg Glu Lys Ile His  Tyr Ile Arg Thr Glu  Gly Asn His
    1145                 1150                 1155

Gly Leu  Glu Lys Leu Ser Cys  Asp Ala Asp Leu Val  Ile Leu Leu
    1160                 1165                 1170
```

-continued

```
Ser Leu Phe Glu Glu Glu Ile Met Ser Tyr Val Pro Leu Gln Ala
    1175                1180                1185

Ala Phe His Pro Gly Tyr Ser Phe Ser Pro Arg Cys Ser Pro Cys
    1190                1195                1200

Ser Ser Pro Gln Asn Ser Pro Gly Leu Gln Arg Ala Ser Ala Arg
    1205                1210                1215

Ala Pro Ser Pro Tyr Arg Arg Asp Phe Glu Ala Lys Leu Arg Asn
    1220                1225                1230

Phe Tyr Arg Lys Leu Glu Ala Lys Gly Phe Gly Gln Gly Pro Gly
    1235                1240                1245

Lys Ile Lys Leu Ile Ile Arg Arg Asp His Leu Leu Glu Gly Thr
    1250                1255                1260

Phe Asn Gln Val Met Ala Tyr Ser Arg Lys Glu Leu Gln Arg Asn
    1265                1270                1275

Lys Leu Tyr Val Thr Phe Val Gly Glu Glu Gly Leu Asp Tyr Ser
    1280                1285                1290

Gly Pro Ser Arg Glu Phe Phe Phe Leu Leu Ser Gln Glu Leu Phe
    1295                1300                1305

Asn Pro Tyr Tyr Gly Leu Phe Glu Tyr Ser Ala Asn Asp Thr Tyr
    1310                1315                1320

Thr Val Gln Ile Ser Pro Met Ser Ala Phe Val Glu Asn His Leu
    1325                1330                1335

Glu Trp Phe Arg Phe Ser Gly Arg Ile Leu Gly Leu Ala Leu Ile
    1340                1345                1350

His Gln Tyr Leu Leu Asp Ala Phe Phe Thr Arg Pro Phe Tyr Lys
    1355                1360                1365

Ala Leu Leu Arg Leu Pro Cys Asp Leu Ser Asp Leu Glu Tyr Leu
    1370                1375                1380

Asp Glu Glu Phe His Gln Ser Leu Gln Trp Met Lys Asp Asn Asn
    1385                1390                1395

Ile Thr Asp Ile Leu Asp Leu Thr Phe Thr Val Asn Glu Glu Val
    1400                1405                1410

Phe Gly Gln Val Thr Glu Arg Glu Leu Lys Ser Gly Gly Ala Asn
    1415                1420                1425

Thr Gln Val Thr Glu Lys Asn Lys Lys Glu Tyr Ile Glu Arg Met
    1430                1435                1440

Val Lys Trp Arg Val Glu Arg Gly Val Val Gln Gln Thr Glu Ala
    1445                1450                1455

Leu Val Arg Gly Phe Tyr Glu Val Val Asp Ser Arg Leu Val Ser
    1460                1465                1470

Val Phe Asp Ala Arg Glu Leu Glu Leu Val Ile Ala Gly Thr Ala
    1475                1480                1485

Glu Ile Asp Leu Asn Asp Trp Arg Asn Asn Thr Glu Tyr Arg Gly
    1490                1495                1500

Gly Tyr His Asp Gly His Leu Val Ile Arg Trp Phe Trp Ala Ala
    1505                1510                1515

Val Glu Arg Phe Asn Asn Glu Gln Arg Leu Arg Leu Leu Gln Phe
    1520                1525                1530

Val Thr Gly Thr Ser Ser Val Pro Tyr Glu Gly Phe Ala Ala Leu
    1535                1540                1545

Arg Gly Ser Asn Gly Leu Arg Arg Phe Cys Ile Glu Lys Trp Gly
    1550                1555                1560

Lys Ile Thr Ser Leu Pro Arg Ala His Thr Cys Phe Asn Arg Leu
```

```
    1565                1570                1575

Asp Leu  Pro Pro Tyr Pro Ser  Tyr Ser Met Leu Tyr  Glu Lys Leu
    1580                1585                1590

Leu Thr  Ala Val Glu Glu Thr  Ser Thr Phe Gly Leu  Glu
    1595                1600                1605


<210> SEQ ID NO 14
<211> LENGTH: 1572
<212> TYPE: PRT
<213> ORGANISM: Homo Sapiens

<400> SEQUENCE: 14

Met Ala Ser Ser Ala Arg Glu His Leu Leu Phe Val Arg Arg Arg Asn
1               5                   10                  15

Pro Gln Met Arg Tyr Thr Leu Ser Pro Glu Asn Leu Gln Ser Leu Ala
            20                  25                  30

Ala Gln Ser Ser Met Pro Glu Asn Met Thr Leu Gln Arg Ala Asn Ser
        35                  40                  45

Asp Thr Asp Leu Val Thr Ser Glu Ser Arg Ser Ser Leu Thr Ala Ser
    50                  55                  60

Met Tyr Glu Tyr Thr Leu Gly Gln Ala Gln Asn Leu Ile Ile Phe Trp
65                  70                  75                  80

Asp Ile Lys Glu Glu Val Asp Pro Ser Asp Trp Ile Gly Leu Tyr His
                85                  90                  95

Ile Asp Glu Asn Ser Pro Ala Asn Phe Trp Asp Ser Lys Asn Arg Gly
            100                 105                 110

Val Thr Gly Thr Gln Lys Gly Gln Ile Val Trp Arg Ile Glu Pro Gly
        115                 120                 125

Pro Tyr Phe Met Glu Pro Glu Ile Lys Ile Cys Phe Lys Tyr Tyr His
    130                 135                 140

Gly Ile Ser Gly Ala Leu Arg Ala Thr Thr Pro Cys Ile Thr Val Lys
145                 150                 155                 160

Asn Pro Ala Val Met Met Gly Ala Glu Gly Met Glu Gly Gly Ala Ser
                165                 170                 175

Gly Asn Leu His Ser Arg Lys Leu Val Ser Phe Thr Leu Ser Asp Leu
            180                 185                 190

Arg Ala Val Gly Leu Lys Lys Gly Met Phe Phe Asn Pro Asp Pro Tyr
        195                 200                 205

Leu Lys Met Ser Ile Gln Pro Gly Lys Lys Ser Ser Phe Pro Thr Cys
    210                 215                 220

Ala His His Gly Gln Glu Arg Arg Ser Thr Ile Ile Ser Asn Thr Thr
225                 230                 235                 240

Asn Pro Ile Trp His Arg Glu Lys Tyr Ser Phe Phe Ala Leu Leu Thr
                245                 250                 255

Asp Val Leu Glu Ile Glu Ile Lys Asp Lys Phe Ala Lys Ser Arg Pro
            260                 265                 270

Ile Ile Lys Arg Phe Leu Gly Lys Leu Thr Ile Pro Val Gln Arg Leu
        275                 280                 285

Leu Glu Arg Gln Ala Ile Gly Asp Gln Met Leu Ser Tyr Asn Leu Gly
    290                 295                 300

Arg Arg Leu Pro Ala Asp His Val Ser Gly Tyr Leu Gln Phe Lys Val
305                 310                 315                 320

Glu Val Thr Ser Ser Val His Glu Asp Ala Ser Pro Glu Ala Val Gly
                325                 330                 335
```

-continued

```
Thr Ile Leu Gly Val Asn Ser Val Asn Gly Asp Leu Gly Ser Pro Ser
            340                 345                 350

Asp Asp Glu Asp Met Pro Gly Ser His His Asp Ser Gln Val Cys Ser
        355                 360                 365

Asn Gly Pro Val Ser Glu Asp Ser Ala Ala Asp Gly Thr Pro Lys His
    370                 375                 380

Ser Phe Arg Thr Ser Ser Thr Leu Glu Ile Asp Thr Glu Glu Leu Thr
385                 390                 395                 400

Ser Thr Ser Ser Arg Thr Ser Pro Pro Arg Gly Arg Gln Asp Ser Leu
                405                 410                 415

Asn Asp Tyr Leu Asp Ala Ile Glu His Asn Gly His Ser Arg Pro Gly
            420                 425                 430

Thr Ala Thr Cys Ser Glu Arg Ser Met Gly Ala Ser Pro Lys Leu Arg
        435                 440                 445

Ser Ser Phe Pro Thr Asp Thr Arg Leu Asn Ala Met Leu His Ile Asp
    450                 455                 460

Ser Asp Glu Glu Asp His Glu Phe Gln Gln Asp Leu Gly Tyr Pro Ser
465                 470                 475                 480

Ser Leu Glu Glu Glu Gly Gly Leu Ile Met Phe Ser Arg Ala Ser Arg
                485                 490                 495

Ala Asp Asp Gly Ser Leu Thr Ser Gln Thr Lys Leu Glu Asp Asn Pro
            500                 505                 510

Val Glu Asn Glu Glu Ala Ser Thr His Glu Ala Ala Ser Phe Glu Asp
        515                 520                 525

Lys Pro Glu Asn Leu Pro Glu Leu Ala Glu Ser Ser Leu Pro Ala Gly
    530                 535                 540

Pro Ala Pro Glu Glu Gly Glu Gly Gly Pro Glu Pro Gln Pro Ser Ala
545                 550                 555                 560

Asp Gln Gly Ser Ala Glu Leu Cys Gly Ser Gln Glu Val Asp Gln Pro
                565                 570                 575

Thr Ser Gly Ala Asp Thr Gly Thr Ser Asp Ala Ser Gly Gly Ser Arg
            580                 585                 590

Arg Ala Val Ser Glu Thr Glu Ser Leu Asp Gln Gly Ser Glu Pro Ser
        595                 600                 605

Gln Val Ser Ser Glu Thr Glu Pro Ser Asp Pro Ala Arg Thr Glu Ser
    610                 615                 620

Val Ser Glu Ala Ser Thr Arg Pro Glu Gly Glu Ser Asp Leu Glu Cys
625                 630                 635                 640

Ala Asp Ser Ser Cys Asn Glu Ser Val Thr Thr Gln Leu Ser Ser Val
                645                 650                 655

Asp Thr Arg Cys Ser Ser Leu Glu Ser Ala Arg Phe Pro Glu Thr Pro
            660                 665                 670

Ala Phe Ser Ser Gln Glu Glu Glu Asp Gly Ala Cys Ala Ala Glu Pro
        675                 680                 685

Thr Ser Ser Gly Pro Ala Glu Gly Ser Gln Glu Ser Val Cys Thr Ala
    690                 695                 700

Gly Ser Leu Pro Val Val Gln Val Pro Ser Gly Glu Asp Glu Gly Pro
705                 710                 715                 720

Gly Ala Glu Ser Ala Thr Val Pro Asp Gln Glu Glu Leu Gly Glu Val
                725                 730                 735

Trp Gln Arg Arg Gly Ser Leu Glu Gly Ala Ala Ala Ala Ala Glu Ser
            740                 745                 750

Pro Pro Gln Glu Glu Gly Ser Ala Gly Glu Ala Gln Gly Thr Cys Glu
```

-continued

```
        755                 760                 765

Gly Ala Thr Ala Gln Glu Glu Gly Ala Thr Gly Gly Ser Gln Ala Asn
    770                 775                 780

Gly His Gln Pro Leu Arg Ser Leu Pro Ser Val Arg Gln Asp Val Ser
785                 790                 795                 800

Arg Tyr Gln Arg Val Asp Glu Ala Leu Pro Pro Asn Trp Glu Ala Arg
                805                 810                 815

Ile Asp Ser His Gly Arg Ile Phe Tyr Val Asp His Val Asn Arg Thr
            820                 825                 830

Thr Thr Trp Gln Arg Pro Thr Ala Pro Pro Ala Pro Gln Val Leu Gln
        835                 840                 845

Arg Ser Asn Ser Ile Gln Gln Met Glu Gln Leu Asn Arg Arg Tyr Gln
    850                 855                 860

Ser Ile Arg Arg Thr Met Thr Asn Glu Arg Pro Glu Glu Asn Thr Asn
865                 870                 875                 880

Ala Ile Asp Gly Ala Gly Glu Glu Ala Asp Phe His Gln Ala Ser Ala
                885                 890                 895

Asp Phe Arg Arg Glu Asn Ile Leu Pro His Ser Thr Ser Arg Ser Arg
            900                 905                 910

Ile Thr Leu Leu Leu Gln Ser Pro Pro Val Lys Phe Leu Ile Ser Pro
        915                 920                 925

Glu Phe Phe Thr Val Leu His Ser Asn Pro Ser Ala Tyr Arg Met Phe
    930                 935                 940

Thr Asn Asn Thr Cys Leu Lys His Met Ile Thr Lys Val Arg Arg Asp
945                 950                 955                 960

Thr His His Phe Glu Arg Tyr Gln His Asn Arg Asp Leu Val Gly Phe
                965                 970                 975

Leu Asn Met Phe Ala Asn Lys Gln Leu Glu Leu Pro Arg Gly Trp Glu
            980                 985                 990

Met Lys His Asp His Gln Gly Lys  Ala Phe Phe Val Asp  His Asn Ser
        995                 1000                1005

Arg Thr  Thr Thr Phe Ile Asp  Pro Arg Leu Pro Leu  Gln Ser Ser
    1010                1015                1020

Arg Pro  Thr Ser Ala Leu Val  His Arg Gln His Leu  Thr Arg Gln
    1025                1030                1035

Arg Ser  His Ser Ala Gly Glu  Val Gly Glu Asp Ser  Arg His Ala
    1040                1045                1050

Gly Pro  Pro Val Leu Pro Arg  Pro Ser Ser Thr Phe  Asn Thr Val
    1055                1060                1065

Ser Arg  Pro Gln Tyr Gln Asp  Met Val Pro Val Ala  Tyr Asn Asp
    1070                1075                1080

Lys Ile  Val Ala Phe Leu Arg  Gln Pro Asn Ile Phe  Glu Ile Leu
    1085                1090                1095

Gln Glu  Arg Gln Pro Asp Leu  Thr Arg Asn His Ser  Leu Arg Glu
    1100                1105                1110

Lys Ile  Gln Phe Ile Arg Thr  Glu Gly Thr Pro Gly  Leu Val Arg
    1115                1120                1125

Leu Ser  Ser Asp Ala Asp Leu  Val Met Leu Leu Ser  Leu Phe Glu
    1130                1135                1140

Glu Glu  Ile Met Ser Tyr Val  Pro Pro His Ala Leu  Leu His Pro
    1145                1150                1155

Ser Tyr  Cys Gln Ser Pro Arg  Gly Ser Pro Val Ser  Ser Pro Gln
    1160                1165                1170
```

-continued

```
Asn Ser  Pro Gly Thr Gln Arg  Ala Asn Ala Arg Ala  Pro Ala Pro
    1175                 1180                 1185

Tyr Lys  Arg Asp Phe Glu Ala  Lys Leu Arg Asn Phe  Tyr Arg Lys
    1190                 1195                 1200

Leu Glu  Thr Lys Gly Tyr Gly  Gln Gly Pro Gly Lys  Leu Lys Leu
    1205                 1210                 1215

Ile Ile  Arg Arg Asp His Leu  Leu Glu Asp Ala Phe  Asn Gln Ile
    1220                 1225                 1230

Met Gly  Tyr Ser Arg Lys Asp  Leu Gln Arg Asn Lys  Leu Tyr Val
    1235                 1240                 1245

Thr Phe  Val Gly Glu Glu Gly  Leu Asp Tyr Ser Gly  Pro Ser Arg
    1250                 1255                 1260

Glu Phe  Phe Phe Leu Val Ser  Arg Glu Leu Phe Asn  Pro Tyr Tyr
    1265                 1270                 1275

Gly Leu  Phe Glu Tyr Ser Ala  Asn Asp Thr Tyr Thr  Val Gln Ile
    1280                 1285                 1290

Ser Pro  Met Ser Ala Phe Val  Asp Asn His His Glu  Trp Phe Arg
    1295                 1300                 1305

Phe Ser  Gly Arg Ile Leu Gly  Leu Ala Leu Ile His  Gln Tyr Leu
    1310                 1315                 1320

Leu Asp  Ala Phe Phe Thr Arg  Pro Phe Tyr Lys Ala  Leu Leu Arg
    1325                 1330                 1335

Ile Leu  Cys Asp Leu Ser Asp  Leu Glu Tyr Leu Asp  Glu Glu Phe
    1340                 1345                 1350

His Gln  Ser Leu Gln Trp Met  Lys Asp Asn Asp Ile  His Asp Ile
    1355                 1360                 1365

Leu Asp  Leu Thr Phe Thr Val  Asn Glu Glu Val Phe  Gly Gln Ile
    1370                 1375                 1380

Thr Glu  Arg Glu Leu Lys Pro  Gly Gly Ala Asn Ile  Pro Val Thr
    1385                 1390                 1395

Glu Lys  Asn Lys Lys Glu Tyr  Ile Glu Arg Met Val  Lys Trp Arg
    1400                 1405                 1410

Ile Glu  Arg Gly Val Val Gln  Gln Thr Glu Ser Leu  Val Arg Gly
    1415                 1420                 1425

Phe Tyr  Glu Val Val Asp Ala  Arg Leu Val Ser Val  Phe Asp Ala
    1430                 1435                 1440

Arg Glu  Leu Glu Leu Val Ile  Ala Gly Thr Ala Glu  Ile Asp Leu
    1445                 1450                 1455

Ser Asp  Trp Arg Asn Asn Thr  Glu Tyr Arg Gly Gly  Tyr His Asp
    1460                 1465                 1470

Asn His  Ile Val Ile Arg Trp  Phe Trp Ala Ala Val  Glu Arg Phe
    1475                 1480                 1485

Asn Asn  Glu Gln Arg Leu Arg  Leu Leu Gln Phe Val  Thr Gly Thr
    1490                 1495                 1500

Ser Ser  Ile Pro Tyr Glu Gly  Phe Ala Ser Leu Arg  Gly Ser Asn
    1505                 1510                 1515

Gly Pro  Arg Arg Phe Cys Val  Glu Lys Trp Gly Lys  Ile Thr Ala
    1520                 1525                 1530

Leu Pro  Arg Ala His Thr Cys  Phe Asn Arg Leu Asp  Leu Pro Pro
    1535                 1540                 1545

Tyr Pro  Ser Phe Ser Met Leu  Tyr Glu Lys Leu Leu  Thr Ala Val
    1550                 1555                 1560
```

```
Glu Glu  Thr Ser Thr Phe Gly  Leu Glu
    1565                 1570


<210> SEQ ID NO 15
<211> LENGTH: 433
<212> TYPE: PRT
<213> ORGANISM: Homo Sapiens

<400> SEQUENCE: 15

Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile His Asp Val Arg Thr Ile Ala Glu
    210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270

Ala Thr Val Thr Leu Pro Val Phe Ile Gly Asn Ile Ala Val Asn His
        275                 280                 285

Ala Pro Val Ser Pro Arg Pro Gly Leu Gly Leu Pro Pro Gly Ala Pro
    290                 295                 300

Pro Leu Val Val Pro Ser Ala Pro Pro Gln Glu Glu Ala Glu Ala Glu
305                 310                 315                 320

Ala Ala Ala Gly Gly Pro His Phe Leu Asp Pro Val Phe Leu Ser Thr
                325                 330                 335

Lys Ser His Ser Gln Arg Gln Pro Leu Leu Ala Thr Leu Ser Ser Val
            340                 345                 350

Pro Gly Ala Pro Glu Pro Cys Pro Gln Asp Gly Ser Pro Ala Ser His
        355                 360                 365
```

```
Pro Leu His Pro Pro Leu Cys Ile Ser Thr Gly Ala Thr Val Pro Tyr
    370                 375                 380

Phe Ala Glu Gly Ser Gly Gly Pro Val Pro Thr Thr Ser Thr Leu Ile
385                 390                 395                 400

Leu Pro Pro Glu Tyr Ser Ser Trp Gly Tyr Pro Tyr Glu Ala Pro Pro
                405                 410                 415

Ser Tyr Glu Gln Ser Cys Gly Gly Val Glu Pro Ser Leu Thr Pro Glu
            420                 425                 430

Ser


<210> SEQ ID NO 16
<211> LENGTH: 434
<212> TYPE: PRT
<213> ORGANISM: Mus musculus

<400> SEQUENCE: 16

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
            20                  25                  30

Gly Ala Pro Leu Pro Phe Arg Ala Ile Arg Val Thr Cys Met Gly Ser
        35                  40                  45

Cys Gly Val Ser Thr Lys Ala Asn Asp Gly Ala Trp Val Val Glu Glu
    50                  55                  60

Ser Tyr Phe Asn Ser Ser Leu Ser Leu Ala Asp Lys Gly Ser Leu Pro
65                  70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile Tyr Asp Val Arg Thr Ile Ala Glu
    210                 215                 220

Val Glu Gly Thr Gly Val Lys Ala Trp Arg Arg Ala Gln Trp Gln Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Met Lys Ala Pro Glu
            260                 265                 270

Ala Thr Val Thr Leu Pro Leu Phe Val Gly Asn Ile Ala Val Asn Gln
        275                 280                 285

Thr Pro Leu Ser Pro Cys Pro Gly Arg Glu Ser Ser Pro Gly Thr Leu
    290                 295                 300
```

```
Ser Leu Val Val Pro Ser Ala Pro Pro Gln Glu Glu Ala Glu Ala Val
305                 310                 315                 320

Ala Ser Gly Pro His Phe Ser Asp Pro Val Ser Leu Ser Thr Lys Ser
                325                 330                 335

His Ser Gln Gln Gln Pro Leu Ser Ala Pro Leu Gly Ser Val Ser Val
            340                 345                 350

Thr Thr Thr Glu Pro Trp Val Gln Val Gly Ser Pro Ala Arg His Ser
        355                 360                 365

Leu His Pro Pro Leu Cys Ile Ser Ile Gly Ala Thr Val Pro Tyr Phe
    370                 375                 380

Ala Glu Gly Ser Ala Gly Pro Val Pro Thr Thr Ser Ala Leu Ile Leu
385                 390                 395                 400

Pro Pro Glu Tyr Ser Ser Trp Gly Tyr Pro Tyr Glu Ala Pro Pro Ser
                405                 410                 415

Tyr Glu Gln Ser Cys Gly Ala Ala Gly Thr Asp Leu Gly Leu Ile Pro
            420                 425                 430

Gly Ser


<210> SEQ ID NO 17
<211> LENGTH: 433
<212> TYPE: PRT
<213> ORGANISM: Mus musculus

<400> SEQUENCE: 17

Met Gly Arg Val Gln Leu Phe Glu Ile Arg Leu Ser Gln Gly Arg Val
1               5                   10                  15

Val Tyr Gly Pro Gly Glu Pro Leu Ala Gly Thr Val His Leu Arg Leu
            20                  25                  30

Gly Ala Pro Leu Pro Phe Arg Ala Ile Arg Val Thr Cys Met Gly Ser
        35                  40                  45

Cys Gly Val Ser Thr Lys Ala Asn Asp Gly Ala Trp Val Val Glu Glu
    50                  55                  60

Ser Tyr Phe Asn Ser Ser Leu Ser Leu Ala Asp Lys Gly Ser Leu Pro
65                  70                  75                  80

Ala Gly Glu His Asn Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ser Ile Asp Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Thr Thr Lys Lys Phe Ser Tyr Lys Leu
145                 150                 155                 160

Val Lys Thr Gly Asn Val Val Leu Thr Ala Ser Thr Asp Leu Arg Gly
                165                 170                 175

Tyr Val Val Gly Gln Val Leu Arg Leu Gln Ala Asp Ile Glu Asn Gln
            180                 185                 190

Ser Gly Lys Asp Thr Ser Pro Val Val Ala Ser Leu Leu Gln Val Ser
        195                 200                 205

Tyr Lys Ala Lys Arg Trp Ile Tyr Asp Val Arg Thr Ile Ala Glu Val
    210                 215                 220

Glu Gly Thr Gly Val Lys Ala Trp Arg Arg Ala Gln Trp Gln Glu Gln
225                 230                 235                 240
```

-continued

Ile Leu Val Pro Ala Leu Pro Gln Ser Ala Leu Pro Gly Cys Ser Leu
245 250 255

Ile His Ile Asp Tyr Tyr Leu Gln Val Ser Met Lys Ala Pro Glu Ala
260 265 270

Thr Val Thr Leu Pro Leu Phe Val Gly Asn Ile Ala Val Asn Gln Thr
275 280 285

Pro Leu Ser Pro Cys Pro Gly Arg Glu Ser Ser Pro Gly Thr Leu Ser
290 295 300

Leu Val Val Pro Ser Ala Pro Pro Gln Glu Glu Ala Glu Ala Val Ala
305 310 315 320

Ser Gly Pro His Phe Ser Asp Pro Val Ser Leu Ser Thr Lys Ser His
325 330 335

Ser Gln Gln Gln Pro Leu Ser Ala Pro Leu Gly Ser Val Ser Val Thr
340 345 350

Thr Thr Glu Pro Trp Val Gln Val Gly Ser Pro Ala Arg His Ser Leu
355 360 365

His Pro Pro Leu Cys Ile Ser Ile Gly Ala Thr Val Pro Tyr Phe Ala
370 375 380

Glu Gly Ser Ala Gly Pro Val Pro Thr Thr Ser Ala Leu Ile Leu Pro
385 390 395 400

Pro Glu Tyr Ser Ser Trp Gly Tyr Pro Tyr Glu Ala Pro Pro Ser Tyr
405 410 415

Glu Gln Ser Cys Gly Ala Ala Gly Thr Asp Leu Gly Leu Ile Pro Gly
420 425 430

Ser

<210> SEQ ID NO 18
<211> LENGTH: 65
<212> TYPE: PRT
<213> ORGANISM: Homo Sapiens

<400> SEQUENCE: 18

Pro Leu Pro Pro Gly Trp Glu Gln Arg Val Asp Gln His Gly Arg Val
1 5 10 15

Tyr Tyr Val Asp His Val Glu Lys Arg Thr Thr Trp Asp Arg Pro Glu
20 25 30

Pro Leu Pro Pro Gly Trp Glu Arg Arg Val Asp Asn Met Gly Arg Ile
35 40 45

Tyr Tyr Val Asp His Phe Thr Arg Thr Thr Thr Trp Gln Arg Pro Thr
50 55 60

Leu
65

<210> SEQ ID NO 19
<211> LENGTH: 185
<212> TYPE: PRT
<213> ORGANISM: Homo Sapiens

<400> SEQUENCE: 19

Pro Leu Pro Pro Gly Trp Glu Gln Arg Val Asp Gln His Gly Arg Val
1 5 10 15

Tyr Tyr Val Asp His Val Glu Lys Arg Thr Thr Trp Asp Arg Pro Glu
20 25 30

Pro Leu Pro Pro Gly Trp Glu Arg Arg Val Asp Asn Met Gly Arg Ile
35 40 45

```
Tyr Tyr Val Asp His Phe Thr Arg Thr Thr Thr Trp Gln Arg Pro Thr
    50                  55                  60

Leu Glu Ser Val Arg Asn Tyr Glu Gln Trp Gln Leu Gln Arg Ser Gln
65                  70                  75                  80

Leu Gln Gly Ala Met Gln Gln Phe Asn Gln Arg Phe Ile Tyr Gly Asn
                85                  90                  95

Gln Asp Leu Phe Ala Thr Ser Gln Ser Lys Glu Phe Asp Pro Leu Gly
            100                 105                 110

Pro Leu Pro Pro Gly Trp Glu Lys Arg Thr Asp Ser Asn Gly Arg Val
        115                 120                 125

Tyr Phe Val Asn His Asn Thr Arg Ile Thr Gln Trp Glu Asp Pro Arg
    130                 135                 140

Ser Gln Gly Gln Leu Asn Glu Lys Pro Leu Pro Glu Gly Trp Glu Met
145                 150                 155                 160

Arg Phe Thr Val Asp Gly Ile Pro Tyr Phe Val Asp His Asn Arg Arg
                165                 170                 175

Thr Thr Thr Tyr Ile Asp Pro Arg Thr
            180                 185


<210> SEQ ID NO 20
<211> LENGTH: 390
<212> TYPE: PRT
<213> ORGANISM: Homo Sapiens

<400> SEQUENCE: 20

Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240
```

```
Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390


<210> SEQ ID NO 21
<211> LENGTH: 391
<212> TYPE: PRT
<213> ORGANISM: Mus musculus

<400> SEQUENCE: 21

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
        115                 120                 125

Gln Ile Met Ile Val Ile Phe Gly Glu Glu Pro Pro Val Phe Ser Arg
    130                 135                 140

Pro Thr Val Ser Ala Ser Tyr Pro Pro Tyr Thr Ala Thr Gly Pro Pro
145                 150                 155                 160

Asn Thr Ser Tyr Met Pro Gly Met Pro Ser Gly Ile Ser Ala Tyr Pro
                165                 170                 175

Ser Gly Tyr Pro Pro Asn Pro Ser Gly Tyr Pro Gly Cys Pro Tyr Pro
            180                 185                 190

Pro Ala Gly Pro Tyr Pro Ala Thr Thr Ser Ser Gln Tyr Pro Ser Gln
        195                 200                 205

Pro Pro Val Thr Thr Val Gly Pro Ser Arg Asp Gly Thr Ile Ser Glu
```

```
    210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
        275                 280                 285

Ile Glu Leu Leu Lys Lys Lys Asp Glu Glu Leu Ser Ser Ala Leu Glu
    290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
        355                 360                 365

Arg Lys Gln Phe Gln Leu Arg Ala Leu Met Gln Lys Ala Arg Lys Thr
    370                 375                 380

Ala Gly Leu Ser Asp Leu Tyr
385                 390


<210> SEQ ID NO 22
<211> LENGTH: 391
<212> TYPE: PRT
<213> ORGANISM: Rattus norvegicus

<400> SEQUENCE: 22

Met Ala Val Ser Glu Ser Gln Leu Lys Lys Met Met Ser Lys Tyr Lys
1               5                   10                  15

Tyr Arg Asp Leu Thr Val Arg Gln Thr Val Asn Val Ile Ala Met Tyr
            20                  25                  30

Lys Asp Leu Lys Pro Val Leu Asp Ser Tyr Val Phe Asn Asp Gly Ser
        35                  40                  45

Ser Arg Glu Leu Val Asn Leu Thr Gly Thr Ile Pro Val Arg Tyr Arg
    50                  55                  60

Gly Asn Ile Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Asp Trp Lys His Pro Arg Ser Glu Leu Leu Glu Leu Ile
        115                 120                 125

Gln Ile Met Ile Val Ile Phe Gly Glu Glu Pro Pro Val Phe Ser Arg
    130                 135                 140

Pro Thr Val Ser Ala Ser Tyr Pro Pro Tyr Thr Ala Ala Gly Pro Pro
145                 150                 155                 160

Asn Thr Ser Tyr Leu Pro Ser Met Pro Ser Gly Ile Ser Ala Tyr Pro
                165                 170                 175

Ser Gly Tyr Pro Pro Asn Pro Ser Gly Tyr Pro Gly Cys Pro Tyr Pro
            180                 185                 190
```

```
Pro Ala Gly Pro Tyr Pro Ala Thr Thr Ser Ser Gln Tyr Pro Ser Gln
        195                 200                 205

Pro Pro Val Thr Thr Ala Gly Pro Ser Arg Asp Gly Thr Ile Ser Glu
    210                 215                 220

Asp Thr Ile Arg Ala Ser Leu Ile Ser Ala Val Ser Asp Lys Leu Arg
225                 230                 235                 240

Trp Arg Met Lys Glu Glu Met Asp Gly Ala Gln Ala Glu Leu Asn Ala
                245                 250                 255

Leu Lys Arg Thr Glu Glu Asp Leu Lys Lys Gly His Gln Lys Leu Glu
            260                 265                 270

Glu Met Val Thr Arg Leu Asp Gln Glu Val Ala Glu Val Asp Lys Asn
        275                 280                 285

Ile Glu Leu Leu Lys Lys Lys Asp Glu Glu Leu Ser Ser Ala Leu Glu
    290                 295                 300

Lys Met Glu Asn Gln Ser Glu Asn Asn Asp Ile Asp Glu Val Ile Ile
305                 310                 315                 320

Pro Thr Ala Pro Leu Tyr Lys Gln Ile Leu Asn Leu Tyr Ala Glu Glu
                325                 330                 335

Asn Ala Ile Glu Asp Thr Ile Phe Tyr Leu Gly Glu Ala Leu Arg Arg
            340                 345                 350

Gly Val Ile Asp Leu Asp Val Phe Leu Lys His Val Arg Leu Leu Ser
        355                 360                 365

Arg Lys Gln Phe Gln Leu Arg Ala Leu Met Gln Lys Ala Arg Lys Thr
    370                 375                 380

Ala Gly Leu Ser Asp Leu Tyr
385                 390
```

<210> SEQ ID NO 23
<211> LENGTH: 3475
<212> TYPE: DNA
<213> ORGANISM: Homo Sapiens

<400> SEQUENCE: 23

```
gaattcgcgg ccgcgtcgac cgcttctgtg gccacggcag atgaaacaga aaggctaaag     60

agggctggag tcaggggact tctcttccac cagcttcacg gtgatgatat ggcatctgcc    120

agctctagcc gggcaggagt ggccctgcct tttgagaagt ctcagctcac tttgaaagtg    180

gtgtccgcaa agcccaaggt gcataatcgt caacctcgaa ttaactccta cgtggaggtg    240

gcggtggatg gactccccag tgagaccaag aagactggga agcgcattgg gagctctgag    300

cttctctgga atgagatcat cattttgaat gtcacggcac agagtcattt agatttaaag    360

gtctggagct gccatacctt gagaaatgaa ctgctaggca ccgcatctgt caacctctcc    420

aacgtcttga agaacaatgg gggcaaaatg gagaacatgc agctgaccct gaacctgcag    480

acggagaaca aaggcagcgt tgtctcaggc ggaaaactga caattttcct ggacgggcca    540

actgttgatc tgggaaatgt gcctaatggc agtgccctga cagatggatc acagctgcct    600

tcgagagact ccagtggaac agcagtagct ccagagaacc ggcaccagcc ccccagcaca    660

aactgctttg gtggaagatc ccggacgcac agacattcgg gtgcttcagc cagaacaacc    720

ccagcaaccg gcgagcaaag ccccggtgct cggagccggc accgccagcc cgtcaagaac    780

tcaggccaca gtggcttggc caatggcaca gtgaatgatg aacccacaac agccactgat    840

cccgaagaac cttccgttgt tggtgtgacg tccccacctg ctgcaccctt gagtgtgacc    900

ccgaatccca acacgacttc tctccctgcc ccagccacac cggctgaagg agaggaaccc    960
```

-continued

```
agcacttcgg gtacacagca gctcccagcg gctgcccagg cccccgacgc tctgcctgct   1020
ggatgggaac agcgagagct gcccaacgga cgtgtctatt atgttgacca caataccaag   1080
accaccacct gggagcggcc ccttcctcca ggctgggaaa aacgcacaga tccccgaggc   1140
aggttttact atgtggatca caatactcgg accaccacct ggcagcgtcc gaccgcggag   1200
tacgtgcgca actatgagca gtggcagtcg cagcggaatc agctccaggg ggccatgcag   1260
cacttcagcc aaagattcct ataccagttt tggagtgctt cgactgacca tgatcccctg   1320
ggcccccctcc ctcctggttg ggagaaaaga caggacaatg gacgggtgta ttacgtgaac   1380
cataacactc gcacgaccca gtgggaggat ccccggaccc aggggatgat ccaggaacca   1440
gctttgcccc caggatggga gatgaaatac accagcgagg gggtgcgata ctttgtggac   1500
cacaataccc gcaccaccac ctttaaggat cctcgcccgg ggtttgagtc ggggacgaag   1560
caaggttccc ctggtgctta tgaccgcagt tttcggtgga agtatcacca gttccgtttc   1620
ctctgccatt caaatgccct acctagccac gtgaagatca gcgtttccag gcagacgctt   1680
ttcgaagatt ccttccaaca gatcatgaac atgaaaccct atgacctgcg ccgccggctt   1740
tacatcatca tgcgtggcga ggagggcctg gactatgggg gcatcgccag agagtggttt   1800
ttcctcctgt ctcacgaggt gctcaaccct atgtattgtt tatttgaata tgccggaaag   1860
aacaattact gcctgcagat caaccccgcc tcctccatca acccggacca cctcacctac   1920
tttcgcttta taggcagatt catcgccatg gcgctgtacc atggaaagtt catcgacacg   1980
ggcttcaccc tccctttcta caagcggatg ctcaataaga gaccaaccct gaaagacctg   2040
gagtccattg accctgagtt ctacaactcc attgtctgga tcaaagagaa caacctggaa   2100
gaatgtggcc tggagctgta cttcatccag gacatggaga tactgggcaa ggtgacgacc   2160
cacgagctga aggagggcgg cgagagcatc cgggtcacgg aggagaacaa ggaagagtac   2220
atcatgctgc tgactgactg gcgtttcacc cgaggcgtgg aagagcagac caaagccttc   2280
ctggatggct tcaacgaggt ggccccgctg gagtggctgc gctactttga cgagaaagag   2340
ctggagctga tgctgtgcgg catgcaggag atagacatga gcgactggca gaagagcacc   2400
atctaccggc actacaccaa gaacagcaag cagatccagt ggttctggca ggtggtgaag   2460
gagatggaca acgagaagag gatccggctg ctgcagtttg tcaccggtac ctgccgcctg   2520
cccgtcgggg gatttgccga actcatcggt agcaacggac cacagaagtt ttgcattgac   2580
aaagttggca aggaaacctg gctgcccaga agccacacct gcttcaaccg tctggatctt   2640
ccaccctaca agagctacga acagctgaga gagaagctgc tgtatgccat tgaggagacc   2700
gagggctttg gacaggagta accgaggccg cccctcccac gccccccagc gcacatgtag   2760
tcctgagtcc tccctgcctg agaggccact ggccccgcag cccttgggag gcccccgtgg   2820
atgtggccct gtgtgggacc acactgtcat ctcgctgctg gcagaaaagc ctgatcccag   2880
gaggccctgc agttccccccg acccgcggat ggcagtctgg aataaagccc cctagttgcc   2940
tttggcccca cctttgcaaa gttccagagg gctgaccctc tctgcaaaac tctcccctgt   3000
cctctagacc ccaccctggg tgtatgtgag tgtgcaaggg aaggtgttgc atccccaggg   3060
gctgccgcag aggccggaga cctcctggac tagttcggcg aggagactgg ccactggggg   3120
tggctgttcg ggactgagag cgccaagggt ctttgccagc aaaggaggtt ctgcctgtaa   3180
ttgagcctct ctgatgatgg agatgaagtg aaggtctgag ggacgggccc tggggctagg   3240
ccatctctgc ctgcctccct agcaggcgcc agcggtggag gctgagtcgc aggacacatg   3300
ccggccagtt aattcattct cagcaaatga aggtttgtct aagctgcctg ggtatccacg   3360
```

-continued ggacaaaaac agcaaactcc ctccagactt tgtccatgtt ataaacttga aagttggttg 3420
ttgtttgtta ggtttgccag gtttttttgt ttacgcctgc tgtcactttc ctgtc 3475

<210> SEQ ID NO 24
<211> LENGTH: 3475
<212> TYPE: DNA
<213> ORGANISM: Homo Sapiens

<400> SEQUENCE: 24
gaattcgcgg ccgcgtcgac cgcttctgtg gccacggcag atgaaacaga aaggctaaag 60
agggctggag tcaggggact tctcttccac cagcttcacg gtgatgatat ggcatctgcc 120
agctctagcc gggcaggagt ggccctgcct tttgagaagt ctcagctcac tttgaaagtg 180
gtgtccgcaa agcccaaggt gcataatcgt caacctcgaa ttaactccta cgtggaggtg 240
gcggtggatg gactccccag tgagaccaag aagactggga agcgcattgg gagctctgag 300
cttctctgga atgagatcat cattttgaat gtcacggcac agagtcattt agatttaaag 360
gtctggagct gccatacctt gagaaatgaa ctgctaggca ccgcatctgt caacctctcc 420
aacgtcttga agaacaatgg gggcaaaatg gagaacatgc agctgaccct gaacctgcag 480
acggagaaca aaggcagcgt tgtctcaggc ggaaaactga caatttttcct ggacgggcca 540 actgttgatc tgggaaatgt gcctaatggc agtgccctga cagatggatc acagctgcct 600
tcgagagact ccagtggaac agcagtagct ccagagaacc ggcaccagcc ccccagcaca 660
aactgctttg gtggaagatc ccggacgcac agacattcgg gtgcttcagc cagaacaacc 720
ccagcaaccg gcgagcaaag ccccggtgct cggagccggc accgccagcc cgtcaagaac 780
tcaggccaca gtggcttggc caatggcaca gtgaatgatg aacccacaac agccactgat 840
cccgaagaac cttccgttgt tggtgtgacg tccccacctg ctgcaccctt gagtgtgacc 900
ccgaatccca acacgacttc tctccctgcc ccagccacac cggctgaagg agaggaaccc 960
agcacttcgg gtacacagca gctcccagcg gctgcccagg cccccgacgc tctgcctgct 1020
ggatgggaac agcgagagct gcccaacgga cgtgtctatt atgttgacca caataccaag 1080
accaccacct gggagcggcc ccttcctcca ggctgggaaa aacgcacaga tccccgaggc 1140
aggttttact atgtggatca caatactcgg accaccacct ggcagcgtcc gaccgcggag 1200
tacgtgcgca actatgagca gtggcagtcg cagcggaatc agctccaggg ggccatgcag 1260
cacttcagcc aaagattcct ataccagttt tggagtgctt cgactgacca tgatcccctg 1320 ggcccccctcc ctcctggttg ggagaaaaga caggacaatg gacgggtgta ttacgtgaac 1380
cataacactc gcacgaccca gtgggaggat ccccggaccc aggggatgat ccaggaacca 1440
gctttgcccc caggatggga gatgaaatac accagcgagg gggtgcgata ctttgtggac 1500
cacaataccc gcaccaccac ctttaaggat cctcgcccgg ggtttgagtc ggggacgaag 1560
caaggttccc ctggtgctta tgaccgcagt tttcggtgga agtatcacca gttccgtttc 1620
ctctgccatt caaatgccct acctagccac gtgaagatca gcgtttccag gcagacgctt 1680
ttcgaagatt ccttccaaca gatcatgaac atgaaaccct atgacctgcg ccgccggctt 1740
tacatcatca tgcgtggcga ggagggcctg gactatgggg gcatcgccag agagtggttt 1800
ttcctcctgt ctcacgaggt gctcaaccct atgtattgtt tatttgaata tgccggaaag 1860
aacaattact gcctgcagat caaccccgcc tcctccatca acccggacca cctcacctac 1920
tttcgcttta taggcagatt catcgccatg gcgctgtacc atggaaagtt catcgacacg 1980

-continued

```
ggcttcaccc tccctttcta caagcggatg ctcaataaga gaccaaccct gaaagacctg   2040

gagtccattg accctgagtt ctacaactcc attgtctgga tcaaagagaa caacctggaa   2100

gaatgtggcc tggagctgta cttcatccag gacatggaga tactgggcaa ggtgacgacc   2160

cacgagctga aggagggcgg cgagagcatc cgggtcacgg aggagaacaa ggaagagtac   2220

atcatgctgc tgactgactg gcgtttcacc cgaggcgtgg aagagcagac caaagccttc   2280

ctggatggct tcaacgaggt ggccccgctg gagtggctgc gctactttga cgagaaagag   2340

ctggagctga tgctgtgcgg catgcaggag atagacatga gcgactggca gaagagcacc   2400

atctaccggc actacaccaa gaacagcaag cagatccagt ggttctggca ggtggtgaag   2460

gagatggaca acgagaagag gatccggctg ctgcagtttg tcaccggtac ctgccgcctg   2520

cccgtcgggg gatttgccga actcatcggt agcaacggac cacagaagtt ttgcattgac   2580

aaagttggca aggaaacctg gctgcccaga agccacacct gcttcaaccg tctggatctt   2640

ccaccctaca agagctacga acagctgaga gagaagctgc tgtatgccat tgaggagacc   2700

gagggctttg gacaggagta accgaggccg cccctcccac gccccccagc gcacatgtag   2760

tcctgagtcc tccctgcctg agaggccact ggccccgcag cccttgggag gcccccgtgg   2820

atgtggccct gtgtgggacc acactgtcat ctcgctgctg gcagaaaagc ctgatcccag   2880

gaggccctgc agttcccccg acccgcggat ggcagtctgg aataaagccc cctagttgcc   2940

tttggcccca cctttgcaaa gttccagagg gctgaccctc tctgcaaaac tctcccctgt   3000

cctctagacc ccaccctggg tgtatgtgag tgtgcaaggg aaggtgttgc atccccaggg   3060

gctgccgcag aggccggaga cctcctggac tagttcggcg aggagactgg ccactggggg   3120

tggctgttcg ggactgagag cgccaagggt ctttgccagc aaaggaggtt ctgcctgtaa   3180

ttgagcctct ctgatgatgg agatgaagtg aaggtctgag ggacgggccc tggggctagg   3240

ccatctctgc ctgcctccct agcaggcgcc agcggtggag gctgagtcgc aggacacatg   3300

ccggccagtt aattcattct cagcaaatga aggtttgtct aagctgcctg ggtatccacg   3360

ggacaaaaac agcaaactcc ctccagactt tgtccatgtt ataaacttga aagttggttg   3420

ttgtttgtta ggtttgccag gttttttgt ttacgcctgc tgtcactttc ctgtc        3475
```

<210> SEQ ID NO 25
<211> LENGTH: 2914
<212> TYPE: DNA
<213> ORGANISM: Homo Sapiens

<400> SEQUENCE: 25

```
acagttgcct gccctgggcg ggggcgagcg cgtccggttt gctggaagcg ttcggaaatg     60

gcaacttgcg cggtggaggt gttcgggctc ctggaggacg aggaaaattc acgaattgtg    120

agagtaagag ttatagccgg aataggcctt gccaagaagg atatattggg agctagtgat    180

ccttacgtga gagtgacgtt atatgaccca atgaatggag ttcttacaag tgtgcaaaca    240

aaaaccatta aaaagagttt gaatccaaag tggaatgaag aaatattatt cagagttcat    300

cctcagcagc accggcttct ttttgaagtg tttgacgaaa accgattgac aagagatgat    360

ttcctaggtc aagtggatgt tccactttat ccattaccga cagaaaatcc aagattggag    420

agaccatata catttaagga ttttgttctt catccaagaa gtcacaaatc aagagttaaa    480

ggttatctga gactaaaaat gacttattta cctaaaacca gtggctcaga agatgataat    540

gcagaacagg ctgaggaatt agagcctggc tgggttgttt tggaccaacc agatgctgct    600

tgccatttgc agcaacaaca agaaccttct cctctacctc cagggtggga agagaggcag    660
```

```
gatatccttg gaaggaccta ttatgtaaac catgaatcta gaagaacaca gtggaaaaga    720
ccaacccctc aggacaacct aacagatgct gagaatggca acattcaact gcaagcacaa    780
cgtgcattta ccaccaggcg gcagatatcc gaggaaacag aaagtgttga caaccaagag    840
tcttccgaga actgggaaat tataagagaa gatgaagcca ccatgtatag cagccaggcc    900
ttcccatcac ctccaccgtc aagtaacttg gatgttccaa ctcatcttgc agaagaattg    960
aatgccagac tcaccatttt tggaaattca gccgtgagcc agccagcatc gagctcaaat   1020
cattccagca gaagaggcag cttacaagcc tatacttttg aggaacaacc tacacttcct   1080
gtgcttttgc ctacttcatc tggattacca ccaggttggg aagaaaaaca agatgaaaga   1140
ggaagatcat attatgtaga tcacaattcc agaacgacta cttggacaaa gcccactgta   1200
caggccacag tggagaccag tcagctgacc tcaagccaga gttctgcagg ccctcaatca   1260
caagcctcca ccagtgattc aggccagcag gtgacccagc catctgaaat tgagcaagga   1320
ttccttccta aaggctggga agtccggcat gcaccaaatg ggaggccttt ctttattgac   1380
cacaacacta aaaccaccac ctgggaagat ccaagattga aaattccagc ccatctgaga   1440
ggaaagacat cacttgatac ttccaatgat ctagggcctt tacctccagg atgggaagag   1500
agaactcaca cagatggaag aatcttctac ataaatcaca atataaaaag aacacaatgg   1560
gaagatcctc ggttggagaa tgtagcaata actggaccag cagtgcccta ctccagggat   1620
tacaaaagaa agtatgagtt cttccgaaga aagttgaaga agcagaatga cattccaaac   1680
aaatttgaaa tgaaacttcg ccgagcaact gttcttgaag actcttaccg gagaattatg   1740
ggtgtcaaga gagcagactt cctgaaggct cgactgtgga ttgagtttga tggtgaaaag   1800
ggattggatt atggaggagt tgccagagaa tggttcttcc tgatctcaaa ggaaatgttt   1860
aacccttatt atgggttgtt tgaatattct gctacggaca attataccct acagataaat   1920
ccaaactctg gattgtgtaa cgaagatcac ctctcttact tcaagtttat tggtcgggta   1980
gctggaatgg cagtttatca tggcaaactg ttggatggtt ttttcatccg cccattttac   2040
aagatgatgc ttcacaaacc aataaccctt catgatatgg aatctgtgga tagtgaatat   2100
tacaattccc taagatggat tcttgaaaat gacccaacag aattggacct caggtttatc   2160
atagatgaag aactttttgg acagacacat caacatgagc tgaaaaatgg tggatcagaa   2220
atagttgtca ccaataagaa caaaaaggaa tatatttatc ttgtaataca atggcgattt   2280
gtaaaccgaa tccagaagca aatggctgct tttaaagagg gattctttga actaatacca   2340
caggatctca tcaaaatttt tgatgaaaat gaactagagc ttcttatgtg tggaccggga   2400
gatgttgatg tgaatgactg gagggaacat acaaagtata aaaatggcta cagtgcaaat   2460
catcaggtta tacagtggtt ttggaaggct gttttaatga tggattcaga aaaaagaata   2520
agattacttc agtttgtcac tggcacatct cgggtgccta tgaatggatt tgctgaacta   2580
tacggttcaa atggaccaca gtcatttaca gttgaacagt ggggtactcc tgaaaagctg   2640
ccaagagctc atacctgttt taatcgcctg gacttgccac cttatgaatc atttgaagaa   2700
ttatgggata aacttcagat ggcaattgaa aacacccagg gctttgatgg agttgattag   2760
attacaaata acaatctgta gtgtttttac tgccatagtt ttataaccaa aatcttgact   2820
taaaattttc cggggaacta ctaaaatgtg gccactgagt cttcccagat cttgaagaaa   2880
atcatataaa aagcatttga agaaatagta cgac                                2914
```

<210> SEQ ID NO 26

<211> LENGTH: 2868
<212> TYPE: DNA
<213> ORGANISM: Homo Sapiens

<400> SEQUENCE: 26

```
atggcgaccg ggctcgggga gccggtctat ggactttccg aagacgaggg agagtcccgt     60
attctcagag taaaagttgt ttctggaatt gatctcgcca aaaaggacat ctttggagcc    120
agtgatccgt atgtgaaact ttcattgtac gtagcggatg agaatagaga acttgctttg    180
gtccagacaa aaacaattaa aaagacactg aacccaaaat ggaatgaaga attttatttc    240
agggtaaacc catctaatca cagactccta tttgaagtat ttgacgaaaa tagactgaca    300
cgagacgact tcctgggcca ggtggacgtg ccccttagtc accttccgac agaagatcca    360
accatggagc gaccctatac atttaaggac tttctcctca gaccaagaag tcataagtct    420
cgagttaagg gatttttgcg attgaaaatg gcctatatgc caaaaaatgg aggtcaagat    480
gaagaaaaca gtgaccagag ggatgacatg gagcatggat gggaagttgt tgactcaaat    540
gactcggctt ctcagcacca agaggaactt cctcctcctc ctctgcctcc cgggtgggaa    600
gaaaaagtgg acaatttagg ccgaacttac tatgtcaacc acaacaaccg gaccactcag    660
tggcacagac caagcctgat ggacgtgtcc tcggagtcgg acaataacat cagacagatc    720
aaccaggagg cagcacaccg gcgcttccgc tcccgcaggc acatcagcga agacttggag    780
cccgagccct cggagggcgg ggatgtcccc gagccttggg agaccatttc agaggaagtg    840
aatatcgctg gagactctct cggtctggct ctgcccccac caccggcctc cccaggatct    900
cggaccagcc ctcaggagct gtcagaggaa ctaagcagaa ggcttcagat cactccagac    960
tccaatgggg aacagttcag ctctttgatt caaagagaac cctcctcaag gttgaggtca   1020
tgcagtgtca ccgacgcagt tgcagaacag ggccatctac caccgccatc agtggcctat   1080
gtacatacca cgccgggtct gccttcaggc tgggaagaaa gaaaagatgc taaggggcgc   1140
acatactatg tcaatcataa caatcgaacc acaacttgga ctcgacctat catgcagctt   1200
gcagaagatg gtgcgtccgg atcagccaca aacagtaaca accatctaat cgagcctcag   1260
atccgccggc ctcgtagcct cagctcgcca acagtaactt tatctgcccc gctggagggt   1320
gccaaggact cacccgtacg tcgggctgtg aaagacaccc tttccaaccc acagtcccca   1380
cagccatcac cttacaactc ccccaaacca caacacaaag tcacacagag cttcttgcca   1440
cccggctggg aaatgaggat agcgccaaac ggccggccct tcttcattga tcataacaca   1500
aagactacaa cctgggaaga tccacgtttg aaatttccag tacatatgcg gtcaaagaca   1560
tctttaaacc ccaatgacct tggccccctt cctcctggct gggaagaaag aattcacttg   1620
gatggccgaa cgttttatat tgatcataat agcaaaatta ctcagtggga agacccaaga   1680
ctgcagaacc cagctattac tggtccggct gtcccttact ccagagaatt taagcagaaa   1740
tatgactact tcaggaagaa attaaagaaa cctgctgata tccccaatag gtttgaaatg   1800
aaacttcaca gaaataacat atttgaagag tcctatcgga gaattatgtc cgtgaaaaga   1860
ccagatgtcc taaaagctag actgtggatt gagtttgaat cagagaaagg tcttgactat   1920
gggggtgtgg ccagagaatg gttcttctta ctgtccaaag agatgttcaa cccctactac   1980
ggcctctttg agtactctgc cacggacaac tacacccttc agatcaaccc taattcaggc   2040
ctctgtaatg aggatcattt gtcctacttc acttttattg gaagagttgc tggtctggcc   2100
gtatttcatg ggaagctctt agatggtttc ttcattagac cattttacaa gatgatgttg   2160
ggaaagcaga taaccctgaa tgacatggaa tctgtggata gtgaatatta caactctttg   2220
```

-continued

```
aaatggatcc tggagaatga ccctactgag ctggacctca tgttctgcat agacgaagaa   2280

aactttggac agacatatca agtggatttg aagcccaatg ggtcagaaat aatggtcaca   2340

aatgaaaaca aaagggaata tatcgactta gtcatccagt ggagatttgt gaacagggtc   2400

cagaagcaga tgaacgcctt cttggaggga ttcacagaac tacttcctat tgatttgatt   2460

aaaatttttg atgaaaatga gctggagttg ctcatgtgcg gcctcggtga tgtggatgtg   2520

aatgactgga gacagcattc tatttacaag aacggctact gcccaaacca ccccgtcatt   2580

cagtggttct ggaaggctgt gctactcatg gacgccgaaa agcgtatccg gttactgcag   2640

tttgtcacag ggacatcgcg agtacctatg aatggatttg ccgaacttta tggttccaat   2700

ggtcctcagc tgtttacaat agagcaatgg ggcagtcctg agaaactgcc cagagctcac   2760

acatgcttta atcgccttga cttacctcca tatgaaacct ttgaagattt acgagagaaa   2820

cttctcatgg ccgtggaaaa tgctcaagga tttgaagggg tggattaa                2868
```

<210> SEQ ID NO 27
<211> LENGTH: 2274
<212> TYPE: DNA
<213> ORGANISM: Homo Sapiens

<400> SEQUENCE: 27

```
atgtcgaacc ccgggacacg caggaacggc tccagcatca agatccgtct gacagtgtta     60

tgtgccaaga accttgcaaa gaaagacttc ttcaggctcc ctgacccttt tgcaaagatt    120

gtcgtggatg ggtctgggca gtgccactca accgacactg tgaaaaacac attggaccca    180

aagtggaacc agcactatga tctatatgtt gggaaaacgg attcgataac cattagcgtg    240

tggaaccata agaaaattca caagaaacag ggagctggct tcctgggctg tgtgcggctg    300

ctctccaatg ccatcagcag attaaaagat accggatacc agcgtttgga tctatgcaaa    360

ctaaacccct cagatactga tgcagttcgt ggccagatag tggtcagttt acagacacga    420

gacagaatag gaaccggcgg ctcggtggtg gactgcagag gactgttaga aaatgaagga    480

acggtgtatg aagactccgg gcctgggagg ccgctcagct gcttcatgga ggaaccagcc    540

ccttacacag atagcaccgg tgctgctgct ggaggaggga attgcaggtt cgtggagtcc    600

ccaagtcaag atcaaagact tcaggcacag cggcttcgaa accctgatgt gcgaggttca    660

ctacagacgc cccagaaccg accacacggc caccagtccc cggaactgcc cgaaggctac    720

gaacaaagaa caacagtcca gggccaagtt tacttttttgc atacacagac tggagttagc    780

acgtggcacg accccaggat accaagtccc tcggggacca ttcctggggg agatgcagct    840

tttctatacg aattccttct acaaggccat acatctgagc ccagagacct taacagtgtg    900

aactgtgatg aacttggacc actgccgcca ggctgggaag tcagaagtac agtttctggg    960

aggatatatt ttgtagatca taataaccga acaacccagt ttacagaccc aaggttacac   1020

cacatcatga atcaccagtg ccaactcaag gagcccagcc agccgctgcc actgcccagt   1080

gagggctctc tggaggacga ggagcttcct gcccagagat acgaaagaga tctagtccag   1140

aagctgaaag tcctcagaca cgaactgtcg cttcagcagc cccaagctgg tcattgccgc   1200

atcgaagtgt ccagagaaga aatctttgag gagtcttacc gccagataat gaagatgcga   1260

ccgaaagact tgaaaaaacg gctgatggtg aaattccgtg gggaagaagg tttggattac   1320

ggtggtgtgg ccagggagtg gctttacttg ctgtgccatg aaatgctgaa tccttattac   1380

gggctcttcc agtattctac ggacaatatt tacatgttgc aaataaatcc ggattcttca   1440
```

-continued

```
atcaaccccg accacttgtc ttatttccac tttgtggggc ggatcatggg gctggctgtg   1500

ttccatggac actacatcaa cggggggcttc acagtgccct tctacaagca gctgctgggg   1560

aagcccatcc agctctcaga tctggaatct gtggacccag agctgcataa gagcttggtg   1620

tggatcctag agaacgacat cacgcctgta ctggaccaca ccttctgcgt ggaacacaac   1680

gccttcgggc ggatcctgca gcatgaactg aaacccaatg gcagaaatgt gccagtcaca   1740

gaggagaata agaaagaata cgtccggttg tatgtaaact ggaggtttat gagaggaatc   1800

gaagcccagt tcttagctct gcagaagggg ttcaatgagc tcatccctca acatctgctg   1860

aagccttttg accagaagga actggagctg atcataggcg gcctggataa aatagacttg   1920

aacgactgga agtcgaacac gcggctgaag cactgtgtgg ccgacagcaa catcgtgcgg   1980

tggttctggc aagcggtgga gacgttcgat gaagaaagga gggccaggct cctgcagttt   2040

gtgactgggt ccacgcgagt cccgctccaa ggcttcaagg ctttgcaagg ttctacaggc   2100

gcggcagggc cccggctgtt caccatccac ctgatagacg cgaacacaga caaccttccg   2160

aaggcccata cctgctttaa ccggatcgac attccaccat atgagtccta tgagaagctc   2220

tacgagaagc tgctgacagc cgtggaggag acctgcgggt ttgctgtgga gtga         2274
```

<210> SEQ ID NO 28
<211> LENGTH: 2247
<212> TYPE: DNA
<213> ORGANISM: Homo Sapiens

<400> SEQUENCE: 28

```
atgtctaacc ccggacgccg gaggaacggg cccgtcaagc tgcgcctgac agtactctgt     60

gcaaaaaacc tggtgaaaaa ggattttttc cgacttcctg atccatttgc taaggtggtg    120

gttgatggat ctgggcaatg ccattctaca gatactgtga agaatacgct tgatccaaag    180

tggaatcagc attatgacct gtatattgga aagtctgatt cagttacgat cagtgtatgg    240

aatcacaaga agatccataa gaaacaaggt gctggatttc tcggttgtgt tcgtcttctt    300

tccaatgcca tcaaccgcct caaagacact ggttatcaga ggttggattt atgcaaactc    360

gggccaaatg acaatgatac agttagagga cagatagtag taagtcttca gtccagagac    420

cgaataggca caggaggaca agttgtggac tgcagtcgtt tatttgataa cgatttacca    480

gacggctggg aagaaaggag aaccgcctct ggaagaatcc agtatctaaa ccatataaca    540

agaactacgc aatgggagcg cccaacacga ccggcatccg aatattctag ccctggcaga    600

cctcttagct gctttgttga tgagaacact ccaattagtg gaacaaatgg tgcaacatgt    660

ggacagtctt cagatcccag gctggcagag aggagagtca ggtcacaacg acatagaaat    720

tacatgagca gaacacattt acatactcct ccagacctac cagaaggcta tgaacagagg    780

acaacgcaac aaggccaggt gtatttctta catacacaga ctggtgtgag cacatggcat    840

gatccaagag tgcccaggga tcttagcaac atcaattgtg aagagcttgg tccattgcct    900

cctggatggg agatccgtaa tacggcaaca ggcagagttt atttcgttga ccataacaac    960

agaacaacac aatttacaga tcctcggctg tctgctaact tgcatttagt tttaaatcgg   1020

cagaaccaat tgaaagacca acagcaacag caagtggtat cgttatgtcc tgatgacaca   1080

gaatgcctga cagtcccaag gtacaagcga gacctggttc agaaactaaa aattttgcgg   1140

caagaacttt cccaacaaca gcctcaggca ggtcattgcc gcattgaggt ttccagggaa   1200

gagatttttg aggaatcata tcgacaggtc atgaaaatga gaccaaaaga tctctggaag   1260

cgattaatga taaaatttcg tggagaagaa ggccttgact atggaggcgt tgccagggaa   1320
```

tggttgtatc tcttgtcaca tgaaatgttg aatccatact atggcctctt ccagtattca 1380
agagatgata tttatacatt gcagatcaat cctgattctg cagttaatcc ggaacattta 1440
tcctatttcc actttgttgg acgaataatg ggaatggctg tgtttcatgg acattatatt 1500
gatggtggtt tcacattgcc tttttataag caattgcttg ggaagtcaat taccttggat 1560
gacatggagt tagtagatcc ggatcttcac aacagtttag tgtggatact tgagaatgat 1620
attacaggtg ttttggacca taccttctgt gttgaacata atgcatatgg tgaaattatt 1680
cagcatgaac ttaaaccaaa tggcaaaagt atccctgtta atgaagaaaa taaaaaagaa 1740
tatgtcaggc tctatgtgaa ctggagattt ttacgaggca ttgaggctca attcttggct 1800
ctgcagaaag gatttaatga agtaattcca caacatctgc tgaagacatt tgatgagaag 1860
gagttagagc tcattatttg tggacttgga aagatagatg ttaatgactg gaaggtaaac 1920
acccggttaa aacactgtac accagacagc aacattgtca aatggttctg gaaagctgtg 1980 gagtttttg atgaagagcg acgagcaaga ttgcttcagt ttgtgacagg atcctctcga 2040
gtgcctctgc agggcttcaa agcattgcaa ggtgctgcag gcccgagact ctttaccata 2100
caccagattg atgcctgcac taacaacctg ccgaaagccc acacttgctt caatcgaata 2160
gacattccac cctatgaaag ctatgaaaag ctatatgaaa agctgctaac agccattgaa 2220
gaaacatgtg gatttgctgt ggaatga 2247

<210> SEQ ID NO 29
<211> LENGTH: 2869
<212> TYPE: DNA
<213> ORGANISM: Homo Sapiens

<400> SEQUENCE: 29
ggagtcgccg ccgccccgag ttccggtacc atgcatttca cggtggcctt gtggagacaa 60
cgccttaacc caaggaagtg actcaaactg tgagaactcc aggttttcca acctattggt 120
ggtatgtctg acagtggatc acaacttggt tcaatgggta gcctcaccat gaaatcacag 180
cttcagatca ctgtcatctc agcaaaactt aaggaaaata agaagaattg gtttggacca 240
agtccttacg tagaggtcac agtagatgga cagtcaaaga agacagaaaa atgcaacaac 300
acaaacagtc ccaagtggaa gcaacccctt acagttatcg ttacccctgt gagtaaatta 360
cattttcgtg tgtggagtca ccagacactg aaatctgatg ttttgttggg aactgctgca 420
ttagatattt atgaaacatt aaagtcaaac aatatgaaac ttgaagaagt agttgtgact 480
ttgcagcttg gaggtgacaa agagccaaca gagacaatag gagacttgtc aatttgtctt 540
gatgggctac agttagagtc tgaagttgtt accaatggtg aaactacatg ttcagaaagt 600
gcttctcaga atgatgatgg ctccagatcc aaggatgaaa caagagtgag cacaaatgga 660
tcagatgacc ctgaagatgc aggagctggt gaaaatagga gagtcagtgg gaataattct 720
ccatcactct caaatggtgg ttttaaacct tctagacctc caagaccttc acgaccacca 780
ccacccaccc cacgtagacc agcatctgtc aatggttcac catctgccac ttctgaaagt 840
gatgggtcta gtacaggctc tctgccgccg acaaatacaa atacaaatac atctgaagga 900
gcaacatctg gattaataat tcctcttact atatctggag gctcaggccc taggccatta 960
aatcctgtaa ctcaagctcc cttgccacct ggttgggagc agagagtgga ccagcacggg 1020
cgagtttact atgtagatca tgttgagaaa agaacaacat gggatagacc agaacctcta 1080
cctcctggct gggaacggcg ggttgacaac atgggacgta tttattatgt tgaccatttc 1140

-continued

```
acaagaacaa caacgtggca gaggccaaca ctggaatccg tccggaacta tgaacaatgg   1200

cagctacagc gtagtcagct tcaaggagca atgcagcagt ttaaccagag attcatttat   1260

gggaatcaag atttatttgc tacatcacaa agtaaagaat ttgatcctct tggtccattg   1320

ccacctggat gggagaagag aacagacagc aatggcagag tatatttcgt caaccacaac   1380

acacgaatta cacaatggga agaccccaga agtcaaggtc aattaaatga aaagccctta   1440

cctgaaggtt gggaaatgag attcacagtg gatggaattc catattttgt ggaccacaat   1500

agaagaacta ccacctatat agatccccgc acaggaaaat ctgccctaga caatggacct   1560

cagatagcct atgttcggga cttcaaagca aaggttcagt atttccggtt ctggtgtcag   1620

caactggcca tgccacagca cataaagatt acagtgacaa gaaaaacatt gtttgaggat   1680

tcctttcaac agataatgag cttcagtccc caagatctgc gaagacgttt gtgggtgatt   1740

tttccaggag aagaaggttt agattatgga ggtgtagcaa gagaatggtt ctttcttttg   1800

tcacatgaag tgttgaaccc aatgtattgc ctgtttgaat atgcagggaa ggataactac   1860

tgcttgcaga taaaccccgc ttcttacatc aatccagatc acctgaaata ttttcgtttt   1920

attggcagat ttattgccat ggctctgttc catgggaaat tcatagacac gggtttttct   1980

ttaccattct ataagcgtat cttgaacaaa ccagttggac tcaaggattt agaatctatt   2040

gatccagaat tttacaattc tctcatctgg gttaaggaaa acaatattga ggaatgtgat   2100

ttggaaatgt acttctccgt tgacaaagaa attctaggtg aaattaagag tcatgatctg   2160

aaacctaatg gtggcaatat tcttgtaaca gaagaaaata aagaggaata catcagaatg   2220

gtagctgagt ggaggttgtc tcgaggtgtt gaagaacaga cacaagcttt ctttgaaggc   2280

tttaatgaaa ttcttcccca gcaatatttg caatactttg atgcaaagga attagaggtc   2340

cttttatgtg gaatgcaaga gattgatttg aatgactggc aaagacatgc catctaccgt   2400

cattatgcaa ggaccagcaa acaaatcatg tggttttggc agtttgttaa agaaattgat   2460

aatgagaaga gaatgagact tctgcagttt gttactggaa cctgccgatt gccagtagga   2520

ggatttgctg atctcatggg gagcaatgga ccacagaaat tctgcattga aaaagttggg   2580

aaagaaaatt ggctacccag aagtcatacc tgttttaatc gcctggacct gccaccatac   2640

aagagctatg agcaactgaa ggaaaagctg ttgtttgcca tagaagaaac agaaggattt   2700

ggacaagagt aacttctgag aacttgcacc atgaatgggc aagaacttat ttgcaatgtt   2760

tgtccttctc tgcctgttgc acatcttgta aaattggaca atggctcttt agagagttat   2820

ctgagtgtaa gtaaattaat gttctcattt aaaaaaaaaa aaaaaaaaa               2869
```

<210> SEQ ID NO 30
<211> LENGTH: 5169
<212> TYPE: DNA
<213> ORGANISM: Homo Sapiens

<400> SEQUENCE: 30

```
gcgcatcagg cgctgttgtt ggagccggaa caccgtgcga ctctgaccga accggccccc     60

tcctcgcgca cacactcgcc gagccgcgcg cgcccctccg ccgtgacagt ggccgtggcc    120

tccgctctct cggggcaccc ggcagccaga gcgcagcgag agcgggcggt cgccagggtc    180

ccctccccag ccagtcccag gcgcccggtg cactatgcgg ggcacgtgcg ccccccagct    240

ctaatctgcg cgctgacagg agcatgatct gtgcccaggc cagggctgcc aaggaattga    300

tgcgcgtaca cgtggtgggt cattatgctg ctacacctgt gtagtgtgaa gaatctgtac    360

cagaacaggt ttttaggcct ggccgccatg gcgtctcctt ctagaaactc ccagagccga    420
```

-continued

```
cgccggtgca aggagccgct ccgatacagc tacaaccccg accagttcca caacatggac    480
ctcaggggcg gcccccacga tggcgtcacc attccccgct ccaccagcga cactgacctg    540
gtcacctcgg acagccgctc cacgctcatg gtcagcagct cctactattc catcgggcac    600
tctcaggacc tggtcatcca ctgggacata aaggaggaag tggacgctgg ggactggatt    660
ggcatgtacc tcattgatga ggtcttgtcc gaaaactttc tggactataa aaaccgtgga    720
gtcaatggtt ctcatcgggg ccagatcatc tggaagatcg atgccagctc gtactttgtg    780
gaacctgaaa ctaagatctg cttcaaatac taccatggag tgagtggggc cctgcgagca    840
accacccccca gtgtcacggt caaaaactcg gcagctccta tttttaaaag cattggtgct    900
gatgagaccg tccaaggaca aggaagtcgg aggctgatca gcttctctct ctcagatttc    960
caagccatgg ggttgaagaa agggatgttt ttcaacccag acccttatct gaagatttcc   1020
attcagcctg ggaaacacag catcttcccc gccctccctc accatggaca ggagaggaga   1080
tccaagatca taggcaacac cgtgaacccc atctggcagg ccgagcaatt cagttttgtg   1140
tccttgccca ctgacgtgct ggaaattgag gtgaaggaca agtttgccaa gagccgcccc   1200
atcatcaagc gcttcttggg aaagctgtcg atgcccgttc aaagactcct ggagagacac   1260
gccatagggg atagggtggt cagctacaca cttggccgca ggcttccaac agatcatgtg   1320
agtggacagc tgcaattccg atttgagatc acttcctcca tccacccaga tgatgaggag   1380
atttccctga gtaccgagcc tgagtcagcc caaattcagg acagccccat gaacaacctg   1440
atggaaagcg gcagtgggga acctcggtct gaggcaccag agtcctctga gagctggaag   1500
ccagagcagc tgggtgaggg cagtgtcccc gatggtccag ggaaccaaag catagagctt   1560
tccagaccag ctgaggaagc agcagtcatc acggaggcag gagaccaggg catggtctct   1620
gtgggacctg aaggggctgg ggagctcctg gcccaggtgc aaaaggacat ccagcctgcc   1680
cccagtgcag aagagctggc cgagcagctg gacctgggtg aggaggcatc agcactgctg   1740
ctggaagacg gtgaagcccc agccagcacc aaggaggagc ccttggagga ggaagcaacg   1800
acccagagcc gggctggaag ggaagaagag gagaaggagc aggaggagga gggagatgtg   1860
tctaccctgg agcagggaga gggcaggctg cagctgcggg cctcggtgaa gagaaaaagc   1920
aggccctgct ccttgcctgt gtccgagctg gagacggtga tcgcgtcagc ctgcggggac   1980
cccgagaccc cgcggacaca ctacatccgc atccacaccc tgctgcacag catgccctcc   2040
gcccagggcg gcagcgcggc agaggaggag gacggcgcgg aggaggagtc caccctcaag   2100
gactcctcgg agaaggatgg gctcagcgag gtggacacgg tggccgctga cccgtctgcc   2160
ctggaagagg acagagaaga gcccgagggg gctactccag gcacggcgca ccctggccac   2220
tccgggggcc acttccccag cctggccaat ggcgcggccc aggatggcga cacgcacccc   2280
agcaccggga gcgagagcga ctccagcccc aggcaaggcg gggaccacag ttgcgagggc   2340
tgtgacgcgt cctgctgcag cccctcgtgc tacagctcct cgtgctacag cacgtcctgc   2400
tacagcagct cgtgctacag cgcctcgtgc tacagcccct cctgctacaa cggcaacagg   2460
ttcgccagcc acacgcgctt ctcctccgtg gacagcgcca agatctccga gagcacggtc   2520
ttctcctcgc aagacgacga ggaggaggag aacagcgcgt tcgagtcggt acccgactcc   2580
atgcagagcc ctgagctgga cccggagtcc acgaacggcg ctgggccgtg gcaagacgag   2640
ctggccgccc ctagcgggca cgtggaaaga agcccggaag gtctggaatc cccccgtggca  2700
ggtccaagca atcggagaga agactgggaa gctcgaattg acagccacgg gcgggtcttt   2760
```

-continued tatgtggacc acgtgaaccg cacaaccacc tggcagcgtc cgacggcagc agccaccccg 2820
gatggcatgc ggagatcggg gtccatccag cagatggagc aactcaacag gcggtatcaa 2880
aacattcagc gaaccattgc aacagagagg tccgaagaag attctggcag ccaaagctgc 2940
gagcaagccc cagcaggagg aggcggaggt ggagggagtg actcagaagc cgaatcttcc 3000
cagtccagct tagatctaag gagagagggg tcactttctc cagtgaactc acaaaaaatc 3060
accttgctgc tgcagtcccc agcggtcaag ttcatcacca accccgagtt cttcactgtg 3120
ctacacgcca attatagtgc ctaccgagtc ttcaccagta gcacctgctt aaagcacatg 3180
attctgaaag tccgacggga tgctcgcaat tttgaacgct accagcacaa ccgggacttg 3240
gtgaatttca tcaacatgtt cgcagacact cggctggaac tgccccgggg ctgggagatc 3300
aaaacggacc agcagggaaa gtctttttttc gtggaccaca acagtcgagc taccactttc 3360
attgaccccc gaatccctct tcagaacggt cgtcttccca atcatctaac tcaccgacag 3420
cacctccaga ggctccgaag ttacagcgcc ggagaggcct cagaagtttc tagaaacaga 3480
ggagcctctt tactggccag gccaggacac agcttagtag ctgctattcg aagccaacat 3540
caacatgagt cattgccact ggcatataat gacaagattg tggcatttct tcgccagcca 3600
aacatttttg aaatgctgca agagcgtcag ccaagcttag caagaaacca cacactcagg 3660
gagaaaatcc attacattcg gactgagggt aatcacgggc ttgagaagtt gtcctgtgat 3720
gcggatctgg tcattttgct gagtctcttt gaagaagaga ttatgtccta cgtccccctg 3780
caggctgcct tccaccctgg gtatagcttc tctccccgat gttcaccctg ttcttcacct 3840
cagaactccc caggtttaca gagagccagt gcaagagccc cttcccccta ccgaagagac 3900
tttgaggcca agctccgcaa tttctacaga aaactggaag ccaaaggatt tggtcagggt 3960
ccggggaaaa ttaagctcat tattcgccgg gatcatttgt tggagggaac cttcaatcag 4020
gtgatggcct attcgcggaa agagctccag cgaaacaagc tctacgtcac ctttgttgga 4080
gaggagggcc tggactacag tggcccctcg cgggagttct tcttccttct gtctcaggag 4140
ctcttcaacc cttactatgg actctttgag tactcggcaa atgatactta cacggtgcag 4200
atcagcccca tgtccgcatt tgtagaaaac catcttgagt ggttcaggtt tagcggtcgc 4260
atcctgggtc tggctctgat ccatcagtac cttcttgacg ctttcttcac gaggcccttc 4320
tacaaggcac tcctgagact gccctgtgat ttgagtgacc tggaatattt ggatgaggaa 4380
ttccaccaga gtttgcagtg gatgaaggac aacaacatca cagacatctt agacctcact 4440
ttcactgtta atgaagaggt ttttggacag gtcacggaaa gggagttgaa gtctggagga 4500
gccaacacac aggtgacgga gaaaaacaag aaggagtaca tcgagcgcat ggtgaagtgg 4560
cgggtggagc gcggcgtggt acagcagacc gaggcgctgg tgcgcggctt ctacgaggtt 4620
gtagactcga ggctggtgtc cgtgtttgat gccagggagc tggagctggt gatagctggc 4680
accgcggaaa tcgacctaaa tgactggcgg aataacactg agtaccgggg aggttaccac 4740
gatgggcatc ttgtgatccg ctggttctgg gctgcggtgg agcgcttcaa taatgagcag 4800
aggctgagat tactgcagtt tgtcacggga acatccagcg tgccctacga aggcttcgca 4860
gccctccgtg ggagcaatgg gcttcggcgc ttctgcatag agaaatgggg gaaaattact 4920
tctctcccca gggcacacac atgcttcaac cgactggatc ttccaccgta tccctcgtac 4980
tccatgttgt atgaaaagct gttaacagca gtagaggaaa ccagcacctt tggacttgag 5040
tgaggacatg gaacctcgcc tgacattttc ctggccagtg acatcaccct tcctgggatg 5100 atccccttttt ccctttccct taatcaactc tcctttgatt ttggtattcc atgattttta 5160
ttttcaaac 5169

<210> SEQ ID NO 31
<211> LENGTH: 2715
<212> TYPE: DNA
<213> ORGANISM: Homo Sapiens

<400> SEQUENCE: 31
agagttccat cagagcctgc agtggatgaa agacaatgat atccatgaca tcctagacct 60
cacgttcact gtgaacgaag aagtatttgg gcagataact gaacgagaat taaagccagg 120
gggtgccaat atcccagtta cagagaagaa caagaaggag tacatcgaga ggatggtgaa 180
gtggaggatt gagaggggtg ttgtacagca aacagagagc ttagtgcgtg gcttctatga 240
ggtggtggat gccaggctgg tatctgtttt tgatgcaaga gaactggaat tggtcatcgc 300
aggcacagct gaaatagacc taagtgattg gagaaacaac acagaatata gaggaggata 360
ccatgacaat catattgtaa ttcggtggtt ctgggctgca gtggaaagat tcaacaatga 420
acaacgacta aggttgttac agtttgttac aggcacatcc agcattccct atgaaggatt 480
tgcttcactc cgagggagta acggcccaag aagattctgt gtggagaaat gggggaaaat 540
cactgctctt cccagagcgc atacatgttt taaccgtctg gatctgcctc cctacccatc 600
cttttccatg ctttatgaaa aactgttgac agcagttgaa gaaaccagta cttttggact 660
tgagtgacct ggaagctgaa tgcccatctc tgtggacagg cagtttcaga agctgccttc 720
tagaagaatg attgaacatt ggaagtttca agaggatgct tcctttagga taaagctacg 780
tgctgttgtt ttccaggaac aagtgctctg tcacatttgg ggactggaga tgagtcctct 840
tggaaggatt tgggtgagct tgatgcccag ggaacaaccc aaccgtcttt caatcaacag 900
ttcttgactg ccaaactttt tccatttgtt atgttccaag acaaagatga acccatacat 960
gatcagctcc acggtaattt ttagggactc aggagaatct tgaaacttac ccttgaacgt 1020
ggttcaagcc aaactggcag catttggccc aatctccaaa ttagagcaag ttaaataata 1080
taataaaagt aaatatattt cctgaaagta cattcattta agccctaagt tataacagaa 1140
tattcatttc ttgcttatga gtgcctgcat ggtgtgcacc ataggtttcc gctttcatgg 1200
gacatgagtg aaaatgaaac caagtcaata tgaggtacct ttacagattt gcaataagat 1260
ggtctgtgac aatgtatatg caagtggtat gtgtgtaatt atggctaaag acaaaccatt 1320
attcagtgaa ttactaatga cagattttat gctttataat gcatgaaaac aattttaaaa 1380
taactagcaa ttaatcacag catatcagga aaaagtacac agtgagttct gtttattttt 1440
tgtaggctca ttatgtttat gttctttaag atgtatataa gaacctactt atcatgctgt 1500
atgtatcact cattccattt tcatgttcca tgcatactcg ggcatcatgc taatatgtat 1560
ccttttaagc actctcaagg aaacaaaagg gccttttatt tttataaagg taaaaaaaat 1620
tccccaaata ttttgcactg aatgtaccaa aggtgaaggg acattacaat atgactaaca 1680
gcaactccat cacttgagaa gtataataga aaatagcttc taaatcaaac ttccttcaca 1740
gtgccgtgtc taccactaca aggactgtgc atctaagtaa taatttttta agattcacta 1800
tatgtgatag tatgatatgc atttatttaa aatgcattag actctcttcc atccatcaaa 1860
tactttacag gatggcattt aatacagata tttcgtattt cccccactgc tttttatttg 1920
tacagcatca ttaaacacta agctcagtta aggagccatc agcaacactg aagagatcag 1980
tagtaagaat tccattttcc ctcatcagtg aagacaccac aaattgaaac tcagaactat 2040

-continued atttctaagc ctgcattttc actgatgcat aattttctta ttaatattaa gagacagttt 2100
ttctatggca tctccaaaac tgcatgacat cactagtctt acttctgctt aattttatga 2160
gaaggtattc ttcattttaa ttgcttttgg gattactcca catctttgtt tatttcttga 2220
ctaatcagat tttcaataga gtgaagttaa attgggggtc ataaaagcat tggattgaca 2280
tatggtttgc cagcctatgg gtttacaggc attgcccaaa catttctttg agatctatat 2340
ttataagcag ccatggaatt cctattatgg gatgttggca atcttacatt ttatagaggt 2400
catatgcata gttttcatag gtgttttgta agaactgatt gctctcctgt gagttaagct 2460
atgtttacta ctgggaccct caagaggaat accacttatg ttacactcct gcactaaagg 2520
cacgtactgc agtgtgaaga aatgttctga aaaagggtta tagaaatctg gaaataagaa 2580
aggaagagct ctctgtattc tataattgga agagaaaaaa agaaaaactt ttaactggaa 2640
atgttagttt gtacttattg atcatgaata caagtatata tttaattttg caaaaaaaaa 2700
aaaaaaaaaa aaaag 2715

<210> SEQ ID NO 32
<211> LENGTH: 195
<212> TYPE: DNA
<213> ORGANISM: Homo Sapiens

<400> SEQUENCE: 32
cccttgccac ctggttggga gcagagagtg gaccagcacg ggcgagttta ctatgtagat 60
catgttgaga aaagaacaac atgggataga ccagaacctc tacctcctgg ctgggaacgg 120
cgggttgaca acatgggacg tatttattat gttgaccatt tcacaagaac aacaacgtgg 180
cagaggccaa cactg 195

<210> SEQ ID NO 33
<211> LENGTH: 555
<212> TYPE: DNA
<213> ORGANISM: Homo Sapiens

<400> SEQUENCE: 33
cccttgccac ctggttggga gcagagagtg gaccagcacg ggcgagttta ctatgtagat 60
catgttgaga aaagaacaac atgggataga ccagaacctc tacctcctgg ctgggaacgg 120
cgggttgaca acatgggacg tatttattat gttgaccatt tcacaagaac aacaacgtgg 180
cagaggccaa cactggaatc cgtccggaac tatgaacaat ggcagctaca gcgtagtcag 240
cttcaaggag caatgcagca gtttaaccag agattcattt atgggaatca agatttattt 300
gctacatcac aaagtaaaga atttgatcct cttggtccat tgccacctgg atgggagaag 360
agaacagaca gcaatggcag agtatatttc gtcaaccaca acacacgaat tacacaatgg 420
gaagacccca gaagtcaagg tcaattaaat gaaaagccct tacctgaagg ttgggaaatg 480
agattcacag tggatggaat tccatatttt gtggaccaca atagaagaac taccacctat 540
atagatcccc gcaca 555

<210> SEQ ID NO 34
<211> LENGTH: 8506
<212> TYPE: DNA
<213> ORGANISM: Artificial Sequence
<220> FEATURE:
<223> OTHER INFORMATION: Synthetic Polynucleotide

<400> SEQUENCE: 34
gagggcctat ttcccatgat tccttcatat ttgcatatac gatacaaggc tgttagagag 60
ataattggaa ttaatttgac tgtaaacaca aagatattag tacaaaatac gtgacgtaga 120
aagtaataat ttcttgggta gtttgcagtt ttaaaattat gttttaaaat ggactatcat 180
atgcttaccg taacttgaaa gtatttcgat ttcttggctt tatatatctt gtggaaagga 240
cgaaacaccg ggtcttcgag aagacctgtt ttagagctag aaatagcaag ttaaaataag 300
gctagtccgt tatcaacttg aaaaagtggc accgagtcgg tgcttttttg ttttagagct 360
agaaatagca agttaaaata aggctagtcc gtttttagcg cgtgcgccaa ttctgcagac 420
aaatggctct agaggtaccc gttacataac ttacggtaaa tggcccgcct ggctgaccgc 480
ccaacgaccc ccgcccattg acgtcaatag taacgccaat agggactttc cattgacgtc 540
aatgggtgga gtatttacgg taaactgccc acttggcagt acatcaagtg tatcatatgc 600
caagtacgcc ccctattgac gtcaatgacg gtaaatggcc cgcctggcat tgtgcccagt 660
acatgacctt atgggacttt cctacttggc agtacatcta cgtattagtc atcgctatta 720
ccatggtcga ggtgagcccc acgttctgct tcactctccc catctccccc ccctccccac 780
ccccaatttt gtatttattt atttttaat tattttgtgc agcgatgggg gcgggggggg 840
gggggggcg cgcgccaggc ggggcggggc ggggcgaggg gcggggcggg gcgaggcgga 900
gaggtgcggc ggcagccaat cagagcggcg cgctccgaaa gtttcctttt atggcgaggc 960
ggcggcggcg gcggccctat aaaaagcgaa gcgcgcggcg ggcgggagtc gctgcgacgc 1020
tgccttcgcc ccgtgccccg ctccgccgcc gcctcgcgcc gcccgccccg gctctgactg 1080
accgcgttac tcccacaggt gagcgggcgg gacggccctt ctcctccggg ctgtaattag 1140
ctgagcaaga ggtaagggtt taagggatgg ttggttggtg gggtattaat gtttaattac 1200
ctggagcacc tgcctgaaat cacttttttt caggttggac cggtgccacc atggactata 1260
aggaccacga cggagactac aaggatcatg atattgatta caaagacgat gacgataaga 1320
tggccccaaa gaagaagcgg aaggtcggta tccacggagt cccagcagcc gacaagaagt 1380
acagcatcgg cctggacatc ggcaccaact ctgtgggctg ggccgtgatc accgacgagt 1440
acaaggtgcc cagcaagaaa ttcaaggtgc tgggcaacac cgaccggcac agcatcaaga 1500
agaacctgat cggagccctg ctgttcgaca gcggcgaaac agccgaggcc acccggctga 1560
agagaaccgc cagaagaaga tacaccagac ggaagaaccg gatctgctat ctgcaagaga 1620
tcttcagcaa cgagatggcc aaggtggacg acagcttctt ccacagactg gaagagtcct 1680
tcctggtgga agaggataag aagcacgagc ggcaccccat cttcggcaac atcgtggacg 1740
aggtggccta ccacgagaag taccccacca tctaccacct gagaaagaaa ctggtggaca 1800
gcaccgacaa ggccgacctg cggctgatct atctggccct ggcccacatg atcaagttcc 1860
ggggccactt cctgatcgag ggcgacctga accccgacaa cagcgacgtg gacaagctgt 1920
tcatccagct ggtgcagacc tacaaccagc tgttcgagga aaaccccatc aacgccagcg 1980
gcgtggacgc caaggccatc ctgtctgcca gactgagcaa gagcagacgg ctggaaaatc 2040
tgatcgccca gctgcccggc gagaagaaga atggcctgtt cggaaacctg attgccctga 2100
gcctgggcct gacccccaac ttcaagagca acttcgacct ggccgaggat gccaaactgc 2160
agctgagcaa ggacacctac gacgacgacc tggacaacct gctggcccag atcggcgacc 2220
agtacgccga cctgtttctg gccgccaaga acctgtccga cgccatcctg ctgagcgaca 2280
tcctgagagt gaacaccgag atcaccaagg ccccctgag cgcctctatg atcaagagat 2340
acgacgagca ccaccaggac ctgaccctgc tgaaagctct cgtgcggcag cagctgcctg 2400

-continued

```
agaagtacaa agagattttc ttcgaccaga gcaagaacgg ctacgccggc tacattgacg   2460
gcggagccag ccaggaagag ttctacaagt tcatcaagcc catcctggaa aagatggacg   2520
gcaccgagga actgctcgtg aagctgaaca gagaggacct gctgcggaag cagcggacct   2580
tcgacaacgg cagcatcccc caccagatcc acctgggaga gctgcacgcc attctgcggc   2640
ggcaggaaga tttttaccca ttcctgaagg acaaccggga aaagatcgag aagatcctga   2700
ccttccgcat cccctactac gtgggccctc tggccagggg aaacagcaga ttcgcctgga   2760
tgaccagaaa gagcgaggaa accatcaccc cctggaactt cgaggaagtg gtggacaagg   2820
gcgcttccgc ccagagcttc atcgagcgga tgaccaactt cgataagaac ctgcccaacg   2880
agaaggtgct gcccaagcac agcctgctgt acgagtactt caccgtgtat aacgagctga   2940
ccaaagtgaa atacgtgacc gagggaatga gaaagcccgc cttcctgagc ggcgagcaga   3000
aaaaggccat cgtggacctg ctgttcaaga ccaaccggaa agtgaccgtg aagcagctga   3060
aagaggacta cttcaagaaa atcgagtgct tcgactccgt ggaaatctcc ggcgtggaag   3120
atcggttcaa cgcctccctg ggcacatacc acgatctgct gaaaattatc aaggacaagg   3180
acttcctgga caatgaggaa aacgaggaca ttctggaaga tatcgtgctg accctgacac   3240
tgtttgagga cagagagatg atcgaggaac ggctgaaaac ctatgcccac ctgttcgacg   3300
acaaagtgat gaagcagctg aagcggcgga gatacaccgg ctggggcagg ctgagccgga   3360
agctgatcaa cggcatccgg gacaagcagt ccggcaagac aatcctggat ttcctgaagt   3420
ccgacggctt cgccaacaga aacttcatgc agctgatcca cgacgacagc ctgaccttta   3480
aagaggacat ccagaaagcc caggtgtccg gccagggcga tagcctgcac gagcacattg   3540
ccaatctggc cggcagcccc gccattaaga agggcatcct gcagacagtg aaggtggtgg   3600
acgagctcgt gaaagtgatg ggccggcaca agcccgagaa catcgtgatc gaaatggcca   3660
gagagaacca gaccacccag aagggacaga agaacagccg cgagagaatg aagcggatcg   3720
aagagggcat caaagagctg ggcagccaga tcctgaaaga acaccccgtg gaaaacaccc   3780
agctgcagaa cgagaagctg tacctgtact acctgcagaa tgggcgggat atgtacgtgg   3840
accaggaact ggacatcaac cggctgtccg actacgatgt ggaccatatc gtgcctcaga   3900
gctttctgaa ggacgactcc atcgacaaca aggtgctgac cagaagcgac aagaaccggg   3960
gcaagagcga caacgtgccc tccgaagagg tcgtgaagaa gatgaagaac tactggcggc   4020
agctgctgaa cgccaagctg attacccaga gaaagttcga caatctgacc aaggccgaga   4080
gaggcggcct gagcgaactg gataaggccg gcttcatcaa gagacagctg gtggaaaccc   4140
ggcagatcac aaagcacgtg gcacagatcc tggactcccg gatgaacact aagtacgacg   4200
agaatgacaa gctgatccgg gaagtgaaag tgatcaccct gaagtccaag ctggtgtccg   4260
atttccggaa ggatttccag ttttacaaag tgcgcgagat caacaactac caccacgccc   4320
acgacgccta cctgaacgcc gtcgtgggaa ccgccctgat caaaaagtac cctaagctgg   4380
aaagcgagtt cgtgtacggc gactacaagg tgtacgacgt gcggaagatg atcgccaaga   4440
gcgagcagga aatcggcaag gctaccgcca agtacttctt ctacagcaac atcatgaact   4500
ttttcaagac cgagattacc ctggccaacg gcgagatccg gaagcggcct ctgatcgaga   4560
caaacggcga aaccggggag atcgtgtggg ataagggccg ggattttgcc accgtgcgga   4620
aagtgctgag catgccccaa gtgaatatcg tgaaaaagac cgaggtgcag acaggcggct   4680
tcagcaaaga gtctatcctg cccaagagga acagcgataa gctgatcgcc agaaagaagg   4740
actgggaccc taagaagtac ggcggcttcg acagccccac cgtggcctat tctgtgctgg   4800
```

-continued tggtggccaa agtggaaaag ggcaagtcca agaaactgaa gagtgtgaaa gagctgctgg 4860
ggatcaccat catggaaaga agcagcttcg agaagaatcc catcgacttt ctggaagcca 4920
agggctacaa agaagtgaaa aaggacctga tcatcaagct gcctaagtac tccctgttcg 4980
agctggaaaa cggccggaag agaatgctgg cctctgccgg cgaactgcag aagggaaacg 5040
aactggccct gccctccaaa tatgtgaact tcctgtacct ggccagccac tatgagaagc 5100
tgaagggctc cccgaggat aatgagcaga aacagctgtt tgtggaacag cacaagcact 5160
acctggacga gatcatcgag cagatcagcg agttctccaa gagagtgatc ctggccgacg 5220
ctaatctgga caaagtgctg tccgcctaca acaagcaccg ggataagccc atcagagagc 5280
aggccgagaa tatcatccac ctgtttaccc tgaccaatct gggagcccct gccgccttca 5340
agtactttga caccaccatc gaccggaaga ggtacaccag caccaaagag gtgctggacg 5400
ccaccctgat ccaccagagc atcaccggcc tgtacgagac acggatcgac ctgtctcagc 5460
tgggaggcga caaaaggccg gcggccacga aaaaggccgg ccaggcaaaa aagaaaaagt 5520
aagaattcct agagctcgct gatcagcctc gactgtgcct tctagttgcc agccatctgt 5580
tgtttgcccc tcccccgtgc cttccttgac cctggaaggt gccactccca ctgtcctttc 5640
ctaataaaat gaggaaattg catcgcattg tctgagtagg tgtcattcta ttctgggggg 5700
tggggtgggg caggacagca agggggagga ttgggaagag aatagcaggc atgctgggga 5760
gcggccgcag gaacccctag tgatggagtt ggccactccc tctctgcgcg ctcgctcgct 5820
cactgaggcc gggcgaccaa aggtcgcccg acgcccgggc tttgcccggg cggcctcagt 5880
gagcgagcga gcgcgcagct gcctgcaggg gcgcctgatg cggtattttc tccttacgca 5940
tctgtgcggt atttcacacc gcatacgtca aagcaaccat agtacgcgcc ctgtagcggc 6000
gcattaagcg cggcgggtgt ggtggttacg cgcagcgtga ccgctacact tgccagcgcc 6060
ctagcgcccg ctcctttcgc tttcttccct tcctttctcg ccacgttcgc cggctttccc 6120
cgtcaagctc taaatcgggg gctcccttta gggttccgat ttagtgcttt acggcacctc 6180
gaccccaaaa aacttgattt gggtgatggt tcacgtagtg ggccatcgcc ctgatagacg 6240
gtttttcgcc ctttgacgtt ggagtccacg ttctttaata gtggactctt gttccaaact 6300
ggaacaacac tcaaccctat ctcgggctat tcttttgatt tataagggat tttgccgatt 6360
tcggcctatt ggttaaaaaa tgagctgatt taacaaaaat ttaacgcgaa ttttaacaaa 6420
atattaacgt ttacaatttt atggtgcact ctcagtacaa tctgctctga tgccgcatag 6480
ttaagccagc cccgacaccc gccaacaccc gctgacgcgc cctgacgggc ttgtctgctc 6540
ccggcatccg cttacagaca agctgtgacc gtctccggga gctgcatgtg tcagaggttt 6600
tcaccgtcat caccgaaacg cgcgagacga aagggcctcg tgatacgcct atttttatag 6660
gttaatgtca tgataataat ggtttcttag acgtcaggtg gcacttttcg gggaaatgtg 6720
cgcggaaccc ctatttgttt atttttctaa atacattcaa atatgtatcc gctcatgaga 6780
caataaccct gataaatgct tcaataatat tgaaaaagga agagtatgag tattcaacat 6840
ttccgtgtcg cccttattcc cttttttgcg gcattttgcc ttcctgtttt tgctcaccca 6900
gaaacgctgg tgaaagtaaa agatgctgaa gatcagttgg gtgcacgagt gggttacatc 6960
gaactggatc tcaacagcgg taagatcctt gagagttttc gccccgaaga acgttttcca 7020
atgatgagca cttttaaagt tctgctatgt ggcgcggtat tatcccgtat tgacgccggg 7080
caagagcaac tcggtcgccg catacactat tctcagaatg acttggttga gtactcacca 7140

-continued

```
gtcacagaaa agcatcttac ggatggcatg acagtaagag aattatgcag tgctgccata   7200

accatgagtg ataacactgc ggccaactta cttctgacaa cgatcggagg accgaaggag   7260

ctaaccgctt ttttgcacaa catgggggat catgtaactc gccttgatcg ttgggaaccg   7320

gagctgaatg aagccatacc aaacgacgag cgtgacacca cgatgcctgt agcaatggca   7380

acaacgttgc gcaaactatt aactggcgaa ctacttactc tagcttcccg gcaacaatta   7440

atagactgga tggaggcgga taaagttgca ggaccacttc tgcgctcggc ccttccggct   7500

ggctggttta ttgctgataa atctggagcc ggtgagcgtg gaagccgcgg tatcattgca   7560

gcactggggc cagatggtaa gccctcccgt atcgtagtta tctacacgac ggggagtcag   7620

gcaactatgg atgaacgaaa tagacagatc gctgagatag gtgcctcact gattaagcat   7680

tggtaactgt cagaccaagt ttactcatat atactttaga ttgatttaaa acttcatttt   7740

taatttaaaa ggatctaggt gaagatcctt tttgataatc tcatgaccaa aatcccttaa   7800

cgtgagtttt cgttccactg agcgtcagac cccgtagaaa agatcaaagg atcttcttga   7860

gatccttttt ttctgcgcgt aatctgctgc ttgcaaacaa aaaaaccacc gctaccagcg   7920

gtggtttgtt tgccggatca agagctacca actctttttc cgaaggtaac tggcttcagc   7980

agagcgcaga taccaaatac tgtccttcta gtgtagccgt agttaggcca ccacttcaag   8040

aactctgtag caccgcctac atacctcgct ctgctaatcc tgttaccagt ggctgctgcc   8100

agtggcgata agtcgtgtct taccgggttg gactcaagac gatagttacc ggataaggcg   8160

cagcggtcgg gctgaacggg gggttcgtgc acacagccca gcttggagcg aacgacctac   8220

accgaactga gatacctaca gcgtgagcta tgagaaagcg ccacgcttcc cgaagggaga   8280

aaggcggaca ggtatccggt aagcggcagg gtcggaacag gagagcgcac gagggagctt   8340

ccagggggaa acgcctggta tctttatagt cctgtcgggt ttcgccacct ctgacttgag   8400

cgtcgatttt tgtgatgctc gtcagggggg cggagcctat ggaaaaacgc cagcaacgcg   8460

gcctttttac ggttcctggc cttttgctgg ccttttgctc acatgt                  8506
```

<210> SEQ ID NO 35
<211> LENGTH: 238
<212> TYPE: PRT
<213> ORGANISM: Aequorea victoria

<400> SEQUENCE: 35

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
```

```
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235


<210> SEQ ID NO 36
<211> LENGTH: 34
<212> TYPE: PRT
<213> ORGANISM: Homo Sapiens

<400> SEQUENCE: 36

Glu Thr Leu Pro Ser Gly Trp Glu Gln Arg Lys Asp Pro His Gly Arg
1               5                   10                  15

Thr Tyr Tyr Val Asp His Asn Thr Arg Thr Thr Thr Trp Glu Arg Pro
            20                  25                  30

Gln Pro


<210> SEQ ID NO 37
<211> LENGTH: 34
<212> TYPE: PRT
<213> ORGANISM: Homo Sapiens

<400> SEQUENCE: 37

Gln Pro Leu Pro Pro Gly Trp Glu Arg Arg Val Asp Asp Arg Arg Arg
1               5                   10                  15

Val Tyr Tyr Val Asp His Asn Thr Arg Thr Thr Thr Trp Gln Arg Pro
            20                  25                  30

Thr Met


<210> SEQ ID NO 38
<211> LENGTH: 39
<212> TYPE: PRT
<213> ORGANISM: Homo Sapiens

<400> SEQUENCE: 38

Glu Asn Asp Pro Tyr Gly Pro Leu Pro Pro Gly Trp Glu Lys Arg Val
1               5                   10                  15

Asp Ser Thr Asp Arg Val Tyr Phe Val Asn His Asn Thr Lys Thr Thr
            20                  25                  30

Gln Trp Glu Asp Pro Arg Thr
        35


<210> SEQ ID NO 39
<211> LENGTH: 34
<212> TYPE: PRT
<213> ORGANISM: Homo Sapiens

<400> SEQUENCE: 39

Glu Pro Leu Pro Glu Gly Trp Glu Ile Arg Tyr Thr Arg Glu Gly Val
1               5                   10                  15
```

Arg Tyr Phe Val Asp His Asn Thr Arg Thr Thr Thr Phe Lys Asp Pro
20 25 30

Arg Asn

<210> SEQ ID NO 40
<211> LENGTH: 34
<212> TYPE: PRT
<213> ORGANISM: Homo Sapiens

<400> SEQUENCE: 40

Asp Ala Leu Pro Ala Gly Trp Glu Gln Arg Glu Leu Pro Asn Gly Arg
1 5 10 15

Val Tyr Tyr Val Asp His Asn Thr Lys Thr Thr Thr Trp Glu Arg Pro
20 25 30

Leu Pro

<210> SEQ ID NO 41
<211> LENGTH: 33
<212> TYPE: PRT
<213> ORGANISM: Homo Sapiens

<400> SEQUENCE: 41

Pro Leu Pro Pro Gly Trp Glu Lys Arg Thr Asp Pro Arg Gly Arg Phe
1 5 10 15

Tyr Tyr Val Asp His Asn Thr Arg Thr Thr Thr Trp Gln Arg Pro Thr
20 25 30

Ala

<210> SEQ ID NO 42
<211> LENGTH: 37
<212> TYPE: PRT
<213> ORGANISM: Homo Sapiens

<400> SEQUENCE: 42

His Asp Pro Leu Gly Pro Leu Pro Pro Gly Trp Glu Lys Arg Gln Asp
1 5 10 15

Asn Gly Arg Val Tyr Tyr Val Asn His Asn Thr Arg Thr Thr Gln Trp
20 25 30

Glu Asp Pro Arg Thr
35

<210> SEQ ID NO 43
<211> LENGTH: 34
<212> TYPE: PRT
<213> ORGANISM: Homo Sapiens

<400> SEQUENCE: 43

Pro Ala Leu Pro Pro Gly Trp Glu Met Lys Tyr Thr Ser Glu Gly Val
1 5 10 15

Arg Tyr Phe Val Asp His Asn Thr Arg Thr Thr Thr Phe Lys Asp Pro
20 25 30

Arg Pro

<210> SEQ ID NO 44
<211> LENGTH: 34
<212> TYPE: PRT
<213> ORGANISM: Homo Sapiens

<400> SEQUENCE: 44

```
Ser Pro Leu Pro Pro Gly Trp Glu Glu Arg Gln Asp Ile Leu Gly Arg
1               5                   10                  15

Thr Tyr Tyr Val Asn His Glu Ser Arg Arg Thr Gln Trp Lys Arg Pro
            20                  25                  30

Thr Pro


<210> SEQ ID NO 45
<211> LENGTH: 34
<212> TYPE: PRT
<213> ORGANISM: Homo Sapiens

<400> SEQUENCE: 45

Ser Gly Leu Pro Pro Gly Trp Glu Glu Lys Gln Asp Glu Arg Gly Arg
1               5                   10                  15

Ser Tyr Tyr Val Asp His Asn Ser Arg Thr Thr Thr Trp Thr Lys Pro
            20                  25                  30

Thr Val


<210> SEQ ID NO 46
<211> LENGTH: 34
<212> TYPE: PRT
<213> ORGANISM: Homo Sapiens

<400> SEQUENCE: 46

Gly Phe Leu Pro Lys Gly Trp Glu Val Arg His Ala Pro Asn Gly Arg
1               5                   10                  15

Pro Phe Phe Ile Asp His Asn Thr Lys Thr Thr Thr Trp Glu Asp Pro
            20                  25                  30

Arg Leu


<210> SEQ ID NO 47
<211> LENGTH: 34
<212> TYPE: PRT
<213> ORGANISM: Homo Sapiens

<400> SEQUENCE: 47

Gly Pro Leu Pro Pro Gly Trp Glu Glu Arg Thr His Thr Asp Gly Arg
1               5                   10                  15

Ile Phe Tyr Ile Asn His Asn Ile Lys Arg Thr Gln Trp Glu Asp Pro
            20                  25                  30

Arg Leu


<210> SEQ ID NO 48
<211> LENGTH: 34
<212> TYPE: PRT
<213> ORGANISM: Homo Sapiens

<400> SEQUENCE: 48

Pro Glu Leu Pro Glu Gly Tyr Glu Gln Arg Thr Thr Val Gln Gly Gln
1               5                   10                  15

Val Tyr Phe Leu His Thr Gln Thr Gly Val Ser Thr Trp His Asp Pro
            20                  25                  30

Arg Ile


<210> SEQ ID NO 49
<211> LENGTH: 34
<212> TYPE: PRT
<213> ORGANISM: Homo Sapiens

<400> SEQUENCE: 49
```

Gly Pro Leu Pro Pro Gly Trp Glu Val Arg Ser Thr Val Ser Gly Arg
1 5 10 15

Ile Tyr Phe Val Asp His Asn Asn Arg Thr Thr Gln Phe Thr Asp Pro
20 25 30

Arg Leu

<210> SEQ ID NO 50
<211> LENGTH: 34
<212> TYPE: PRT
<213> ORGANISM: Homo Sapiens

<400> SEQUENCE: 50

Asn Asp Leu Pro Asp Gly Trp Glu Glu Arg Arg Thr Ala Ser Gly Arg
1 5 10 15

Ile Gln Tyr Leu Asn His Ile Thr Arg Thr Thr Gln Trp Glu Arg Pro
20 25 30

Thr Arg

<210> SEQ ID NO 51
<211> LENGTH: 34
<212> TYPE: PRT
<213> ORGANISM: Homo Sapiens

<400> SEQUENCE: 51

Pro Asp Leu Pro Glu Gly Tyr Glu Gln Arg Thr Thr Gln Gln Gly Gln
1 5 10 15

Val Tyr Phe Leu His Thr Gln Thr Gly Val Ser Thr Trp His Asp Pro
20 25 30

Arg Val

<210> SEQ ID NO 52
<211> LENGTH: 34
<212> TYPE: PRT
<213> ORGANISM: Homo Sapiens

<400> SEQUENCE: 52

Gly Pro Leu Pro Pro Gly Trp Glu Ile Arg Asn Thr Ala Thr Gly Arg
1 5 10 15

Val Tyr Phe Val Asp His Asn Asn Arg Thr Thr Gln Phe Thr Asp Pro
20 25 30

Arg Leu

<210> SEQ ID NO 53
<211> LENGTH: 34
<212> TYPE: PRT
<213> ORGANISM: Homo Sapiens

<400> SEQUENCE: 53

Ala Pro Leu Pro Pro Gly Trp Glu Gln Arg Val Asp Gln His Gly Arg
1 5 10 15

Val Tyr Tyr Val Asp His Val Glu Lys Arg Thr Thr Trp Asp Arg Pro
20 25 30

Glu Pro

<210> SEQ ID NO 54
<211> LENGTH: 34
<212> TYPE: PRT
<213> ORGANISM: Homo Sapiens

<400> SEQUENCE: 54

Glu Pro Leu Pro Pro Gly Trp Glu Arg Arg Val Asp Asn Met Gly Arg
1 5 10 15

Ile Tyr Tyr Val Asp His Phe Thr Arg Thr Thr Thr Trp Gln Arg Pro
20 25 30

Thr Leu

<210> SEQ ID NO 55
<211> LENGTH: 34
<212> TYPE: PRT
<213> ORGANISM: Homo Sapiens

<400> SEQUENCE: 55

Gly Pro Leu Pro Pro Gly Trp Glu Lys Arg Thr Asp Ser Asn Gly Arg
1 5 10 15

Val Tyr Phe Val Asn His Asn Thr Arg Ile Thr Gln Trp Glu Asp Pro
20 25 30

Arg Ser

<210> SEQ ID NO 56
<211> LENGTH: 34
<212> TYPE: PRT
<213> ORGANISM: Homo Sapiens

<400> SEQUENCE: 56

Lys Pro Leu Pro Glu Gly Trp Glu Met Arg Phe Thr Val Asp Gly Ile
1 5 10 15

Pro Tyr Phe Val Asp His Asn Arg Arg Thr Thr Thr Tyr Ile Asp Pro
20 25 30

Arg Thr

<210> SEQ ID NO 57
<211> LENGTH: 33
<212> TYPE: PRT
<213> ORGANISM: Homo Sapiens

<400> SEQUENCE: 57

Pro Leu Pro Pro Asn Trp Glu Ala Arg Ile Asp Ser His Gly Arg Val
1 5 10 15

Phe Tyr Val Asp His Val Asn Arg Thr Thr Thr Trp Gln Arg Pro Thr
20 25 30

Ala

<210> SEQ ID NO 58
<211> LENGTH: 34
<212> TYPE: PRT
<213> ORGANISM: Homo Sapiens

<400> SEQUENCE: 58

Leu Glu Leu Pro Arg Gly Trp Glu Ile Lys Thr Asp Gln Gln Gly Lys
1 5 10 15

Ser Phe Phe Val Asp His Asn Ser Arg Ala Thr Thr Phe Ile Asp Pro
20 25 30

Arg Ile

<210> SEQ ID NO 59
<211> LENGTH: 34
<212> TYPE: PRT
<213> ORGANISM: Homo Sapiens

<400> SEQUENCE: 59

Glu Ala Leu Pro Pro Asn Trp Glu Ala Arg Ile Asp Ser His Gly Arg
1 5 10 15

Ile Phe Tyr Val Asp His Val Asn Arg Thr Thr Thr Trp Gln Arg Pro
20 25 30

Thr Ala

<210> SEQ ID NO 60
<211> LENGTH: 34
<212> TYPE: PRT
<213> ORGANISM: Homo Sapiens

<400> SEQUENCE: 60

Leu Glu Leu Pro Arg Gly Trp Glu Met Lys His Asp His Gln Gly Lys
1 5 10 15

Ala Phe Phe Val Asp His Asn Ser Arg Thr Thr Thr Phe Ile Asp Pro
20 25 30

Arg Leu

<210> SEQ ID NO 61
<211> LENGTH: 27
<212> TYPE: PRT
<213> ORGANISM: Homo Sapiens

<400> SEQUENCE: 61

Gly Trp Glu Glu Lys Val Asp Asn Leu Gly Arg Thr Tyr Tyr Val Asn
1 5 10 15

His Asn Asn Arg Thr Thr Gln Trp His Arg Pro
20 25

<210> SEQ ID NO 62
<211> LENGTH: 29
<212> TYPE: PRT
<213> ORGANISM: Homo Sapiens

<400> SEQUENCE: 62

Pro Ser Gly Trp Glu Glu Arg Lys Asp Ala Lys Gly Arg Thr Tyr Tyr
1 5 10 15

Val Asn His Asn Asn Arg Thr Thr Thr Trp Thr Arg Pro
20 25

<210> SEQ ID NO 63
<211> LENGTH: 31
<212> TYPE: PRT
<213> ORGANISM: Homo Sapiens

<400> SEQUENCE: 63

Pro Pro Gly Trp Glu Met Arg Ile Ala Pro Asn Gly Arg Pro Phe Phe
1 5 10 15

Ile Asp His Asn Thr Lys Thr Thr Thr Trp Glu Asp Pro Arg Leu
20 25 30

<210> SEQ ID NO 64
<211> LENGTH: 31
<212> TYPE: PRT
<213> ORGANISM: Homo Sapiens

<400> SEQUENCE: 64

Pro Pro Gly Trp Glu Glu Arg Ile His Leu Asp Gly Arg Thr Phe Tyr
1 5 10 15

Ile Asp His Asn Ser Lys Ile Thr Gln Trp Glu Asp Pro Arg Leu
20 25 30

<210> SEQ ID NO 65
<211> LENGTH: 101
<212> TYPE: PRT
<213> ORGANISM: Artificial Sequence
<220> FEATURE:
<223> OTHER INFORMATION: Synthetic Polypeptide

<400> SEQUENCE: 65

Met Glu Pro Val Asp Pro Arg Leu Glu Pro Trp Lys His Pro Gly Ser
1 5 10 15

Gln Pro Arg Thr Pro Cys Thr Thr Cys Tyr Cys Lys Lys Cys Cys Phe
20 25 30

His Cys Gln Val Cys Phe Thr Thr Lys Ala Leu Gly Ile Ser Tyr Gly
35 40 45

Arg Lys Lys Arg Arg Gln Arg Arg Arg Pro Pro Gln Gly Ser Gln Thr
50 55 60

His Gln Val Ser Leu Ser Lys Gln Pro Ser Ser Gln Pro Arg Gly Asp
65 70 75 80

Gln Thr Gly Pro Lys Glu Ser Lys Lys Lys Val Glu Arg Glu Thr Glu
85 90 95

Ala Asp Pro Lys Pro
100

<210> SEQ ID NO 66
<211> LENGTH: 86
<212> TYPE: PRT
<213> ORGANISM: Artificial Sequence
<220> FEATURE:
<223> OTHER INFORMATION: Synthetic Polypeptide

<400> SEQUENCE: 66

Met Glu Pro Val Asp Pro Arg Leu Glu Pro Trp Lys His Pro Gly Ser
1 5 10 15

Gln Pro Arg Thr Pro Cys Thr Thr Cys Tyr Cys Lys Lys Cys Cys Phe
20 25 30

His Cys Gln Val Cys Phe Thr Thr Lys Ala Leu Gly Ile Ser Tyr Gly
35 40 45

Arg Lys Lys Arg Arg Gln Arg Arg Arg Pro Pro Gln Gly Ser Gln Thr
50 55 60

His Gln Val Ser Leu Ser Lys Gln Pro Ser Ser Gln Pro Arg Gly Asp
65 70 75 80

Gln Thr Gly Pro Lys Glu
85

<210> SEQ ID NO 67
<211> LENGTH: 36
<212> TYPE: PRT
<213> ORGANISM: Artificial Sequence
<220> FEATURE:
<223> OTHER INFORMATION: Synthetic Polypeptide

<400> SEQUENCE: 67

Cys Phe Thr Thr Lys Ala Leu Gly Ile Ser Tyr Gly Arg Lys Lys Arg
1 5 10 15

Arg Gln Arg Arg Arg Pro Pro Gln Gly Ser Gln Thr His Gln Val Ser
20 25 30

Leu Ser Lys Gln
        35

<210> SEQ ID NO 68
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 68

Met Glu Pro Val Asp Pro Arg Leu Glu Pro Trp Lys His Pro Gly Ser
1               5                   10                  15

Gln Pro Arg Thr Pro Cys Thr Thr Cys Tyr Cys Lys Lys Cys Cys Phe
            20                  25                  30

His Cys Gln Val Cys Phe Thr Thr Lys Ala Leu Gly Ile
        35                  40                  45

<210> SEQ ID NO 69
<211> LENGTH: 38
<212> TYPE: PRT
<213> ORGANISM: Artificial Sequence
<220> FEATURE:
<223> OTHER INFORMATION: Synthetic Polypeptide

<400> SEQUENCE: 69

Arg Lys Lys Arg Arg Gln Arg Arg Arg Pro Pro Gln Gly Ser Gln Thr
1               5                   10                  15

His Gln Val Ser Leu Ser Lys Gln Pro Ser Ser Gln Pro Arg Gly Asp
            20                  25                  30

Gln Thr Gly Pro Lys Glu
        35

<210> SEQ ID NO 70
<211> LENGTH: 35
<212> TYPE: PRT
<213> ORGANISM: Artificial Sequence
<220> FEATURE:
<223> OTHER INFORMATION: Synthetic Polypeptide

<400> SEQUENCE: 70

Arg Arg Gln Arg Arg Arg Pro Pro Gln Gly Ser Gln Thr His Gln Val
1               5                   10                  15

Ser Leu Ser Lys Gln Pro Ser Ser Gln Pro Arg Gly Asp Gln Thr Gly
            20                  25                  30

Pro Lys Glu
        35

<210> SEQ ID NO 71
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 71

Arg Arg Arg Pro Pro Gln Gly Ser Gln Thr His Gln Val Ser Leu Ser
1               5                   10                  15

Lys Gln Pro Ser Ser Gln Pro Arg Gly Asp Gln Thr Gly Pro Lys Glu
            20                  25                  30

<210> SEQ ID NO 72
<211> LENGTH: 29

<212> TYPE: PRT
<213> ORGANISM: Artificial Sequence
<220> FEATURE:
<223> OTHER INFORMATION: Synthetic Polypeptide

<400> SEQUENCE: 72

Pro Pro Gln Gly Ser Gln Thr His Gln Val Ser Leu Ser Lys Gln Pro
1 5 10 15

Ser Ser Gln Pro Arg Gly Asp Gln Thr Gly Pro Lys Glu
20 25

<210> SEQ ID NO 73
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 73

Arg Lys Lys Arg Arg Gln Arg Arg Arg
1 5

<210> SEQ ID NO 74
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 74

Arg Lys Lys Arg Arg Gln Arg Arg Arg Pro Pro
1 5 10

<210> SEQ ID NO 75
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 75

Arg Lys Lys Arg Arg Gln Arg Arg Arg Pro Pro Gln Gly
1 5 10

<210> SEQ ID NO 76
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 76

Arg Lys Lys Arg Arg Gln Arg Arg Arg Pro Pro Gln Gly Ser Gln
1 5 10 15

<210> SEQ ID NO 77
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 77

Arg Lys Lys Arg Arg Gln Arg Arg Arg Pro Pro Gln Gly Ser Gln Thr
1 5 10 15

His

<210> SEQ ID NO 78
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 78

```
Cys Phe Thr Thr Lys Ala Leu Gly Ile Ser Tyr Gly Arg Lys Lys Arg
1               5                   10                  15

Arg Gln Arg Arg Arg
            20
```

<210> SEQ ID NO 79
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 79

```
Cys Phe Thr Thr Lys Ala Leu Gly Ile Ser Tyr Gly Arg Lys Lys Arg
1               5                   10                  15

Arg Gln Arg Arg Arg Pro Pro Gln Gly Ser Gln
            20                  25
```

<210> SEQ ID NO 80
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 80

```
Gly Arg Arg Lys Lys Arg Arg Gln Arg Arg Arg Pro
1               5                   10
```

<210> SEQ ID NO 81
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 81

```
Ser Tyr Gly Arg Lys Lys Arg Arg Gln Arg Arg Arg Pro Pro Gln Gly
1               5                   10                  15

Ser Gln Thr His
            20
```

<210> SEQ ID NO 82
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 82

```
Met Glu Thr Pro Leu Lys Ala Pro Glu Gly Ser Leu Gly Ser Tyr Asn
1               5                   10                  15

Glu Pro Ser Ser Cys Thr Ser Glu Gln Asp Ala Ala Ala Gln Gly Leu
            20                  25                  30

Val Ser Pro Gly Asp Glu Ile Leu Tyr Gln Leu Tyr Gln Pro Leu Glu
```

```
        35                  40                  45

Ala Cys Asp Asn Lys Cys Tyr Cys Lys Lys Cys Cys Tyr His Cys Gln
    50                  55                  60

Met Cys Phe Leu Asn Lys Gly Leu Gly Ile Trp Tyr Glu Arg Lys Gly
65                  70                  75                  80

Arg Arg Arg Arg Thr Pro Lys Lys Thr Lys Ala His Ser Ser Ser Ala
                85                  90                  95

Ser Asp Lys Ser Ile Ser Thr Arg Thr Gly Asn Ser Gln Pro Glu Lys
            100                 105                 110

Lys Gln Lys Lys Thr Leu Glu Thr Ala Leu Glu Thr Ile Gly Gly Pro
        115                 120                 125

Gly Arg
    130


<210> SEQ ID NO 83
<211> LENGTH: 103
<212> TYPE: PRT
<213> ORGANISM: Artificial Sequence
<220> FEATURE:
<223> OTHER INFORMATION: Synthetic Polypeptide

<400> SEQUENCE: 83

Met Pro Gly Pro Trp Val Ala Met Ile Met Leu Pro Gln Pro Lys Glu
1               5                   10                  15

Ser Phe Gly Gly Lys Pro Ile Gly Trp Leu Phe Trp Asn Thr Cys Lys
            20                  25                  30

Gly Pro Arg Arg Asp Cys Pro His Cys Cys Cys Pro Ile Cys Ser Trp
        35                  40                  45

His Cys Gln Leu Cys Phe Leu Gln Lys Asn Leu Gly Ile Asn Tyr Gly
    50                  55                  60

Ser Gly Pro Arg Arg Arg Gly Thr Arg Gly Lys Gly Arg Arg Ile Arg
65                  70                  75                  80

Arg Thr Ala Ser Gly Gly Asp Gln Arg Arg Glu Ala Asp Ser Gln Arg
                85                  90                  95

Ser Phe Thr Asn Met Asp Gln
            100


<210> SEQ ID NO 84
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 84

Ser Gly Pro Arg Pro Arg Gly Thr Arg Gly Lys Gly Arg Arg Ile Arg
1               5                   10                  15

Arg


<210> SEQ ID NO 85
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 85

gggcccggag accagacgag ccgggagccc ggcaacaggg aacccacg                48
```

<210> SEQ ID NO 86
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 86
gggcccggag accagacgag ccgggccggc aacagggaac ccacg 45

<210> SEQ ID NO 87
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 87
gggcccggag accagacgag ccgggagccc ggcaacaggg aacc 44

<210> SEQ ID NO 88
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 88
agacgagccg ggagccc 17

<210> SEQ ID NO 89
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 89
gccggagccg ggaagcccga gc 22

<210> SEQ ID NO 90
<211> LENGTH: 15
<212> TYPE: DNA
<213> ORGANISM: Artificial Sequence
<220> FEATURE:
<223> OTHER INFORMATION: Synthetic Polynucleotide

<400> SEQUENCE: 90
cggagccaag cccga 15

<210> SEQ ID NO 91
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 91
ggcgggcgca gcgcaagcga cggacaggcc 30

<210> SEQ ID NO 92
<211> LENGTH: 28
<212> TYPE: DNA
<213> ORGANISM: Artificial Sequence
<220> FEATURE:
<223> OTHER INFORMATION: Synthetic Polypeptide

<400> SEQUENCE: 92
ggcggaccga ccggacggag aaacagcc 28

<210> SEQ ID NO 93
<211> LENGTH: 116
<212> TYPE: PRT
<213> ORGANISM: Artificial Sequence
<220> FEATURE:
<223> OTHER INFORMATION: Synthetic Polypeptide

<400> SEQUENCE: 93

Met Ala Gly Arg Ser Gly Asp Ser Asp Glu Glu Leu Ile Arg Thr Val
1 5 10 15

Arg Leu Ile Lys Leu Leu Tyr Gln Ser Asn Pro Pro Pro Asn Pro Glu
20 25 30

Gly Thr Arg Gln Ala Arg Arg Asn Arg Arg Arg Arg Trp Arg Glu Arg
35 40 45

Gln Arg Gln Ile His Ser Ile Ser Glu Arg Ile Leu Gly Thr Tyr Leu
50 55 60

Gly Arg Ser Ala Glu Pro Val Pro Leu Gln Leu Pro Pro Leu Glu Arg
65 70 75 80

Leu Thr Leu Asp Cys Asn Glu Asp Cys Gly Thr Ser Gly Thr Gln Gly
85 90 95

Val Gly Ser Pro Gln Ile Leu Val Glu Ser Pro Thr Val Leu Glu Ser
100 105 110

Gly Thr Lys Glu
115

<210> SEQ ID NO 94
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 94

Thr Arg Gln Ala Arg Arg Asn Arg Arg Arg Arg Trp Arg Glu Arg Gln
1 5 10 15

Arg

<210> SEQ ID NO 95
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 95

Arg Asp Arg Arg Arg Arg Gly Ser Arg Pro Ser Gly Ala Glu Arg Arg
1 5 10 15

Arg Arg Arg Ala Ala Ala Ala
20

<210> SEQ ID NO 96
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 96
acaugaggau uacccaugu 19

<210> SEQ ID NO 97
<211> LENGTH: 18
<212> TYPE: RNA
<213> ORGANISM: Artificial Sequence
<220> FEATURE:
<223> OTHER INFORMATION: Synthetic Polynucleotide

<400> SEQUENCE: 97
ccggaggauc accacggg 18

<210> SEQ ID NO 98
<211> LENGTH: 14
<212> TYPE: RNA
<213> ORGANISM: Artificial Sequence
<220> FEATURE:
<223> OTHER INFORMATION: Synthetic Polynucleotide

<400> SEQUENCE: 98
ccacagucac uggg 14

<210> SEQ ID NO 99
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 99

```
Ala Ser Asn Phe Thr Gln Phe Val Leu Val Asp Asn Gly Gly Thr Gly
1               5                   10                  15

Asp Val Thr Val Ala Pro Ser Asn Phe Ala Asn Gly Val Ala Glu Trp
            20                  25                  30

Ile Ser Ser Asn Ser Arg Ser Gln Ala Tyr Lys Val Thr Cys Ser Val
        35                  40                  45

Arg Gln Ser Ser Ala Gln Asn Arg Lys Tyr Thr Ile Lys Val Glu Val
    50                  55                  60

Pro Lys Val Ala Thr Gln Thr Val Gly Gly Val Glu Leu Pro Val Ala
65                  70                  75                  80

Ala Trp Arg Ser Tyr Leu Asn Met Glu Leu Thr Ile Pro Ile Phe Ala
                85                  90                  95

Thr Asn Ser Asp Cys Glu Leu Ile Val Lys Ala Met Gln Gly Leu Leu
            100                 105                 110

Lys Asp Gly Asn Pro Ile Pro Ser Ala Ile Ala Ala Asn Ser Gly Ile
        115                 120                 125

Tyr
```

<210> SEQ ID NO 100
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 100

```
Asn Ala Lys Thr Arg Arg His Glu Arg Arg Arg Lys Leu Ala Ile Glu
1               5                   10                  15

Arg Asp Thr Ile
            20
```

<210> SEQ ID NO 101
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 101

```
Gly Ser Met Asp Ala Gln Thr Arg Arg Arg Glu Arg Arg Ala Glu Lys
1               5                   10                  15

Gln Ala Gln Trp Lys Ala Ala Asn
            20
```

<210> SEQ ID NO 102
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 102

```
Gly Thr Ala Lys Ser Arg Tyr Lys Ala Arg Arg Ala Glu Leu Ile Ala
1               5                   10                  15

Glu Arg Arg
```

<210> SEQ ID NO 103
<211> LENGTH: 55
<212> TYPE: PRT
<213> ORGANISM: Artificial Sequence
<220> FEATURE:
<223> OTHER INFORMATION: Synthetic Polypeptide

<400> SEQUENCE: 103

```
Met Gln Lys Gly Asn Phe Arg Asn Gln Arg Lys Thr Val Lys Cys Phe
1               5                   10                  15

Asn Cys Gly Lys Glu Gly His Ile Ala Lys Asn Cys Arg Ala Pro Arg
            20                  25                  30

Lys Lys Gly Cys Trp Lys Cys Gly Lys Glu Gly His Gln Met Lys Asp
        35                  40                  45

Cys Thr Glu Arg Gln Ala Asn
    50                  55
```

<210> SEQ ID NO 104
<211> LENGTH: 15
<212> TYPE: RNA
<213> ORGANISM: Artificial Sequence
<220> FEATURE:
<223> OTHER INFORMATION: Synthetic Polynucleotide

<400> SEQUENCE: 104

```
gcgcugacaa agcgc                                                    15
```

<210> SEQ ID NO 105
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 105

```
gggcccugaa gaagggccc                                                19
```

<210> SEQ ID NO 106
<211> LENGTH: 20

<212> TYPE: RNA
<213> ORGANISM: Artificial Sequence
<220> FEATURE:
<223> OTHER INFORMATION: Synthetic Polynucleotide

<400> SEQUENCE: 106
ucucaaccua accguugaga 20

<210> SEQ ID NO 107
<211> LENGTH: 20
<212> TYPE: RNA
<213> ORGANISM: Artificial Sequence
<220> FEATURE:
<223> OTHER INFORMATION: Synthetic Polynucleotide

<400> SEQUENCE: 107
ggacuagcgg aggcuagucc 20

<210> SEQ ID NO 108
<211> LENGTH: 4104
<212> TYPE: DNA
<213> ORGANISM: Streptococcus pyogenes

<400> SEQUENCE: 108
atggataaga aatactcaat aggcttagat atcggcacaa atagcgtcgg atgggcggtg 60
atcactgatg attataaggt tccgtctaaa aagttcaagg ttctgggaaa tacagaccgc 120
cacagtatca aaaaaaatct tataggggct cttttatttg gcagtggaga gacagcggaa 180
gcgactcgtc tcaaacggac agctcgtaga aggtatacac gtcggaagaa tcgtatttgt 240
tatctacagg agattttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggcag attctactga taaagcggat ttgcgcttaa tctatttggc cttagcgcat 480
atgattaagt ttcgtggtca tttttttgatt gagggagatt taaatcctga taatagtgat 540
gtggacaaac tatttatcca gttggtacaa atctacaatc aattatttga agaaaaccct 600
attaacgcaa gtagagtaga tgctaaagcg attctttctg cacgattgag taaatcaaga 660
cgattagaaa atctcattgc tcagctcccc ggtgagaaga gaaatggctt gtttgggaat 720
ctcattgctt tgtcattggg attgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctatt 900
ttactttcag atatcctaag agtaaatagt gaaataacta aggctcccct atcagcttca 960
atgattaagc gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaggt caaatatgtt actgagggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggcgcct accatgattt gctaaaaatt 1800
attaaagata aagatttttt ggataatgaa gaaaatgaag atatcttaga ggatattgtt 1860
ttaacattga ccttatttga agataggggg atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040
gatttttga aatcagatgg ttttgccaat cgcaatttta tgcagctgat ccatgatgat 2100
agtttgacat ttaaagaaga tattcaaaaa gcacaggtgt ctggacaagg ccatagttta 2160
catgaacaga ttgctaactt agctggcagt cctgctatta aaaaaggtat tttacagact 2220
gtaaaaattg ttgatgaact ggtcaaagta atggggcata agccagaaaa tatcgttatt 2280
gaaatggcac gtgaaaatca gacaactcaa aagggccaga aaaattcgcg agagcgtatg 2340
aaacgaatcg aagaaggtat caaagaatta ggaagtcaga ttcttaaaga gcatcctgtt 2400
gaaaatactc aattgcaaaa tgaaaagctc tatctctatt atctacaaaa tggaagagac 2460
atgtatgtgg accaagaatt agatattaat cgtttaagtg attatgatgt cgatcacatt 2520
gttccacaaa gtttcattaa agacgattca atagacaata aggtactaac gcgttctgat 2580
aaaaatcgtg gtaaatcgga taacgttcca agtgaagaag tagtcaaaaa gatgaaaaac 2640
tattggagac aacttctaaa cgccaagtta atcactcaac gtaagtttga taatttaacg 2700
aaagctgaac gtggaggttt gagtgaactt gataaagctg gttttatcaa acgccaattg 2760
gttgaaactc gccaaatcac taagcatgtg gcacaaattt tggatagtcg catgaatact 2820
aaatacgatg aaaatgataa acttattcga gaggttaaag tgattacctt aaaatctaaa 2880
ttagtttctg acttccgaaa agatttccaa ttctataaag tacgtgagat taacaattac 2940
catcatgccc atgatgcgta tctaaatgcc gtcgttggaa ctgctttgat taagaaatat 3000
ccaaaacttg aatcggagtt tgtctatggt gattataaag tttatgatgt tcgtaaaatg 3060
attgctaagt ctgagcaaga aataggcaaa gcaaccgcaa aatatttctt ttactctaat 3120
atcatgaact tcttcaaaac agaaattaca cttgcaaatg gagagattcg caaacgccct 3180
ctaatcgaaa ctaatgggga aactggagaa attgtctggg ataaagggcg agattttgcc 3240
acagtgcgca aagtattgtc catgccccaa gtcaatattg tcaagaaaac agaagtacag 3300
acaggcggat tctccaagga gtcaatttta ccaaaaagaa attcggacaa gcttattgct 3360
cgtaaaaaag actgggatcc aaaaaaatat ggtggttttg atagtccaac ggtagcttat 3420
tcagtcctag tggttgctaa ggtggaaaaa gggaaatcga agaagttaaa atccgttaaa 3480
gagttactag ggatcacaat tatggaaaga agttcctttg aaaaaaatcc gattgacttt 3540
ttagaagcta aaggatataa ggaagttaaa aaagacttaa tcattaaact acctaaatat 3600
agtctttttg agttagaaaa cggtcgtaaa cggatgctgg ctagtgccgg agaattacaa 3660
aaaggaaatg agctggctct gccaagcaaa tatgtgaatt ttttatattt agctagtcat 3720
tatgaaaagt tgaagggtag tccagaagat aacgaacaaa aacaattgtt tgtggagcag 3780
cataagcatt atttagatga gattattgag caaatcagtg aattttctaa gcgtgttatt 3840
ttagcagatg ccaatttaga taaagttctt agtgcatata acaaacatag agacaaacca 3900
atacgtgaac aagcagaaaa tattattcat ttatttacgt tgacgaatct tggagctccc 3960
gctgctttta aatattttga tacaacaatt gatcgtaaac gatatacgtc tacaaaagaa 4020
gttttagatg ccactcttat ccatcaatcc atcactggtc tttatgaaac acgcattgat 4080
ttgagtcagc taggaggtga ctga 4104

<210> SEQ ID NO 109
<211> LENGTH: 1493
<212> TYPE: PRT
<213> ORGANISM: Artificial Sequence
<220> FEATURE:
<223> OTHER INFORMATION: Synthetic Polypeptide

<400> SEQUENCE: 109

Met Pro Leu Pro Pro Gly Trp Glu Gln Arg Val Asp Gln His Gly Arg
1 5 10 15

Val Tyr Tyr Val Asp His Val Glu Lys Arg Thr Thr Trp Asp Arg Pro
20 25 30

Glu Pro Leu Pro Pro Gly Trp Glu Arg Arg Val Asp Asn Met Gly Arg
35 40 45

Ile Tyr Tyr Val Asp His Phe Thr Arg Thr Thr Thr Trp Gln Arg Pro
50 55 60

Thr Leu Thr Gly Ala Thr Met Asp Tyr Lys Asp His Asp Gly Asp Tyr
65 70 75 80

Lys Asp His Asp Ile Asp Tyr Lys Asp Asp Asp Asp Lys Met Ala Pro
85 90 95

Lys Lys Lys Arg Lys Val Gly Ile His Gly Val Pro Ala Ala Asp Lys
100 105 110

Lys Tyr Ser Ile Gly Leu Asp Ile Gly Thr Asn Ser Val Gly Trp Ala
115 120 125

Val Ile Thr Asp Glu Tyr Lys Val Pro Ser Lys Lys Phe Lys Val Leu
130 135 140

Gly Asn Thr Asp Arg His Ser Ile Lys Lys Asn Leu Ile Gly Ala Leu
145 150 155 160

Leu Phe Asp Ser Gly Glu Thr Ala Glu Ala Thr Arg Leu Lys Arg Thr
165 170 175

Ala Arg Arg Arg Tyr Thr Arg Arg Lys Asn Arg Ile Cys Tyr Leu Gln
180 185 190

Glu Ile Phe Ser Asn Glu Met Ala Lys Val Asp Asp Ser Phe Phe His
195 200 205

Arg Leu Glu Glu Ser Phe Leu Val Glu Glu Asp Lys Lys His Glu Arg
210 215 220

His Pro Ile Phe Gly Asn Ile Val Asp Glu Val Ala Tyr His Glu Lys
225 230 235 240

Tyr Pro Thr Ile Tyr His Leu Arg Lys Lys Leu Val Asp Ser Thr Asp
245 250 255

Lys Ala Asp Leu Arg Leu Ile Tyr Leu Ala Leu Ala His Met Ile Lys
260 265 270

Phe Arg Gly His Phe Leu Ile Glu Gly Asp Leu Asn Pro Asp Asn Ser
275 280 285

Asp Val Asp Lys Leu Phe Ile Gln Leu Val Gln Thr Tyr Asn Gln Leu
290 295 300

Phe Glu Glu Asn Pro Ile Asn Ala Ser Gly Val Asp Ala Lys Ala Ile
305 310 315 320

-continued

```
Leu Ser Ala Arg Leu Ser Lys Ser Arg Arg Leu Glu Asn Leu Ile Ala
                325                 330                 335

Gln Leu Pro Gly Glu Lys Lys Asn Gly Leu Phe Gly Asn Leu Ile Ala
            340                 345                 350

Leu Ser Leu Gly Leu Thr Pro Asn Phe Lys Ser Asn Phe Asp Leu Ala
        355                 360                 365

Glu Asp Ala Lys Leu Gln Leu Ser Lys Asp Thr Tyr Asp Asp Asp Leu
    370                 375                 380

Asp Asn Leu Leu Ala Gln Ile Gly Asp Gln Tyr Ala Asp Leu Phe Leu
385                 390                 395                 400

Ala Ala Lys Asn Leu Ser Asp Ala Ile Leu Leu Ser Asp Ile Leu Arg
                405                 410                 415

Val Asn Thr Glu Ile Thr Lys Ala Pro Leu Ser Ala Ser Met Ile Lys
            420                 425                 430

Arg Tyr Asp Glu His His Gln Asp Leu Thr Leu Leu Lys Ala Leu Val
        435                 440                 445

Arg Gln Gln Leu Pro Glu Lys Tyr Lys Glu Ile Phe Phe Asp Gln Ser
    450                 455                 460

Lys Asn Gly Tyr Ala Gly Tyr Ile Asp Gly Gly Ala Ser Gln Glu Glu
465                 470                 475                 480

Phe Tyr Lys Phe Ile Lys Pro Ile Leu Glu Lys Met Asp Gly Thr Glu
                485                 490                 495

Glu Leu Leu Val Lys Leu Asn Arg Glu Asp Leu Leu Arg Lys Gln Arg
            500                 505                 510

Thr Phe Asp Asn Gly Ser Ile Pro His Gln Ile His Leu Gly Glu Leu
        515                 520                 525

His Ala Ile Leu Arg Arg Gln Glu Asp Phe Tyr Pro Phe Leu Lys Asp
    530                 535                 540

Asn Arg Glu Lys Ile Glu Lys Ile Leu Thr Phe Arg Ile Pro Tyr Tyr
545                 550                 555                 560

Val Gly Pro Leu Ala Arg Gly Asn Ser Arg Phe Ala Trp Met Thr Arg
                565                 570                 575

Lys Ser Glu Glu Thr Ile Thr Pro Trp Asn Phe Glu Glu Val Val Asp
            580                 585                 590

Lys Gly Ala Ser Ala Gln Ser Phe Ile Glu Arg Met Thr Asn Phe Asp
        595                 600                 605

Lys Asn Leu Pro Asn Glu Lys Val Leu Pro Lys His Ser Leu Leu Tyr
    610                 615                 620

Glu Tyr Phe Thr Val Tyr Asn Glu Leu Thr Lys Val Lys Tyr Val Thr
625                 630                 635                 640

Glu Gly Met Arg Lys Pro Ala Phe Leu Ser Gly Glu Gln Lys Lys Ala
                645                 650                 655

Ile Val Asp Leu Leu Phe Lys Thr Asn Arg Lys Val Thr Val Lys Gln
            660                 665                 670

Leu Lys Glu Asp Tyr Phe Lys Lys Ile Glu Cys Phe Asp Ser Val Glu
        675                 680                 685

Ile Ser Gly Val Glu Asp Arg Phe Asn Ala Ser Leu Gly Thr Tyr His
    690                 695                 700

Asp Leu Leu Lys Ile Ile Lys Asp Lys Asp Phe Leu Asp Asn Glu Glu
705                 710                 715                 720

Asn Glu Asp Ile Leu Glu Asp Ile Val Leu Thr Leu Thr Leu Phe Glu
                725                 730                 735

Asp Arg Glu Met Ile Glu Glu Arg Leu Lys Thr Tyr Ala His Leu Phe
```

```
            740                 745                 750

Asp Asp Lys Val Met Lys Gln Leu Lys Arg Arg Arg Tyr Thr Gly Trp
        755                 760                 765

Gly Arg Leu Ser Arg Lys Leu Ile Asn Gly Ile Arg Asp Lys Gln Ser
    770                 775                 780

Gly Lys Thr Ile Leu Asp Phe Leu Lys Ser Asp Gly Phe Ala Asn Arg
785                 790                 795                 800

Asn Phe Met Gln Leu Ile His Asp Asp Ser Leu Thr Phe Lys Glu Asp
                805                 810                 815

Ile Gln Lys Ala Gln Val Ser Gly Gln Gly Asp Ser Leu His Glu His
            820                 825                 830

Ile Ala Asn Leu Ala Gly Ser Pro Ala Ile Lys Lys Gly Ile Leu Gln
        835                 840                 845

Thr Val Lys Val Val Asp Glu Leu Val Lys Val Met Gly Arg His Lys
    850                 855                 860

Pro Glu Asn Ile Val Ile Glu Met Ala Arg Glu Asn Gln Thr Thr Gln
865                 870                 875                 880

Lys Gly Gln Lys Asn Ser Arg Glu Arg Met Lys Arg Ile Glu Glu Gly
                885                 890                 895

Ile Lys Glu Leu Gly Ser Gln Ile Leu Lys Glu His Pro Val Glu Asn
            900                 905                 910

Thr Gln Leu Gln Asn Glu Lys Leu Tyr Leu Tyr Tyr Leu Gln Asn Gly
        915                 920                 925

Arg Asp Met Tyr Val Asp Gln Glu Leu Asp Ile Asn Arg Leu Ser Asp
    930                 935                 940

Tyr Asp Val Asp His Ile Val Pro Gln Ser Phe Leu Lys Asp Asp Ser
945                 950                 955                 960

Ile Asp Asn Lys Val Leu Thr Arg Ser Asp Lys Asn Arg Gly Lys Ser
                965                 970                 975

Asp Asn Val Pro Ser Glu Glu Val Val Lys Lys Met Lys Asn Tyr Trp
            980                 985                 990

Arg Gln Leu Leu Asn Ala Lys Leu  Ile Thr Gln Arg Lys  Phe Asp Asn
        995                 1000                1005

Leu Thr  Lys Ala Glu Arg Gly  Gly Leu Ser Glu Leu  Asp Lys Ala
    1010                1015                1020

Gly Phe  Ile Lys Arg Gln Leu  Val Glu Thr Arg Gln  Ile Thr Lys
    1025                1030                1035

His Val  Ala Gln Ile Leu Asp  Ser Arg Met Asn Thr  Lys Tyr Asp
    1040                1045                1050

Glu Asn  Asp Lys Leu Ile Arg  Glu Val Lys Val Ile  Thr Leu Lys
    1055                1060                1065

Ser Lys  Leu Val Ser Asp Phe  Arg Lys Asp Phe Gln  Phe Tyr Lys
    1070                1075                1080

Val Arg  Glu Ile Asn Asn Tyr  His His Ala His Asp  Ala Tyr Leu
    1085                1090                1095

Asn Ala  Val Val Gly Thr Ala  Leu Ile Lys Lys Tyr  Pro Lys Leu
    1100                1105                1110

Glu Ser  Glu Phe Val Tyr Gly  Asp Tyr Lys Val Tyr  Asp Val Arg
    1115                1120                1125

Lys Met  Ile Ala Lys Ser Glu  Gln Glu Ile Gly Lys  Ala Thr Ala
    1130                1135                1140

Lys Tyr  Phe Phe Tyr Ser Asn  Ile Met Asn Phe Phe  Lys Thr Glu
    1145                1150                1155
```

```
Ile Thr  Leu Ala Asn Gly Glu  Ile Arg Lys Arg Pro  Leu Ile Glu
    1160                 1165                 1170

Thr Asn  Gly Glu Thr Gly Glu  Ile Val Trp Asp Lys  Gly Arg Asp
    1175                 1180                 1185

Phe Ala  Thr Val Arg Lys Val  Leu Ser Met Pro Gln  Val Asn Ile
    1190                 1195                 1200

Val Lys  Lys Thr Glu Val Gln  Thr Gly Gly Phe Ser  Lys Glu Ser
    1205                 1210                 1215

Ile Leu  Pro Lys Arg Asn Ser  Asp Lys Leu Ile Ala  Arg Lys Lys
    1220                 1225                 1230

Asp Trp  Asp Pro Lys Lys Tyr  Gly Gly Phe Asp Ser  Pro Thr Val
    1235                 1240                 1245

Ala Tyr  Ser Val Leu Val Val  Ala Lys Val Glu Lys  Gly Lys Ser
    1250                 1255                 1260

Lys Lys  Leu Lys Ser Val Lys  Glu Leu Leu Gly Ile  Thr Ile Met
    1265                 1270                 1275

Glu Arg  Ser Ser Phe Glu Lys  Asn Pro Ile Asp Phe  Leu Glu Ala
    1280                 1285                 1290

Lys Gly  Tyr Lys Glu Val Lys  Lys Asp Leu Ile Ile  Lys Leu Pro
    1295                 1300                 1305

Lys Tyr  Ser Leu Phe Glu Leu  Glu Asn Gly Arg Lys  Arg Met Leu
    1310                 1315                 1320

Ala Ser  Ala Gly Glu Leu Gln  Lys Gly Asn Glu Leu  Ala Leu Pro
    1325                 1330                 1335

Ser Lys  Tyr Val Asn Phe Leu  Tyr Leu Ala Ser His  Tyr Glu Lys
    1340                 1345                 1350

Leu Lys  Gly Ser Pro Glu Asp  Asn Glu Gln Lys Gln  Leu Phe Val
    1355                 1360                 1365

Glu Gln  His Lys His Tyr Leu  Asp Glu Ile Ile Glu  Gln Ile Ser
    1370                 1375                 1380

Glu Phe  Ser Lys Arg Val Ile  Leu Ala Asp Ala Asn  Leu Asp Lys
    1385                 1390                 1395

Val Leu  Ser Ala Tyr Asn Lys  His Arg Asp Lys Pro  Ile Arg Glu
    1400                 1405                 1410

Gln Ala  Glu Asn Ile Ile His  Leu Phe Thr Leu Thr  Asn Leu Gly
    1415                 1420                 1425

Ala Pro  Ala Ala Phe Lys Tyr  Phe Asp Thr Thr Ile  Asp Arg Lys
    1430                 1435                 1440

Arg Tyr  Thr Ser Thr Lys Glu  Val Leu Asp Ala Thr  Leu Ile His
    1445                 1450                 1455

Gln Ser  Ile Thr Gly Leu Tyr  Glu Thr Arg Ile Asp  Leu Ser Gln
    1460                 1465                 1470

Leu Gly  Gly Asp Lys Arg Pro  Ala Ala Thr Lys Lys  Ala Gly Gln
    1475                 1480                 1485

Ala Lys  Lys Lys Lys
    1490
```

<210> SEQ ID NO 110
<211> LENGTH: 1616
<212> TYPE: PRT
<213> ORGANISM: Artificial Sequence
<220> FEATURE:
<223> OTHER INFORMATION: Synthetic Polypeptide

<400> SEQUENCE: 110

-continued

```
Met Pro Leu Pro Pro Gly Trp Glu Gln Arg Val Asp Gln His Gly Arg
1               5                   10                  15

Val Tyr Tyr Val Asp His Val Glu Lys Arg Thr Thr Trp Asp Arg Pro
            20                  25                  30

Glu Pro Leu Pro Pro Gly Trp Glu Arg Arg Val Asp Asn Met Gly Arg
        35                  40                  45

Ile Tyr Tyr Val Asp His Phe Thr Arg Thr Thr Thr Trp Gln Arg Pro
    50                  55                  60

Thr Leu Glu Ser Val Arg Asn Tyr Glu Gln Trp Gln Leu Gln Arg Ser
65                  70                  75                  80

Gln Leu Gln Gly Ala Met Gln Gln Phe Asn Gln Arg Phe Ile Tyr Gly
                85                  90                  95

Asn Gln Asp Leu Phe Ala Thr Ser Gln Ser Lys Glu Phe Asp Pro Leu
            100                 105                 110

Gly Pro Leu Pro Pro Gly Trp Glu Lys Arg Thr Asp Ser Asn Gly Arg
        115                 120                 125

Val Tyr Phe Val Asn His Asn Thr Arg Ile Thr Gln Trp Glu Asp Pro
    130                 135                 140

Arg Ser Gln Gly Gln Leu Asn Glu Lys Pro Leu Pro Glu Gly Trp Glu
145                 150                 155                 160

Met Arg Phe Thr Val Asp Gly Ile Pro Tyr Phe Val Asp His Asn Arg
                165                 170                 175

Arg Thr Thr Thr Tyr Ile Asp Pro Arg Thr Gly Gly Gly Thr Gly Ala
            180                 185                 190

Thr Met Asp Tyr Lys Asp His Asp Gly Asp Tyr Lys Asp His Asp Ile
        195                 200                 205

Asp Tyr Lys Asp Asp Asp Asp Lys Met Ala Pro Lys Lys Lys Arg Lys
    210                 215                 220

Val Gly Ile His Gly Val Pro Ala Ala Asp Lys Lys Tyr Ser Ile Gly
225                 230                 235                 240

Leu Asp Ile Gly Thr Asn Ser Val Gly Trp Ala Val Ile Thr Asp Glu
                245                 250                 255

Tyr Lys Val Pro Ser Lys Lys Phe Lys Val Leu Gly Asn Thr Asp Arg
            260                 265                 270

His Ser Ile Lys Lys Asn Leu Ile Gly Ala Leu Leu Phe Asp Ser Gly
        275                 280                 285

Glu Thr Ala Glu Ala Thr Arg Leu Lys Arg Thr Ala Arg Arg Arg Tyr
    290                 295                 300

Thr Arg Arg Lys Asn Arg Ile Cys Tyr Leu Gln Glu Ile Phe Ser Asn
305                 310                 315                 320

Glu Met Ala Lys Val Asp Asp Ser Phe Phe His Arg Leu Glu Glu Ser
                325                 330                 335

Phe Leu Val Glu Glu Asp Lys Lys His Glu Arg His Pro Ile Phe Gly
            340                 345                 350

Asn Ile Val Asp Glu Val Ala Tyr His Glu Lys Tyr Pro Thr Ile Tyr
        355                 360                 365

His Leu Arg Lys Lys Leu Val Asp Ser Thr Asp Lys Ala Asp Leu Arg
    370                 375                 380

Leu Ile Tyr Leu Ala Leu Ala His Met Ile Lys Phe Arg Gly His Phe
385                 390                 395                 400

Leu Ile Glu Gly Asp Leu Asn Pro Asp Asn Ser Asp Val Asp Lys Leu
                405                 410                 415
```

```
Phe Ile Gln Leu Val Gln Thr Tyr Asn Gln Leu Phe Glu Glu Asn Pro
            420                 425                 430

Ile Asn Ala Ser Gly Val Asp Ala Lys Ala Ile Leu Ser Ala Arg Leu
        435                 440                 445

Ser Lys Ser Arg Arg Leu Glu Asn Leu Ile Ala Gln Leu Pro Gly Glu
    450                 455                 460

Lys Lys Asn Gly Leu Phe Gly Asn Leu Ile Ala Leu Ser Leu Gly Leu
465                 470                 475                 480

Thr Pro Asn Phe Lys Ser Asn Phe Asp Leu Ala Glu Asp Ala Lys Leu
                485                 490                 495

Gln Leu Ser Lys Asp Thr Tyr Asp Asp Asp Leu Asp Asn Leu Leu Ala
            500                 505                 510

Gln Ile Gly Asp Gln Tyr Ala Asp Leu Phe Leu Ala Ala Lys Asn Leu
        515                 520                 525

Ser Asp Ala Ile Leu Leu Ser Asp Ile Leu Arg Val Asn Thr Glu Ile
    530                 535                 540

Thr Lys Ala Pro Leu Ser Ala Ser Met Ile Lys Arg Tyr Asp Glu His
545                 550                 555                 560

His Gln Asp Leu Thr Leu Leu Lys Ala Leu Val Arg Gln Gln Leu Pro
                565                 570                 575

Glu Lys Tyr Lys Glu Ile Phe Phe Asp Gln Ser Lys Asn Gly Tyr Ala
            580                 585                 590

Gly Tyr Ile Asp Gly Gly Ala Ser Gln Glu Glu Phe Tyr Lys Phe Ile
        595                 600                 605

Lys Pro Ile Leu Glu Lys Met Asp Gly Thr Glu Glu Leu Leu Val Lys
    610                 615                 620

Leu Asn Arg Glu Asp Leu Leu Arg Lys Gln Arg Thr Phe Asp Asn Gly
625                 630                 635                 640

Ser Ile Pro His Gln Ile His Leu Gly Glu Leu His Ala Ile Leu Arg
                645                 650                 655

Arg Gln Glu Asp Phe Tyr Pro Phe Leu Lys Asp Asn Arg Glu Lys Ile
            660                 665                 670

Glu Lys Ile Leu Thr Phe Arg Ile Pro Tyr Tyr Val Gly Pro Leu Ala
        675                 680                 685

Arg Gly Asn Ser Arg Phe Ala Trp Met Thr Arg Lys Ser Glu Glu Thr
    690                 695                 700

Ile Thr Pro Trp Asn Phe Glu Glu Val Val Asp Lys Gly Ala Ser Ala
705                 710                 715                 720

Gln Ser Phe Ile Glu Arg Met Thr Asn Phe Asp Lys Asn Leu Pro Asn
                725                 730                 735

Glu Lys Val Leu Pro Lys His Ser Leu Leu Tyr Glu Tyr Phe Thr Val
            740                 745                 750

Tyr Asn Glu Leu Thr Lys Val Lys Tyr Val Thr Glu Gly Met Arg Lys
        755                 760                 765

Pro Ala Phe Leu Ser Gly Glu Gln Lys Lys Ala Ile Val Asp Leu Leu
    770                 775                 780

Phe Lys Thr Asn Arg Lys Val Thr Val Lys Gln Leu Lys Glu Asp Tyr
785                 790                 795                 800

Phe Lys Lys Ile Glu Cys Phe Asp Ser Val Glu Ile Ser Gly Val Glu
                805                 810                 815

Asp Arg Phe Asn Ala Ser Leu Gly Thr Tyr His Asp Leu Leu Lys Ile
            820                 825                 830

Ile Lys Asp Lys Asp Phe Leu Asp Asn Glu Glu Asn Glu Asp Ile Leu
```

-continued

```
        835                 840                 845

Glu Asp Ile Val Leu Thr Leu Thr Leu Phe Glu Asp Arg Glu Met Ile
    850                 855                 860

Glu Glu Arg Leu Lys Thr Tyr Ala His Leu Phe Asp Asp Lys Val Met
865                 870                 875                 880

Lys Gln Leu Lys Arg Arg Arg Tyr Thr Gly Trp Gly Arg Leu Ser Arg
                885                 890                 895

Lys Leu Ile Asn Gly Ile Arg Asp Lys Gln Ser Gly Lys Thr Ile Leu
            900                 905                 910

Asp Phe Leu Lys Ser Asp Gly Phe Ala Asn Arg Asn Phe Met Gln Leu
        915                 920                 925

Ile His Asp Asp Ser Leu Thr Phe Lys Glu Asp Ile Gln Lys Ala Gln
    930                 935                 940

Val Ser Gly Gln Gly Asp Ser Leu His Glu His Ile Ala Asn Leu Ala
945                 950                 955                 960

Gly Ser Pro Ala Ile Lys Lys Gly Ile Leu Gln Thr Val Lys Val Val
                965                 970                 975

Asp Glu Leu Val Lys Val Met Gly Arg His Lys Pro Glu Asn Ile Val
            980                 985                 990

Ile Glu Met Ala Arg Glu Asn Gln  Thr Thr Gln Lys Gly  Gln Lys Asn
        995                 1000                1005

Ser Arg  Glu Arg Met Lys Arg  Ile Glu Glu Gly Ile  Lys Glu Leu
    1010                1015                1020

Gly Ser  Gln Ile Leu Lys Glu  His Pro Val Glu Asn  Thr Gln Leu
    1025                1030                1035

Gln Asn  Glu Lys Leu Tyr Leu  Tyr Tyr Leu Gln Asn  Gly Arg Asp
    1040                1045                1050

Met Tyr  Val Asp Gln Glu Leu  Asp Ile Asn Arg Leu  Ser Asp Tyr
    1055                1060                1065

Asp Val  Asp His Ile Val Pro  Gln Ser Phe Leu Lys  Asp Asp Ser
    1070                1075                1080

Ile Asp  Asn Lys Val Leu Thr  Arg Ser Asp Lys Asn  Arg Gly Lys
    1085                1090                1095

Ser Asp  Asn Val Pro Ser Glu  Glu Val Val Lys Lys  Met Lys Asn
    1100                1105                1110

Tyr Trp  Arg Gln Leu Leu Asn  Ala Lys Leu Ile Thr  Gln Arg Lys
    1115                1120                1125

Phe Asp  Asn Leu Thr Lys Ala  Glu Arg Gly Gly Leu  Ser Glu Leu
    1130                1135                1140

Asp Lys  Ala Gly Phe Ile Lys  Arg Gln Leu Val Glu  Thr Arg Gln
    1145                1150                1155

Ile Thr  Lys His Val Ala Gln  Ile Leu Asp Ser Arg  Met Asn Thr
    1160                1165                1170

Lys Tyr  Asp Glu Asn Asp Lys  Leu Ile Arg Glu Val  Lys Val Ile
    1175                1180                1185

Thr Leu  Lys Ser Lys Leu Val  Ser Asp Phe Arg Lys  Asp Phe Gln
    1190                1195                1200

Phe Tyr  Lys Val Arg Glu Ile  Asn Asn Tyr His His  Ala His Asp
    1205                1210                1215

Ala Tyr  Leu Asn Ala Val Val  Gly Thr Ala Leu Ile  Lys Lys Tyr
    1220                1225                1230

Pro Lys  Leu Glu Ser Glu Phe  Val Tyr Gly Asp Tyr  Lys Val Tyr
    1235                1240                1245
```

```
Asp Val  Arg Lys Met Ile Ala  Lys Ser Glu Gln Glu  Ile Gly Lys
    1250                 1255                 1260

Ala Thr  Ala Lys Tyr Phe Phe  Tyr Ser Asn Ile Met  Asn Phe Phe
    1265                 1270                 1275

Lys Thr  Glu Ile Thr Leu Ala  Asn Gly Glu Ile Arg  Lys Arg Pro
    1280                 1285                 1290

Leu Ile  Glu Thr Asn Gly Glu  Thr Gly Glu Ile Val  Trp Asp Lys
    1295                 1300                 1305

Gly Arg  Asp Phe Ala Thr Val  Arg Lys Val Leu Ser  Met Pro Gln
    1310                 1315                 1320

Val Asn  Ile Val Lys Lys Thr  Glu Val Gln Thr Gly  Gly Phe Ser
    1325                 1330                 1335

Lys Glu  Ser Ile Leu Pro Lys  Arg Asn Ser Asp Lys  Leu Ile Ala
    1340                 1345                 1350

Arg Lys  Lys Asp Trp Asp Pro  Lys Lys Tyr Gly Gly  Phe Asp Ser
    1355                 1360                 1365

Pro Thr  Val Ala Tyr Ser Val  Leu Val Val Ala Lys  Val Glu Lys
    1370                 1375                 1380

Gly Lys  Ser Lys Lys Leu Lys  Ser Val Lys Glu Leu  Leu Gly Ile
    1385                 1390                 1395

Thr Ile  Met Glu Arg Ser Ser  Phe Glu Lys Asn Pro  Ile Asp Phe
    1400                 1405                 1410

Leu Glu  Ala Lys Gly Tyr Lys  Glu Val Lys Lys Asp  Leu Ile Ile
    1415                 1420                 1425

Lys Leu  Pro Lys Tyr Ser Leu  Phe Glu Leu Glu Asn  Gly Arg Lys
    1430                 1435                 1440

Arg Met  Leu Ala Ser Ala Gly  Glu Leu Gln Lys Gly  Asn Glu Leu
    1445                 1450                 1455

Ala Leu  Pro Ser Lys Tyr Val  Asn Phe Leu Tyr Leu  Ala Ser His
    1460                 1465                 1470

Tyr Glu  Lys Leu Lys Gly Ser  Pro Glu Asp Asn Glu  Gln Lys Gln
    1475                 1480                 1485

Leu Phe  Val Glu Gln His Lys  His Tyr Leu Asp Glu  Ile Ile Glu
    1490                 1495                 1500

Gln Ile  Ser Glu Phe Ser Lys  Arg Val Ile Leu Ala  Asp Ala Asn
    1505                 1510                 1515

Leu Asp  Lys Val Leu Ser Ala  Tyr Asn Lys His Arg  Asp Lys Pro
    1520                 1525                 1530

Ile Arg  Glu Gln Ala Glu Asn  Ile Ile His Leu Phe  Thr Leu Thr
    1535                 1540                 1545

Asn Leu  Gly Ala Pro Ala Ala  Phe Lys Tyr Phe Asp  Thr Thr Ile
    1550                 1555                 1560

Asp Arg  Lys Arg Tyr Thr Ser  Thr Lys Glu Val Leu  Asp Ala Thr
    1565                 1570                 1575

Leu Ile  His Gln Ser Ile Thr  Gly Leu Tyr Glu Thr  Arg Ile Asp
    1580                 1585                 1590

Leu Ser  Gln Leu Gly Gly Asp  Lys Arg Pro Ala Ala  Thr Lys Lys
    1595                 1600                 1605

Ala Gly  Gln Ala Lys Lys Lys  Lys
    1610                 1615
```

<210> SEQ ID NO 111
<211> LENGTH: 4479

<212> TYPE: DNA
<213> ORGANISM: Artificial Sequence
<220> FEATURE:
<223> OTHER INFORMATION: Synthetic Polynucleotide

<400> SEQUENCE: 111
atgcccttgc cacctggttg ggagcagaga gtggaccagc acgggcgagt ttactatgta 60
gatcatgttg agaaaagaac aacatgggat agaccagaac ctctacctcc tggctgggaa 120
cggcgggttg acaacatggg acgtatttat tatgttgacc atttcacaag aacaacaacg 180
tggcagaggc caacactgac cggtgccacc atggactata aggaccacga cggagactac 240
aaggatcatg atattgatta caaagacgat gacgataaga tggccccaaa gaagaagcgg 300
aaggtcggta tccacggagt cccagcagcc gacaagaagt acagcatcgg cctggacatc 360
ggcaccaact ctgtgggctg ggccgtgatc accgacgagt acaaggtgcc cagcaagaaa 420
ttcaaggtgc tgggcaacac cgaccggcac agcatcaaga agaacctgat cggagccctg 480
ctgttcgaca gcggcgaaac agccgaggcc acccggctga agagaaccgc cagaagaaga 540
tacaccagac ggaagaaccg gatctgctat ctgcaagaga tcttcagcaa cgagatggcc 600
aaggtggacg acagcttctt ccacagactg gaagagtcct tcctggtgga agaggataag 660
aagcacgagc ggcaccccat cttcggcaac atcgtggacg aggtggccta ccacgagaag 720
taccccacca tctaccacct gagaaagaaa ctggtggaca gcaccgacaa ggccgacctg 780
cggctgatct atctggccct ggcccacatg atcaagttcc ggggccactt cctgatcgag 840
ggcgacctga accccgacaa cagcgacgtg gacaagctgt tcatccagct ggtgcagacc 900
tacaaccagc tgttcgagga aaaccccatc aacgccagcg gcgtggacgc caaggccatc 960
ctgtctgcca gactgagcaa gagcagacgg ctggaaaatc tgatcgccca gctgcccggc 1020
gagaagaaga atggcctgtt cggaaacctg attgccctga gcctgggcct gacccccaac 1080
ttcaagagca acttcgacct ggccgaggat gccaaactgc agctgagcaa ggacacctac 1140
gacgacgacc tggacaacct gctggcccag atcggcgacc agtacgccga cctgtttctg 1200
gccgccaaga acctgtccga cgccatcctg ctgagcgaca tcctgagagt gaacaccgag 1260
atcaccaagg ccccccctgag cgcctctatg atcaagagat acgacgagca ccaccaggac 1320
ctgaccctgc tgaaagctct cgtgcggcag cagctgcctg agaagtacaa agagattttc 1380
ttcgaccaga gcaagaacgg ctacgccggc tacattgacg gcggagccag ccaggaagag 1440
ttctacaagt tcatcaagcc catcctggaa aagatggacg gcaccgagga actgctcgtg 1500
aagctgaaca gagaggacct gctgcggaag cagcggacct tcgacaacgg cagcatcccc 1560
caccagatcc acctgggaga gctgcacgcc attctgcggc ggcaggaaga tttttaccca 1620
ttcctgaagg acaaccggga aaagatcgag aagatcctga ccttccgcat cccctactac 1680
gtgggccctc tggccagggg aaacagcaga ttcgcctgga tgaccagaaa gagcgaggaa 1740
accatcaccc cctggaactt cgaggaagtg gtggacaagg gcgcttccgc ccagagcttc 1800
atcgagcgga tgaccaactt cgataagaac ctgcccaacg agaaggtgct gcccaagcac 1860
agcctgctgt acgagtactt caccgtgtat aacgagctga ccaaagtgaa atacgtgacc 1920
gagggaatga gaaagcccgc cttcctgagc ggcgagcaga aaaaggccat cgtggacctg 1980
ctgttcaaga ccaaccggaa agtgaccgtg aagcagctga aagaggacta cttcaagaaa 2040
atcgagtgct tcgactccgt ggaaatctcc ggcgtggaag atcggttcaa cgcctccctg 2100
ggcacatacc acgatctgct gaaaattatc aaggacaagg acttcctgga caatgaggaa 2160

-continued

```
aacgaggaca ttctggaaga tatcgtgctg accctgacac tgtttgagga cagagagatg   2220
atcgaggaac ggctgaaaac ctatgcccac ctgttcgacg acaaagtgat gaagcagctg   2280
aagcggcgga gatacaccgg ctggggcagg ctgagccgga agctgatcaa cggcatccgg   2340
gacaagcagt ccggcaagac aatcctggat ttcctgaagt ccgacggctt cgccaacaga   2400
aacttcatgc agctgatcca cgacgacagc ctgaccttta aagaggacat ccagaaagcc   2460
caggtgtccg gccagggcga tagcctgcac gagcacattg ccaatctggc cggcagcccc   2520
gccattaaga agggcatcct gcagacagtg aaggtggtgg acgagctcgt gaaagtgatg   2580
ggccggcaca agcccgagaa catcgtgatc gaaatggcca gagagaacca gaccacccag   2640
aagggacaga agaacagccg cgagagaatg aagcggatcg aagagggcat caaagagctg   2700
ggcagccaga tcctgaaaga acaccccgtg gaaaacaccc agctgcagaa cgagaagctg   2760
tacctgtact acctgcagaa tgggcgggat atgtacgtgg accaggaact ggacatcaac   2820
cggctgtccg actacgatgt ggaccatatc gtgcctcaga gctttctgaa ggacgactcc   2880
atcgacaaca aggtgctgac cagaagcgac aagaaccggg gcaagagcga caacgtgccc   2940
tccgaagagg tcgtgaagaa gatgaagaac tactggcggc agctgctgaa cgccaagctg   3000
attacccaga gaaagttcga caatctgacc aaggccgaga gaggcggcct gagcgaactg   3060
gataaggccg gcttcatcaa gagacagctg gtggaaaccc ggcagatcac aaagcacgtg   3120
gcacagatcc tggactcccg gatgaacact aagtacgacg agaatgacaa gctgatccgg   3180
gaagtgaaag tgatcaccct gaagtccaag ctggtgtccg atttccggaa ggatttccag   3240
ttttacaaag tgcgcgagat caacaactac caccacgccc acgacgccta cctgaacgcc   3300
gtcgtgggaa ccgccctgat caaaaagtac cctaagctgg aaagcgagtt cgtgtacggc   3360
gactacaagg tgtacgacgt gcggaagatg atcgccaaga gcgagcagga aatcggcaag   3420
gctaccgcca agtacttctt ctacagcaac atcatgaact tttcaagac cgagattacc    3480
ctggccaacg gcgagatccg gaagcggcct ctgatcgaga caaacggcga aaccggggag   3540
atcgtgtggg ataagggccg ggattttgcc accgtgcgga aagtgctgag catgccccaa   3600
gtgaatatcg tgaaaaagac cgaggtgcag acaggcggct tcagcaaaga gtctatcctg   3660
cccaagagga acagcgataa gctgatcgcc agaaagaagg actgggaccc taagaagtac   3720
ggcggcttcg acagccccac cgtggcctat tctgtgctgg tggtggccaa agtggaaaag   3780
ggcaagtcca agaaactgaa gagtgtgaaa gagctgctgg ggatcaccat catggaaaga   3840
agcagcttcg agaagaatcc catcgacttt ctggaagcca agggctacaa agaagtgaaa   3900
aaggacctga tcatcaagct gcctaagtac tccctgttcg agctggaaaa cggccggaag   3960
agaatgctgg cctctgccgg cgaactgcag aagggaaacg aactggccct gccctccaaa   4020
tatgtgaact tcctgtacct ggccagccac tatgagaagc tgaagggctc cccgaggat    4080
aatgagcaga aacagctgtt tgtggaacag cacaagcact acctggacga gatcatcgag   4140
cagatcagcg agttctccaa gagagtgatc ctggccgacg ctaatctgga caaagtgctg   4200
tccgcctaca acaagcaccg ggataagccc atcagagagc aggccgagaa tatcatccac   4260
ctgtttaccc tgaccaatct gggagcccct gccgccttca agtactttga caccaccatc   4320
gaccggaaga ggtacaccag caccaaagag gtgctggacg ccaccctgat ccaccagagc   4380
atcaccggcc tgtacgagac acggatcgac ctgtctcagc tgggaggcga caaaaggccg   4440
gcggccacga aaaaggccgg ccaggcaaaa aagaaaaag                          4479
```

<210> SEQ ID NO 112
<211> LENGTH: 4848
<212> TYPE: DNA
<213> ORGANISM: Artificial Sequence
<220> FEATURE:
<223> OTHER INFORMATION: Synthetic Polynucleotide

<400> SEQUENCE: 112
atgcccttgc cacctggttg ggagcagaga gtggaccagc acgggcgagt ttactatgta 60
gatcatgttg agaaaagaac aacatgggat agaccagaac ctctacctcc tggctgggaa 120
cggcgggttg acaacatggg acgtatttat tatgttgacc atttcacaag aacaacaacg 180
tggcagaggc caacactgga atccgtccgg aactatgaac aatggcagct acagcgtagt 240
cagcttcaag gagcaatgca gcagtttaac cagagattca tttatgggaa tcaagattta 300
tttgctacat cacaaagtaa agaatttgat cctcttggtc cattgccacc tggatgggag 360
aagagaacag acagcaatgg cagagtatat ttcgtcaacc acaacacacg aattacacaa 420
tgggaagacc ccagaagtca aggtcaatta aatgaaaagc ccttacctga aggttgggaa 480
atgagattca cagtggatgg aattccatat tttgtggacc acaatagaag aactaccacc 540
tatatagatc cccgcacagg cggaggaacc ggtgccacca tggactataa ggaccacgac 600
ggagactaca aggatcatga tattgattac aaagacgatg acgataagat ggccccaaag 660
aagaagcgga aggtcggtat ccacggagtc ccagcagccg acaagaagta cagcatcggc 720
ctggacatcg gcaccaactc tgtgggctgg gccgtgatca ccgacgagta caaggtgccc 780
agcaagaaat tcaaggtgct gggcaacacc gaccggcaca gcatcaagaa gaacctgatc 840
ggagccctgc tgttcgacag cggcgaaaca gccgaggcca cccggctgaa gagaaccgcc 900
agaagaagat acaccagacg gaagaaccgg atctgctatc tgcaagagat cttcagcaac 960
gagatggcca aggtggacga cagcttcttc cacagactgg aagagtcctt cctggtggaa 1020
gaggataaga agcacgagcg gcaccccatc ttcggcaaca tcgtggacga ggtggcctac 1080
cacgagaagt accccaccat ctaccacctg agaaagaaac tggtggacag caccgacaag 1140
gccgacctgc ggctgatcta tctggccctg gcccacatga tcaagttccg gggccacttc 1200
ctgatcgagg gcgacctgaa ccccgacaac agcgacgtgg acaagctgtt catccagctg 1260
gtgcagacct acaaccagct gttcgaggaa aaccccatca acgccagcgg cgtggacgcc 1320
aaggccatcc tgtctgccag actgagcaag agcagacggc tggaaaatct gatcgcccag 1380
ctgcccggcg agaagaagaa tggcctgttc ggaaacctga ttgccctgag cctgggcctg 1440
acccccaact tcaagagcaa cttcgacctg gccgaggatg ccaaactgca gctgagcaag 1500
gacacctacg acgacgacct ggacaacctg ctggcccaga tcggcgacca gtacgccgac 1560
ctgtttctgg ccgccaagaa cctgtccgac gccatcctgc tgagcgacat cctgagagtg 1620
aacaccgaga tcaccaaggc ccccctgagc gcctctatga tcaagagata cgacgagcac 1680
caccaggacc tgaccctgct gaaagctctc gtgcggcagc agctgcctga gaagtacaaa 1740
gagattttct tcgaccagag caagaacggc tacgccggct acattgacgg cggagccagc 1800
caggaagagt tctacaagtt catcaagccc atcctggaaa agatggacgg caccgaggaa 1860
ctgctcgtga agctgaacag agaggacctg ctgcggaagc agcggacctt cgacaacggc 1920
agcatccccc accagatcca cctgggagag ctgcacgcca ttctgcggcg gcaggaagat 1980
ttttacccat tcctgaagga caaccgggaa aagatcgaga agatcctgac cttccgcatc 2040
ccctactacg tgggccctct ggccagggga aacagcagat tcgcctggat gaccagaaag 2100

```
agcgaggaaa ccatcacccc ctggaacttc gaggaagtgg tggacaaggg cgcttccgcc   2160
cagagcttca tcgagcggat gaccaacttc gataagaacc tgcccaacga gaaggtgctg   2220
cccaagcaca gcctgctgta cgagtacttc accgtgtata acgagctgac caaagtgaaa   2280
tacgtgaccg agggaatgag aaagcccgcc ttcctgagcg gcgagcagaa aaaggccatc   2340
gtggacctgc tgttcaagac caaccggaaa gtgaccgtga agcagctgaa agaggactac   2400
ttcaagaaaa tcgagtgctt cgactccgtg gaaatctccg gcgtggaaga tcggttcaac   2460
gcctccctgg gcacatacca cgatctgctg aaaattatca aggacaagga cttcctggac   2520
aatgaggaaa acgaggacat tctggaagat atcgtgctga ccctgacact gtttgaggac   2580
agagagatga tcgaggaacg gctgaaaacc tatgcccacc tgttcgacga caaagtgatg   2640
aagcagctga agcggcggag atacaccggc tggggcaggc tgagccggaa gctgatcaac   2700
ggcatccggg acaagcagtc cggcaagaca atcctggatt tcctgaagtc cgacggcttc   2760
gccaacagaa acttcatgca gctgatccac gacgacagcc tgacctttaa agaggacatc   2820
cagaaagccc aggtgtccgg ccagggcgat agcctgcacg agcacattgc caatctggcc   2880
ggcagccccg ccattaagaa gggcatcctg cagacagtga aggtggtgga cgagctcgtg   2940
aaagtgatgg gccggcacaa gcccgagaac atcgtgatcg aaatggccag agagaaccag   3000
accacccaga agggacagaa gaacagccgc gagagaatga agcggatcga agagggcatc   3060
aaagagctgg gcagccagat cctgaaagaa caccccgtgg aaaacaccca gctgcagaac   3120
gagaagctgt acctgtacta cctgcagaat gggcgggata tgtacgtgga ccaggaactg   3180
gacatcaacc ggctgtccga ctacgatgtg gaccatatcg tgcctcagag ctttctgaag   3240
gacgactcca tcgacaacaa ggtgctgacc agaagcgaca agaaccgggg caagagcgac   3300
aacgtgccct ccgaagaggt cgtgaagaag atgaagaact actggcggca gctgctgaac   3360
gccaagctga ttacccagag aaagttcgac aatctgacca aggccgagag aggcggcctg   3420
agcgaactgg ataaggccgg cttcatcaag agacagctgg tggaaacccg gcagatcaca   3480
aagcacgtgg cacagatcct ggactcccgg atgaacacta agtacgacga gaatgacaag   3540
ctgatccggg aagtgaaagt gatcaccctg aagtccaagc tggtgtccga tttccggaag   3600
gatttccagt tttacaaagt gcgcgagatc aacaactacc accacgccca cgacgcctac   3660
ctgaacgccg tcgtgggaac cgccctgatc aaaaagtacc ctaagctgga aagcgagttc   3720
gtgtacggcg actacaaggt gtacgacgtg cggaagatga tcgccaagag cgagcaggaa   3780
atcggcaagg ctaccgccaa gtacttcttc tacagcaaca tcatgaactt tttcaagacc   3840
gagattaccc tggccaacgg cgagatccgg aagcggcctc tgatcgagac aaacggcgaa   3900
accggggaga tcgtgtggga taagggccgg gattttgcca ccgtgcggaa agtgctgagc   3960
atgccccaag tgaatatcgt gaaaaagacc gaggtgcaga caggcggctt cagcaaagag   4020
tctatcctgc ccaagaggaa cagcgataag ctgatcgcca gaaagaagga ctgggaccct   4080
aagaagtacg gcggcttcga cagccccacc gtggcctatt ctgtgctggt ggtggccaaa   4140
gtggaaaagg gcaagtccaa gaaactgaag agtgtgaaag agctgctggg gatcaccatc   4200
atggaaagaa gcagcttcga gaagaatccc atcgactttc tggaagccaa gggctacaaa   4260
gaagtgaaaa aggacctgat catcaagctg cctaagtact ccctgttcga gctggaaaac   4320
ggccggaaga gaatgctggc ctctgccggc gaactgcaga agggaaacga actggccctg   4380
ccctccaaat atgtgaactt cctgtacctg gccagccact atgagaagct gaagggctcc   4440
cccgaggata atgagcagaa acagctgttt gtggaacagc acaagcacta cctggacgag   4500
```

```
atcatcgagc agatcagcga gttctccaag agagtgatcc tggccgacgc taatctggac   4560

aaagtgctgt ccgcctacaa caagcaccgg gataagccca tcagagagca ggccgagaat   4620

atcatccacc tgtttaccct gaccaatctg ggagcccctg ccgccttcaa gtactttgac   4680

accaccatcg accggaagag gtacaccagc accaaagagg tgctggacgc caccctgatc   4740

caccagagca tcaccggcct gtacgagaca cggatcgacc tgtctcagct gggaggcgac   4800

aaaaggccgg cggccacgaa aaaggccggc caggcaaaaa agaaaaag                 4848
```

<210> SEQ ID NO 113
<211> LENGTH: 717
<212> TYPE: DNA
<213> ORGANISM: Artificial Sequence
<220> FEATURE:
<223> OTHER INFORMATION: Synthetic Polynucleotide

<400> SEQUENCE: 113

```
atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaag       717
```

<210> SEQ ID NO 114
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 114

Ala Gly Val Phe
1

<210> SEQ ID NO 115
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 115

Pro Pro Ser Tyr
1

<210> SEQ ID NO 116
<211> LENGTH: 433
<212> TYPE: PRT
<213> ORGANISM: Homo Sapiens

<400> SEQUENCE: 116

```
Met Gly Arg Val Gln Leu Phe Glu Ile Ser Leu Ser His Gly Arg Val
1               5                   10                  15

Val Tyr Ser Pro Gly Glu Pro Leu Ala Gly Thr Val Arg Val Arg Leu
            20                  25                  30

Gly Ala Pro Leu Pro Phe Arg Ala Ile Arg Val Thr Cys Ile Gly Ser
        35                  40                  45

Cys Gly Val Ser Asn Lys Ala Asn Asp Thr Ala Trp Val Val Glu Glu
    50                  55                  60

Gly Tyr Phe Asn Ser Ser Leu Ser Leu Ala Asp Lys Gly Ser Leu Pro
65                  70                  75                  80

Ala Gly Glu His Ser Phe Pro Phe Gln Phe Leu Leu Pro Ala Thr Ala
                85                  90                  95

Pro Thr Ser Phe Glu Gly Pro Phe Gly Lys Ile Val His Gln Val Arg
            100                 105                 110

Ala Ala Ile His Thr Pro Arg Phe Ser Lys Asp His Lys Cys Ser Leu
        115                 120                 125

Val Phe Tyr Ile Leu Ser Pro Leu Asn Leu Asn Ser Ile Pro Asp Ile
    130                 135                 140

Glu Gln Pro Asn Val Ala Ser Ala Thr Lys Lys Phe Ser Tyr Lys Leu
145                 150                 155                 160

Val Lys Thr Gly Ser Val Val Leu Thr Ala Ser Thr Asp Leu Arg Gly
                165                 170                 175

Tyr Val Val Gly Gln Ala Leu Gln Leu His Ala Asp Val Glu Asn Gln
            180                 185                 190

Ser Gly Lys Asp Thr Ser Pro Val Val Ala Ser Leu Leu Gln Lys Val
        195                 200                 205

Ser Tyr Lys Ala Lys Arg Trp Ile His Asp Val Arg Thr Ile Ala Glu
    210                 215                 220

Val Glu Gly Ala Gly Val Lys Ala Trp Arg Arg Ala Gln Trp His Glu
225                 230                 235                 240

Gln Ile Leu Val Pro Ala Leu Pro Gln Ser Ala Leu Pro Gly Cys Ser
                245                 250                 255

Leu Ile His Ile Asp Tyr Tyr Leu Gln Val Ser Leu Lys Ala Pro Glu
            260                 265                 270

Ala Thr Val Thr Leu Pro Val Phe Ile Gly Asn Ile Ala Val Asn His
        275                 280                 285

Ala Pro Val Ser Pro Arg Pro Gly Leu Gly Leu Pro Pro Gly Ala Pro
    290                 295                 300

Pro Leu Val Val Pro Ser Ala Pro Pro Gln Glu Glu Ala Glu Ala Glu
305                 310                 315                 320

Ala Ala Ala Gly Gly Pro His Phe Leu Asp Pro Val Phe Leu Ser Thr
                325                 330                 335

Lys Ser His Ser Gln Arg Gln Pro Leu Leu Ala Thr Leu Ser Ser Val
            340                 345                 350

Pro Gly Ala Pro Glu Pro Cys Pro Gln Asp Gly Ser Pro Ala Ser His
        355                 360                 365

Pro Leu His Pro Pro Leu Cys Ile Ser Thr Gly Ala Thr Val Pro Tyr
    370                 375                 380

Phe Ala Glu Gly Ser Gly Gly Pro Val Pro Thr Thr Ser Thr Leu Ile
385                 390                 395                 400

Leu Pro Pro Glu Tyr Ser Ser Trp Gly Tyr Pro Tyr Glu Ala Pro Pro
                405                 410                 415
```

Ser Tyr Glu Gln Ser Cys Gly Gly Val Glu Pro Ser Leu Thr Pro Glu
420 425 430

Ser

<210> SEQ ID NO 117
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 117

Gly Phe Leu Gly
1

<210> SEQ ID NO 118
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 118

Ala Leu Ala Leu
1

<210> SEQ ID NO 119
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 119

Ala Leu Ala Leu Ala
1 5

<210> SEQ ID NO 120
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 120

Leu Pro Xaa Thr Gly
1 5

<210> SEQ ID NO 121
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 121

Asn Asn Ala Gly Ala Ala Trp
1 5

<210> SEQ ID NO 122
<211> LENGTH: 4
<212> TYPE: PRT

```
<213> ORGANISM: Artificial Sequence
<220> FEATURE:
<223> OTHER INFORMATION: Synthetic Polypeptide

<400> SEQUENCE: 122

Pro Ser Ala Pro
1


<210> SEQ ID NO 123
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 123

Pro Thr Ala Pro
1


<210> SEQ ID NO 124
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 124

Pro Pro Glu Tyr
1
```